(12) United States Patent
Dong et al.

(10) Patent No.: US 8,119,655 B2
(45) Date of Patent: Feb. 21, 2012

(54) KINASE INHIBITORS

(75) Inventors: Qing Dong, San Diego, CA (US); Bheema R. Paraselli, San Diego, CA (US); Nicholas Scorah, San Diego, CA (US); Jeffrey A. Stafford, San Diego, CA (US); Michael B. Wallace, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 1235 days.

(21) Appl. No.: 11/539,857

(22) Filed: Oct. 9, 2006

(65) Prior Publication Data

US 2007/0117816 A1 May 24, 2007

Related U.S. Application Data

(60) Provisional application No. 60/724,619, filed on Oct. 7, 2005.

(51) Int. Cl.
*A61K 31/437* (2006.01)
*C07D 471/04* (2006.01)

(52) U.S. Cl. .......................................... 514/292; 546/81
(58) Field of Classification Search .................... 546/81; 514/292
See application file for complete search history.

(56) References Cited

U.S. PATENT DOCUMENTS

| | | | |
|---|---|---|---|
| 4,260,776 A | 4/1981 | Harnisch | |
| 5,491,147 A | 2/1996 | Boyd | |
| 5,739,144 A | 4/1998 | Warrellow | |
| 5,859,034 A | 1/1999 | Warrellow | |
| 5,962,312 A | 10/1999 | Plowman | |
| 5,972,676 A | 10/1999 | Plowman | |
| 6,143,480 A | 11/2000 | Obayashi et al. | |
| 6,207,401 B1 | 3/2001 | Plowman | |
| 6,265,411 B1 | 7/2001 | Thomas et al. | |
| 6,294,532 B1 | 9/2001 | Thomas et al. | |
| 6,352,858 B1 | 3/2002 | Cowsert | |
| 6,455,559 B1 | 9/2002 | Pevarello | |
| 6,528,509 B1 | 3/2003 | Hale | |
| 6,555,329 B2 | 4/2003 | Jenuwein et al. | |
| 6,593,357 B1 | 7/2003 | Green | |
| 6,610,677 B2 | 8/2003 | Davies | |
| 6,613,776 B2 | 9/2003 | Knegtel | |
| 6,638,926 B2 | 10/2003 | Davies | |
| 6,653,300 B2 | 11/2003 | Bebbington | |
| 6,653,301 B2 | 11/2003 | Bebbington | |
| 6,656,939 B2 | 12/2003 | Bebbington | |
| 6,660,731 B2 | 12/2003 | Bebbington | |
| 6,664,247 B2 | 12/2003 | Bebbington | |
| 6,696,452 B2 | 2/2004 | Davies | |
| 6,699,865 B2 | 3/2004 | Hale | |
| 6,706,491 B1 | 3/2004 | Chang | |
| 6,716,575 B2 | 4/2004 | Plowman | |
| 6,727,251 B2 | 4/2004 | Bebbington | |
| 6,743,791 B2 | 6/2004 | Cao | |
| 6,762,179 B2 | 7/2004 | Cochran et al. | |
| 6,770,643 B2 | 8/2004 | Cox | |
| 6,784,195 B2 | 8/2004 | Hale | |
| 6,787,545 B1 | 9/2004 | Ohtani et al. | |
| 6,806,272 B2 | 10/2004 | Bauer | |
| 6,831,091 B2 | 12/2004 | Gant | |
| 6,841,579 B1 | 1/2005 | Plowman | |
| 6,846,928 B2 | 1/2005 | Bebbington | |
| 6,849,653 B2 | 2/2005 | Clare et al. | |
| 6,858,638 B2 | 2/2005 | Damour | |
| 6,861,422 B2 | 3/2005 | Hoffmann | |
| 6,872,533 B2 | 3/2005 | Toland | |
| 6,890,927 B2 | 5/2005 | Bogle | |
| 6,897,207 B2 | 5/2005 | Cox | |
| 6,916,798 B2 | 7/2005 | Green | |
| 6,919,338 B2 | 7/2005 | Mortlock | |
| 6,949,580 B2 | 9/2005 | Hale et al. | |
| 6,956,052 B2 | 10/2005 | Bergmanis et al. | |
| 6,982,265 B1 | 1/2006 | Hunt et al. | |
| 6,989,385 B2 | 1/2006 | Bebbington et al. | |
| 6,989,451 B2 | 1/2006 | Zhang et al. | |
| 7,008,948 B2 | 3/2006 | Bebbington | |
| 7,038,045 B2 | 5/2006 | Guzi et al. | |
| 7,056,944 B2 | 6/2006 | Hale et al. | |
| 7,081,461 B1 | 7/2006 | Mortlock et al. | |

(Continued)

FOREIGN PATENT DOCUMENTS

CA 2517020 8/2005

(Continued)

OTHER PUBLICATIONS

Dorwald F. A. Side Reactions in Organic Synthesis, 2005, Wiley: VCH, Weinheim p. IX of Preface.*
Mulvihill et. al. "1,3-Disubstituted-imidazo[1,5-a]pyrazines as insulin-like growth-factor-I receptor (IGF-IR) inhibitors" Bioorganic & Medicinal Chemistry Letters 2007, 17, 1091-1097.*
3-Amino-1,4-dimethyl-5H-pyrido[4,3-b]indole(Trp-P-1) tiggers apoptosis by DNA double-strand breaks caused by inhibition of topoisomerarase I , Bunsyo Shiotani et al vol. 25, No. 7, 2004.*
Cecil Textbook of Medicine, edited by Bennet, J.C. and Plum F., 20th edition, vol. 1, 1998, pp. 1004-1010.
Fabbro et al. Pharmacology & Therapeutics vol. 93, p. 79-98, 2002.
Mass, R. D. Int. J. Radiation Oncology Bio. Phys. vol. 58 (3): p. 932-40, 2004.
Database Registry ACS; Oct. 20, 2000; XP002368779, retrieved from STN, Database accession No. 297763-91-8/RN abstract.

(Continued)

*Primary Examiner* — Rita Desai
(74) *Attorney, Agent, or Firm* — David Stemerik; C. Amy Smith; Mitchell Brustein

(57) ABSTRACT

Compounds, pharmaceutical compositions, kits and methods are provided for use with kinases that comprise a compound selected from the group consisting of:

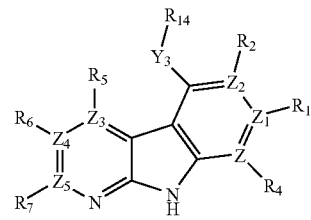

wherein the variables are as defined herein.

17 Claims, No Drawings

U.S. PATENT DOCUMENTS

| | | |
|---|---|---|
| 7,087,603 B2 | 8/2006 | Bebbington et al. |
| 7,091,213 B2 | 8/2006 | Metcalf, III et al. |
| 7,091,343 B2 | 8/2006 | Bebbington et al. |
| 7,098,330 B2 | 8/2006 | Bebbington et al. |
| 7,105,669 B1 | 9/2006 | Mortlock et al. |
| 7,115,739 B2 | 10/2006 | Bebbington et al. |
| 7,151,113 B2 | 12/2006 | Dyckman et al. |
| 7,157,476 B2 | 1/2007 | Come et al. |
| 2002/0151573 A1 | 10/2002 | Gant |
| 2002/0151574 A1 | 10/2002 | Hale |
| 2003/0004161 A1 | 1/2003 | Bebbington |
| 2003/0004164 A1 | 1/2003 | Bebbington |
| 2003/0022885 A1 | 1/2003 | Bebbington |
| 2003/0036543 A1 | 2/2003 | Bebbington |
| 2003/0040536 A1 | 2/2003 | Hale |
| 2003/0055044 A1 | 3/2003 | Davies |
| 2003/0055068 A1 | 3/2003 | Bebbington |
| 2003/0064981 A1 | 4/2003 | Knegtel |
| 2003/0064982 A1 | 4/2003 | Davies |
| 2003/0073687 A1 | 4/2003 | Bebbington |
| 2003/0073692 A1 | 4/2003 | Pulici |
| 2003/0078166 A1 | 4/2003 | Davies |
| 2003/0078275 A1 | 4/2003 | Bebbington |
| 2003/0083327 A1 | 5/2003 | Davies |
| 2003/0092714 A1 | 5/2003 | Cao |
| 2003/0105090 A1 | 6/2003 | Bebbington |
| 2003/0105129 A1 | 6/2003 | Mortlock |
| 2003/0109550 A1 | 6/2003 | Clare |
| 2003/0109697 A1 | 6/2003 | Shepard |
| 2003/0114432 A1 | 6/2003 | Clare et al. |
| 2003/0119856 A1 | 6/2003 | Cochran |
| 2003/0125361 A1 | 7/2003 | Clare |
| 2003/0171357 A1 | 9/2003 | Fancelli |
| 2003/0171359 A1 | 9/2003 | Dahmann |
| 2003/0187002 A1 | 10/2003 | Mortlock |
| 2003/0187007 A1 | 10/2003 | Cao |
| 2003/0208067 A1 | 11/2003 | Cao |
| 2003/0225073 A1 | 12/2003 | Bebbington |
| 2003/0225151 A1 | 12/2003 | Hale |
| 2004/0002496 A1 | 1/2004 | Bebbington |
| 2004/0009974 A1 | 1/2004 | Bebbington |
| 2004/0009981 A1 | 1/2004 | Bebbington |
| 2004/0009983 A1 | 1/2004 | Cox |
| 2004/0010027 A1 | 1/2004 | Casuscelli |
| 2004/0019046 A1 | 1/2004 | Pevarello |
| 2004/0024040 A1 | 2/2004 | Green |
| 2004/0029157 A1 | 2/2004 | Tatsuka |
| 2004/0029857 A1 | 2/2004 | Hale |
| 2004/0029885 A1 | 2/2004 | Bauer |
| 2004/0048849 A1 | 3/2004 | Prevost et al. |
| 2004/0049032 A1 | 3/2004 | Charrier |
| 2004/0053931 A1 | 3/2004 | Cox |
| 2004/0054179 A1 | 3/2004 | Yura et al. |
| 2004/0063715 A1 | 4/2004 | Paruch et al. |
| 2004/0082631 A1 | 4/2004 | Hale |
| 2004/0097501 A1 | 5/2004 | Bebbington |
| 2004/0097531 A1 | 5/2004 | Ledeboer |
| 2004/0102360 A1 | 5/2004 | Barnett |
| 2004/0102506 A1 | 5/2004 | Hale |
| 2004/0106615 A1 | 6/2004 | Cochran |
| 2004/0106667 A1 | 6/2004 | Damour |
| 2004/0110741 A1 | 6/2004 | Bergmanis |
| 2004/0116454 A1 | 6/2004 | Davies |
| 2004/0147524 A1 | 7/2004 | Bauer |
| 2004/0157893 A1 | 8/2004 | Bebbington |
| 2004/0167121 A1 | 8/2004 | Aronov |
| 2004/0167124 A1 | 8/2004 | Chen |
| 2004/0167141 A1 | 8/2004 | Bebbington |
| 2004/0176380 A1 | 9/2004 | Hoffmann |
| 2004/0180881 A1 | 9/2004 | Berta |
| 2004/0198737 A1 | 10/2004 | Cox |
| 2004/0214814 A1 | 10/2004 | Bebbington |
| 2004/0220200 A1 | 11/2004 | Maltais |
| 2004/0224944 A1 | 11/2004 | Bebbington |
| 2004/0229875 A1 | 11/2004 | Cao |
| 2004/0235867 A1 | 11/2004 | Bilodeau |
| 2004/0235919 A1 | 11/2004 | Pevarello |
| 2004/0242559 A1 | 12/2004 | Ugolini |
| 2004/0242613 A1 | 12/2004 | Cardozo |
| 2004/0248853 A1 | 12/2004 | Dyckman |
| 2004/0254177 A1 | 12/2004 | Amici |
| 2004/0265852 A1 | 12/2004 | Plowman |
| 2005/0002938 A1 | 1/2005 | Plowman |
| 2005/0004110 A1 | 1/2005 | Bebbington |
| 2005/0004152 A1 | 1/2005 | Cochran |
| 2005/0004176 A1 | 1/2005 | Dyckman |
| 2005/0009876 A1 | 1/2005 | Bhagwat |
| 2005/0014760 A1 | 1/2005 | Hoffmann |
| 2005/0014761 A1 | 1/2005 | Hoffmann |
| 2005/0020583 A1 | 1/2005 | Pulici |
| 2005/0026984 A1 | 2/2005 | Bigot |
| 2005/0026991 A1 | 2/2005 | Cholody |
| 2005/0032839 A1 | 2/2005 | Fancelli |
| 2005/0032869 A1 | 2/2005 | Berta et al. |
| 2005/0038023 A1 | 2/2005 | Bebbington |
| 2005/0043323 A1 | 2/2005 | Vanotti |
| 2005/0043346 A1 | 2/2005 | Vanotti |
| 2005/0059657 A1 | 3/2005 | Cavicchioli |
| 2005/0059722 A1 | 3/2005 | Damour |
| 2005/0065169 A1 | 3/2005 | Wang |
| 2005/0065171 A1 | 3/2005 | Shakespeare |
| 2005/0070561 A1 | 3/2005 | Jung |
| 2005/0085490 A1 | 4/2005 | Wang |
| 2005/0085531 A1 | 4/2005 | Hodge |
| 2005/0090498 A1 | 4/2005 | Samizu et al. |
| 2005/0107386 A1 | 5/2005 | Narla |
| 2005/0113460 A1 | 5/2005 | Glick |
| 2005/0124640 A1 | 6/2005 | Cardozo |
| 2005/0125852 A1 | 6/2005 | Caenepeel |
| 2005/0130977 A1 | 6/2005 | Lindsley |
| 2005/0137171 A1 | 6/2005 | Cherrier |
| 2005/0137199 A1 | 6/2005 | Jin |
| 2005/0137201 A1 | 6/2005 | Aronov |
| 2005/0143402 A1 | 6/2005 | Cheetham |
| 2005/0170442 A1 | 8/2005 | Kupcho |
| 2006/0004014 A1 | 1/2006 | Hoffmann et al. |
| 2006/0014751 A1 | 1/2006 | Hoffmann et al. |
| 2006/0046990 A1 | 3/2006 | Stadtmueller et al. |
| 2006/0047118 A1 | 3/2006 | Stadtmueller et al. |
| 2006/0148800 A1 | 7/2006 | Stadtmueller et al. |
| 2007/0004684 A1 | 1/2007 | Sennhenn et al. |
| 2007/0093488 A1 | 4/2007 | Deprets et al. |
| 2007/0117816 A1 | 5/2007 | Brown et al. |
| 2007/0161626 A1 | 7/2007 | Halley et al. |
| 2008/0139606 A1 | 6/2008 | Tabart et al. |
| 2008/0146542 A1 | 6/2008 | Barberis et al. |
| 2009/0030034 A1 | 1/2009 | Badorc et al. |
| 2009/0156557 A1 | 6/2009 | Brown |
| 2009/0233924 A1 | 9/2009 | Ple et al. |

FOREIGN PATENT DOCUMENTS

| | | |
|---|---|---|
| DE | 28 44 606 | 4/1980 |
| EP | 1134221 A1 | 9/2001 |
| EP | 1209158 A1 | 5/2002 |
| EP | 1367058 A1 | 12/2003 |
| FR | 1 242 962 | 10/1960 |
| FR | 1242962 | 10/1960 |
| FR | 2818278 | 6/2002 |
| FR | 2876377 | 4/2006 |
| GB | 828 847 | 2/1960 |
| GB | 1268773 | 3/1972 |
| WO | WO 97/42187 | 11/1997 |
| WO | WO 98/18782 A1 | 5/1998 |
| WO | WO 98/28281 A1 | 7/1998 |
| WO | WO 98/41512 A1 | 9/1998 |
| WO | WO 99/10349 | 3/1999 |
| WO | WO 99/37788 | 7/1999 |
| WO | WO 01/07466 A1 | 2/2001 |
| WO | WO 01/21594 A1 | 3/2001 |
| WO | WO 01/21595 A1 | 3/2001 |
| WO | WO 01/21596 A1 | 3/2001 |
| WO | WO 01/21597 A1 | 3/2001 |
| WO | WO 01/25220 A1 | 4/2001 |
| WO | WO 01/32653 A1 | 5/2001 |
| WO | WO 01/47922 A2 | 7/2001 |
| WO | WO 01/47922 A3 | 7/2001 |
| WO | WO 01/55116 A2 | 8/2001 |

| | | | | | | | |
|---|---|---|---|---|---|---|---|
| WO | WO 01/55116 | A3 | 8/2001 | WO | WO 2004/007504 | A1 | 1/2004 |
| WO | WO 01/56993 | A2 | 8/2001 | WO | WO 2004/013144 | A1 | 2/2004 |
| WO | WO 01/56993 | A3 | 8/2001 | WO | WO 2004/013146 | A1 | 2/2004 |
| WO | WO 01/57022 | A2 | 8/2001 | WO | WO 2004/014374 | A1 | 2/2004 |
| WO | WO 01/57022 | A3 | 8/2001 | WO | WO2004/016597 | | 2/2004 |
| WO | WO 01/98299 | A1 | 12/2001 | WO | WO2004/016612 | | 2/2004 |
| WO | WO 02/00649 | A1 | 1/2002 | WO | WO2004/016613 | | 2/2004 |
| WO | WO 02/06280 | A2 | 1/2002 | WO | WO 2004/037814 | A1 | 5/2004 |
| WO | WO 02/12242 | A2 | 2/2002 | WO | WO 2004/043953 | A1 | 5/2004 |
| WO | WO 02/22601 | A1 | 3/2002 | WO | WO 2004/055019 | A1 | 7/2004 |
| WO | WO 02/22602 | A2 | 3/2002 | WO | WO 2004/056812 | A1 | 7/2004 |
| WO | WO 02/22602 | A3 | 3/2002 | WO | WO 2004/056827 | A2 | 7/2004 |
| WO | WO 02/22603 | A1 | 3/2002 | WO | WO 2004/058752 | A1 | 7/2004 |
| WO | WO 02/22604 | A1 | 3/2002 | WO | WO 2004/058781 | A1 | 7/2004 |
| WO | WO 02/22605 | A1 | 3/2002 | WO | WO 2004/058782 | A1 | 7/2004 |
| WO | WO 02/22606 | A1 | 3/2002 | WO | WO 2004/066919 | A2 | 8/2004 |
| WO | WO 02/22607 | A1 | 3/2002 | WO | WO 2004/067516 | A1 | 8/2004 |
| WO | WO 02/22608 | A1 | 3/2002 | WO | WO 2004/070062 | A2 | 8/2004 |
| WO | WO 02/48114 | A1 | 6/2002 | WO | WO 2004/071390 | A2 | 8/2004 |
| WO | WO 02/50065 | A2 | 6/2002 | WO | WO 2004/071507 | A1 | 8/2004 |
| WO | WO 02/50065 | A3 | 6/2002 | WO | WO 2004/076454 | A1 | 9/2004 |
| WO | WO 02/50066 | A2 | 6/2002 | WO | WO 2004/080457 | A1 | 9/2004 |
| WO | WO 02/50066 | A3 | 6/2002 | WO | WO 2004/083203 | A1 | 9/2004 |
| WO | WO 02/057259 | A2 | 7/2002 | WO | WO 2004/087056 | A2 | 10/2004 |
| WO | WO 02/057259 | A3 | 7/2002 | WO | WO 2004/087056 | A3 | 10/2004 |
| WO | WO 02/059111 | A2 | 8/2002 | WO | WO 2004/087707 | A1 | 10/2004 |
| WO | WO 02/059111 | A3 | 8/2002 | WO | WO 2004/090106 | A2 | 10/2004 |
| WO | WO 02/059112 | A2 | 8/2002 | WO | WO 2004/094410 | A1 | 11/2004 |
| WO | WO 02/059112 | A3 | 8/2002 | WO | WO 2004/096129 | A2 | 11/2004 |
| WO | WO 02/062789 | A1 | 8/2002 | WO | WO 2004/096130 | A2 | 11/2004 |
| WO | WO 02/062804 | A1 | 8/2002 | WO | WO 2004/096131 | A2 | 11/2004 |
| WO | WO 02/064586 | A2 | 8/2002 | WO | WO 2004/096135 | A2 | 11/2004 |
| WO | WO 02/064586 | A3 | 8/2002 | WO | WO 2004/098518 | A2 | 11/2004 |
| WO | WO 02/066461 | A1 | 8/2002 | WO | WO 2004/098528 | A2 | 11/2004 |
| WO | WO 02/068415 | A1 | 9/2002 | WO | WO 2004/099156 | A1 | 11/2004 |
| WO | WO 02/079192 | | 10/2002 | WO | WO 2004/104007 | A1 | 12/2004 |
| WO | WO 02/083654 | A1 | 10/2002 | WO | WO 2004/105764 | A1 | 12/2004 |
| WO | WO 02/094809 | A1 | 11/2002 | WO | WO2004/112719 | | 12/2004 |
| WO | WO 02/096867 | A2 | 12/2002 | WO | WO 2004/113324 | A1 | 12/2004 |
| WO | WO 02/096867 | A3 | 12/2002 | WO | WO 2005/002552 | A2 | 1/2005 |
| WO | WO 02/096905 | A1 | 12/2002 | WO | WO 2005/002571 | A1 | 1/2005 |
| WO | WO 03/000688 | A1 | 1/2003 | WO | WO 2005/002576 | A2 | 1/2005 |
| WO | WO 03/000695 | A1 | 1/2003 | WO | WO 2005/004988 | A2 | 1/2005 |
| WO | WO03/000833 | | 1/2003 | WO | WO 2005/004988 | A3 | 1/2005 |
| WO | WO 03/008365 | A2 | 1/2003 | WO | WO 2005/005414 | A2 | 1/2005 |
| WO | WO 03/009852 | | 2/2003 | WO | WO 2005/005414 | A3 | 1/2005 |
| WO | WO 03/011287 | A1 | 2/2003 | WO | WO 2005/005427 | A1 | 1/2005 |
| WO | WO 03/012046 | A2 | 2/2003 | WO | WO 2005/005438 | A1 | 1/2005 |
| WO | WO 03/012046 | A3 | 2/2003 | WO | WO 2005/007641 | A1 | 1/2005 |
| WO | WO 03/020276 | A1 | 3/2003 | WO | WO 2005/009348 | A2 | 2/2005 |
| WO | WO 03/028720 | A1 | 4/2003 | WO | WO 2005/009987 | A1 | 2/2005 |
| WO | WO 03/031606 | A2 | 4/2003 | WO | WO 2005/011675 | A1 | 2/2005 |
| WO | WO 03/031606 | A3 | 4/2003 | WO | WO 2005/012262 | A1 | 2/2005 |
| WO | WO 03/035625 | A1 | 5/2003 | WO | WO 2005/012280 | A1 | 2/2005 |
| WO | WO03/037886 | | 5/2003 | WO | WO 2005/012298 | A1 | 2/2005 |
| WO | WO 03/051358 | A1 | 6/2003 | WO | WO 2005/012304 | A2 | 2/2005 |
| WO | WO 03/053330 | A2 | 7/2003 | WO | WO 2005/012307 | A1 | 2/2005 |
| WO | WO 03/055491 | A1 | 7/2003 | WO | WO 2005/016252 | A2 | 2/2005 |
| WO | WO03/064383 | | 8/2003 | WO | WO 2005/019190 | A2 | 3/2005 |
| WO | WO 03/077921 | A1 | 9/2003 | WO | WO 2005/026150 | A1 | 3/2005 |
| WO | WO 03/078402 | A1 | 9/2003 | WO | WO 2005/026155 | A1 | 3/2005 |
| WO | WO 03/078423 | | 9/2003 | WO | WO 2005/026156 | A1 | 3/2005 |
| WO | WO 03/078426 | A1 | 9/2003 | WO | WO 2005/026157 | A1 | 3/2005 |
| WO | WO 03/078427 | A1 | 9/2003 | WO | WO 2005/027907 | A1 | 3/2005 |
| WO | WO 03/082853 | A1 | 10/2003 | WO | WO 2005/028475 | A2 | 3/2005 |
| WO | WO 03/087395 | A2 | 10/2003 | WO | WO 2005/033102 | | 4/2005 |
| WO | WO 03/087395 | A3 | 10/2003 | WO | WO 2005/034840 | A2 | 4/2005 |
| WO | WO 03/091246 | A1 | 11/2003 | WO | WO 2005/035527 | A1 | 4/2005 |
| WO | WO 03/092607 | A2 | 11/2003 | WO | WO 2005/037797 | A1 | 4/2005 |
| WO | WO 03/092607 | A3 | 11/2003 | WO | WO 2005/037825 | A2 | 4/2005 |
| WO | WO 03/097610 | A1 | 11/2003 | WO | WO 2005/037843 | A1 | 4/2005 |
| WO | WO 03/106417 | A1 | 12/2003 | WO | WO 2005/040133 | A1 | 5/2005 |
| WO | WO 03/106500 | A1 | 12/2003 | WO | WO 2005/040159 | A1 | 5/2005 |
| WO | WO 03/107002 | A1 | 12/2003 | WO | WO 2005/040368 | | 5/2005 |
| WO | WO 03/107002 | A1 | 12/2003 | WO | WO 2005/042525 | A1 | 5/2005 |
| WO | WO 2004/000833 | A1 | 12/2003 | WO | WO 2005/044270 | A1 | 5/2005 |
| WO | WO 2004/005283 | A1 | 1/2004 | WO | WO 2005/047266 | A1 | 5/2005 |
| WO | WO 2004/006838 | A2 | 1/2004 | WO | WO 2005/049033 | A1 | 6/2005 |
| WO | WO 2004/006838 | A3 | 1/2004 | WO | WO 2005/051308 | | 6/2005 |

| | | |
|---|---|---|
| WO | WO 2005/051942 | 6/2005 |
| WO | WO 2005/058923 A1 | 6/2005 |
| WO | WO 2005/063746 A1 | 7/2005 |
| WO | WO 2005/063747 A1 | 7/2005 |
| WO | WO 2005/068473 A1 | 7/2005 |
| WO | WO 2005/070930 A2 | 8/2005 |
| WO | WO 2005/071419 A2 | 8/2005 |
| WO | WO 2005/074922 A1 | 8/2005 |
| WO | WO 2005/075468 A2 | 8/2005 |
| WO | WO 2005/082457 A2 | 9/2005 |
| WO | WO 2005/082908 A1 | 9/2005 |
| WO | WO 2005/094830 A1 | 10/2005 |
| WO | WO 2005/095400 A1 | 10/2005 |
| WO | WO 2005/097758 A1 | 10/2005 |
| WO | WO 2005/097787 A2 | 10/2005 |
| WO | WO 2005/105777 A1 | 11/2005 |
| WO | WO 2005/105788 A1 | 11/2005 |
| WO | WO 2005/111039 A2 | 11/2005 |
| WO | WO 2005/113494 A2 | 12/2005 |
| WO | WO 2005/113507 A1 | 12/2005 |
| WO | WO 2005/113515 A1 | 12/2005 |
| WO | WO 2005/113550 A1 | 12/2005 |
| WO | WO 2005/113550 A1 | 12/2005 |
| WO | WO 2005/116028 A2 | 12/2005 |
| WO | WO 2005/117909 A2 | 12/2005 |
| WO | WO 2005/117943 A2 | 12/2005 |
| WO | WO 2005/117980 A1 | 12/2005 |
| WO | WO 2005/118544 A2 | 12/2005 |
| WO | WO 2005/118587 A1 | 12/2005 |
| WO | WO 2005/120509 A1 | 12/2005 |
| WO | WO 2005/123672 A2 | 12/2005 |
| WO | WO 2005/123696 A1 | 12/2005 |
| WO | WO 2005/123736 A1 | 12/2005 |
| WO | WO 2006/000589 A1 | 1/2006 |
| WO | WO 2006/002236 A1 | 1/2006 |
| WO | WO 2006/002367 A1 | 1/2006 |
| WO | WO 2006/003276 A1 | 1/2006 |
| WO | WO 2006/003378 A1 | 1/2006 |
| WO | WO 2006/003440 A1 | 1/2006 |
| WO | WO 2006/005941 A1 | 1/2006 |
| WO | WO 2006/005955 A1 | 1/2006 |
| WO | WO 2006/007496 A2 | 1/2006 |
| WO | WO 2006/007501 A2 | 1/2006 |
| WO | WO 2006/008028 A1 | 1/2006 |
| WO | WO 2006/008523 A1 | 1/2006 |
| WO | WO 2006/008545 A2 | 1/2006 |
| WO | WO 2006/012624 A2 | 2/2006 |
| WO | WO 2006/014482 A1 | 2/2006 |
| WO | WO 2006/015123 A1 | 2/2006 |
| WO | WO 2006/015312 A2 | 2/2006 |
| WO | WO 2006/017054 A2 | 2/2006 |
| WO | WO 2006/017443 A2 | 2/2006 |
| WO | WO 2006/017549 A2 | 2/2006 |
| WO | WO 2006/018628 A1 | 2/2006 |
| WO | WO 2006/020767 A2 | 2/2006 |
| WO | WO 2006/021544 A1 | 3/2006 |
| WO | WO 2006/021547 A1 | 3/2006 |
| WO | WO 2006/021548 A1 | 3/2006 |
| WO | WO 2006/023083 A1 | 3/2006 |
| WO | WO 2006/023440 A2 | 3/2006 |
| WO | WO 2006/023931 A2 | 3/2006 |
| WO | WO 2006/024836 A1 | 3/2006 |
| WO | WO 2006/024841 A2 | 3/2006 |
| WO | WO 2006/024858 A1 | 3/2006 |
| WO | WO 2006/026500 A1 | 3/2006 |
| WO | WO 2006/026597 A2 | 3/2006 |
| WO | WO 2006/031348 A2 | 3/2006 |
| WO | WO2006/032518 | 3/2006 |
| WO | WO20061026501 | 3/2006 |
| WO | WO 2006/036266 A1 | 4/2006 |
| WO | WO 2006/036395 A2 | 4/2006 |
| WO | WO 2006/036883 A2 | 4/2006 |
| WO | WO 2006/036941 A2 | 4/2006 |
| WO | WO 2006/037032 A2 | 4/2006 |
| WO | WO 2006/040451 A2 | 4/2006 |
| WO | WO 2006/040520 A1 | 4/2006 |
| WO | WO 2006/040568 A1 | 4/2006 |
| WO | WO 2006/041773 A2 | 4/2006 |
| WO | WO2006/044687 | 4/2006 |
| WO | WO2006/046735 | 5/2006 |
| WO | WO2006/050076 | 5/2006 |
| WO | WO2006/052936 | 5/2006 |
| WO | WO2006/055561 | 5/2006 |
| WO | WO2006/055831 | 5/2006 |
| WO | WO2006/058074 | 6/2006 |
| WO | WO2006/067391 | 6/2006 |
| WO | WO2006/067557 | 6/2006 |
| WO | WO2006/070192 | 7/2006 |
| WO | WO2006/070195 | 7/2006 |
| WO | WO2006/070198 | 7/2006 |
| WO | WO2006/075152 | 7/2006 |
| WO | WO 2006/092510 A1 | 9/2006 |
| WO | WO 2006/092573 A1 | 9/2006 |
| WO | WO 2006/092574 A1 | 9/2006 |
| WO | WO2006/114520 | 11/2006 |
| WO | WO2006/117549 | 11/2006 |
| WO | WO2006/117552 | 11/2006 |
| WO | WO2006/117570 | 11/2006 |
| WO | WO2006/124863 | 11/2006 |
| WO | WO2006/130673 | 12/2006 |
| WO | WO 2006/131552 A1 | 12/2006 |
| WO | WO2006/131835 | 12/2006 |
| WO | WO 2007/044779 | 4/2007 |
| WO | WO 2007/117816 | 5/2007 |
| WO | WO 2008/016184 | 2/2008 |
| WO | WO 2008/045834 | 4/2008 |
| WO | WO 2008/054956 | 5/2008 |

OTHER PUBLICATIONS

Database CAPLUS, Chemical Abstracts Service, Columbus, Ohio, US: XP002368789 retrieved from STN, Database accession No. 135:332604/DN abstract RN369597-42-2, -43-3 & JP 2001 294772 A, Oct. 23, 2001.

Database HCAPLUS ACS; XP002368787, retrieved from STN, Database accession No. 57:76580/DN abstract RN95936-94-0 & Sabata, B.K. et al.: Journal of Scientific and Industrial Research, Section B: Physical Sciences, vol. 21B, 1962, pp. 227-229.

Database HCAPLUS ACS; XP002368788 retrieved from STN, Database accession No. 91:176650/DN abstract RN71811-83-1 & Vavrova, Jaroslava et al.: Collection of Czechoslovak Chemical Communications, vol. 44, 1979, pp. 1413-1422.

Database Registry ACS; Apr. 10, 2001; XP002368782, retrieved from STN, Database accession No. 330683-80-2/RN abstract.

Database Registry ACS; Feb. 8, 2001; XP002368783, retrieved from STN, Database accession No. 320741-28-4/RN abstract.

Database Registry ACS; Jan. 11, 2001; XP002368784, retrieved from STN, Database accession No. 313549-01-8/RN abstract.

Database Registry ACS; Jan. 11, 2001; XP002368785, retrieved from STN, Database accession No. 313522-23-5/RN abstract.

Database Registry ACS; Jan. 4, 2001; XP002368786, retrieved from STN, Database accession No. 312755-54-7/RN abstract.

Database Registry ACS; Mar. 18, 2002; XP002368781, retrieved from STN, Database accession No. 401622-65-9/RN abstract.

Database Registry ACS; Oct. 9, 2000; XP002368780, retrieved from STN, Database accession No. 293763-18-5/RN abstract.

Drobnic-Kosorok, M. et al., "Transformations of Some Substituted Methylene Heterocycles with Some Nucleophiles (1)", Journal of Heterocyclic Chemistry, vol. 13, 1976, pp. 1279-1282, XP008060243.

Kurasawa, Y. et al., "A Facile Synthesis of Novel Heterocycle-Conjugated Quinoxalines", Heterocycles vol. 22, No. 5, 1984, pp. 1189-1193, XP008059222 ISSN: 0385-5414.

Kurasawa, Y. et al., "A New Synthesis of 1,5-Dihydropyridazino[3,4-b] quinoxalines and 2-(Pyrazol-4-yl) quinoxalines", J. Heterocyclic Chemistry, vol. 33, 1996, pp. 757-762, XP008060252.

Li Sun et al.: Identification of substituted 3-(4, 5, 6, 7-tetrahydro-1H-indol-2-yl)methylene)-1, 3-dihydroindol-2-ones as growth factor receptor inhibitors for VEGF-R2 (Flk-1/KDR), FGF-R1 and PDGF-Rbeta tyroine kinases, Journal of Medicinal Chemistry, American Chemical Society, Washington, US, vol. 43, Jun. 23, 2000, pp. 2655-2663, XP002222716.

Li Sun et al.: Synthesis and biological evaluation of 3-substituted indolin-2-ones: a novel class of tyrosine kinase inhibitors that exhibit selectivity toward particular receptor tyrosine kinases. Journal of Medicinal and Pharmaceutical Chemistry, American Chemistry Society, Easton, US, vol. 41, No. 14, 1998, pp. 2588-2603, XP002184621.

P. Bruni, G. Guerra: Enolizable cylic ketones. I. Reaction with activated heteroaromatic N-oxides, Annali Di Chimica, vol. 57, No. 6, 1967, pp. 688-697, XP009048877 Rome p. 691, reaction scheme middle of page, last compound.

U.S. Appl. No. 12/706,837, filed Feb. 17, 2010, Qing Dong.

U.S. Appl. No. 12/708,304, filed Feb. 18, 2010, Qing Dong.

U.S. Appl. No. 12/444,957, filed Apr. 9, 2009, Jason W. Brown.

U.S. Appl. No. 12/103,882, filed Apr. 16, 2008, Jason W. Brown.

Bhatti, Inayat A. et al. "Prolysis of 1-substituted pyrazoles and chloroform at 550 C: formation of a-carboline from 1-benzylpyrazoles" Journal of Chemical Society, Perkin Transactions 1: Organic and Bio-Organic Chemistry, (24), 3581-3586 Coden: JCPRB4; ISSN: 0300-922X, 1997, XP002417212 p. 3583; examples 24-27.

Mehta, Lina K. et al. The Eliminatin of an Alkoxy Group in the Photo-Graebe-Ullmann Convension of 1-(2,5-Dialkoxyphenyl)triazolopyridines into Carbolines, and the Preparation of a-,u-and x-Carboine Quinones, 1993.

* cited by examiner

KINASE INHIBITORS

RELATED APPLICATION

This application claims the benefit of U.S. Provisional Application No. 60/724,619 filed Oct. 7, 2005, which is incorporated herein by reference.

FIELD OF THE INVENTION

The invention relates to compounds that may be used to inhibit kinases as well as compositions of matter and kits comprising these compounds. The present invention also relates to methods for inhibiting kinases as well as treatment methods using compounds according to the present invention.

BACKGROUND OF THE INVENTION

The invention relates to inhibitors of enzymes that catalyze phosphoryl transfer and/or that bind ATP/GTP nucleotides, compositions comprising the inhibitors, and methods of using the inhibitors and inhibitor compositions. The inhibitors and compositions comprising them are useful for treating or modulating disease in which phosphoryl transferases, including kinases, may be involved, symptoms of such disease, or the effect of other physiological events mediated by phosphoryl transferases, including kinases. The invention also provides for methods of making the inhibitor compounds and methods for treating diseases in which one or more phosphoryl transferase, including kinase, activities is involved.

Phosphoryl transferases are a large family of enzymes that transfer phosphorous-containing groups from one substrate to another. By the conventions set forth by the Nomenclature Committee of the International Union of Biochemistry and Molecular Biology (IUBMB) enzymes of this type have Enzyme Commission (EC) numbers starting with 2.7.-.- (See, Bairoch A., The ENZYME database in Nucleic Acids Res. 28:204-305 (2000)). Kinases are a class of enzymes that function in the catalysis of phosphoryl transfer. The protein kinases constitute the largest subfamily of structurally related phosphoryl transferases and are responsible for the control of a wide variety of signal transduction processes within the cell. (See, Hardie, G. and Hanks, S. (1995) The Protein Kinase Facts Book, I and II, Academic Press, San Diego, Calif.). Protein kinases are thought to have evolved from a common ancestral gene due to the conservation of their structure and catalytic function. Almost all kinases contain a similar 250-300 amino acid catalytic domain. The protein kinases may be categorized into families by the substrates they phosphorylate (e.g., protein-tyrosine, protein-serine/threonine, histidine, etc.). Protein kinase sequence motifs have been identified that generally correspond to each of these kinase families (See, for example, Hanks, S. K.; Hunter, T., FASEB J. 9:576-596 (1995); Kinghton et al., Science, 253:407-414 (1991); Hiles et al., Cell 70:419-429 (1992); Kunz et al., Cell, 73:585-596 (1993); Garcia-Bustos et al., EMBO J., 13:2352-2361 (1994)). Lipid kinases (e.g. PI3K) constitute a separate group of kinases with structural similarity to protein kinases.

Protein and lipid kinases regulate many different cell processes including, but not limited to, proliferation, growth, differentiation, metabolism, cell cycle events, apoptosis, motility, transcription, translation and other signaling processes, by adding phosphate groups to targets such as proteins or lipids. Phosphorylation events catalyzed by kinases act as molecular on/off switches that can modulate or regulate the biological function of the target protein. Phosphorylation of target proteins occurs in response to a variety of extracellular signals (hormones, neurotransmitters, growth and differentiation factors, etc.), cell cycle events, environmental or nutritional stresses, etc. Protein and lipid kinases can function in signaling pathways to activate or inactivate, or modulate the activity of (either directly or indirectly) the targets. These targets may include, for example, metabolic enzymes, regulatory proteins, receptors, cytoskeletal proteins, ion channels or pumps, or transcription factors. Uncontrolled signaling due to defective control of protein phosphorylation has been implicated in a number of diseases and disease conditions, including, for example, inflammation, cancer, allergy/asthma, diseases and conditions of the immune system, disease and conditions of the central nervous system (CNS), cardiovascular disease, dermatology, and angiogenesis.

Initial interest in protein kinases as pharmacological targets was stimulated by the findings that many viral oncogenes encode structurally modified cellular protein kinases with constitutive enzyme activity. These findings pointed to the potential involvement of oncogene related protein kinases in human proliferatives disorders. Subsequently, deregulated protein kinase activity, resulting from a variety of more subtle mechanisms, has been implicated in the pathophysiology of a number of important human disorders including, for example, cancer, CNS conditions, and immunologically related diseases. The development of selective protein kinase inhibitors that can block the disease pathologies and/or symptoms resulting from aberrant protein kinase activity has therefore generated much interest.

Cancer results from the deregulation of the normal processes that control cell division, differentiation and apoptotic cell death. Protein kinases play a critical role in this regulatory process. A partial non-limiting list of such kinases includes ab1, Aurora-A, Aurora-B, Aurora-C, ATK, bcr-abl, Blk, Brk, Btk, c-Kit, c-Met, c-Src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK-4, Flt-1, Fps, Frk, Fyn, Hck, IGF-1R, INS-R, Jak, KDR, Lck, Lyn, MEK, p38, PDGFR, PIK, PKC, PYK2, Ros, Tie1, Tie2, Trk, Yes and Zap70. In mammalian biology, such protein kinases comprise mitogen activated protein kinase (MAPK) signaling pathways. MAPK signaling pathways are inappropriately activated by a variety of common disease-associated mechanisms such as mutation of ras genes and deregulation of growth factor receptors (Magnuson et al., Seminars in Cancer Biology 5:247-252 (1994)). Therefore the inhibition of protein kinases is an object of the present invention.

Aurora kinases (Aurora-A, Aurora-B, Aurora-C) are serine/threonine protein kinases that have been implicated in human cancer, such as colon, breast and other solid tumors. Aurora-A (also sometimes referred to as AIK) is believed to be involved in protein phosphorylation events that regulate the cell cycle. Specifically, Aurora-A may play a role in controlling the accurate segregation of chromosomes during mitosis. Misregulation of the cell cycle can lead to cellular proliferation and other abnormalities. In human colon cancer tissue, Aurora-A, Aurora-B and Aurora-C have been found to be overexpressed (See, Bischoff et al., EMBO J., 17:3052-3065 (1998); Schumacher et al., J. Cell Biol. 143:1635-1646 (1998); Kimura et al., J. Biol. Chem., 272:13766-13771 (1997)).

There is a continued need to find new therapeutic agents to treat human diseases. The protein kinases, specifically but not limited to Aurora-A, Aurora-B and Aurora-C are especially attractive targets for the discovery of new therapeutics due to their important role in cancer, diabetes, Alzheimer's disease and other diseases.

SUMMARY OF THE INVENTION

The present invention relates to compounds that have activity for inhibiting kinases. The present invention also provides compositions, articles of manufacture and kits comprising these compounds.

In one embodiment, a pharmaceutical composition is provided that comprises a kinase inhibitor according to the present invention as an active ingredient. Pharmaceutical compositions according to the invention may optionally comprise 0.001%-100% of one or more kinase inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with kinases.

In one embodiment, a kit is provided that comprises a composition comprising at least one kinase inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one kinase inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit kinases.

In another embodiment, the compounds, compositions, kits and articles of manufacture are used to treat a disease state for which kinases possesses activity that contributes to the pathology and/or symptomology of the disease state.

In another embodiment, a compound is administered to a subject wherein kinases activity within the subject is altered, preferably reduced.

In another embodiment, a prodrug of a compound is administered to a subject that is converted to the compound in vivo where it inhibits kinases.

In another embodiment, a method of inhibiting kinases is provided that comprises contacting kinases with a compound according to the present invention.

In another embodiment, a method of inhibiting kinases is provided that comprises causing a compound according to the present invention to be present in a subject in order to inhibit kinases in vivo.

In another embodiment, a method of inhibiting kinases is provided that comprises administering a first compound to a subject that is converted in vivo to a second compound wherein the second compound inhibits kinases in vivo. It is noted that the compounds of the present invention may be the first or second compounds.

In another embodiment, a therapeutic method is provided that comprises administering a compound according to the present invention.

In another embodiment, a method of inhibiting cell proliferation is provided that comprises contacting a cell with an effective amount of a compound according to the present invention.

In another embodiment, a method of inhibiting cell proliferation in a patient is provided that comprises administering to the patient a therapeutically effective amount of a compound according to the present invention.

In another embodiment, a method of treating a condition in a patient which is known to be mediated by kinases, or which is known to be treated by kinase inhibitors, comprising administering to the patient a therapeutically effective amount of a compound according to the present invention.

In another embodiment, a method is provided for using a compound according to the present invention in order to manufacture a medicament for use in the treatment of disease state which is known to be mediated by kinases, or which is known to be treated by kinase inhibitors.

In another embodiment, a method is provided for treating a disease state for which kinases possesses activity that contributes to the pathology and/or symptomology of the disease state, the method comprising: causing a compound according to the present invention to be present in a subject in a therapeutically effective amount for the disease state.

In another embodiment, a method is provided for treating a disease state for which kinases possesses activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which kinases possesses activity that contributes to the pathology and/or symptomology of the disease state, the method comprising: administering a compound according to the present invention to a subject such that the compound is present in the subject in a therapeutically effective amount for the disease state.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well know in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting kinases and thus may themselves be prodrugs for another compound. Such prodrugs of another compound may or may not themselves independently have kinase inhibitory activity.

Definitions

Unless otherwise stated, the following terms used in the specification and claims shall have the following meanings for the purposes of this Application.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_{3-8}$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with oxygen (See "oxaalkyl"), oxoalkyl (See "oxoalkyl), sulfur (See "thioalkyl"), or nitrogen atoms (See "azaalkyl") between the carbon atoms. $C_X$ alkyl and $C_{X-Y}$ alkyl are typically used where X and Y indicate the number of carbon atoms in the chain. For example, $C_{1-6}$ alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl) means a straight or branched, saturated or unsaturated aliphatic divalent radical having the number of atoms indicated or when no atoms are indicated means a bond (e.g., $(C_{6-10})$aryl$(C_{1-3})$alkyl includes, benzyl, phenethyl, 1-phenylethyl, 3-phenylpropyl, 2-thienylmethyl, 2-pyridinylmethyl and the like).

"Alkenyl" means a straight or branched, carbon chain that contains at least one carbon-carbon double bond. Examples of alkenyl include vinyl, allyl, isopropenyl, pentenyl, hexenyl, heptenyl, 1-propenyl, 2-butenyl, 2-methyl-2-butenyl, and the like.

"Alkynyl" means a straight or branched, carbon chain that contains at least one carbon-carbon triple bond. Examples of alkynyl include ethynyl, propargyl, 3-methyl-1-pentynyl, 2-heptynyl and the like.

"Alkylene", unless indicated otherwise, means a straight or branched, saturated or unsaturated, aliphatic, divalent radical. $C_X$ alkylene and $C_{X-Y}$ alkylene are typically used where X and Y indicate the number of carbon atoms in the chain. For example, $C_{1-6}$ alkylene includes methylene (—$CH_2$—), ethylene (—$CH_2CH_2$—), trimethylene (—$CH_2CH_2CH_2$—), tetramethylene (—$CH_2CH_2CH_2CH_2$—) 2-butenylene (—$CH_2CH=CHCH_2$—), 2-methyltetramethylene (—$CH_2CH(CH_3)CH_2CH_2$—), pentamethylene (—$CH_2CH_2CH_2CH_2CH_2$—) and the like.

"Alkenylene" means a straight or branched, divalent carbon chain having one or more carbon-carbon double bonds. Examples of alkenylene include ethene-1,2-diyl, propene-1,3-diyl, methylene-1,1-diyl, and the like.

"Alkynylene" means a straight or branched, divalent carbon chain having one or more carbon-carbon triple bonds. Examples of alkynylene include ethyne-1,2-diyl, propyne-1,3-diyl, and the like.

"Alkylidene" means a straight or branched saturated or unsaturated, aliphatic radical connected to the parent molecule by a double bond. $C_X$ alkylidene and $C_{X-Y}$ alkylidene are typically used where X and Y indicate the number of carbon atoms in the chain. For example, $C_{1-6}$ alkylidene includes methylene (=$CH_2$), ethylidene (=$CHCH_3$), isopropylidene (=$C(CH_3)_2$), propylidene (=$CHCH_2CH_3$), allylidene (=CH—CH=$CH_2$), and the like).

"Amino" means a nitrogen moiety having two further substituents where, for example, a hydrogen or carbon atom is attached to the nitrogen. For example, representative amino groups include —$NH_2$, —$NHCH_3$, —$N(CH_3)_2$, —$NHC_{1-10}$-alkyl, —$N(C_{1-10}$-alkyl$)_2$, —NHaryl, —NHheteroaryl, —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Azaalkyl" means an alkyl, as defined above, except where one or more of the carbon atoms forming the alkyl chain are replaced with substituted or unsubstituted nitrogen atoms (—N—). For example, a $(C_{1-10})$azaalkyl refers to a chain comprising between 1 and 10 carbons and one or more nitrogen atoms.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are $sp^2$ hybridized and the total number of pi electrons is equal to 4n+2. An aromatic ring may be such that the ring atoms are only carbon atoms or may include carbon and non-carbon atoms (see Heteroaryl).

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $C_X$ aryl and $C_{X-Y}$ aryl are typically used where X and Y indicate the number of carbon atoms in the ring.

"Bicycloalkyl" means a saturated or partially unsaturated fused bicyclic or bridged polycyclic ring assembly.

"Bicycloaryl" means a bicyclic ring assembly wherein the rings are linked by a single bond or fused and at least one of the rings comprising the assembly is aromatic. $C_X$ bicycloaryl and $C_{X-Y}$ bicycloaryl are typically used where X and Y indicate the number of carbon atoms in the bicyclic ring assembly and directly attached to the ring.

"Bridging ring" as used herein refers to a ring that is bonded to another ring to form a compound having a bicyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NR$_a$R$_b$ where R$_a$ and R$_b$ are each independently two further substituents where a hydrogen or carbon atom is attached to the nitrogen.

"Carbocycle" means a ring consisting of carbon atoms.

"Carbocyclic ketone derivative" means a carbocyclic derivative wherein the ring contains a —CO— moiety.

"Carbonyl" means the radical —CO—. It is noted that the carbonyl radical may be further substituted with a variety of substituents to form different carbonyl groups including acids, acid halides, aldehydes, amides, esters, and ketones.

"Carboxy" means the radical —CO$_2$—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, fused bicyclic or bridged polycyclic ring assembly. $C_X$ cycloalkyl and $C_{X-Y}$ cycloalkyl are typically used where X and Y indicate the number of carbon atoms in the ring assembly. For example, $C_{3-10}$ cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

"Cycloalkylene" means a divalent saturated or partially unsaturated, monocyclic or polycyclic ring assembly. $C_X$ cycloalkylene and $C_{X-Y}$ cycloalkylene are typically used where X and Y indicate the number of carbon atoms in the ring assembly.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g., halo-substituted $(C_{1-3})$alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom" refers to an atom that is not a carbon atom. Particular examples of heteroatoms include, but are not limited to nitrogen, oxygen, and sulfur.

"Heteroatom moiety" includes a moiety where the atom by which the moiety is attached is not a carbon. Examples of heteroatom moieties include —N=, —NR$_c$—, —N$^+$(O$^-$)=, —O—, —S— or —S(O)$_2$—, wherein R$_c$ is further substituent.

"Heteroalkyl" means alkyl, as defined in this Application, provided that one or more of the atoms within the alkyl chain is a heteroatom.

"Heterobicycloalkyl" means bicycloalkyl, as defined in this Application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like.

"Heterocycloalkylene" means cycloalkylene, as defined in this Application, provided that one or more of the ring member carbon atoms is replaced by a heteroatom.

"Heteroaryl" means a monocyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted.

"Heterobicycloaryl" means bicycloaryl, as defined in this Application, provided that one or more of the atoms within the ring is a heteroatom. For example, hetero($C_{4-12}$)bicycloaryl as used in this Application includes, but is not limited to, 2-amino-4-oxo-3,4-dihydropteridin-6-yl, tetrahydroisoquinolinyl, and the like.

"Heterocycloalkyl" means cycloalkyl, as defined in this Application, provided that one or more of the atoms forming the ring is a heteroatom selected, independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl, tetrazolyl and the like.

"Hydroxy" means the radical —OH.

"$IC_{50}$" means the molar concentration of an inhibitor that produces 50% inhibition of the target enzyme.

"Iminoketone derivative" means a derivative comprising the moiety —C(NR)—, wherein R comprises a hydrogen or carbon atom attached to the nitrogen.

"Isomers" mean any compound having an identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Nitro" means the radical —$NO_2$.

"Oxaalkyl" means an alkyl, as defined above, except where one or more of the carbon atoms forming the alkyl chain are replaced with oxygen atoms (—O—). For example, a ($C_{1-10}$) oxaalkyl refers to a chain comprising between 1 and 10 carbons and one or more oxygen atoms.

"Oxoalkyl" means an alkyl, further substituted with a carbonyl group. In particular, "oxoalkyl" refers to an alkyl, as defined above, wherein one or more of the carbon atoms forming the alkyl chain is substituted with an oxo group (=O). The carbonyl group may be an aldehyde, ketone, ester, amide, acid or acid chloride. For example, a ($C_{2-10}$)oxoalkyl refers to a chain comprising between 2 and 10 carbon atoms wherein one or more of the carbon atoms is substituted with an oxo group to form a carbonyl.

"Oxy" means the radical —O—. It is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound that is convertible in vivo metabolically into an inhibitor according to the present invention. The prodrug itself may or may not also have kinase inhibitory activity. For example, an inhibitor comprising a hydroxy group may be administered as an ester that is converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, an inhibitor comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis,* 3rd edition, John Wiley & Sons, Inc. 1999.

"Ring" means a carbocyclic or a heterocyclic system.

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —CH$_3$. In general, a non-hydrogen substituent may be any substituent that may be bound to an atom of the given moiety that is specified to be substituted. Examples of substituents include, but are not limited to, aldehyde, alicyclic, aliphatic, (C$_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl.

"Sulfinyl" means the radical —SO—. It is noted that the sulfinyl radical may be further substituted with a variety of substituents to form different sulfinyl groups including sulfinic acids, sulfinamides, sulfinyl esters, and sulfoxides.

"Sulfonyl" means the radical —SO$_2$—. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thioalkyl" means an alkyl, as defined above, except where one or more of the carbon atoms forming the alkyl chain are replaced with sulfur atoms (—S—). For example, a (C$_{1-10}$)thiooalkyl refers to a chain comprising between 1 and 10 carbons and one or more sulfur atoms.

"Thiocarbonyl" means the radical —CS—. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a C$_1$ alkyl comprises methyl (i.e., —CH$_3$) as well as —CR$_a$R$_b$R$_c$ where R$_a$, R$_b$, and R$_c$ may each independently be hydrogen or any other substituent where the atom attached to the carbon is a heteroatom or cyano. Hence, CF$_3$, CH$_2$OH and CH$_2$CN, for example, are all C$_1$ alkyls.

Kinase Inhibitors

In one embodiment, kinase inhibitors of the present invention comprise the formula:

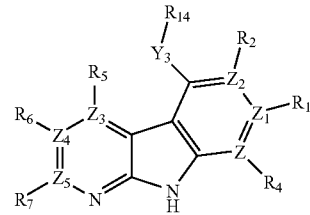

wherein

Z, Z$_1$, Z$_2$, Z$_3$, Z$_4$ and Z$_5$ are each independently selected from the group consisting of C and N;

R$_1$ is —Y$_1$—R$_{12}$, or R$_1$ is absent when Z$_1$ is N;

R$_2$ is —Y$_2$—R$_{13}$, or R$_2$ is absent when Z$_2$ is N, or R$_1$ and R$_2$ are taken together to form a ring;

Y$_1$, Y$_2$ and Y$_3$ are each independently absent or a linker providing 1 or 2 atom separation between R$_{12}$, R$_{13}$ or R$_{14}$ and the ring to which Y$_1$, Y$_2$ or Y$_3$ is attached, wherein the atoms of the linker providing the separation are selected from the group consisting of carbon, oxygen, nitrogen, and sulfur;

R$_4$ is selected from the group consisting of hydrogen, halo, nitro, cyano, thio, oxy, hydroxy, carbonyloxy, alkoxy, carbonyl, amino, (C$_{1-5}$)alkylamino, (C$_{1-5}$)alkyl, halo(C$_{1-5}$)alkyl, carbonyl(C$_{1-3}$)alkyl, sulfonyl(C$_{1-3}$)alkyl, amino (C$_{1-5}$)alkyl, aryl(C$_{1-5}$)alkyl, heteroaryl(C$_{1-5}$)alkyl, (C$_{3-6}$)cycloalkyl and hetero(C$_{3-6}$)cycloalkyl, each substituted or unsubstituted, with the proviso that R$_4$ is absent when the atom to which it is bound is N;

R$_5$ and R$_6$ are each independently selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-2}$)

bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;

$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N;

$R_{12}$ and $R_{13}$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{12}$ and $R_{13}$ are taken together to form a ring; and $R_{14}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In one variation of the above embodiment, —$Y_3$—$R_{14}$ is not H when Z, $Z_1$, $Z_2$, $Z_3$ and $Z_5$ are all C; $R_5$ is a substituted amino group; and $R_2$ is methoxy or $R_7$ is methyl or amino. In another variation of the above embodiment and variation, $R_{14}$ is not 3-chlorophenyl when $R_1$, $R_5$, $R_6$ and $R_7$ are each H; Z and $Z_2$ are each N; $R_2$ and $R_4$ are absent; $Z_1$, $Z_3$, $Z_4$ and $Z_5$ are all C; and $Y_3$ is NH.

In another embodiment, kinase inhibitors of the present invention comprise the formula:

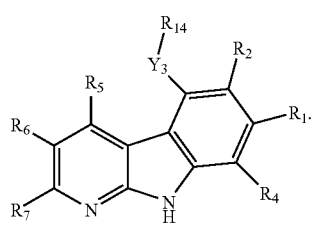

In still another embodiment, kinase inhibitors of the present invention comprise the formula:

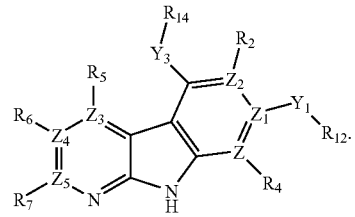

In yet another embodiment, kinase inhibitors of the present invention comprise the formula:

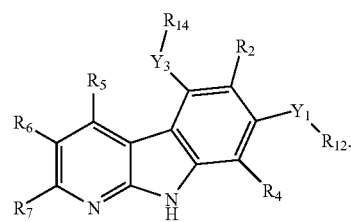

In a further embodiment, kinase inhibitors of the present invention comprise the formula:

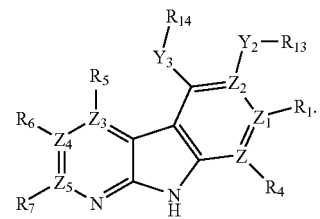

In still a further embodiment, kinase inhibitors of the present invention comprise the formula:

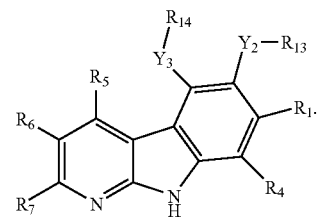

In yet a further embodiment, kinase inhibitors of the present invention comprise the formula:

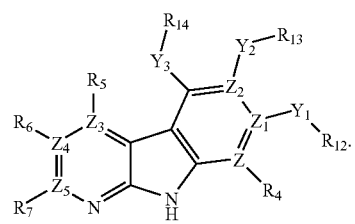

In one variation of the above embodiment, —$Y_1$—$R_{12}$ is absent when $Z_1$ is N and —$Y_2$—$R_{13}$ is absent when $Z_2$ is N.

In another embodiment, kinase inhibitors of the present invention comprise the formula:

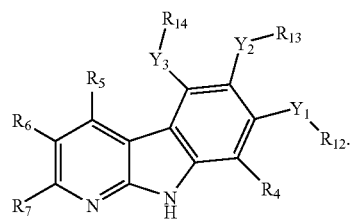

In still another embodiment, kinase inhibitors of the present invention comprise the formula:

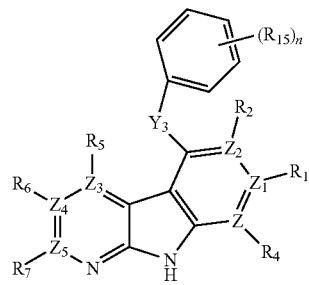

wherein n is selected from the group consisting of 0, 1, 2, 3, 4 and 5; and $R_{15}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{15}$ are taken together to form a ring.

In one variation of the above embodiment, $R_{15}$ is not 3-chloro when n is 1; $R_1$, $R_5$, $R_6$ and $R_7$ are each H; Z and $Z_2$ are each N; $R_2$ and $R_4$ are absent; $Z_1$, $Z_3$, $Z_4$ and $Z_5$ are all C; and $Y_3$ is NH.

In yet another embodiment, kinase inhibitors of the present invention comprise the formula:

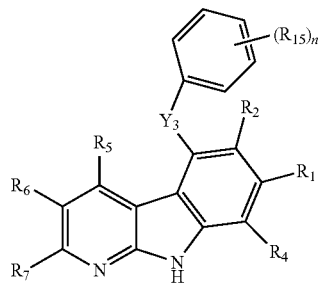

wherein n is selected from the group consisting of 0, 1, 2, 3, 4 and 5; and $R_{15}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{15}$ are taken together to form a ring.

In a further embodiment, kinase inhibitors of the present invention comprise the formula:

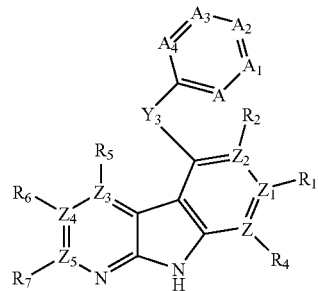

wherein

A, $A_1$, $A_2$, $A_3$ and $A_4$ are each independently selected from the group consisting of $CR_{25}$ and N; and $R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a ring.

In one variation of the above embodiment, $A_1$ is not CCl when $A, A_2, A_3$ and $A_4$ are each CH; $R_1, R_5, R_6$ and $R_7$ are each H; Z and $Z_2$ are each N; $R_2$ and $R_4$ are absent; $Z_1, Z_3, Z_4$ and $Z_5$ are all C; and $Y_3$ is NH.

In still a further embodiment, kinase inhibitors of the present invention comprise the formula:

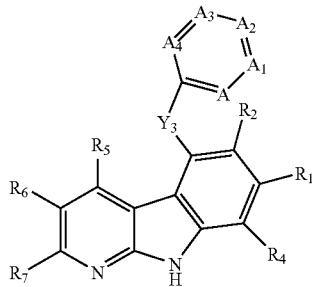

wherein $A, A_1, A_2, A_3$ and $A_4$ are each independently selected from the group consisting of $CR_{25}$ and N; and $R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a ring.

In yet a further embodiment, kinase inhibitors of the present invention comprise the formula:

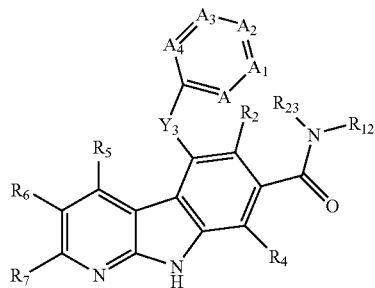

wherein $A, A_1, A_2, A_3$ and $A_4$ are each independently selected from the group consisting of $CR_{25}$ and N;

$R_{23}$ is selected from the group consisting of hydrogen, carbonyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted, or $R_{23}$ and $R_{12}$ are taken together to form a ring; and $R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a ring.

In another embodiment, kinase inhibitors of the present invention comprise the formula:

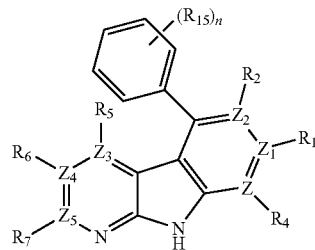

wherein n is selected from the group consisting of 0, 1, 2, 3, 4 and 5; and $R_{15}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{15}$ are taken together to form a ring.

In still another embodiment, kinase inhibitors of the present invention comprise the formula:

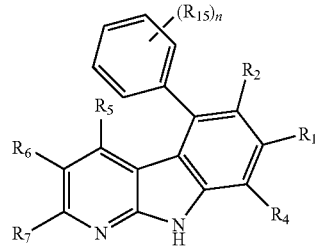

wherein n is selected from the group consisting of 0, 1, 2, 3, 4 and 5; and $R_{15}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{15}$ are taken together to form a ring.

In yet another embodiment, kinase inhibitors of the present invention comprise the formula:

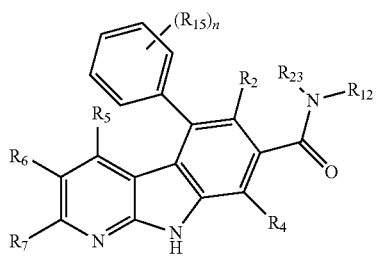

wherein n is selected from the group consisting of 0, 1, 2, 3, 4 and 5;

$R_{15}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{15}$ are taken together to form a ring; and $R_{23}$ is selected from the group consisting of hydrogen, carbonyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted, or $R_{23}$ and $R_{12}$ are taken together to form a ring.

In a further embodiment, kinase inhibitors of the present invention comprise the formula:

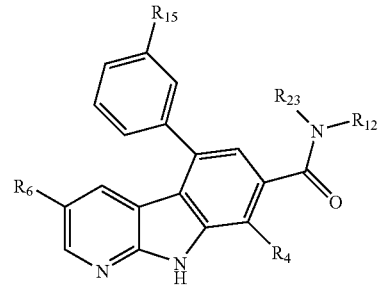

wherein $R_{15}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{23}$ is selected from the group consisting of hydrogen, carbonyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted, or $R_{23}$ and $R_{12}$ are taken together to form a ring.

In still a further embodiment, kinase inhibitors of the present invention comprise the formula:

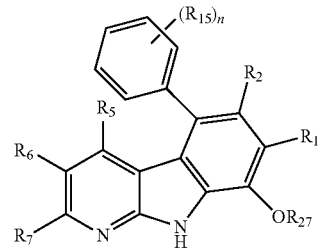

wherein n is selected from the group consisting of 0, 1, 2, 3, 4 and 5;

$R_{15}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{15}$ are taken together to form a ring; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In yet a further embodiment, kinase inhibitors of the present invention comprise the formula:

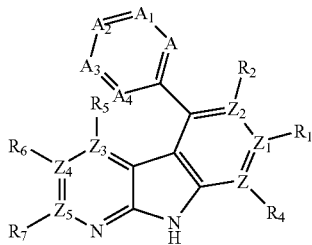

wherein $A, A_1, A_2, A_3$ and $A_4$ are each independently selected from the group consisting of $CR_{25}$ and N; and $R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a ring.

In another embodiment, kinase inhibitors of the present invention comprise the formula:

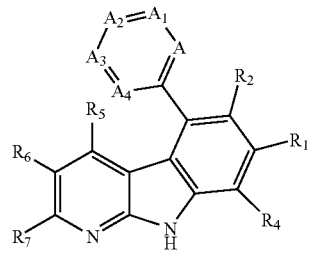

wherein $A, A_1, A_2, A_3$ and $A_4$ are each independently selected from the group consisting of $CR_{25}$ and N; and $R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a ring.

In still another embodiment, kinase inhibitors of the present invention comprise the formula:

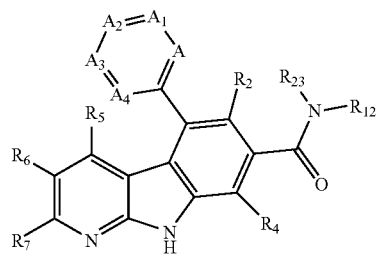

wherein $A, A_1, A_2, A_3$ and $A_4$ are each independently selected from the group consisting of $CR_{25}$ and N;

$R_{23}$ is selected from the group consisting of hydrogen, carbonyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted, or $R_{23}$ and $R_{12}$ are taken together to form a ring; and $R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a ring.

In yet another embodiment, kinase inhibitors of the present invention comprise the formula:

23

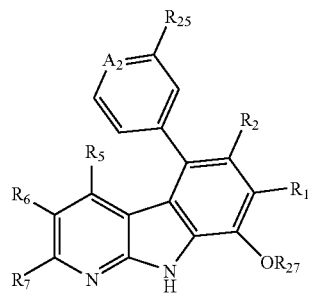

wherein
A$_2$ is selected from the group consisting of CR$_{25}$ and N;
R$_{25}$ is selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or any two R$_{25}$ are taken together to form a ring; and
R$_{27}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted.

In a further embodiment, kinase inhibitors of the present invention comprise the formula:

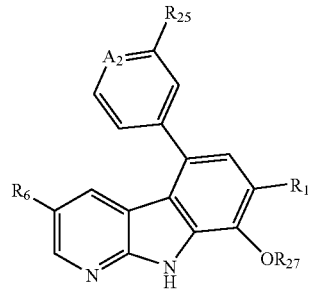

wherein
A$_2$ is selected from the group consisting of CR$_{25}$ and N;

24

R$_{25}$ is selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or any two R$_{25}$ are taken together to form a ring; and
R$_{27}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, (C$_{1-10}$)oxaalkyl, (C$_{1-10}$)oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted.

In still a further embodiment, kinase inhibitors of the present invention comprise the formula:

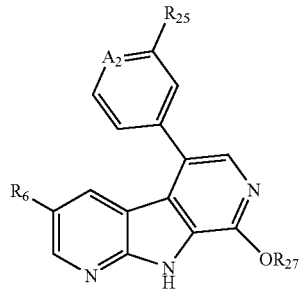

wherein
A$_2$ is selected from the group consisting of CR$_{25}$ and N;
R$_{25}$ is selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, or any two R$_{25}$ are taken together to form a ring; and $R_{27}$ is selected from the group consisting of hydrogen, halo, nitro, cyano, thio, oxy, hydroxy, carbonyloxy,(£ $C_{1-10}$)alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In yet a further embodiment, kinase inhibitors of the present invention comprise the formula:

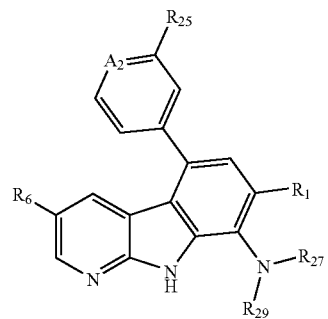

wherein $A_2$ is selected from the group consisting of $CR_{25}$ and N;

$R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{25}$ are taken together to form a ring; and $R_{27}$ and $R_{29}$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero $(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{27}$ and $R_{29}$ are taken together to form a substituted or unsubstituted ring.

In another embodiment, kinase inhibitors of the present invention comprise the formula:

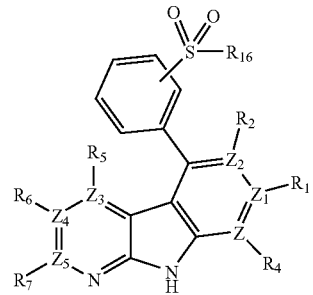

wherein $R_{16}$ is selected from the group consisting of amino, $(C_{1-10})$alkylamino, $(C_{1-10})$alkyl, halo$(C_{1-10})$alkyl, hydroxy$(C_{1-5})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted.

In still another embodiment, kinase inhibitors of the present invention comprise the formula:

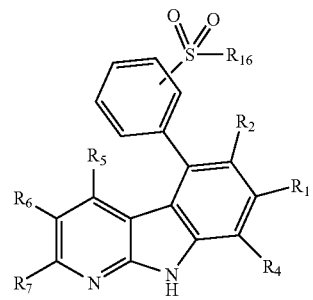

wherein $R_{16}$ is selected from the group consisting of amino, $(C_{1-10})$alkylamino, $(C_{1-10})$alkyl, halo$(C_{1-10})$alkyl, hydroxy$(C_{1-5})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted.

In yet another embodiment, kinase inhibitors of the present invention comprise the formula:

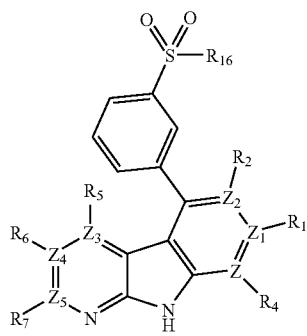

wherein
R$_{16}$ is selected from the group consisting of amino, (C$_{1-10}$) alkylamino, (C$_{1-10}$)alkyl, halo(C$_{1-10}$)alkyl, hydroxy (C$_{1-5}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, amino (C$_{1-10}$)alkyl, (C$_{3-12}$)cycloalkyl(C$_{1-5}$)alkyl, hetero (C$_{3-12}$)cycloalkyl(C$_{1-5}$)alkyl, aryl(C$_{1-10}$)alkyl, heteroaryl(C$_{1-5}$)alkyl, (C$_{3-12}$)cycloalkyl, hetero(C$_{3-12}$)cycloalkyl, aryl and heteroaryl, each substituted or unsubstituted.

In a further embodiment, kinase inhibitors of the present invention comprise the formula:

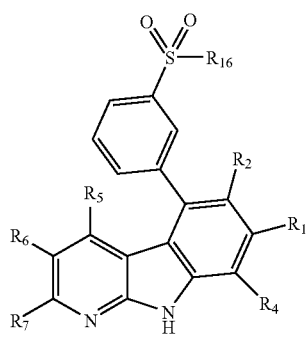

wherein
R$_{16}$ is selected from the group consisting of amino, (C$_{1-10}$) alkylamino, (C$_{1-10}$)alkyl, halo(C$_{1-10}$)alkyl, hydroxy (C$_{1-5}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, amino (C$_{1-10}$)alkyl, (C$_{3-12}$)cycloalkyl(C$_{1-5}$)alkyl, hetero (C$_{3-12}$)cycloalkyl(C$_{1-5}$)alkyl, aryl(C$_{1-10}$)alkyl, heteroaryl(C$_{1-5}$)alkyl, (C$_{3-12}$)cycloalkyl, hetero(C$_{3-12}$)cycloalkyl, aryl and heteroaryl, each substituted or unsubstituted.

In still a further embodiment, kinase inhibitors of the present invention comprise the formula:

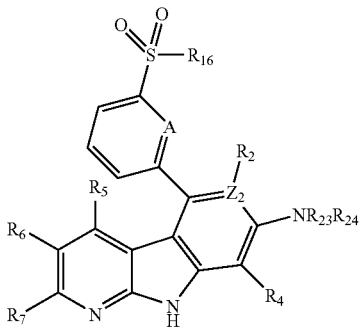

wherein
A is selected from the group consisting of CR$_{25}$ and N;
R$_{16}$ is selected from the group consisting of amino, (C$_{1-10}$) alkylamino, (C$_{1-10}$)alkyl, halo(C$_{1-10}$)alkyl, hydroxy (C$_{1-5}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, amino (C$_{1-10}$)alkyl, (C$_{3-12}$)cycloalkyl(C$_{1-5}$)alkyl, hetero (C$_{3-12}$)cycloalkyl(C$_{1-5}$)alkyl, aryl(C$_{1-10}$)alkyl, heteroaryl(C$_{1-5}$)alkyl, (C$_{3-12}$)cycloalkyl, hetero(C$_{3-12}$)cycloalkyl, aryl and heteroaryl, each substituted or unsubstituted;
R$_{23}$ and R$_{24}$ are each independently selected from the group consisting of hydrogen, carbonyl, (C$_{1-10}$)alkyl, halo(C$_{1-10}$)alkyl, carbonyl(C$_{1-3}$)alkyl, thiocarbonyl (C$_{1-3}$)alkyl, sulfonyl(C$_{1-3}$)alkyl, sulfinyl(C$_{1-3}$)alkyl, amino(C$_{1-10}$)alkyl, imino(C$_{1-3}$)alkyl, (C$_{3-12}$)cycloalkyl (C$_{1-5}$)alkyl, hetero(C$_{3-12}$)cycloalkyl(C$_{1-5}$)alkyl, aryl (C$_{1-10}$)alkyl, heteroaryl(C$_{1-5}$)alkyl, (C$_{3-12}$)cycloalkyl, hetero(C$_{3-12}$)cycloalkyl, aryl and heteroaryl, each substituted or unsubstituted, or R$_{23}$ and R$_{24}$ are taken together to form a ring; and
R$_{25}$ is selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo (C$_{1-10}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted.

In yet a further embodiment, kinase inhibitors of the present invention comprise the formula:

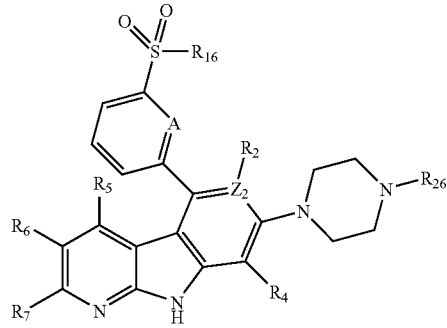

wherein
A is selected from the group consisting of $CR_{25}$ and N;
$R_{16}$ is selected from the group consisting of amino, $(C_{1-10})$alkylamino, $(C_{1-10})$alkyl, halo$(C_{1-10})$alkyl, hydroxy $(C_{1-5})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted;
$R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and
$R_{26}$ is selected from the group consisting of hydrogen, carbonyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted.

In another embodiment, kinase inhibitors of the present invention comprise the formula:

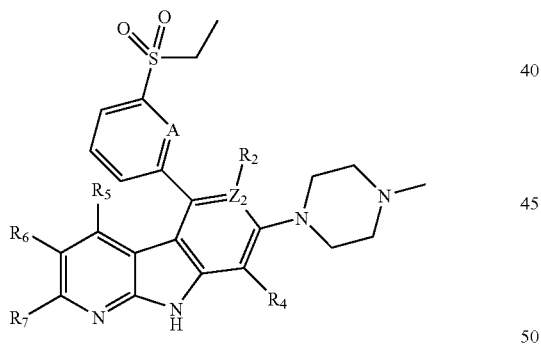

wherein
A is selected from the group consisting of $CR_{25}$ and N; and
$R_{25}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In still another embodiment, kinase inhibitors of the present invention comprise the formula:

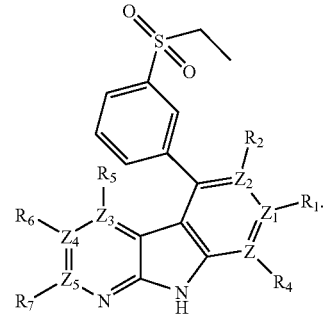

In yet another embodiment, kinase inhibitors of the present invention comprise the formula:

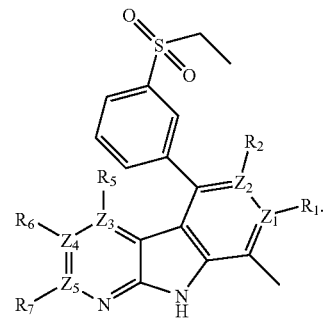

In a further embodiment, kinase inhibitors of the present invention comprise the formula:

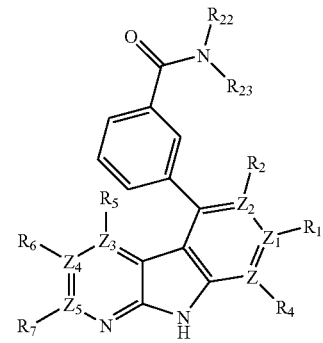

wherein
$R_{22}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and R$_{23}$ is selected from the group consisting of hydrogen, carbonyl, (C$_{1-10}$)alkyl, halo(C$_{1-10}$)alkyl, carbonyl(C$_{1-3}$) alkyl, thiocarbonyl(C$_{1-3}$)alkyl, sulfonyl(C$_{1-3}$)alkyl, sulfinyl(C$_{1-3}$)alkyl, amino(C$_{1-10}$)alkyl, imino(C$_{1-3}$) alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$) alkyl, (C$_{3-12}$)cycloalkyl, hetero(C$_{3-12}$)cycloalkyl, aryl and heteroaryl, each substituted or unsubstituted, or R$_{23}$ and R$_{22}$ are taken together to form a ring.

In another of its aspects, the present invention relates to processes for preparing compounds of the present invention. In one embodiment, the process comprises:

reacting a compound comprising the formula

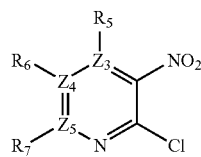

with a compound comprising the formula

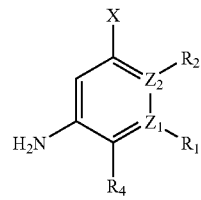

under conditions that form a first reaction product comprising the formula

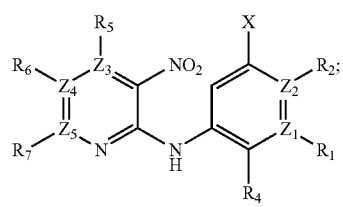

treating the first reaction product under conditions that form a second reaction product comprising the formula

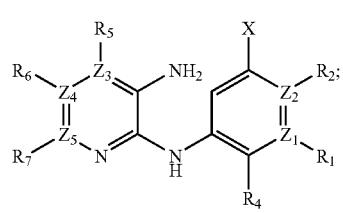

treating the second reaction product under conditions that form a third reaction product comprising the formula

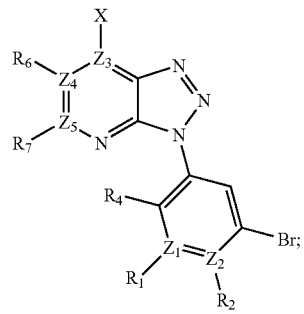

treating the third reaction product under conditions that form a fourth reaction product comprising the formula

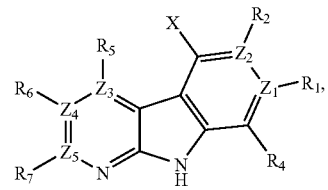

wherein

Z$_1$, Z$_2$, Z$_3$, Z$_4$ and Z$_5$ are each independently selected from the group consisting of C and N;

R$_1$ is —Y$_1$—R$_{12}$, or R$_1$ is absent when Z$_1$ is N;

R$_2$ is —Y$_2$—R$_{13}$, or R$_2$ is absent when Z$_2$ is N, or R$_1$ and R$_2$ are taken together to form a ring;

Y$_1$ and Y$_2$ are each independently absent or a linker providing 1 or 2 atom separation between R$_{12}$ or R$_{13}$ and the ring to which Y$_1$ or Y$_2$ is attached, wherein the atoms of the linker providing the separation are selected from the group consisting of carbon, oxygen, nitrogen, and sulfur;

R$_4$ is selected from the group consisting of hydrogen, halo, nitro, cyano, thio, oxy, hydroxy, carbonyloxy, alkoxy, carbonyl, amino, (C$_{1-5}$)alkylamino, (C$_{1-5}$)alkyl, halo(C$_{1-5}$)alkyl, carbonyl(C$_{1-3}$)alkyl, sulfonyl(C$_{1-3}$)alkyl, amino(C$_{1-5}$)alkyl, aryl(C$_{1-5}$)alkyl, heteroaryl(C$_{1-5}$) alkyl, (C$_{3-6}$)cycloalkyl and hetero(C$_{3-6}$)cycloalkyl, each substituted or unsubstituted, with the proviso that R$_4$ is absent when the atom to which it is bound is N;

R$_5$ and R$_6$ are each independently selected from the group consisting of hydrogen, halo, nitro, cyano, thio, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino(C$_{1-10}$)alkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted, with the proviso that each of R$_5$ and R$_6$ is absent when the atom to which it is bound is N;

R$_7$ is selected from the group consisting of hydrogen, halo, hydroxy, alkoxy, amino and (C$_{1-5}$)alkyl, each substituted or unsubstituted, with the proviso that R$_7$ is absent when the atom to which it is bound is N;

$R_{12}$ and $R_{13}$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{12}$ and $R_{13}$ are taken together to form a ring; and X is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In one variation of the above embodiment, the process further comprises:

treating the fourth reaction product under conditions that form a compound comprising the formula

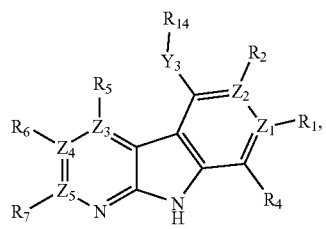

wherein $Y_3$ is absent or a linker providing 1 or 2 atom separation between $R_{14}$ and the ring to which $Y_3$ is attached, wherein the atoms of the linker providing the separation are selected from the group consisting of carbon, oxygen, nitrogen, and sulfur; and $R_{14}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In another embodiment, the process comprises:
reacting a compound comprising the formula

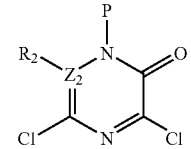

with a compound comprising the formula

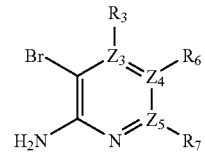

under conditions that form a first reaction product comprising the formula

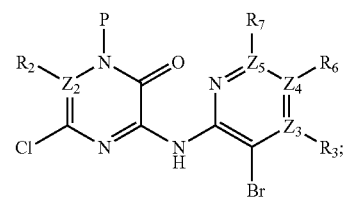

reacting the first reaction product with ethynyltrimethylsilane under conditions that form a second reaction product comprising the formula

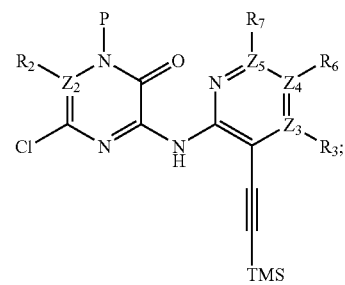

treating the second reaction product under conditions that form a third reaction product comprising the formula

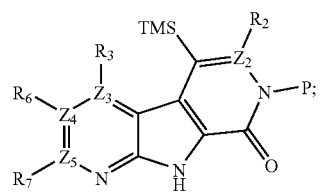

treating the third reaction product under conditions that form a fourth reaction product comprising the formula

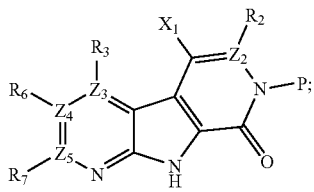

treating the fourth reaction product under conditions that form a fifth reaction product comprising the formula

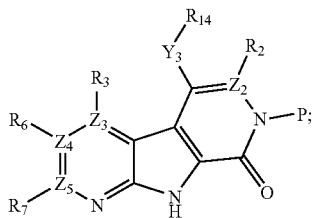

treating the fifth reaction product under conditions that form a sixth reaction product comprising the formula

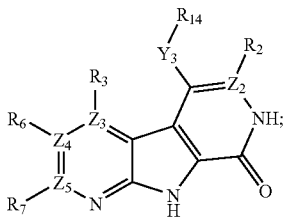

treating the sixth reaction product under conditions that form a seventh reaction product comprising the formula

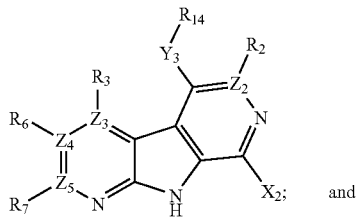

and treating the seventh reaction product under conditions that form a compound comprising the formula

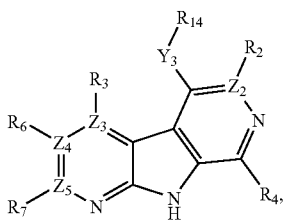

wherein $Z_2$, $Z_3$, $Z_4$ and $Z_5$ are each independently selected from the group consisting of C and N;

$R_2$ is —$Y_2$—$R_{13}$, or $R_2$ is absent when $Z_2$ is N;

$Y_2$ and $Y_3$ are each independently absent or a linker providing 1 or 2 atom separation between $R_{13}$ or $R_{14}$ and the ring to which $Y_2$ or $Y_3$ is attached, wherein the atoms of the linker providing the separation are selected from the group consisting of carbon, oxygen, nitrogen, and sulfur;

$R_4$ is selected from the group consisting of hydrogen, halo, nitro, cyano, thio, oxy, hydroxy, carbonyloxy, alkoxy, carbonyl, amino, ($C_{1-5}$)alkylamino, ($C_{1-5}$)alkyl, halo($C_{1-5}$)alkyl, carbonyl($C_{1-3}$)alkyl, sulfonyl($C_{1-3}$)alkyl, amino($C_{1-5}$)alkyl, aryl($C_{1-5}$)alkyl, heteroaryl($C_{1-5}$)alkyl, ($C_{3-6}$)cycloalkyl and hetero($C_{3-6}$)cycloalkyl, each substituted or unsubstituted, with the proviso that $R_4$ is absent when the atom to which it is bound is N;

$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;

$R_{13}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;

$R_{14}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;

P is a protecting group; and $X_1$ and $X_2$ are each independently selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In still another embodiment, the process comprises:

reacting a compound comprising the formula

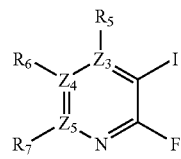

with a compound comprising the formula

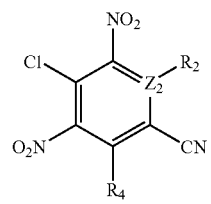

under conditions that form a first reaction product comprising the formula

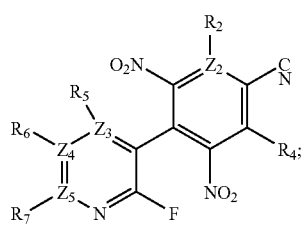

treating the first reaction product under conditions that form a second reaction product comprising the formula

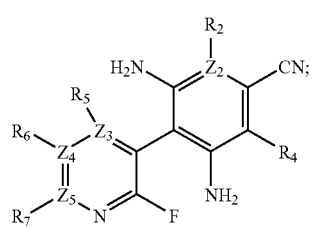

treating the second reaction product under conditions that form a third reaction product comprising the formula

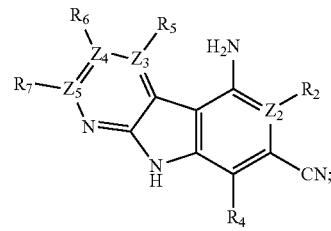

treating the third reaction product under conditions that form a fourth reaction product comprising the formula

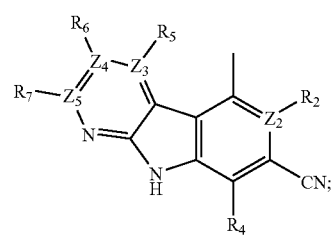

treating the fourth reaction product under conditions that form a fifth reaction product comprising the formula

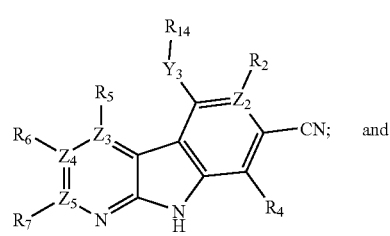

treating the fifth reaction product under conditions that form a compound comprising the formula

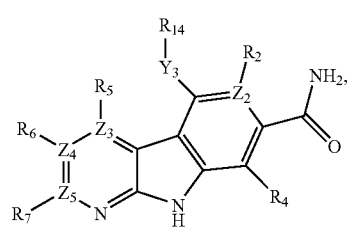

wherein $Z_2$, $Z_3$, $Z_4$ and $Z_5$ are each independently selected from the group consisting of C and N;

$R_2$ is —$Y_2$—$R_{13}$, or $R_2$ is absent when $Z_2$ is N;

$Y_2$ and $Y_3$ are each independently absent or a linker providing 1 or 2 atom separation between $R_{13}$ or $R_{14}$ and the ring to which $Y_2$ or $Y_3$ is attached, wherein the atoms of the linker providing the separation are selected from the group consisting of carbon, oxygen, nitrogen, and sulfur;

$R_4$ is selected from the group consisting of hydrogen, halo, nitro, cyano, thio, oxy, hydroxy, carbonyloxy, alkoxy, carbonyl, amino, ($C_{1-5}$)alkylamino, ($C_{1-5}$)alkyl, halo($C_{1-5}$)alkyl, carbonyl($C_{1-3}$)alkyl, sulfonyl($C_{1-3}$)alkyl, amino($C_{1-5}$)alkyl, aryl($C_{1-5}$)alkyl, heteroaryl($C_{1-5}$)alkyl, ($C_{3-6}$)cycloalkyl and hetero($C_{3-6}$)cycloalkyl, each substituted or unsubstituted, with the proviso that $R_4$ is absent when the atom to which it is bound is N;

$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;

$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N;

$R_{13}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and $R_{14}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In yet another embodiment, the process comprises:

reacting a compound comprising the formula

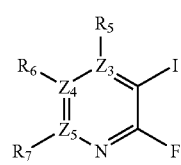

with a compound comprising the formula

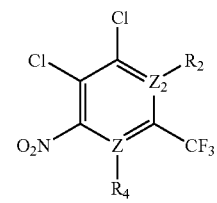

under conditions that form a first reaction product comprising the formula

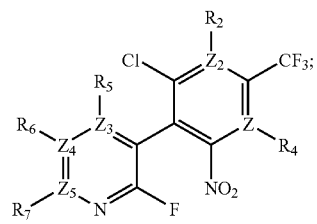

treating the first reaction product under conditions that form a second reaction product comprising the formula

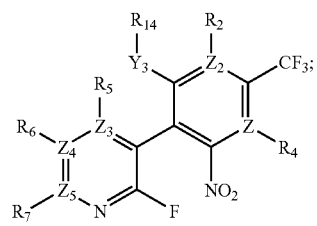

treating the second reaction product under conditions that form a third reaction product comprising the formula

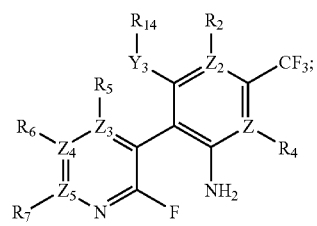

treating the third reaction product under conditions that form a fourth reaction product comprising the formula

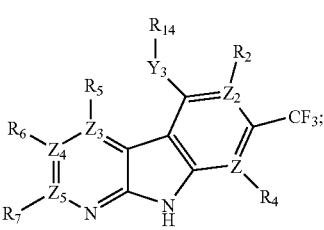

treating the fourth reaction product under conditions that form a fifth reaction product comprising the formula

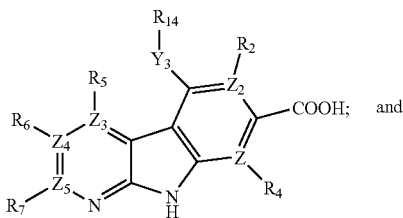

reacting the fifth reaction product with a compound comprising the formula $HNR_{23}R_{24}$ under conditions that form a compound comprising the formula

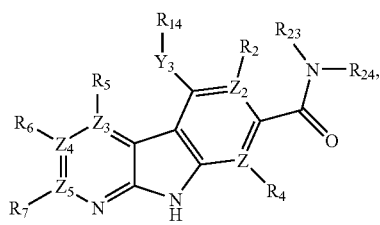

wherein

Z, $Z_2$, $Z_3$, $Z_4$ and $Z_5$ are each independently selected from the group consisting of C and N;

$R_2$ is —$Y_2$—$R_{13}$, or $R_2$ is absent when $Z_2$ is N;

$Y_2$ and $Y_3$ are each independently absent or a linker providing 1 or 2 atom separation between $R_{13}$ or $R_{14}$ and the ring to which $Y_2$ or $Y_3$ is attached, wherein the atoms of the linker providing the separation are selected from the group consisting of carbon, oxygen, nitrogen, and sulfur;

$R_4$ is selected from the group consisting of hydrogen, halo, nitro, cyano, thio, oxy, hydroxy, carbonyloxy, alkoxy, carbonyl, amino, $(C_{1-5})$alkylamino, $(C_{1-5})$alkyl, halo$(C_{1-5})$alkyl, carbonyl$(C_{1-3})$alkyl, sulfonyl$(C_{1-3})$alkyl, amino$(C_{1-5})$alkyl, aryl$(C_{1-5})$alkyl, heteroaryl$(C_{1-5})$alkyl, $(C_{3-6})$cycloalkyl and hetero$(C_{3-6})$cycloalkyl, each substituted or unsubstituted, with the proviso that $R_4$ is absent when the atom to which it is bound is N;

$R_5$ and $R_6$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that each of $R_5$ and $R_6$ is absent when the atom to which it is bound is N;

$R_7$ is selected from the group consisting of hydrogen, halo, hydroxy, alkoxy, amino and $(C_{1-5})$alkyl, each substituted or unsubstituted, with the proviso that $R_7$ is absent when the atom to which it is bound is N;

$R_{13}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;

$R_{14}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino$(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl$(C_{1-5})$ alkyl, $(C_{9-12})$bicycloaryl$(C_{1-5})$alkyl, hetero$(C_{8-12})$ bicycloaryl$(C_{1-5})$alkyl, $(C_{3-12})$cycloalkyl, hetero$(C_{3-12})$ cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{23}$ and $R_{24}$ are each independently selected from the group consisting of hydrogen, carbonyl, $(C_{1-10})$alkyl, halo$(C_{1-10})$alkyl, carbonyl$(C_{1-3})$alkyl, thiocarbonyl $(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl $(C_{1-5})$alkyl, hetero$(C_{3-12})$cycloalkyl$(C_{1-5})$alkyl, aryl $(C_{1-10})$alkyl, heteroaryl$(C_{1-5})$alkyl, $(C_{3-12})$cycloalkyl, hetero$(C_{3-12})$cycloalkyl, aryl and heteroaryl, each substituted or unsubstituted, or $R_{23}$ and $R_{24}$ are taken together to form a ring.

In another embodiment, the process comprises:

reacting a compound comprising the formula

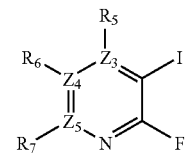

with a compound comprising the formula

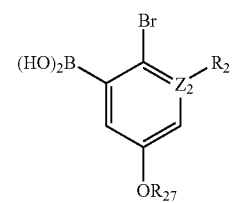

under conditions that form a first reaction product comprising the formula

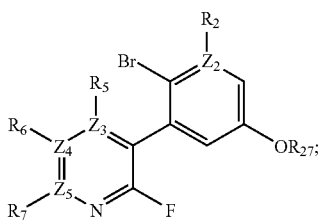

treating the first reaction product under conditions that form a second reaction product comprising the formula

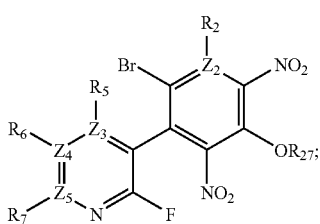

treating the second reaction product under conditions that form a third reaction product comprising the formula

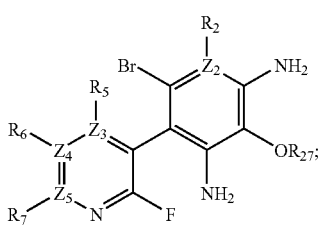

treating the third reaction product under conditions that form a fourth reaction product comprising the formula

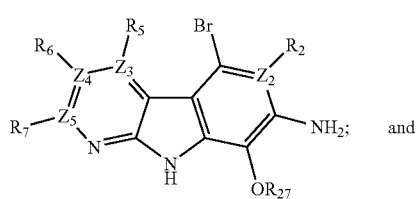

treating the fourth reaction product under conditions that form a fifth reaction product comprising the formula

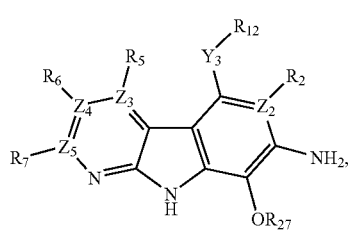

wherein $Z_2$, $Z_3$, $Z_4$ and $Z_5$ are each independently selected from the group consisting of C and N;

$R_2$ is —$Y_2$—$R_{13}$, or $R_2$ is absent when $Z_2$ is N;

$Y_2$ and $Y_3$ are each independently absent or a linker providing 1 or 2 atom separation between $R_{13}$ or $R_{14}$ and the ring to which $Y_2$ or $Y_3$ is attached, wherein the atoms of the linker providing the separation are selected from the group consisting of carbon, oxygen, nitrogen, and sulfur;

$R_5$ and $R_6$ are each independently selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that each of $R_5$ and $R_6$ is absent when the atom to which it is bound is N;

$R_7$ is selected from the group consisting of hydrogen, halo, hydroxy, alkoxy, amino and $(C_{1-5})$alkyl, each substituted or unsubstituted, with the proviso that $R_7$ is absent when the atom to which it is bound is N;

$R_{13}$ is selected from the group consisting of hydrogen, halo, nitro, cyano, thio, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$ alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$ alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$ cycloalkyl, hetero$(C_{3-12})$cycloalkyl, $(C_{9-12})$ bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$ bicycloaryl, each substituted or unsubstituted.

In one variation of the above embodiment, the process further comprises treating the fifth reaction product under conditions that form a compound comprising the formula

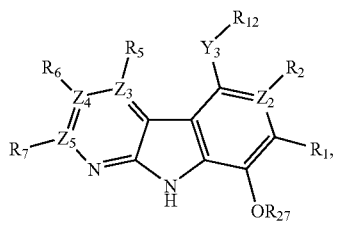

wherein $R_1$ is —$Y_1$—$R_{12}$;

$Y_1$ is absent or a linker providing 1 or 2 atom separation between $R_{12}$ and the ring to which $Y_1$ is attached, wherein the atoms of the linker providing the separation are selected from the group consisting of carbon, oxygen, nitrogen, and sulfur; and $R_{12}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In still another of its aspects, the present invention relates to compounds useful in preparing compounds of the present invention. In one embodiment, such compounds comprise a formula

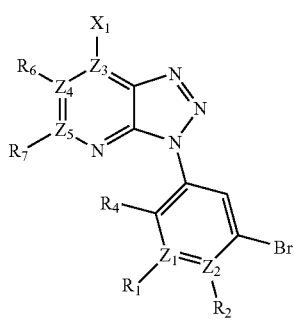

wherein $X_1$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

$Z_1$, $Z_2$, $Z_3$, $Z_4$ and $Z_5$ are each independently selected from the group consisting of C and N;

$R_1$ is —$Y_1$—$R_{12}$, or $R_1$ is absent when $Z_1$ is N;

$R_2$ is —$Y_2$—$R_{13}$, or $R_2$ is absent when $Z_2$ is N, or $R_1$ and $R_2$ are taken together to form a ring;

$Y_1$ and $Y_2$ are each independently absent or a linker providing 1 or 2 atom separation between $R_{12}$ or $R_{13}$ and the ring to which $Y_1$ or $Y_2$ is attached, wherein the atoms of the linker providing the separation are selected from the group consisting of carbon, oxygen, nitrogen, and sulfur;

$R_4$ is selected from the group consisting of hydrogen, halo, nitro, cyano, thio, oxy, hydroxy, carbonyloxy, alkoxy, carbonyl, amino, ($C_{1-5}$)alkylamino, ($C_{1-5}$)alkyl, halo($C_{1-5}$)alkyl, carbonyl($C_{1-3}$)alkyl, sulfonyl($C_{1-3}$)alkyl, amino($C_{1-5}$)alkyl, aryl($C_{1-5}$)alkyl, heteroaryl($C_{1-5}$)alkyl, ($C_{3-6}$)cycloalkyl and hetero($C_{3-6}$)cycloalkyl, each substituted or unsubstituted, with the proviso that $R_4$ is absent when the atom to which it is bound is N;

$R_6$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that $R_6$ is absent when the atom to which it is bound is N;

$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N; and $R_{12}$ and $R_{13}$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{12}$ and $R_{13}$ are taken together to form a ring.

In another embodiment, such compounds comprise a formula

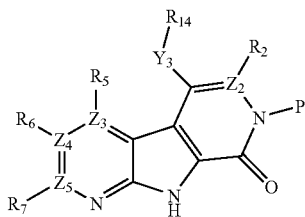

wherein $Z_2$, $Z_3$, $Z_4$ and $Z_5$ are each independently selected from the group consisting of C and N;

$R_2$ is —$Y_2$—$R_{13}$, or $R_2$ is absent when $Z_2$ is N;

$Y_2$ and $Y_3$ are each independently absent or a linker providing 1 or 2 atom separation between $R_{13}$ or $R_{14}$ and the ring to which $Y_2$ or $Y_3$ is attached, wherein the atoms of the linker providing the separation are selected from the group consisting of carbon, oxygen, nitrogen, and sulfur;

$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;

$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N;

$R_{13}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;

$R_{14}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and P is a protecting group.

In still another embodiment, such compounds comprise a formula

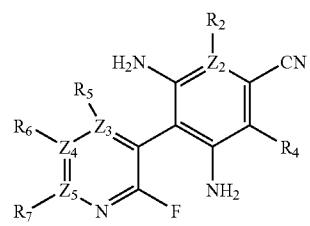

wherein $Z_2$, $Z_3$, $Z_4$ and $Z_5$ are each independently selected from the group consisting of C and N;

$R_2$ is —$Y_2$—$R_{13}$, or $R_2$ is absent when $Z_2$ is N;

$Y_2$ is absent or a linker providing 1 or 2 atom separation between $R_{13}$ and the ring to which $Y_2$ is attached, wherein the atoms of the linker providing the separation are selected from the group consisting of carbon, oxygen, nitrogen, and sulfur;

$R_4$ is selected from the group consisting of hydrogen, halo, nitro, cyano, thio, oxy, hydroxy, carbonyloxy, alkoxy, carbonyl, amino, ($C_{1-5}$)alkylamino, ($C_{1-5}$)alkyl, halo($C_{1-5}$)alkyl, carbonyl($C_{1-3}$)alkyl, sulfonyl($C_{1-3}$)alkyl, amino($C_{1-5}$)alkyl, aryl($C_{1-5}$)alkyl, heteroaryl($C_{1-5}$)alkyl, ($C_{3-6}$)cycloalkyl and hetero($C_{3-6}$)cycloalkyl, each substituted or unsubstituted, with the proviso that $R_4$ is absent when the atom to which it is bound is N;

$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;

$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N; and $R_{13}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)

cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In yet another embodiment, such compounds comprise a formula

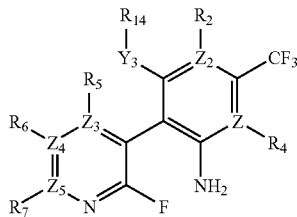

wherein
Z, $Z_2$, $Z_3$, $Z_4$ and $Z_5$ are each independently selected from the group consisting of C and N;
$R_2$ is —$Y_2$—$R_{13}$, or $R_2$ is absent when $Z_2$ is N;
$Y_2$ and $Y_3$ are each independently absent or a linker providing 1 or 2 atom separation between $R_{13}$ or $R_{14}$ and the ring to which $Y_2$ or $Y_3$ is attached, wherein the atoms of the linker providing the separation are selected from the group consisting of carbon, oxygen, nitrogen, and sulfur;
$R_4$ is selected from the group consisting of hydrogen, halo, nitro, cyano, thio, oxy, hydroxy, carbonyloxy, alkoxy, carbonyl, amino, ($C_{1-5}$)alkylamino, ($C_{1-5}$)alkyl, halo($C_{1-5}$)alkyl, carbonyl($C_{1-3}$)alkyl, sulfonyl($C_{1-3}$)alkyl, amino($C_{1-5}$)alkyl, aryl($C_{1-5}$)alkyl, heteroaryl($C_{1-5}$)alkyl, ($C_{3-6}$)cycloalkyl and hetero($C_{3-6}$)cycloalkyl, each substituted or unsubstituted, with the proviso that $R_4$ is absent when the atom to which it is bound is N;
$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;
$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N;
$R_{13}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and
$R_{14}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In another embodiment, such compounds comprise a formula

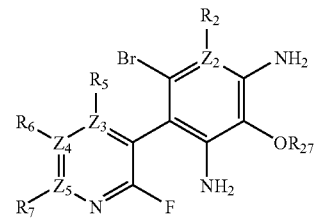

wherein $Z_2$, $Z_3$, $Z_4$ and $Z_5$ are each independently selected from the group consisting of C and N;
$R_2$ is —$Y_2$—$R_{13}$, or $R_2$ is absent when $Z_2$ is N;
$Y_2$ is absent or a linker providing 1 or 2 atom separation between $R_{13}$ and the ring to which $Y_2$ is attached, wherein the atoms of the linker providing the separation are selected from the group consisting of carbon, oxygen, nitrogen, and sulfur;
$R_5$ and $R_6$ are each independently selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that each of $R_5$ and $R_6$ is absent when the atom to which it is bound is N;
$R_7$ is selected from the group consisting of hydrogen, halo, hydroxy, alkoxy, amino and ($C_{1-5}$)alkyl, each substituted or unsubstituted, with the proviso that $R_7$ is absent when the atom to which it is bound is N;
$R_{13}$ is selected from the group consisting of hydrogen, halo, nitro, cyano, thio, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)

alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and $R_{27}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$) alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{1-10}$)azaalkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$) alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted.

In one variation of the compounds and processes of each of the above embodiments and variations, A is $CR_{25}$. In another variation of the compounds and processes of each of the above embodiments and variations, $A_1$ is $CR_{25}$. In still another variation of the compounds and processes of each of the above embodiments and variations, $A_2$ is $CR_{25}$. In yet another variation of the compounds and processes of each of the above embodiments and variations, $A_3$ is $CR_{25}$. In a further variation of the compounds and processes of each of the above embodiments and variations, $A_4$ is $CR_{25}$.

In another variation of the compounds and processes of each of the above embodiments and variations, $Y_1$ is selected from the group consisting of —$CH_2$—, —NH—, —O— and —S—.

In still another variation of the compounds and processes of each of the above embodiments and variations, $Y_1$ is selected from the group consisting of —O—, —($CR_{19}R_{20})_m$—, —$NR_{21}$—, —S— and —S—$CH_2$—; m is selected from the group consisting of 0, 1, 2, 3, 4 and 5; $R_{19}$ and $R_{20}$ are selected from the group consisting of hydrogen, halo, cyano, thio, oxy, hydroxy, carbonyloxy, alkoxy, aryloxy, heteroaryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl($C_{1-5}$) alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$) cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{19}$ and $R_{12}$ are taken together to form a substituted or unsubstituted ring; and $R_{21}$ is selected from the group consisting of hydrogen, carbonyloxy, alkoxy, aryloxy, heteroaryloxy, carbonyl, oxycarbonyl, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$) alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl ($C_{1-10}$)alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{21}$ and $R_{12}$ are taken together to form a substituted or unsubstituted ring.

In yet another variation of the compounds and processes of each of the above embodiments and variations, $Y_1$ is —C(O)—$NR_{23}$—; and $R_{23}$ is selected from the group consisting of hydrogen, carbonyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$) alkyl, sulfinyl($C_{1-3}$)alkyl, amino($C_{1-10}$)alkyl, imino($C_{1-3}$) alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{3-12}$) cycloalkyl, hetero($C_{3-12}$)cycloalkyl, aryl and heteroaryl, each substituted or unsubstituted, or $R_{23}$ and $R_{12}$ are taken together to form a substituted or unsubstituted ring.

In a further variation of the compounds and processes of each of the above embodiments and variations, $Y_1$ is —C(O)—O—.

In still a further variation of the compounds and processes of each of the above embodiments and variations, $Y_1$ is —$NR_{23}$—C(O)—; and $R_{23}$ is selected from the group consisting of hydrogen, carbonyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$) alkyl, sulfinyl($C_{1-3}$)alkyl, amino($C_{1-10}$)alkyl, imino($C_{1-3}$) alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{3-12}$) cycloalkyl, hetero($C_{3-12}$)cycloalkyl, aryl and heteroaryl, each substituted or unsubstituted, or $R_{23}$ and $R_{12}$ are taken together to form a ring.

In yet a further variation of the compounds and processes of each of the above embodiments and variations, $Y_2$ is selected from the group consisting of —$CH_2$—, —NH—, —O— and —S—.

In another variation of the compounds and processes of each of the above embodiments and variations, $Y_2$ is selected from the group consisting of —O—, —($CR_{19}R_{20})_m$—, —$NR_{21}$—, —S— and —S—$CH_2$; m is selected from the group consisting of 0, 1, 2, 3, 4 and 5; $R_{19}$ and $R_{20}$ are selected from the group consisting of hydrogen, halo, cyano, thio, oxy, hydroxy, carbonyloxy, alkoxy, aryloxy, heteroaryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl($C_{1-5}$) alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$) cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{19}$ and $R_{13}$ are taken together to form a substituted or unsubstituted ring; and $R_{21}$ is selected from the group consisting of hydrogen, carbonyloxy, alkoxy, aryloxy, heteroaryloxy, carbonyl, oxycarbonyl, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$) alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl ($C_{1-10}$)alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_{21}$ and $R_{13}$ are taken together to form a substituted or unsubstituted ring.

In still another variation of the compounds and processes of each of the above embodiments and variations, $Y_3$ is selected from the group consisting of —$CH_2$—, —NH—, —O— and —S—.

In yet another variation of the compounds and processes of each of the above embodiments and variations, $Y_3$ is selected from the group consisting of —O—, —$(CR_{19}R_{20})_m$—, —$NR_{21}$—, —S— and —S—$CH_2$—; m is selected from the group consisting of 0, 1, 2, 3, 4 and 5; $R_{19}$ and $R_{20}$ are selected from the group consisting of hydrogen, halo, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{21}$ is selected from the group consisting of hydrogen, carbonyloxy, alkoxy, aryloxy, heteroaryloxy, carbonyl, oxycarbonyl, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In a further variation of the compounds and processes of each of the above embodiments and variations, $Y_3$ is absent.

In still a further variation of the compounds and processes of each of the above embodiments and variations, —$Y_3$—$R_{14}$ is selected from the group consisting of aryl, heteroaryl, $(C_{9-12})$bicycloaryl and hetero$(C_{4-12})$bicycloaryl, each substituted or unsubstituted.

In yet a further variation of the compounds and processes of each of the above embodiments and variations, Z is N. In another variation of the compounds and processes of each of the above embodiments and variations, $Z_1$ is N. In still another variation of the compounds and processes of each of the above embodiments and variations, $Z_2$ is N. In yet another variation of the compounds and processes of each of the above embodiments and variations, $Z_3$ is N. In a further variation of the compounds and processes of each of the above embodiments and variations, $Z_4$ is N. In still a further variation of the compounds and processes of each of the above embodiments and variations, $Z_5$ is N. In yet a further variation of the compounds and processes of each of the above embodiments and variations, Z, $Z_2$, $Z_3$, $Z_4$ and $Z_5$ are each C. In another variation of the compounds and processes of each of the above embodiments and variations, Z, $Z_1$, $Z_2$, $Z_3$, $Z_4$ and $Z_5$ are each C.

In still another variation of the compounds and processes of each of the above embodiments and variations, $R_1$ is selected from the group consisting of hydrogen, halo, amino, alkoxy, carbonyloxy, aminocarbonyl, sulfonyl, carbonylamino, sulfonylamino, $(C_{1-10})$alkyl, hetero$(C_{3-12})$cycloalkyl and aryl, each substituted or unsubstituted. In yet another variation of the compounds and processes of each of the above embodiments and variations, $R_1$ is a substituted or unsubstituted piperadinyl. In a further variation of the compounds and processes of each of the above embodiments and variations, $R_1$ is a substituted or unsubstituted 1-methyl(piperadin-4-yl).

In still a further variation of the compounds and processes of each of the above embodiments and variations, $R_2$ is selected from the group consisting of hydrogen, halo, amino, alkoxy, $(C_{1-10})$alkyl, hetero$(C_{3-12})$cycloalkyl and aryl, each substituted or unsubstituted. In yet a further variation of the compounds and processes of each of the above embodiments and variations, $R_2$ is hydrogen.

In another variation of the compounds and processes of each of the above embodiments and variations, $R_4$ is selected from the group consisting of hydrogen, halo and substituted or unsubstituted $(C_{1-5})$alkyl. In still another variation of the compounds and processes of each of the above embodiments and variations, $R_4$ is methyl. In yet another variation of the compounds and processes of each of the above embodiments and variations, $R_4$ is trifluoromethyl. In a further variation of the compounds and processes of each of the above embodiments and variations, $R_4$ is a substituted or unsubstituted oxaalkyl. In still a further variation of the compounds and processes of each of the above embodiments and variations, $R_4$ is a substituted or unsubstituted alkoxy. In yet a further variation of the compounds and processes of each of the above embodiments and variations, $R_4$ is a substituted or unsubstituted aryloxy.

In another variation of the compounds and processes of each of the above embodiments and variations, $R_4$ is —$Y_4$—$R_{27}$; $Y_4$ is absent or a linker providing 1 or 2 atom separation between $R_{27}$ and the ring to which $Y_4$ is attached; and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted. In one variation, $Y_4$ is selected from the group consisting of —$CH_2$—, —NH—, —O— and —S—. In another variation, $Y_4$ is absent.

In still another variation of the compounds and processes of each of the above embodiments and variations, $R_4$ is —$OR_{27}$ and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In yet another variation of the compounds and processes of each of the above embodiments and variations, $R_4$ is —$SR_{27}$ and $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-2})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In a further variation of the compounds and processes of each of the above embodiments and variations, $R_4$ is —$NR_{28}$—$R_{27}$; $R_{27}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and $R_{28}$ is selected from the group consisting of hydrogen, oxy, hydroxy, carbonyloxy, $(C_{1-10})$alkoxy, $(C_{4-12})$aryloxy, hetero$(C_{1-10})$aryloxy, carbonyl, oxycarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted. In one variation, $R_{28}$ is selected from the group consisting of hydrogen and a substituted or unsubstituted $(C_{1-5})$alkyl.

In still a further variation of the compounds and processes of each of the above embodiments and variations, $R_5$ is selected from the group consisting of hydrogen, halo and substituted or unsubstituted $(C_{1-5})$alkyl. In yet a further variation of the compounds and processes of each of the above embodiments and variations, $R_5$ is hydrogen.

In another variation of the compounds and processes of each of the above embodiments and variations, $R_6$ is selected from the group consisting of hydrogen, halo, amino, carbonyl, alkoxy and $(C_{1-5})$alkyl, each substituted or unsubstituted. In a further variation of the compounds and processes of each of the above embodiments and variations, $R_6$ is a substituted or unsubstituted $(C_{1-5})$alkyl. In still another variation of the compounds and processes of each of the above embodiments and variations, $R_6$ is halo. In yet another variation of the compounds and processes of each of the above embodiments and variations, $R_6$ is selected from the group consisting of methyl, ethyl, isopropyl and cyclopropyl, each substituted or unsubstituted.

In a further variation of the compounds and processes of each of the above embodiments and variations, $R_7$ is selected from the group consisting of hydrogen, hydroxy, amino and $(C_{1-5})$alkyl, each substituted or unsubstituted. In still a further variation of the compounds and processes of each of the above embodiments and variations, $R_7$ is hydrogen.

In yet a further variation of the compounds and processes of each of the above embodiments and variations, $R_{12}$ is selected from the group consisting of hydrogen, halo, amino, alkoxy, carbonyloxy, aminocarbonyl, sulfonyl, carbonylamino, sulfonylamino, $(C_{1-10})$alkyl, hetero$(C_{3-12})$cycloalkyl and aryl, each substituted or unsubstituted.

In another variation of the compounds and processes of each of the above embodiments and variations, $R_{13}$ is selected from the group consisting of hydrogen, halo, amino, alkoxy, carbonyloxy, aminocarbonyl, sulfonyl, carbonylamino, sulfonylamino, $(C_{1-10})$alkyl, hetero$(C_{3-12})$cycloalkyl and aryl, each substituted or unsubstituted.

In still another variation of the compounds and processes of each of the above embodiments and variations, $R_{14}$ is selected from the group consisting of halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-2})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted. In yet another variation of the compounds and processes of each of the above embodiments and variations, $R_{14}$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted. In a further variation of the compounds and processes of each of the above embodiments and variations, $R_{14}$ is selected from the group consisting of aryl and heteroaryl, each substituted with a substituent selected from the group consisting of halo, carbonyl, $(C_{1-5})$alkyl, alkoxy, aminocarbonyl, amino and sulfonyl, each substituted or unsubstituted.

In still a further variation of the compounds and processes of each of the above embodiments and variations, $R_{15}$ is selected from the group consisting of $(C_{1-10})$alkyl, —$OR_{22}$, —$C(O)$—$R_{22}$, —$NR_{23}$—$C(O)$—$R_{22}$, —$C(O)$—$NR_{23}$—$R_{22}$, —$SO_2R_{22}$, —$NR_{23}$—$SO_2$—$R_{22}$ and —$SO_2$—$NR_{23}R_{24}$; $R_{22}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{23}$ and $R_{24}$ are each independently selected from the group consisting of hydrogen, carbonyl, $(C_{1-10})$alkyl, halo$(C_{1-10})$alkyl, carbonyl$(C_{1-3})$alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{3-12}$)cycloalkyl, aryl and heteroaryl, each substituted or unsubstituted, or $R_{23}$ and $R_{24}$ are taken together to form a ring.

In yet a further variation of the compounds and processes of each of the above embodiments and variations, $R_{16}$ is —$NR_{23}$—C(O)—$R_{22}$; $R_{22}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$) alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and $R_{23}$ is selected from the group consisting of hydrogen, carbonyl, ($C_{1-10}$) alkyl, halo($C_{1-10}$)alkyl, carbonyl($C_{1-3}$)alkyl, thiocarbonyl ($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{3-12}$)cycloalkyl, hetero($C_{3-12}$)cycloalkyl, aryl and heteroaryl, each substituted or unsubstituted, or $R_{23}$ and $R_{24}$ are taken together to form a ring.

In another variation of the compounds and processes of each of the above embodiments and variations, $R_{22}$ is a substituted or unsubstituted ($C_{3-6}$)cycloalkyl. In still another variation of the compounds and processes of each of the above embodiments and variations, $R_{22}$ is a substituted or unsubstituted cyclopropyl.

In yet another variation of the compounds and processes of each of the above embodiments and variations, $R_{23}$ and $R_{24}$ are taken together to form a carbocyclic or heterocyclic ($C_{5-10}$) ring. In a further variation of the compounds and processes of each of the above embodiments and variations, $R_{23}$ and $R_{24}$ are taken together to form a substituted or unsubstituted piperazine.

In still a further variation of the compounds and processes of each of the above embodiments and variations, $R_{23}$ is hydrogen.

In yet a further variation of the compounds and processes of each of the above embodiments and variations, $R_{25}$ is hydrogen.

In another variation of the compounds and processes of each of the above embodiments and variations, $R_{27}$ is a substituted or unsubstituted heterocycloalkyl($C_{1-3}$)alkyl. In still another variation of the compounds and processes of each of the above embodiments and variations, $R_{27}$ is a substituted or unsubstituted piperadinyl($C_{1-3}$)alkyl. In yet another variation of the compounds and processes of each of the above embodiments and variations, $R_{27}$ is a substituted or unsubstituted 1-methyl(piperadin-4-yl)($C_{1-3}$)alkyl. In a further variation of the compounds and processes of each of the above embodiments and variations, $R_{27}$ is a substituted or unsubstituted 1-methyl(piperadin-4-yl)methyl. In still a further variation of the compounds and processes of each of the above embodiments and variations, $R_{27}$ is a substituted or unsubstituted amino($C_{1-5}$)alkyl. In yet a further variation of the compounds and processes of each of the above embodiments and variations, $R_{27}$ is a substituted or unsubstituted dimethylaminopropyl.

In another variation of the compounds and processes of each of the above embodiments and variations, P is selected from the group consisting of benzyl and p-methoxybenzyl.

Particular examples of compounds according to the present invention include, but are not limited to:
  5-bromo-9H-pyrido[2,3-b]indole;
  5-bromo-8-methyl-9H-pyrido[2,3-b]indole;
  5-bromo-3,8-dimethyl-9H-pyrido[2,3-b]indole;
  5-phenyl-9H-pyrido[2,3-b]indole;
  5-(3-(methylsulfonyl)phenyl)-9H-pyrido[2,3-b]indole;
  5-(3-(ethylsulfonyl)phenyl)-9H-pyrido[2,3-b]indole;
  N-(3-(9H-pyrido[2,3-b]indol-5-yl)phenyl)ethanesulfonamide;
  5-m-tolyl-9H-pyrido[2,3-b]indole;
  N-cyclopropyl-3-(9H-pyrido[2,3-b]indol-5-yl)benzenesulfonamide;
  5-(3-methoxyphenyl)-9H-pyrido[2,3-b]indole;
  5-(3,8-dimethyl-9H-pyrido[2,3-b]indol-5-yl)-2-methoxy-N-methylbenzenesulfonamide;
  3-(3,8-dimethyl-9H-pyrido[2,3-b]indol-5-yl)-N-methylbenzenesulfonamide;
  3-(3,8-dimethyl-9H-pyrido[2,3-b]indol-5-yl)-N,N-dimethylbenzenesulfonamide;
  5-(3-(ethylsulfonyl)phenyl)-8-methyl-9H-pyrido[2,3-b]indole;
  5-(3-(ethylsulfonyl)phenyl)-3,8-dimethyl-9H-pyrido[2,3-b]indole;
  N-(3-(3,8-dimethyl-9H-pyrido[2,3-b]indol-5-yl)phenyl) propionamide;
  N-cyclopropyl-3-(3,8-dimethyl-9H-pyrido[2,3-b]indol-5-yl)benzamide;
  N-(4-(9H-pyrido[2,3-b]indol-5-ylthio)phenyl)acetamide;
  5-(benzylthio)-9H-pyrido[2,3-b]indole;
  5-(phenylthio)-9H-pyrido[2,3-b]indole;
  5-(benzylthio)-8-methyl-9H-pyrido[2,3-b]indole;
  5-(benzylthio)-3,8-dimethyl-9H-pyrido[2,3-b]indole;
  7-Benzyl-5-(3-ethanesulfonyl-phenyl)-3-methyl-7,9-dihydro-dipyrido[2,3-b;4',3'-d]pyrrol-8-one;
  8-Chloro-5-(3-ethanesulfonyl-phenyl)-3-methyl-9H-dipyrido[2,3-b;4',3'-d]pyrrole;
  N'-[5-(3-Ethanesulfonyl-phenyl)-3-methyl-9H-dipyrido[2,3-b;4',3'-d]pyrrol-8-yl]-N,N-dimethyl-ropane-1,3-diamine;
  N'-[5-(3-Ethanesulfonyl-phenyl)-3-methyl-9H-dipyrido[2,3-b;4',3'-d]pyrrol-8-yl]-N,N-dimethyl-ethane-1,2-diamine;
  [5-(3-Ethanesulfonyl-phenyl)-3-methyl-9H-dipyrido[2,3-b;4',3'-d]pyrrol-8-yl]-(3-morpholin-4-yl-propyl)-amine;
  [5-(3-Ethanesulfonyl-phenyl)-3-methyl-9H-dipyrido[2,3-b;4',3'-d]pyrrol-8-yl]-(1-methyl-piperidin-4-yl)-amine;
  2-[5-(3-Ethanesulfonyl-phenyl)-3-methyl-9H-dipyrido[2,3-b;4',3'-d]pyrrol-8-ylamino]-ethanol;
  [5-(3-Ethanesulfonyl-phenyl)-3-methyl-9H-dipyrido[2,3-b;4',3'-d]pyrrol-8-yl]-(1-methyl-piperidin-4-ylmethyl)-amine;
  5-(3-Ethanesulfonyl-phenyl)-3,8-dimethyl-9H-dipyrido[2,3-b;4',3'-d]pyrrole;
  5-(3-Ethanesulfonyl-phenyl)-8-ethyl-3-methyl-9H-dipyrido[2,3-b;4',3'-d]pyrrole;
  5-(3-Ethanesulfonyl-phenyl)-3-methyl-9H-dipyrido[2,3-b;4',3'-d]pyrrole-8-carbonitrile;
  5-(3-Ethanesulfonyl-phenyl)-3-methyl-9H-dipyrido[2,3-b;4',3'-d]pyrrole-8-carboxylic acid amide;
  5-(3-Ethanesulfonyl-phenyl)-8-ethoxy-3-methyl-9H-dipyrido[2,3-b;4',3'-d]pyrrole;

{3-[5-(3-Ethanesulfonyl-phenyl)-3-methyl-9H-dipyrido[2,3-b;4',3'-]pyrrol-8-yloxy]-propyl}-dimethyl-amine;
2-[5-(3-Ethanesulfonyl-phenyl)-3-methyl-9H-dipyrido[2,3-b;4',3'-d]pyrrol-8-yloxy]-ethanol;
5-(3-Ethanesulfonyl-phenyl)-3-methyl-8-(1-methyl-piperidin-4-ylmethoxy)-9H-dipyrido[2,3-b;4',3'-d]pyrrole;
3-[5-(3-Ethanesulfonyl-phenyl)-3-methyl-9H-dipyrido[2,3-b;4',3'-d]pyrrol-8-yloxy]-propan-1-ol;
(R)-2-[5-(3-Ethanesulfonyl-phenyl)-3-methyl-9H-dipyrido[2,3-b;4',3'-d]pyrrol-8-yloxymethyl]-propane-1,3-diol;
(S)-2-[5-(3-Ethanesulfonyl-phenyl)-3-methyl-9H-dipyrido[2,3-b;4',3'-d]pyrrol-8-yloxymethyl]-propane-1,3-diol;
1-[5-(3-Ethanesulfonyl-phenyl)-3-methyl-9H-dipyrido[2,3-b;4',3'-d]pyrrol-8-yloxy]-2-methyl-propan-2-ol;
5-(3-Ethanesulfonyl-phenyl)-3-methyl-8-phenoxy-9H-dipyrido[2,3-b;4',3'-d]pyrrole;
5-(3-Ethanesulfonyl-phenyl)-3-methyl-8-(thiazol-5-ylmethoxy)-9H-dipyrido[2,3-b;4',3'-d]pyrrole;
5-(3-Ethanesulfonyl-phenyl)-8-(1-ethyl-piperidin-4-ylmethoxy)-3-methyl-9H-dipyrido[2,3-b;4',3'-d]pyrrole;
(S)-1-[5-(3-Ethanesulfonyl-phenyl)-3-methyl-9H-dipyrido[2,3-b;4',3'-d]pyrrol-8-yloxy]-propan-2-ol;
(R)-1-[5-(3-Ethanesulfonyl-phenyl)-3-methyl-9H-dipyrido[2,3-b;4',3'-d]pyrrol-8-yloxy]-propan-2-ol;
L-Valine-2-[5-(3-ethanesulfonyl-phenyl)-3-methyl-9H-dipyrido[2,3-b;4',3'-d]pyrrol-8-yloxy]-ethyl ester;
L-Alanine-(R)-2-[5-(3-ethanesulfonyl-phenyl)-3-methyl-9H-dipyrido[2,3-b;4',3'-d]pyrrol-8-yloxy]-1-methyl-ethyl ester;
3-(3-Bromo-5-chloro-pyridin-2-ylamino)-5-chloro-1-(4-methoxy-benzyl)-1H-pyrazin-2-one;
3,8-Dichloro-5-(3-ethanesulfonyl-phenyl)-9H-dipyrido[2,3-b;4',3'-d]pyrrole;
3-Chloro-5-(3-ethanesulfonyl-phenyl)-8-(1-methyl-piperidin-4-ylmethoxy)-9H-dipyrido[2,3-b;4',3'-d]pyrrole;
(R)-1-[3-Chloro-5-(3-ethanesulfonyl-phenyl)-9H-dipyrido[2,3-b;4',3'-d]pyrrol-8-yloxy]-propan-2-ol;
2-[5-(3-Ethanesulfonyl-phenyl)-3-methyl-9H-dipyrido[2,3-b;4',3'-d]pyrrol-8-yl]methyl amine;
2-[5-(3-Ethanesulfonyl-phenyl)-3-methyl-9H-dipyrido[2,3-b;4',3'-d]pyrrol-8-yl]methanethiol;
2-[5-(3-Ethanesulfonyl-phenyl)-3-methyl-9H-dipyrido[2,3-b;4',3'-d]pyrrol-8-yl]ethanethiol;
8-Chloro-5-[3-(cyclopropylcarboxamide)phenyl]-3-methyl-9H-dipyrido[2,3-b;4',3'-d]pyrrole;
2-[5-(3-cyclopropylcarbonylamino-phenyl)-3-methyl-9H-dipyrido[2,3-b;4',3'-d]pyrrol-8-yl]ethanethiol;
9-(3-Ethanesulfonyl-phenyl)-5H-pyrazino[2,3-b]indole;
5-(3-(ethylsulfonyl)phenyl)-3,8-dimethyl-7-(trifluoromethyl)-9H-pyrido[2,3-b]indole acetate;
5-(3-(ethylsulfonyl)phenyl)-3,8-dimethyl-9H-pyrido[2,3-b]indole-7-carboxylic acid;
N-(2-(dimethylamino)ethyl)-5-(3-(ethylsulfonyl)phenyl)-3,8-dimethyl-9H-pyrido[2,3-b]indole-7-carboxamide;
N-(2-(methylamino)ethyl)-5-(3-(ethylsulfonyl)phenyl)-3,8-dimethyl-9H-pyrido[2,3-b]indole-7-carboxamide;
N-(2-(methoxy)ethyl)-5-(3-(ethylsulfonyl)phenyl)-3,8-dimethyl-9H-pyrido[2,3-b]indole-7-carboxamide;
N-(2-(dimethylamino)ethyl)-N-methyl-5-(3-(ethylsulfonyl)phenyl)-3,8-dimethyl-9H-pyrido[2,3-b]indole-7-carboxamide;
N,N-dimethyl-5-(3-(ethylsulfonyl)phenyl)-3,8-dimethyl-9H-pyrido[2,3-b]indole-7-methylcarboxamide;
5-(3-(ethylsulfonyl)phenyl)-3,8-dimethyl-9H-pyrido[2,3-b]indole-7-yl)(4-methylpiperazin-1-yl)methanone;
5-(3-(ethylsulfonyl)phenyl)-3,8-dimethyl-N-(2-piperazin-1-yl)ethyl)-9H-pyrido[2,3-b]indole-7-carboxamide;
5-(3-(ethylsulfonyl)phenyl)-3,8-dimethyl-N-(3-(4-methylpiperazin-1-yl)propyl)-9H-pyrido[2,3-b]indole-7-carboxamide;
5-(3-(ethylsulfonyl)phenyl)-3,8-dimethyl-9H-pyrido[2,3-b]indole-7-yl)(morpholino)methanone;
azetidin-1-yl(5-(3-(ethylsulfonyl)phenyl)-3,8-dimethyl-9H-pyrido[2,3-b]indol-7-yl)methanone;
(5-(3-(ethylsulfonyl)phenyl)-3,8-dimethyl-9H-pyrido[2,3-b]indol-7-yl)(thaiazolidin-3-yl)methanone;
(R)-5-(3-(ethylsulfonyl)phenyl)-N-(2-hydroxypropyl)-3,8-dimethyl-9H-pyrido[2,3-b]indole-7-carboxamide;
(S)-5-(3-(ethylsulfonyl)phenyl)-N-(2-hydroxypropyl)-3,8-dimethyl-9H-pyrido[2,3-b]indole-7-carboxamide;
5-(3-(ethylsulfonyl)phenyl)-N-(2-hydroxyethyl)-3,8-dimethyl-9H-pyrido[2,3-b]indole-7-carboxamide;
N-(2,3-dihydroxypropyl)-5-(3-(ethylsulfonyl)phenyl)-3,8-dimethyl-9H-pyrido[2,3-b]indole-7-carboxamide;
5-(3-(ethylsulfonyl)phenyl)-N-(2-hydroxy-2methylpropyl)-3,8-dimethyl-9H-pyrido[2,3-b]indole-7-carboxamide;
5-(3-(ethylsulfonyl)phenyl)-N-(1-isopropylpiperidin-4-yl)-3,8-dimethyl-9H-pyrido[2,3-b]indole-7-carboxamide;
N-(1-ethylpiperidin-4-yl)-5-(3-(ethylsulfonyl)phenyl)-3,8-dimethyl-9H-pyrido[2,3-b]indole-7-carboxamide;
5-(3-(ethylsulfonyl)phenyl)-3,8-dimethyl-N-thiazol-2-yl)-9H-pyrido[2,3-b]indole-7-carboxamide;
5-(3-(ethylsulfonyl)phenyl)-3,8-dimethyl-N-(2-(2,2,2-trifluoroethoxy)ethyl-9H-pyrido[2,3-b]indole-7-carboxamide;
5-(3-(ethylsulfonyl)phenyl)-3,8-dimethyl-N-(piperidin-3-yl)-9H-pyrido[2,3-b]indole-7-carboxamide;
5-(3-(ethylsulfonyl)phenyl)-3,8-dimethyl-N-(piperidin-4-yl)-9H-pyrid o[2,3-b]indole-7-carboxamide;
5-(3-(ethylsulfonyl)phenyl)-3,8-dimethyl- N-(piperidin-3-yl)-9H-pyrido[2,3-b]indole-7-carboxamide;
5-(3-(ethylsulfonyl)phenyl)-N-(2-(2-hydroxyethoxy)ethyl-3,8-dimethyl-9H-pyrido[2,3-b]indole-7-carboxamide;
5-(3-(cyclopropanecarboxamido)phenyl)-N-(2-(dimethylamino)ethyl)-3, 8-dimethyl-9H-pyrido[2,3-b]indole-7-carboxamide;
5-(3-(ethylsulfonyl)phenyl)-3,8-dimethyl-N-(1-methylpiperidin-4-yl)-9H-pyrido[2,3-b]indole-7-carboxamide;
5-(3-(ethylsulfonyl)phenyl)-3,8-dimethyl-N-((1-methylpiperidin-4-yl)methyl)-9H-pyrido[2,3-b]indole-7-carboxamide;
N-(3-(dimethylamino)propyl)-5-(3-(ethylsulfonyl)phenyl)-3,8-dimethyl-9H-pyrido[2,3-b]indole-7-carboxamide;
5-(3-(ethylsulfonyl)phenyl)-3,8-dimethyl-N-(2-(pyrrolidin-1-yl)ethyl)-9H-pyrido[2,3-b]indole-7-carboxamide;
(S)-5-(3-(ethylsulfonyl)phenyl)-3,8-dimethyl-N-(1-methylpiperidin-3-yl)-9H-pyrido[2,3-b]indole-7-carboxamide;
(R)-5-(3-(ethylsulfonyl)phenyl)-3,8-dimethyl-N-(1-methylpiperidin-3-yl)-9H-pyrido[2,3-b]indole-7-carboxamide;
5-chloro-3,8-dimethyl-N-(1-methylpiperidin-4-yl)-9H-pyrido[2,3-b]indole-7-carboxamide;
5-(3-(cyclopropanecarboxamido)phenyl)-3,8-dimethyl-N-(1-methyl-piperidin-4-yl)-9H-pyrido[2,3-b]indole-7-carboxamide;

5-chloro-N-(2-(dimethylamino)ethyl)-3,8-dimethyl-9H-pyrido[2,3-b]indole-7-carboxamide;
5-(3-(cyclopropylcarbamoyl)phenyl)-N-(2-(dimethylamino)ethyl)-3,8-dimethyl-9H-pyrido[2,3-b]indole-7-carboxamide;
5-Amino-3-methyl-9H-pyrido[2,3-b]indole-7-carbonitrile;
5-Iodo-3-methyl-9H-pyrido[2,3-b]indole-7-carbonitrile;
5-(3-Ethanesulfonyl-phenyl)-3-methyl-9H-pyrido[2,3-b]indole-7-carbonitrile;
5-(3-Ethanesulfonyl-phenyl)-3-methyl-9H-pyrido[2,3-b]indole-7-carboxylic acid amide;
5-Amino-3-methyl-9H-pyrido[2,3-b]indole-7-carboxylic acid methyl ester;
5-Iodo-3-methyl-9H-pyrido[2,3-b]indole-7-carboxylic acid methyl ester;
5-(3-Ethanesulfonyl-phenyl)-3-methyl-9H-pyrido[2,3-b]indole-7-carboxylic acid methyl ester;
[5-(3-Ethanesulfonyl-phenyl)-3-methyl-9H-pyrido[2,3-b]indol-7-yl]-methanol;
[5-(3-Ethanesulfonyl-phenyl)-3-methyl-9H-pyrido[2,3-b]indol-7-ylmethyl]-dimethyl-amine;
5-(3-Ethanesulfonyl-phenyl)-3-methyl-7-morpholin-4-ylmethyl-9H-pyrido[2,3-b]indole;
5-(3-Ethanesulfonyl-phenyl)-3-methyl-7-(4-methyl-piperazin-1-ylmethyl)-9H-pyrido[2,3-b]indole;
5-(3-Ethanesulfonyl-phenyl)-3-methyl-7-pyrrolidin-1-ylmethyl-9H-pyrido[2,3-b]indole;
[5-(3-Ethanesulfonyl-phenyl)-3-methyl-9H-pyrido[2,3-b]indol-7-ylmethyl]-ethyl-amine;
5-(3-Ethanesulfonyl-phenyl)-3-methyl-9H-pyrido[2,3-b]indole-7-carboxylic acid;
[5-(3-Ethanesulfonyl-phenyl)-3-methyl-9H-pyrido[2,3-b]indol-7-yl]-(4-methyl-piperazin-1-yl)-methanone;
5-(3-Ethanesulfonyl-phenyl)-3-methyl-9H-pyrido[2,3-b]indole-7-carboxylic acid(2-dimethylamino-ethyl)-amide;
5-(3-Ethanesulfonyl-phenyl)-3-methyl-9H-pyrido[2,3-b]indole-7-carboxylic acid(3-dimethylamino-propyl)-amide;
5-(3-Ethanesulfonyl-phenyl)-3-methyl-7-(2H-tetrazol-5-yl)-9H-pyrido[2,3-b]indole;
(3-Dimethylamino-pyrrolidin-1-yl)-[5-(3-ethanesulfonyl-phenyl)-3-methyl-9H-pyrido[2,3-b]indol-7-yl]-methanone;
N-ethyl-5-(3-(ethylsulfonyl)phenyl)-3-methyl-9H-pyrido[2,3-b]indole-7-carboxamide;
6-Bromo-5-(3-ethanesulfonyl-phenyl)-3-methyl-9H-pyrido[2,3-b]indole-7-carboxylic acid methyl ester;
8-Bromo-5-(3-ethanesulfonyl-phenyl)-3-methyl-9H-pyrido[2,3-b]indole-7-carboxylic acid methyl ester;
6-Chloro-5-(3-ethanesulfonyl-phenyl)-3-methyl-9H-pyrido[2,3-b]indole-7-carboxylic acid methyl ester;
8-Chloro-5-(3-ethanesulfonyl-phenyl)-3-methyl-9H-pyrido[2,3-b]indole-7-carboxylic acid methyl ester;
5-(benzylthio)-3-methyl-9H-pyrido[2,3-b]indole-7-carboxylic acid;
5-(benzylthio)-N-(2-(dimethylamino)ethyl)-3-methyl-9H-pyrido[2,3-b]indole-7-carboxamide;
5-(3-(N-ethylsulfamoyl)phenyl)-8-methoxy-3-methyl-N-(1-methylpiperidin-4-yl)-9H-pyrido[2,3-b]indole-7-carboxamide;
5-(3-(cyclopropylsulfonyl)phenyl)-3,8-dimethyl-N-(1-methylpiperidin-4-yl)-9H-pyrido[2,3-b]indole-7-carboxamide;
5-choloro-8-methoxy-9H-pyrido[2,3-b]indole;
5-(3-(ethylsulfonyl)phenyl-8-methoxy-3-methyl-9H-pyrido[2,3-b]indole;
5-(3-(ethylsulfonyl)phenyl)-3-methyl-9H-pyrido[2,3-b]indol-8-ol;
8-methoxy-3-methyl-5-(3-(pyrrolidin-1-ylsulfonyl)phenyl)-9H-pyrido[2,3-b]indole;
(R)-8-methoxy-3-methyl-5-(3-(pyrrolidin-3-ylsulfonyl)phenyl)-9H-pyrido[2,3-b]indole;
N-cyclopropyl-4-(8-methoxy-3-methyl-9H-pyrido[2,3-b]indol-5-yl)picolinamide;
N-(3-(8-methoxy-3-methyl-9H-pyrido[2,3-b]indol-5-yl)phenyl)acetamide;
N-(3-(8-methoxy-3-methyl-9H-pyrido[2,3-b]indol-5-yl)phenyl)cyclopropanecarboxamide;
N-cyclopropyl-3-(8-methoxy-3-methyl-9H-pyrido[2,3-b]indol-5-yl)benzamide;
N,N-diethyl-3-(8-methoxy-3-methyl-9H-pyrido[2,3-b]indol-5-yl)benzamide;
5-(benzo[d][1,3]dioxol-5-yl)-8-methoxy-3-methyl-9H-pyrido[2,3-b]indole;
6-(8-methoxy-3-methyl-9H-pyrido[2,3-b]indol-5-yl)-4H-chromen-4-one;
N-(2-hydroxyethyl)-3-(8-methoxy-3-methyl-9H-pyrido[2,3-b]indol-5-yl)benzamide;
(3-(8-methoxy-3-methyl-9H-pyrido[2,3-b]indol-5-yl)phenyl)(pyrrolidin-1-yl)methanone;
N-ethyl-3-(8-methoxy-3-methyl-9H-pyrido[2,3-b]indol-5-yl)benzenesulfonamide;
8-ethoxy-5-(3-(ethylsulfonyl)phenyl)-3-methyl-9H-pyrido[2,3-b]indole;
8-(difluoromethoxy)-5-(3-(ethylsulfonyl)phenyl)-3-methyl-9H-pyrido[2,3-b]indole;
5-(3-(ethylsulfonyl)phenyl)-3-methyl-8-(2,2,2-trifluoroethoxy)-9H-pyrido[2,3-b]indole;
5-(3-(ethylsulfonyl)phenyl)-3-methyl-8-((1-methylpiperidin-4-yl)methoxy)-9H-pyrido[2,3-b]indole;
N-cyclopropyl-3-(3-methyl-8-((1-methylpiperidin-4-yl)methoxy)-9H-pyrido[2,3-b]indol-5-yl)benzamide;
5-(3-(cyclopropylsulfonyl)phenyl)-3-methyl-8-((1-methylpiperidin-4-yl)methoxy)-9H-pyrido[2,3-b]indole;
N-methyl-3-(3-methyl-8-((1-methylpiperidin-4-yl)methoxy)-9H-pyrido[2,3-b]indole-5-yl)benzenesulfonamide;
N,N-dimethyl-3-(3-methyl-8-((1-methylpiperidin-4-yl)methoxy)-9H-pyrido[2,3-b]indole-5-yl)benzenesulfonamide;
N-(3-(3-methyl-8-((1-methylpiperidin-4-yl)methoxy)-9H-pyrido[2,3-b]indol-5-yl)phenyl)cyclopropanecarboxamide;
5-(3-(ethylthio)phenyl)-3-methyl-8-((1-methylpiperidin-4-yl)methoxy)-9H-pyrido[2,3-b]indole;
5-(3-ethoxyphenyl)-3-methyl-8-((1-methylpiperidin-4-yl)methoxy)-9H-pyrido[2,3-b]indole;
5-(3-(ethylsulfonyl)phenyl)-3-methyl-8-(piperidin-4-ylmethoxy)-9H-pyrido[2,3-b]indole;
(S)-5-(3-(ethylsulfonyl)phenyl)-3-methyl-8-((1-methylpyrrolidin-3-yl)methoxy)-9H-pyrido[2,3-b]indole;
(R)-5-(3-(ethylsulfonyl)phenyl)-3-methyl-8-((1-methylpyrrolidin-3-yl)methoxy)-9H-pyrido[2,3-b]indole;
(S)-5-(3-(ethylsulfonyl)phenyl)-3-methyl-8-((1-methylpyrrolidin-2-yl)methoxy)-9H-pyrido[2,3-b]indole;
(S)-5-(3-(ethylsulfonyl)phenyl)-3-methyl-8-(pyrrolidin-3-ylmethoxy)-9H-pyrido[2,3-b]indole;
(R)-5-(3-(ethylsulfonyl)phenyl)-3-methyl-8-(pyrrolidin-3-ylmethoxy)-9H-pyrido[2,3-b]indole;
3-(5-chloro-3-methyl-9H-pyrido[2,3-b]indol-8-yloxy)-N,N-dimethylpropan-1-amine;

N-(3-(8-(3-(dimethylamino)propoxy)-3-methyl-9H-pyrido[2,3-b]indol-5-yl)phenyl)cyclopropanecarboxamide;

N-cyclopropyl-3-(8-(3-(dimethylamino)propoxy)-3-methyl-9H-pyrido[2,3-b]indol-5-yl)benzamide;

3-(8-(3-(dimethylamino)propoxy)-3-methyl-9H-pyrido[2,3-b]indol-5-yl)-N-methylbenzenesulfonamide;

3-(8-(3-(dimethylamino)propoxy)-3-methyl-9H-pyrido[2,3-b]indol-5-yl)-N-N-dimethylbenzenesulfonamide;

3-chloro-5-(3-(ethylsulfonyl)phenyl)-8-((1-methylpiperidin-4-yl)methoxy)-9H-pyrido[2,3-b]indole;

3-chloro-5-(3-(ethylsulfonyl)phenyl)-8-(piperidin-4-ylmethoxy)-9H-pyrido[2,3-b]indole;

5-(3-(ethylsulfonyl)phenyl)-8-((1-methylpiperidin-4-yl)methoxy)-3-(trifluoromethyl)-9H-pyrido[2,3-b]indole;

5-(3-(ethylsulfonyl)phenyl)-8-((1-methylpiperidin-4-yl)methoxy)-9H-pyrido[2,3-b]indole-3-carbonitrile;

2-(5-(3-(ethylsulfonyl)phenyl)-7-fluoro-3-methyl-9H-pyrido[2,3-b]indol-8-yloxy)-N,N-dimethylethanamine;

3-(3-chloro-5-(3-(ethylsulfonyl)phenyl)-7-fluoro-9H-pyrido[2,3-b]indol-8-yloxy)-N,N-dimethylpropan-1-amine;

3-(5-(3-(ethylsulfonyl)phenyl)-3-methyl-9H-pyrido[2,3-b]indol-8-yloxy)-N,N-dimethylpropan-1-amine;

2-(5-(3-(ethylsulfonyl)phenyl)-3-methyl-9H-pyrido[2,3-b]indol-8-yloxy)-N,N-dimethylethanamine;

5-(3-(ethylsulfonyl)phenyl)-8-(2-methoxyethoxy)-3-methyl-9H-pyrido[2,3-b]indole;

2-(5-(3-(ethylsulfonyl)phenyl)-3-methyl-9H-pyrido[2,3-b]indol-8-yloxy)acetonitrile;

3-(5-(3-(ethylsulfonyl)phenyl)-3-methyl-9H-pyrido[2,3-b]indol-8-yloxy)propanenitrile;

(R)-8-(1-tert-butyldiphenylsilyloxy)propan-2-yloxy)-(5-(3-(ethylsulfonyl)phenyl)-3-methyl-9H-pyrido[2,3-b]indole;

(R)-2-(5-(3-(ethylsulfonyl)phenyl)-3-methyl-9H-pyrido[2,3-b]indol-8-yloxy)propan-1-ol;

(S)-2-(5-(3-(ethylsulfonyl)phenyl)-3-methyl-9H-pyrido[2,3-b]indol-8-yloxy)propan-1-ol;

1-(5-(3-(ethylsulfonyl)phenyl)-3-methyl-9H-pyrido[2,3-b]indol-8-yloxy)propan-2-ol;

(S)-4-(5-(3-(ethylsulfonyl)phenyl)-3-methyl-9H-pyrido[2,3-b]indol-8-yloxy)-2-methylpentan-2-ol;

2-(5-(3-(ethylsulfonyl)phenyl)-3-methyl-9H-pyrido[2,3-b]indol-8-yloxy)ethanol;

3-(5-(3-(ethylsulfonyl)phenyl)-3-methyl-9H-pyrido[2,3-b]indol-8-yloxy)propan-1-ol;

3-(3-chloro-5-(3-(ethylsulfonyl)phenyl)-8-methoxy-9H-pyrido[2,3-b]indol-8-ol;

(3-chloro-5-(3-(ethylsulfonyl)phenyl)-9H-pyrido[2,3-b]indol-8-ol;

3-(3-chloro-5-(3-(ethylsulfonyl)phenyl)-9H-pyrido[2,3-b]indol-8-yloxy)-N,N-dimethylpropan-1-amine;

2-(3-chloro-5-(3-(ethylsulfonyl)phenyl)-9H-pyrido[2,3-b]indol-8-yloxy)-N,N-diethylethanamine;

2-(3-chloro-5-(3-(ethylsulfonyl)phenyl)-9H-pyrido[2,3-b]indol-8-yloxy)-N,N-dimethylethanamine;

3-chloro-5-(3-(ethylsulfonyl)phenyl)-8-(2-(pyrrolidin-1-yl)ethoxy)-9H-pyrido[2,3-b]indole;

3-chloro-5-(3-(ethylsulfonyl)phenyl)-8-(2-(4-methylpiperazin-1-yl)ethoxy)-9H-pyrido[2,3-b]indole;

2-(3-chloro-5-(3-(ethylsulfonyl)phenyl)-9H-pyrido[2,3-b]indol-8-yloxy)ethanol;

3-(3-chloro-5-(3-(ethylsulfonyl)phenyl)-9H-pyrido[2,3-b]indol-8-yloxy)propan-1-ol;

(S)-2-(5-(3-(ethylsulfonyl)phenyl)-3-methyl-9H-pyrido[2,3-b]indol-8-yloxy)ethyl 2-aminopropanoate;

(S)-3-(5-(3-(ethylsulfonyl)phenyl)-3-methyl-9H-pyrido[2,3-b]indol-8-yloxy)propyl 2-aminopropanoate;

(S)-3-(3-chloro-5-(3-(ethylsulfonyl)phenyl)-9H-pyrido[2,3-b]indol-8-yloxy)propyl 2-aminopropanoate;

(R)-8-((2,2-dimethyl-1,3-dioxolan-4-yl)methoxy-5-(3-ethylsulfonyl)phenyl)-3-methyl-9H-pyrido[2,3-b]indole;

(S)-3-(5-(3-(ethylsulfonyl)phenyl)-3-methyl-9H-pyrido[2,3-b]indol-8-yloxy)propane-1,2-diol;

(R)-3-(5-(3-(ethylsulfonyl)phenyl)-3-methyl-9H-pyrido[2,3-b]indol-8-yloxy)propane-1,2-diol;

(R)-1-(dimethylamino)-3-(5-(3-(ethylsulfonyl)phenyl)-3-methyl-9H-pyrido[2,3-b]indol-8-yloxy)propan-2-ol;

(R)-1-(5-(3-(ethylsulfonyl)phenyl)-3-methyl-9H-pyrido[2,3-b]indol-8-yloxy)propan-2-ol;

(S)-1-(5-(3-(ethylsulfonyl)phenyl)-3-methyl-9H-pyrido[2,3-b]indol-8-yloxy)propan-2-ol;

5-bromo-8-methoxy-3-methyl-9H-pyrido[2,3-b]indol-7-amine;

(5-(3-(ethylsulfonyl)phenyl)-8-methoxy-3-methyl-9H-pyrido[2,3-b]indol-7-amine;

N-(3-(7-amino-8-methoxy-3-methyl-9H-pyrido[2,3-b]indol-5-yl)phenyl)-cyclopropanecarboxamide;

3-(dimethylamino)-N-(5-(3-(ethylsulfonyl)phenyl)-8-methoxy-3-methyl-9H-pyrido[2,3-b]indol-7-yl)propanamide;

N-(5-(3-(ethylsulfonyl)phenyl)-8-methoxy-3-methyl-9H-pyrido[2,3-b]indol-7-yl)-cyclopropanecarboxamide;

1-acetyl-N-(5-(3-(ethylsulfonyl)phenyl)-8-methoxy-3-methyl-9H-pyrido[2,3-b]indol-7-yl)piperidine-4-carboxamide;

3-(7-amino-8-methoxy-3-methyl-9H-pyrido[2,3-b]indol-5-yl)-N-cyclopropylbenzamide;

3-(7-(cyclopropanecarboxamido)-8-methoxy-3-methyl-9H-pyrido[2,3-b]indol-5-yl)-N-cyclopropylbenzamide;

7-chloro-5-(3-(ethylsulfonyl)phenyl)-8-methoxy-3-methyl-9H-pyrido[2,3-b]indole;

7-chloro-5-(3-(ethylsulfonyl)phenyl)-3-methyl-9H-pyrido[2,3-b]indol-8-ol;

3-(7-chloro-5-(3-(ethylsulfonyl)phenyl)-3-methyl-9H-pyrido[2,3-b]indol-8-yloxy)propan-1-ol;

N-(5-(3-(ethylsulfonyl)phenyl)-8-methoxy-3-methyl-9H-pyrido[2,3-b]indol-7-yl)-N-methylcyclopropanecarboxamide;

3-(dimethylamino)-N-(5-(3-(ethylsulfonyl)phenyl)-8-methoxy-3-methyl-9H-pyrido[2,3-b]indol-7-yl)-N-methylpropanamide;

5-(3-(cyclopropylcarbamoyl)phenyl)-3,8-dimethyl-N-(1-methylpiperidin-4-yl)-9H-pyrido[2,3-b]indole-7-carboxamide;

4-(2-(3-chloro-5-(3-(ethylsulfonyl)phenyl)-9H-pyrido[2,3-b]indol-8-yloxy)ethyl)morpholine;

3-(3-chloro-5-(3-(ethylsulfonyl)phenyl)-9H-pyrido[2,3-b]indol-8-yloxy)propanenitrile;

3-chloro-5-(3-(ethylsulfonyl)phenyl)-8-(1-methylpiperidin-4-yloxy)-9H-pyrido[2,3-b]indole;

3-(5-(3-(ethylsulfonyl)phenyl)-3-(trifluoromethyl)-9H-pyrido[2,3-b]indol-8-yloxy)-N,N-dimethylpropan-1-amine;

(3-(8-methoxy-3-methyl-9H-pyrido[2,3-b]indol-5-yl)phenyl)(morpholino)methanone;

N-methoxy-3-(8-methoxy-3-methyl-9H-pyrido[2,3-b]indol-5-yl)benzamide;

5-(3-Ethanesulfonyl-phenyl)-8-(cyclopropylmethoxy)-3-methyl-9H-dipyrido[2,3-b;4',3'-d]pyrrole;

N-(2-(diethylamino)ethyl)-5-(3-(ethylsulfonyl)phenyl)-3,8-dimethyl-9H-pyrido[2,3-b]indole-7-carboxamide; and 5-(3-(ethylsulfonyl)phenyl)-3,8-dimethyl-N-(3-morpholinopropyl)-9H-pyrido[2,3-b]indole-7-carboxamide.

Particular examples of compounds according to the present invention also include, but are not limited to:

5-(3-(ethylsulfonyl)phenyl)-3,8-dimethyl-N-(1-methylpiperidin-4-yl)-9H-pyrido[2,3-b]indole-7-carboxamide HCl salt;

5-(3-(ethylsulfonyl)phenyl)-3-methyl-8-((1-methylpiperidin-4-yl)methoxy)-9H-pyrido[2,3-b]indole HCl salt;

3-chloro-5-(3-(ethylsulfonyl)phenyl)-8-((1-methylpiperidin-4-yl)methoxy)-9H-pyrido[2,3-b]indole HCl salt;

3-(5-(3-(ethylsulfonyl)phenyl)-3-methyl-9H-pyrido[2,3-b]indol-8-yloxy)-N,N-dimethylpropan-1-amine HCl salt;

3-(3-chloro-5-(3-(ethylsulfonyl)phenyl)-9H-pyrido[2,3-b]indol-8-yloxy)-N,N-dimethylpropan-1-amine HCl salt; and N-cyclopropyl-3-(3-methyl-8-((1-methylpiperidin-4-yl)methoxy)-9H-pyrido[2,3-b]indol-5-yl)benzamide HCl salt.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent such as a hydrogen.

It is further noted that the compounds of the present invention may optionally be solely or predominantly in the enol tautomer in its active state. It is further noted that the compound may be present in a mixture of stereoisomers, or the compound comprises a single stereoisomer.

The invention also provides pharmaceutical compositions comprising, as an active ingredient, a compound according to any one of the above embodiments and variations. In addition, the composition may be a solid or liquid formulation adapted for oral administration. In a further variation, the pharmaceutical composition may be a tablet. In yet another variation, the pharmaceutical composition may be a liquid formulation adapted for parenteral administration.

In one embodiment, there is provided the pharmaceutical composition comprising a compound according to any one of the above embodiments and variations wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

The invention also provides a kit comprising a compound or composition according to any one of the above embodiments and variations, and instructions which comprise one or more forms of information selected from the group consisting of indicating a disease state for which the compound is to be administered, storage information for the compound, dosing information and instructions regarding how to administer the compound. In one variation, the kit comprises the compound or composition in a multiple dose form.

In another embodiment, the present invention provides an article of manufacture comprising a compound or composition according to any one of the above embodiments and variations, and packaging materials. In one variation, the packaging material comprises a container for housing the compound or composition. The container optionally comprises a label indicating a disease state for which the compound or composition is to be administered, storage information, dosing information and/or instructions regarding how to administer the compound or composition. In regard to the above embodiments and variations, the article of manufacture optionally comprises the compound or composition in a multiple dose form.

In another embodiment, the present invention provides a therapeutic method comprising administering a compound or composition according to any one of the above embodiments and variations to a subject.

In yet another embodiment, the present invention provides a method of inhibiting a kinase comprising contacting a kinase with a compound or composition according to any one of the above embodiments and variations.

In still another embodiment, there is provided a method of inhibiting kinase comprising causing a compound or composition according to any one of the above embodiments and variations to be present in a subject in order to inhibit kinase in vivo.

The present invention also provides a method of inhibiting a kinase comprising administering a first compound to a subject that is converted in vivo to a second compound wherein the second compound inhibits kinase in vivo, the second compound being a compound according to any one of the above embodiments and variations.

In yet another embodiment, there is provided a method of preventing or treating a disease state for which a kinase possesses activity that contributes to the pathology and/or symptomology of the disease state comprising causing a compound or composition according to any one of the above embodiments and variations to be present in a subject in a therapeutically effective amount for the disease state.

The present invention also provides a method of preventing or treating a disease state for which a kinase possesses activity that contributes to the pathology and/or symptomology of the disease state comprising administering a first compound to a subject that is converted in vivo to a second compound according to any one of the above embodiments and variations wherein the second compound is present in a subject in a therapeutically effective amount for the disease state.

In addition, there is provided a method of preventing or treating a disease state for which a kinase possesses activity that contributes to the pathology and/or symptomology of the disease state comprising administering a compound or composition according to any one of the above embodiments and variations, wherein the compound or composition is present in the subject in a therapeutically effective amount for the disease state.

In each of the above embodiments and variations, the kinase is optionally an Aurora kinase. In particular variations of each of the above embodiments and variations, the kinase is an Aurora-B kinase.

In another embodiment, there is provided a method for treating cancer comprising administering a therapeutically effective amount of a compound or composition of the present invention to a mammalian species in need thereof. In one embodiment, the cancer is selected from the group consisting of squamous cell carcinoma, astrocytoma, Kaposi's sarcoma, glioblastoma, non small-cell lung cancer, bladder cancer, head and neck cancer, melanoma, ovarian cancer, prostate cancer, breast cancer, small-cell lung cancer, glioma, colorectal cancer, genitourinary cancer, gastrointestinal cancer, thyroid cancer and skin cancer.

In another embodiment, there is provided a method for treating inflammation, inflammatory bowel disease, psoriasis, or transplant rejection, comprising administration to a mammalian species in need thereof of a therapeutically effective amount of a compound or composition according to the present invention.

In another embodiment, there is provided a method for preventing or treating amyotrophic lateral sclerosis, corticobasal degeneration, Down syndrome, Huntington's Disease, Parkinson's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss and contraceptive medication, comprising administration to a mammalian species in need thereof of a therapeutically effective amount of a compound or composition according to any one of the above embodiments.

In yet another embodiment, there is provided a method for preventing or treating mild Cognitive Impairment, Age-Associated Memory Impairment, Age-Related Cognitive Decline, Cognitive Impairment No Dementia, mild cognitive decline, mild neurocognitive decline, Late-Life Forgetfulness, memory impairment and cognitive impairment and androgenetic alopecia, comprising administering to a mammal, including man in need of such prevention and/or treatment, a therapeutically effective amount of a compound or composition according to any one of the above embodiments.

In a further embodiment, there is provided a method for preventing or treating dementia related diseases, Alzheimer's Disease and conditions associated with kinases, comprising administration to a mammalian species in need thereof of a therapeutically effective amount of a compound or composition according to any one of the above embodiments. In one particular variation, the dementia related diseases are selected from the group consisting of Frontotemporal dementia Parkinson's Type, Parkinson dementia complex of Guam, HIV dementia, diseases with associated neurofibrillar tangle pathologies, predemented states, vascular dementia, dementia with Lewy bodies, Frontotemporal dementia and dementia pugilistica.

In another embodiment, there is provided a method for treating arthritis comprising administration to a mammalian species in need thereof of a therapeutically effective amount of a compound or composition according to any one of the above embodiment.

In still another embodiment, there is provided a compound according to any one of the above embodiments and variations for use as a medicament.

In yet another embodiment, there is provided a compound according to any one of the above embodiments and variations for use in the manufacture of a medicament for inhibiting a kinase.

In a further embodiment, there is provided a compound according to any one of the above embodiments and variations for use in the manufacture of a medicament for treating a disease state for which a kinase possesses activity that contributes to the pathology and/or symptomology of the disease state.

In still a further embodiment, there is provided a compound according to any one of the above embodiments and variations for use in the manufacture of a medicament for treating cancer, inflammation, inflammatory bowel disease, psoriasis, transplant rejection, amyotrophic lateral sclerosis, corticobasal degeneration, Down syndrome, Huntington's Disease, Parkinson's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss, contraception, mild Cognitive Impairment, Age-Associated Memory Impairment, Age-Related Cognitive Decline, Cognitive Impairment No Dementia, mild cognitive decline, mild neurocognitive decline, Late-Life Forgetfulness, memory impairment, cognitive impairment, androgenetic alopecia, dementia related diseases, and Alzheimer's Disease.

Salts, Hydrates, and Prodrugs of Kinase Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine(tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as $(C_{1-4})$alkyl halides, e.g., methyl, ethyl, iso-propyl and tert-butyl chlorides, bromides and iodides; di $(C_{1-4})$alkyl sulfates, e.g., dimethyl, diethyl and diamyl sulfates; $(C_{10-18})$ alkyl halides, e.g., decyl, dodecyl, lauryl, myristyl and stearyl chlorides, bromides and iodides; and aryl $(C_{1-4})$alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in T. W. Greene, *Protecting Groups in Organic Synthesis*, 3$^{rd}$ edition, John Wiley & Sons, Inc. 1999.

Compounds of the present invention may also be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Preparation of Kinase Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Composition Comprising Kinase Inhibitors

A wide variety of compositions and administration methods may be used in conjunction with the kinase inhibitors of the present invention. Such compositions may include, in addition to the kinase inhibitors of the present invention, conventional pharmaceutical excipients, and other conventional, pharmaceutically inactive agents. Additionally, the compositions may include active agents in addition to the kinase inhibitors of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising kinase inhibitors of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The kinase inhibitors and compositions comprising them may be administered or coadministered in any conventional dosage form. Co-administration in the context of this invention is intended to mean the administration of more than one therapeutic agent, one of which includes a kinase inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When kinase inhibitors according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding kinase inhibitors according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more kinase inhibitors according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of a kinase inhibitor of the present invention to reduce kinases activity in vivo, thereby treating the disease state of the subject.

Dosage forms or compositions may optionally comprise one or more kinase inhibitors according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more kinase inhibitors, optionally 0.1-95%, and optionally 1-95%.

Salts, preferably sodium salts, of the kinase inhibitors may be prepared with carriers that protect the compound against rapid elimination from the body, such as time release formulations or coatings. The formulations may further include other active compounds to obtain desired combinations of properties.

Formulations For Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, kinase inhibitors according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water soluble FD and C dyes, mixtures thereof, and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The kinase inhibitors of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising kinase inhibitors of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. Nos. Re 28,819 and 4,358,603.

Injectables, Solutions, and Emulsions

The present invention is also directed to compositions designed to administer the kinase inhibitors of the present invention by parenteral administration, generally characterized by injection, either subcutaneously, intramuscularly or intravenously. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions include EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of a kinase inhibitor in the parenteral formulation may be adjusted so that an injection administers a pharmaceutically effective amount sufficient to produce the desired pharmacological effect. The exact concentration of a kinase inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is know and practiced in the art.

Injectables may be designed for local and systemic administration. Typically a therapeutically effective dosage is formulated to contain a concentration of at least about 0.1% w/w up to about 90% w/w or more, preferably more than 1% w/w of the kinase inhibitor to the treated tissue(s). The kinase inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The kinase inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The kinase inhibitors of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a kinase inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the kinase inhibitor.

Topical Administration

The kinase inhibitors of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The kinase inhibitors may be formulated as aerosols for topical application, such as by inhalation (see, U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The kinase inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the kinase inhibitor alone or in combination with other pharmaceutically acceptable excipients can also be administered.

Formulations for Other Routes of Administrations

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

EXAMPLES OF FORMULATIONS

The following are particular examples of oral, intravenous and tablet formulations that may optionally be used with compounds of the present invention. It is noted that these formulations may be varied depending on the particular compound being used and the indication for which the formulation is going to be used.

Oral Formulation

| Compound of the Present Invention | 10-100 mg |
|---|---|
| Citric Acid Monohydrate | 105 mg |
| Sodium Hydroxide | 18 mg |
| Flavoring | |
| Water | q.s. to 100 mL |

Intravenous Formulation

| Compound of the Present Invention | 0.1-10 mg |
|---|---|
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

Tablet Formulation

| Compound of the Present Invention | 1% |
|---|---|
| Microcrystalline Cellulose | 73% |
| Stearic Acid | 25% |
| Colloidal Silica | 1%. |

Kits Comprising Kinase Inhibitors

The invention is also directed to kits and other articles of manufacture for treating diseases associated with kinases. It is noted that diseases are intended to cover all conditions for which the kinases possesses activity that contributes to the pathology and/or symptomology of the condition.

In one embodiment, a kit is provided that comprises a composition comprising at least one kinase inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one kinase inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

1. Preparation of Kinase Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al.(1994), *Bioorganic and Medicinal Chemistry Letters*, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, *Protecting Groups in Organic Synthesis*, $3^{rd}$ edition, John Wiley & Sons, Inc. 1999.

Compounds according to the present invention may be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or thee-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
i.v. (intravenous); Hz (Hertz);
MHz (megahertz); mol (moles);
mmol (millimoles); RT (ambient temperature);
min (minutes); h (hours);
mp (melting point); TLC (thin layer chromatography);
Tr (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); EtOAc (ethyl acetate);
DME (1,2-dimethoxyethane); DCM (dichloromethane);
DCE (dichloroethane); DMF (N,N-dimethylformamide);

DMPU (N,N'-dimethylpropyleneurea); CDI (1,1-carbonyldiimidazole);
IBCF (isobutyl chloroformate); HOAc (acetic acid);
HOSu (N-hydroxysuccinimide); HOBT (1-hydroxybenzotriazole);
$Et_2O$ (diethyl ether); EDCI (ethylcarbodiimide hydrochloride);
BOC (tert-butyloxycarbonyl);FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); Me (methyl);
OMe (methoxy); Et (ethyl);
Et (ethyl); tBu (tert-butyl);
HPLC (high pressure liquid chromatography);
BOP (bis(2-oxo-3-oxazolidinyl)phosphinic chloride);
TBAF (tetra-n-butylammonium fluoride);
mCPBA (meta-chloroperbenzoic acid.

All references to ether or $Et_2O$ are to diethyl ether; brine refers to a saturated aqueous solution of NaCl. Unless otherwise indicated, all temperatures are expressed in ° C. (degrees Centigrade). All reactions conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

The entire disclosure of all documents cited throughout this application are incorporated herein by reference.

2. Synthetic Schemes for Kinase Inhibitors of the Present Invention

Kinase inhibitors according to the present invention may be synthesized according to the reaction scheme shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Experimental Methods

General synthetic routes for producing compounds of the present invention are shown in Schemes 1-5.

Scheme 1:

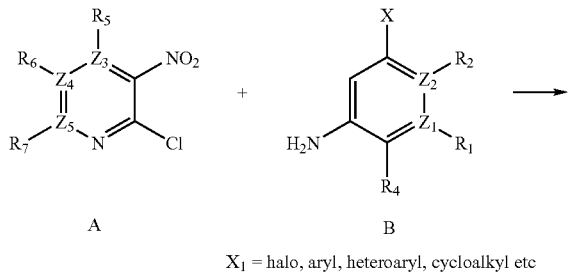

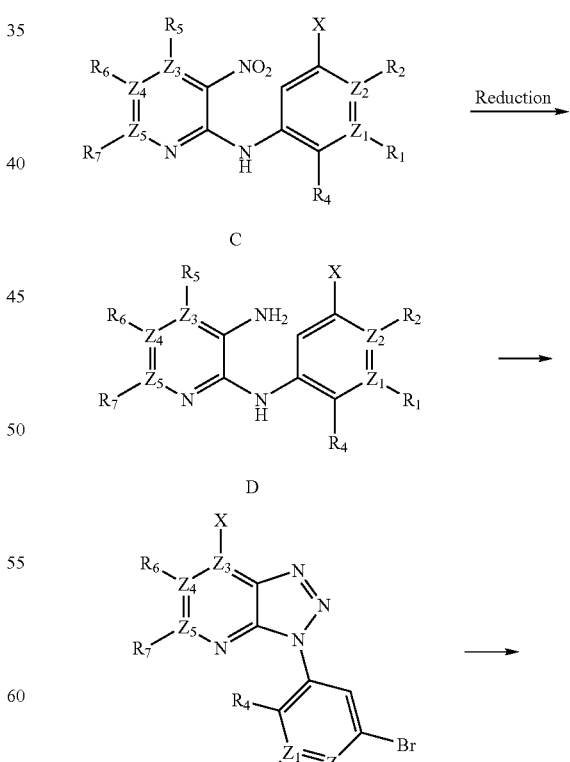

-continued

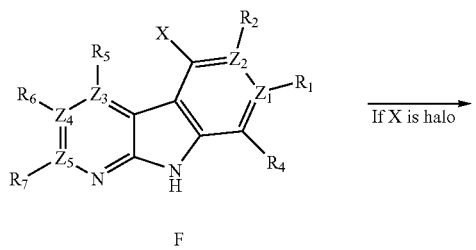

F

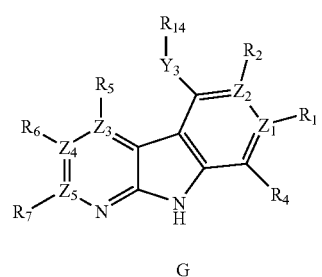

G

Referring to Scheme 1, Compound A and Compound B are mixed and treated under a variety of conditions to form Compound C. For example, the mixture of Compound A and Compound B can be treated with microwaves, either neat or in an appropriate solvent, at temperatures ranging from 80° C. to 200° C. The nitro group in Compound C is reduced by, for example, catalytic hydrogenation or metal reductions (eg., with SnCl$_2$) to form Compound D. Compound D is converted to Compound E using NaNO$_2$ under suitable conditions (eg., in AcOH). Compound E is treated with an acid (e.g., o-phosphoric acid) or under flash vacuum at 150° C. to 350° C. to obtain Compound F. If X in Compound F is halo, Compound F can be further converted to Compound G either by treating with alcohol, amine, thiol or by Suzuki type coupling.

Scheme 2:

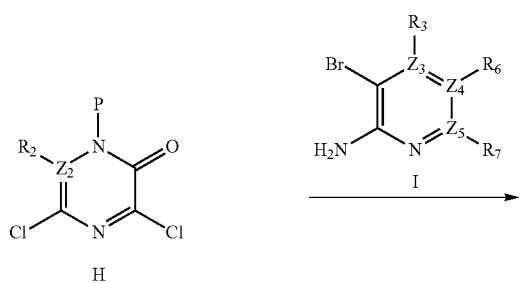

H

P = protecting group such as benzyl, PMB etc.

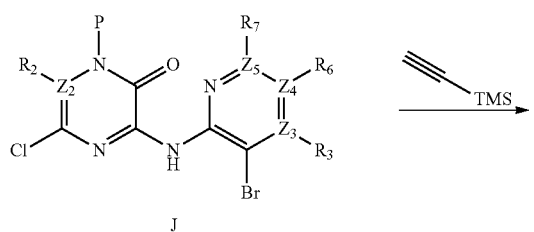

J

-continued

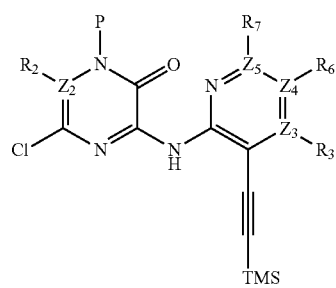

K

Diels-Alder
100-200° C.

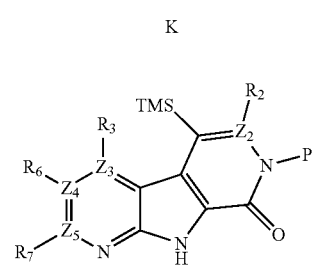

L (X$_1$)$_2$, AgBF$_4$
X = halo

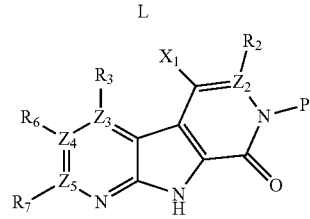

M

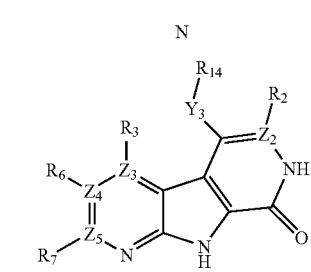

N deprotection

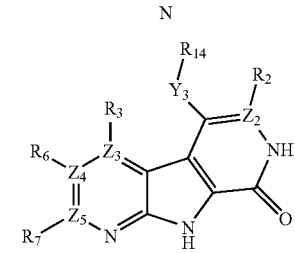

O

PO(X$_2$)$_3$
X = halo

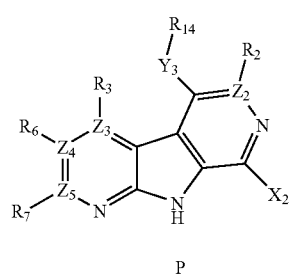

P

-continued

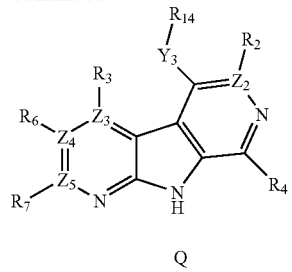

Q

R₄ = alkyl, alkoxy, amino, tioalktl, aryloxy, cycloalkyloxy, heteroaryloxy etc

Referring to Scheme 2, Compound H is reacted with Compound I to give Compound J. Compound J is reacted with ethynyltrimethylsilane under suitable conditions (e.g., Pd mediated in the presence or absence of a base) to provide Compound K. Compound K is transformed to Compound L under Diels-Alder reaction conditions (e.g., heating to a temperature between 100° C. and 200° C.). The TMS group in Compound L is converted to a halo group to yield Compound M. Compound M is further converted to Compound N either by treating with alcohol, amine or thiol, or by Suzuki type coupling. Deprotection of Compound N provides Compound O. Compound O is treated with POX₃ to obtain Compound P. Compound P is further converted to Compound Q either by treating with alcohol, amine or thiol, or by Suzuki type coupling.

Scheme 3:

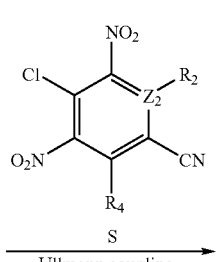

R

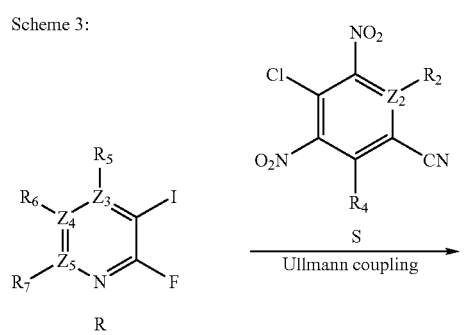

S

Ullmann coupling

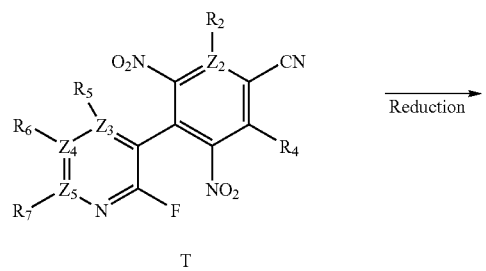

T

Reduction

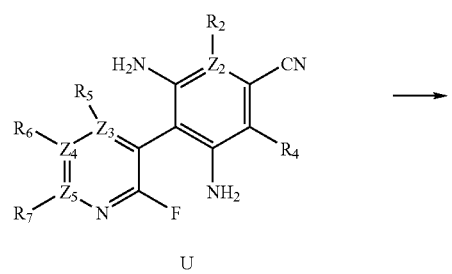

U

-continued

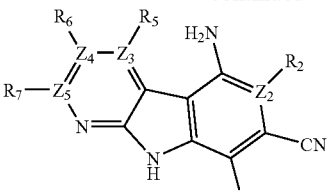

V

Sandmeyer

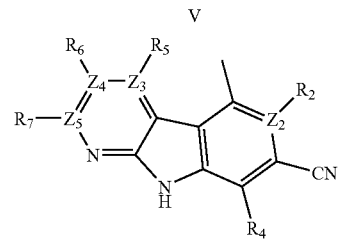

W

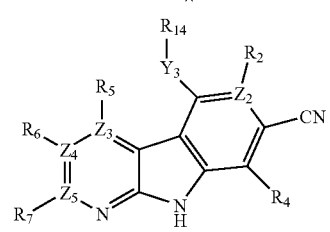

X

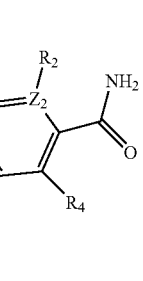

Y

Referring to Scheme 3, Ullmann coupling of Compound R with Compound S provides Compound T. The nitro group in Compound T is reduced (e.g., by catalytic hydrogenation or metal reductions such as with Fe) to form Compound U. Compound U is cyclized to form Compound V. Compound V subjected to Sandmeyer reaction conditions to provide Compound W. Compound W is further converted to Compound X either by treating with alcohol, amine or thiol, or by Suzuki type coupling. Compound X is treated with a base (e.g., KOH) to obtain Compound Y.

Scheme 4:

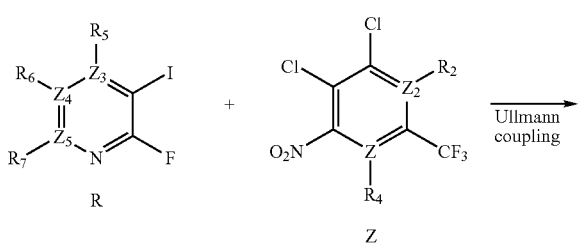

Ullmann coupling

R            Z

-continued

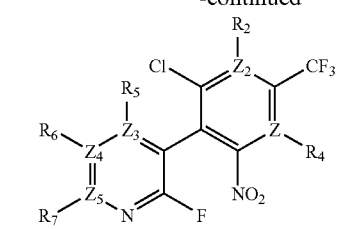
AA

 Reduction

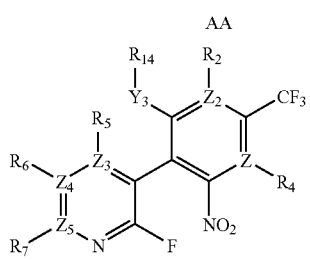
AB

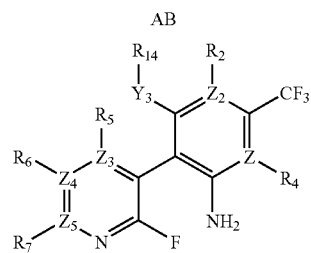
AC

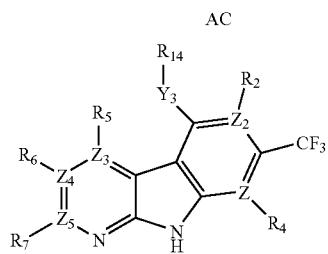
AD

 HNR$_{23}$R$_{24}$ peptide coupling

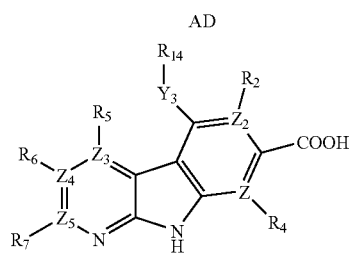
AE

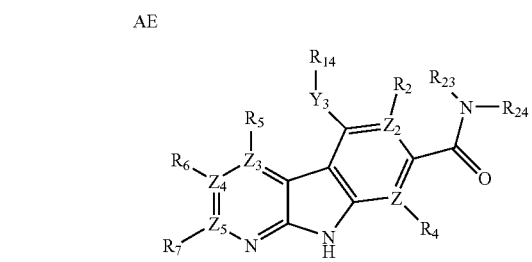
AF

R$_{23}$ and R$_{24}$ = H, alkyl, cycloalkyl, heterocyclylalkyl etc

Referring to Scheme 4, Ullmann coupling of Compound R with Compound Z provides Compound AA. Compound AA is further converted to Compound AB either by treating with alcohol, amine or thiol, or by Suzuki type coupling. The nitro group in Compound AB is reduced (e.g., by catalytic hydrogenation or metal reductions such as with Fe) to form Compound AC. Compound AC is cyclized to form Compound AD. Compound AD is treated with acid to provide Compound AE. Peptide coupling of Compound AE with amine provides Compound AF.

Scheme 5:

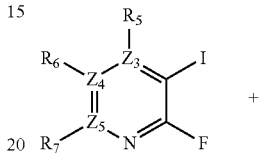
AY

+

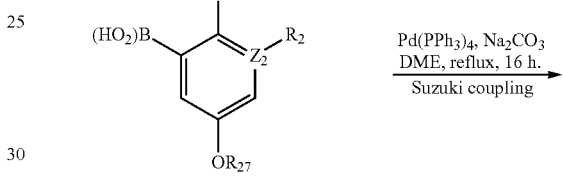
AZ

Pd(PPh$_3$)$_4$, Na$_2$CO$_3$
DME, reflux, 16 h.
Suzuki coupling

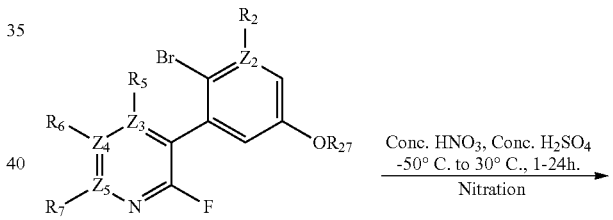
BA

Conc. HNO$_3$, Conc. H$_2$SO$_4$
-50° C. to 30° C., 1-24h.
Nitration

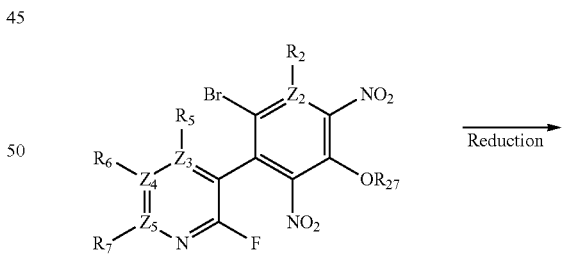
BB

Reduction

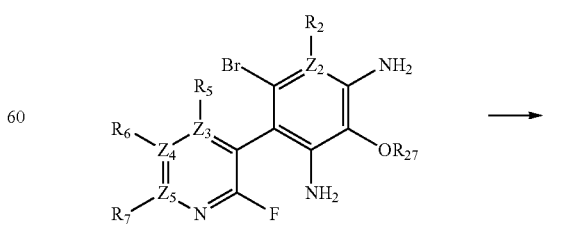
BC

91
-continued

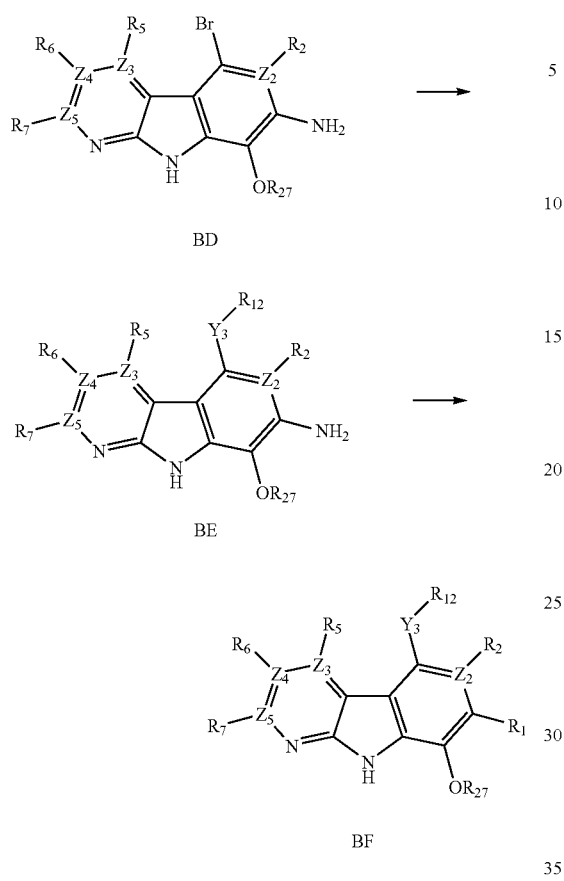

BD

BE

BF

Referring to Scheme 5, Suzuki type coupling of Compound AY with a boronic acid (Compound AZ) under Pd mediated conditions (e.g., tetrakis in presence of base such as $Na_2CO_3$ in a suitable solvent at temperatures ranging from 50° C. to 200° C.) provides Compound BA. Compound BA is subjected to nitration conditions (erg., $HNO_3/H_2SO_4$) to obtain Compound BB. The nitro groups in Compound BB are reduced (eg., by catalytic hydrogenation or metal reductions such as with Fe) to form Compound BC. Compound BC is cyclized to form Compound BD. Compound BD is further converted to Compound BE either by treating with alcohol, amine or thiol, or by Suzuki type coupling. Compound BE can be converted to a halo by Sandmeyers reaction or converted to amides by peptide coupling with suitable acids.

In each of the above reaction procedures or schemes, the various substituents may be selected from among the various substituents otherwise taught herein.

Descriptions of the syntheses of particular compounds according to the present invention based on the above reaction scheme are set forth herein.

3. Examples of Kinase Inhibitors

The present invention is further exemplified, but not limited by, the following examples that describe the synthesis of particular compounds according to the invention.

92

Compound 1:
N-(3-bromophenyl)-3-nitropyridin-2-amine

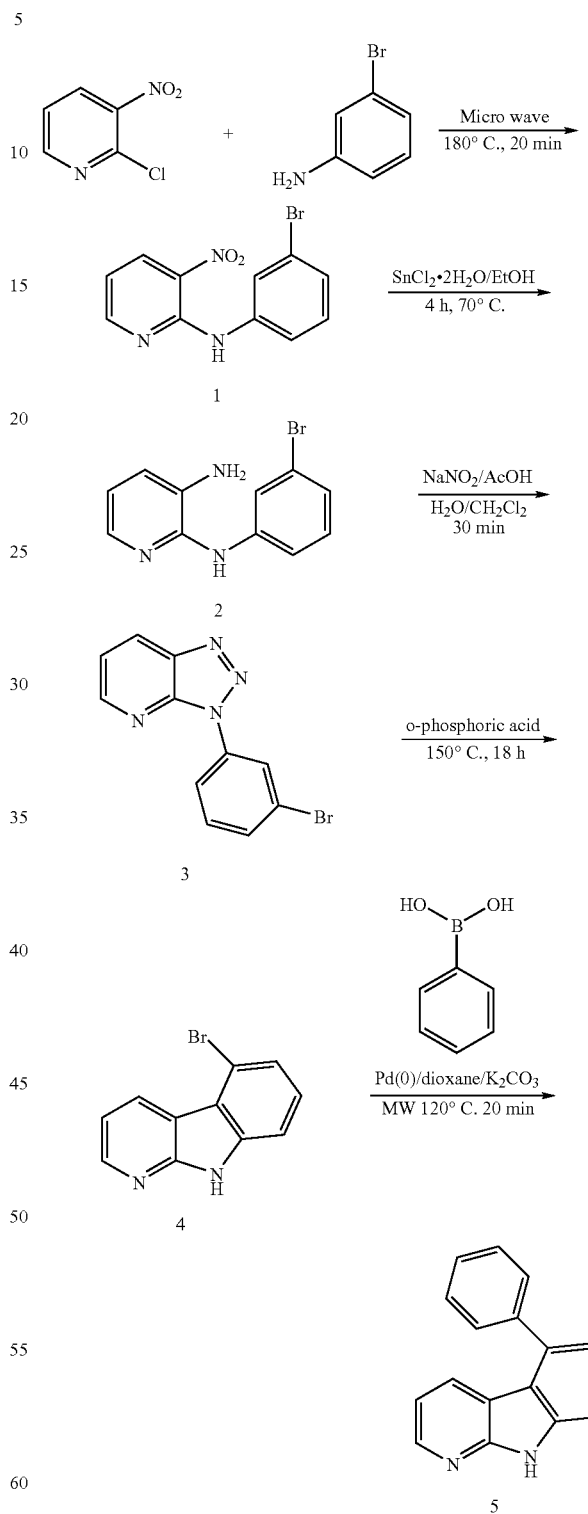

2-chloro-3-nitropyridine (2.0 g, 12.6 mmol, 1 eq) was reacted with 5-Bromoaniline (4.12 ml, 37.8 mmol, 3 eq) for 20 minutes at 180° C. in a microwave reactor. The product was isolated by column chromatography to provide the title compound as a red solid (4.9 g). [M+H] calc'd for $C_{11}H_8BrN_3O_2$, 293; found 293.

Compound 2:
N2-(3-bromophenyl)pyridine-2,3-diamine

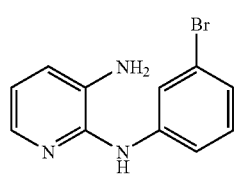

Compound 1 (4.9 g, 16.6 mmol) was dissolved in ethanol (20 ml). Tin (II) Chloride dihydrate (7.5 g, 33.3 mmol) was added and the solution stirred at 70° C. for 4 hours to provide the title compound. The product was confirmed by LC-MS. Addition of excess triethylamine caused a solid to form. The solid was filtered and the solution evaporated to leave an off white solid. The solid as recrystallized from ethanol to leave the title compound (3.8 g, 86%). [M+H] calc'd for $C_{11}H_{10}BrN_3$, 265; found 265.

Compound 3: 3-(3-bromophenyl)-3H-[1,2,3]triazolo [4,5-b]pyridine

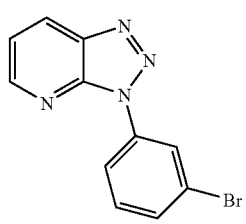

Compound 2 (3.8 g, 14.4 mmol) was dissolved in a mixture of acetic acid (4 ml), water (4 ml) and methylene chloride (4 ml). The mixture was cooled to 0° C., then sodium nitrate (1.29 g, 18.7 mmol) was slowly added. Upon completion of the addition of sodium nitrate, the mixture was brought to room temperature and stirred for 20 minutes. The intended product was confirmed by LC-MS. Methylene chloride (30 ml) was added to the solution and the solution was then washed with water (3×30 ml). The organic layer was dried over magnesium sulfate and then evaporated to provide the title compound (2.9 g, 73%). [M+H] calc'd for $C_{11}H_7BrN_4$, 274; found, 274.

Compound 4: 5-bromo-9H-pyrido[2,3-b]indole

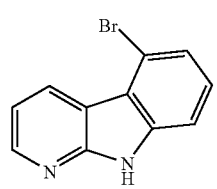

Compound 3 (2.8 g, 10.2 mmol) was dissolved in ortho-phosphoric acid (40 ml). The mixture was heated to 150° C. for 18 hours, and the intended product confirmed by LC-MS. The mixture was cooled to 0° C. and the acid neutralized with concentrated NaOH. Extraction with methylene chloride afforded a mixture of Compounds 4 and 4', which was then purified by HPLC to provide Compound 4 (180 mg, 9%). $^1$H NMR (400 MHz, CD$_3$OD) δ 9.16 (d, J=7.8 Hz 1 H) 8.48 (s, 1 H) 7.62 (d, J=7.8 Hz 1 H) 7.52 (d, J=6.8 Hz 1 H) 7.44 (m, 2 H). [M+H] calc'd for $C_{17}H_{12}N_2$, 245; found 245.

Compound 5: 5-phenyl-9H-pyrido[2,3-b]indole

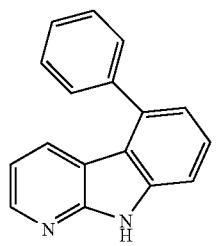

Compound 4 (20 mg, 0.081 mmol) was mixed with phenylboronic acid (20 mg, 0.16 mmol) and Tetrakis Pd(0) catalyst (19 mg, 0.016 mmol) in a solution comprising dioxane (3 ml) and a saturated K$_2$CO$_3$ solution (1 ml). The mixture was heated in a microwave reactor at 150° C. for 20 minutes. Purification by HPLC afforded the title compound as a tan solid (4 mg, 22%). $^1$H NMR (400 MHz, CD$_3$OD) δ 8.39 (s, 1 H) 8.10 (d, J=7.84 Hz, 1 H) 7.67 (m, 2 H), 7.60 (m, 5 H) 7.27 (m, 2 H). [M+H] calc'd for $C_{17}H_{12}N_2$, 245; found 245.

Compound 6:
5-bromo-8-methyl-9H-pyrido[2,3-b]indole

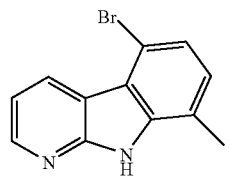

The title compound was synthesized using an analogous procedure to that described in Scheme 1 except that 5-bromo-2-methylaniline was used as the starting material. $^1$H NMR (400 MHz, CD$_3$OD) δ 9.16 (d, J=7.8 Hz 1 H) 8.48 (s, 1 H) 7.62 (d, J=7.8 Hz 1 H) 7.52 (d, J=6.8 Hz 1 H) 7.44 (m, 2 H) 2.27 (s, 3 H). [M+H] calc'd for $C_{17}H_{12}N_2$, 257; found 257.

Compound 7:
5-bromo-3,8-dimethyl-9H-pyrido[2,3-b]indole

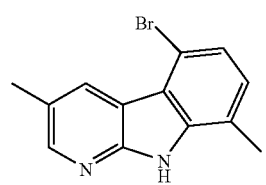

The title compound was synthesized using an analogous procedure to that described in Scheme 1. $^1$H NMR (400 MHz, DMSO-d$_6$) δ ppm 2.48 (s, 3 H) 2.52 (s, 3 H) 7.18 (d, J=7.83 Hz, 1 H) 7.31 (d, J=7.83 Hz, 1 H) 8.37 (d, J=2.02 Hz, 1 H) 8.65 (d, J=1.77 Hz, 1 H) 12.01 (s, 1 H). [M+H] calc'd for C$_{13}$H$_{11}$BrN$_2$ 275, 277; found, 275.2, 277.2.

Compound 8: 5-(3-(methylsulfonyl)phenyl)-9H-pyrido[2,3-b]indole

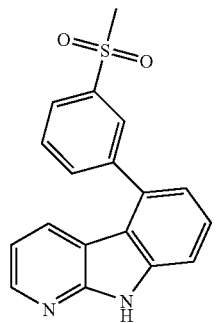

The title compound was synthesized using an analogous procedure to that described in the preparation of compound 7 using 3-methylsulfonylphenylboronic acid. Yield=27%. $^1$H NMR (400 MHz, DMSO) δ 8.40 (d, J=0.076 Hz, 1 H) 8.15 (s, 1 H) 8.08 (d, J=8.56 Hz, 1 H) 8.02 (d, J=7.6 Hz, 1 H) 7.87 (t, 1 H) 7.68 (d, J=6.04, 1 H) 7.59 (m, 2 H) 7.19 (d, J=8.6 Hz, 1 H) 7.03 (m, 1 H) 3.32 (s, 3 H). [M+H] calc'd for C$_{18}$H$_{14}$N$_2$O$_2$S, 323; found, 323.

Compound 9:
5-(3-(ethylsulfonyl)phenyl)-9H-pyrido[2,3-b]indole

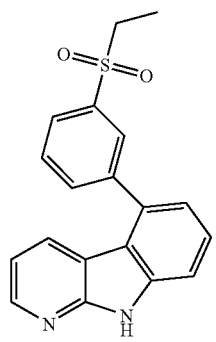

The title compound was synthesized using an analogous procedure to that described in the preparation of compound 7 using 3-ethylsulfonylphenylboronic acid. Yield=48%. $^1$H NMR (400 MHz, CH$_3$OD) δ 8.46 (s, 1 H) 8.15 (s, 1 H) 8.09 (t, 2 H) 8.02 (d, J=7.84 Hz, 1 H) 7.88 (t, 1 H) 7.74 (m, 2 H) 7.35 (m, 2 H) 3.30 (s, 2 H) 1.28 (m, 3 H). [M+H] calc'd for C$_{19}$H$_{16}$N$_2$O$_2$S, 337; found 337.

Compound 10: N-(3-(9H-pyrido[2,3-b]indol-5-yl)phenyl)ethanesulfonamide

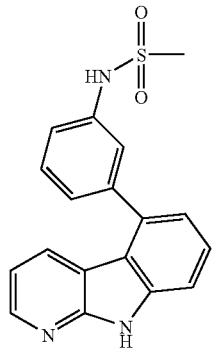

The title compound was synthesized using an analogous procedure to that described in the preparation of compound 7 using 3-(methanesulfonylamino) phenylboronic acid. Yield=63%. $^1$H NMR (400 MHz, CH$_3$OD) δ 8.42 (s, 1 H) 8.28 (d, J=7.6 Hz 1 H) 7.70 (d, J=4.04 Hz 2 H) 7.57 (t, 1 H) 7.52 (s, 1 H) 7.41 (m, 1 H) 7.32 (d, J=7.32 Hz 1 H) 7.24 (d, J=8.6 Hz, 1 H) 7.31 (t, 1 H) 2.93 (s, 3 H). [M+H] calc'd for C$_{18}$H$_{15}$N$_3$O$_2$S, 338; found 338.

Compound 11: 5-m-tolyl-9H-pyrido[2,3-b]indole

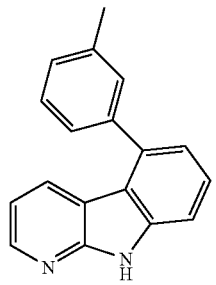

The title compound was synthesized using an analogous procedure to that described in the preparation of compound 7 using m-tolylboronic acid. Yield=18%. $^1$H NMR (400 MHz, CH$_3$OD) δ 8.35 (s, 1 H) 8.01 (d, J=7.84 Hz 1 H) 7.62 (d, J=4.8 Hz 2 H) 7.45 (t, 1 H) 7.39 (m, 3 H) 7.21 (t, 1 H) 7.16 (m, 1 H) 3.30 (m, 3 H). [M+H] calc'd for C$_{18}$H$_{14}$N$_2$ 259; found 259.

Compound 12: N-cyclopropyl-3-(9H-pyrido[2,3-b]indol-5-yl)benzenesulfonamide

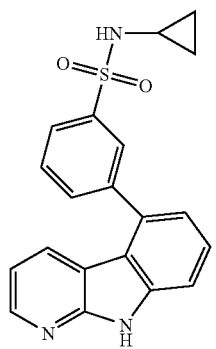

The title compound was synthesized using an analogous procedure to that described in the preparation of compound 7 using 3-(N-cyclopropylsulfamoyl)phenylboronic. Yield=19%. $^1$H NMR (400 MHz, CH$_3$OD) δ 8.38 (s, 1 H) 8.12 (s, 1 H) 8.06 (d, J=7.84 Hz 1 H) 7.97 (d, J=8.6 Hz 1 H) 7.90 (m, 1 H) 7.81 (t, 1 H) 7.68 (m, 2 H) 7.28 (d, J=6.32 Hz 1 H) 7.18 (t, 1 H) 2.26 (m, 1 H) 1.28 (s, 2 H) 0.53 (m, 2 H). [M+H] calc'd for C$_{20}$H$_{17}$N$_3$O$_2$S 364; found 364.

Compound 13:
5-(3-methoxyphenyl)-9H-pyrido[2,3-b]indole

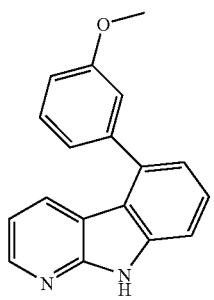

The title compound was synthesized using an analogous procedure to that described in the preparation of compound 7 using 3-methoxyphenylboronic acid. Yield=42%. $^1$H NMR (400 MHz, CH$_3$OD) δ 8.02 (d, J=7.08 1 H) 7.60 (m, 2 H) 7.48 (t, 1 H) 7.22 (m, 1 H) 7.17 (d, J=8.08 Hz 2 H) 7.12 (m, 1 H) 7.10 (d, J=9.08 Hz 1 H) 3.85 (s, 3 H). [M+H] calc'd for C$_{18}$H$_{14}$N$_2$O 275; found, 275.

Compound 14: 5-(3,8-dimethyl-9H-pyrido[2,3-b]indol-5-yl)-2-methoxy-N-methylbenzenesulfonamide

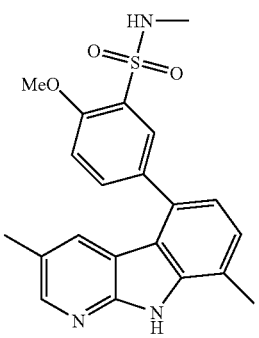

The title compound was synthesized using an analogous procedure to that described in the preparation of compound 7. $^1$H NMR (400 MHz, DMSO-d$_6$) δ ppm 2.27 (s, 3 H) 2.53 (d, J=5.05 Hz, 3 H) 2.59 (s, 3 H) 4.01 (s, 3 H) 7.00 (d, J=7.33 Hz, 1 H) 7.18 (q, J=5.05 Hz, 1 H) 7.32 (d, J=7.58 Hz, 1 H) 7.43 (d, J=8.59 Hz, 1 H) 7.58 (d, J=1.52 Hz, 1 H) 7.82 (dd, J=8.34, 2.27 Hz, 1 H) 7.92 (d, J=2.27 Hz, 1 H) 8.27 (d, J=2.02 Hz, 1 H) 11.91 (s, 1 H). [M+H] calc'd for C$_{21}$H$_{21}$N$_3$O$_3$S 396; found, 396.3.

Compound 15: 3-(3,8-dimethyl-9H-pyrido[2,3-b]indol-5-yl)-N-methylbenzenesulfonamide

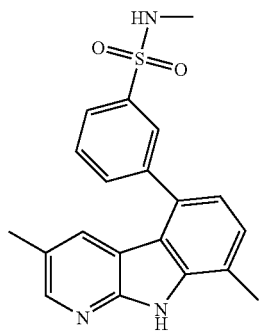

The title compound was synthesized using an analogous procedure to that described in the preparation of compound 7. $^1$H NMR (400 MHz, DMSO-d$_6$) δ ppm 2.26 (s, 3 H) 2.48 (s, 3 H) 2.61 (s, 3 H) 7.06 (d, J=7.33 Hz, 1 H) 7.36 (d, J=6.82 Hz, 1 H) 7.51 (d, J=2.02 Hz, 1 H) 7.60 (q, J=5.05 Hz, 1 H) 7.82 (d, J=7.58 Hz, 1 H) 7.86-7.93 (m, 2 H) 8.00 (t, J=1.52 Hz, 1 H) 8.27 (d, J=2.02 Hz, 1 H) 11.96 (s, 1 H). [M+H] calc'd for C$_{20}$H$_{19}$N$_3$O$_2$S 366; found, 366.3.

Compound 16: 3-(3,8-dimethyl-9H-pyrido[2,3-b]indol-5-yl)-N,N-dimethylbenzenesulfonamide

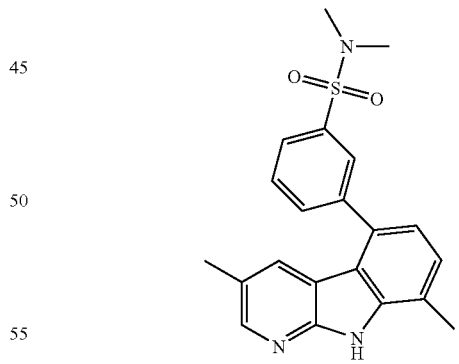

The title compound was synthesized using an analogous procedure to that described in the preparation of compound 7. $^1$H NMR (400 MHz, DMSO-d$_6$) δ ppm 2.27 (s, 3 H) 2.62 (s, 3 H) 2.70 (s, 6 H) 7.08 (d, J=7.58 Hz, 1 H) 7.38 (d, J=7.33 Hz, 1 H) 7.51 (s, 1 H) 7.86-7.96 (m, 4 H) 8.31 (br. s., 1 H) 12.11 (s, 1 H). [M+H] calc'd for C$_{21}$H$_{21}$N$_3$O$_2$S 380; found 380.3.

Compound 17: 5-(3-(ethylsulfonyl)phenyl)-8-methyl-9H-pyrido[2,3-b]indole

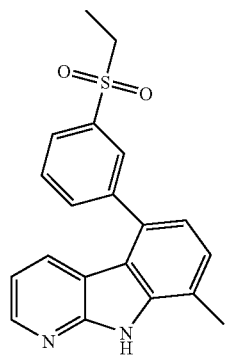

The title compound was synthesized using an analogous procedure to that described in the preparation of compound 7. Yield=51%. $^1$H NMR (400 MHz, CH$_3$OD) δ 8.41 (s, 1 H) 8.13 (s, 1 H) 8.08 (d, J=8.08 Hz 1 H) 7.99 (t, 2 H) 7.86 (t, 1 H) 7.52 (d, J=8.08 Hz 1 H) 7.23 (m, 2 H) 2.70 (s, 3 H) 1.28 (m, 3 H). [M+H] calc'd for C$_{20}$H$_{18}$N$_2$O$_2$S 351; found, 351.

Example 18

5-(3-(ethylsulfonyl)phenyl)-3,8-dimethyl-9H-pyrido[2,3-b]indole

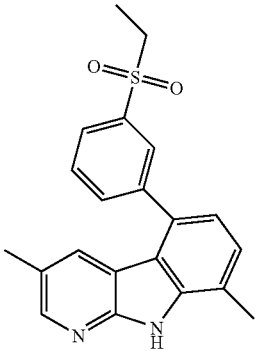

The title compound was synthesized using an analogous procedure to that described in the preparation of compound 7. $^1$H NMR (400 MHz, CH$_3$OD) δ 8.27 (s, 1 H) 8.17 (t, J=3.83 Hz, 1 H) 8.07 (d, J=7.83 Hz 1 H) 7.98 (d, J=8.08 Hz, 1 H) 7.92 (s, 1 H) 7.86 (t, J=7.71 Hz, 1 H) 7.51 (d, J=8.59 Hz, 1 H) 7.23 (d, J=7.58 Hz, 1 H) 2.68 (s, 3 H) 2.38 (s, 3 H) 1.28 (t, J=7.33 Hz, 3 H). [M+H] calc'd for C$_{21}$H$_{20}$N$_2$O$_2$S; found, 364.

Compound 19: N-(3-(3,8-dimethyl-9H-pyrido[2,3-b]indol-5-yl)phenyl)propionamide

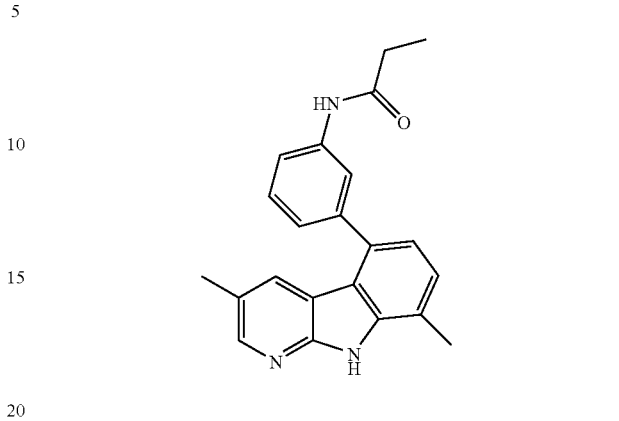

The title compound was synthesized using an analogous procedure to that described in the preparation of compound 7. $^1$H NMR (400 MHz, MeOD) δ ppm 1.20 (t, J=7.58 Hz, 3 H) 1.93 (s, 2 H) 2.41 (s, 3 H) 2.68 (s, 3 H) 7.21 (d, J=7.58 Hz, 1 H) 7.31 (dt, J=7.07, 1.64 Hz, 1 H) 7.50 (d, J=8.84 Hz, 1 H) 7.47 (s, 1 H) 7.54 (dd, J=3.41, 1.64 Hz, 2 H) 7.97 (t, J=1.64 Hz, 1 H) 8.29 (br. s., 1 H) [M+H] calc'd for C$_{22}$H$_{21}$N$_3$O, 344; found, 344.

Compound 20

N-cyclopropyl-3-(3,8-dimethyl-9H-pyrido[2,3-b]indol-5-yl)benzamide

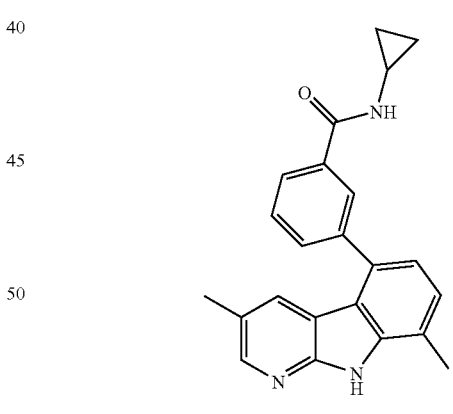

The title compound was synthesized using an analogous procedure to that described in the preparation of compound 7. $^1$H NMR (400 MHz, MeOD) δ ppm 0.65 (dd, J=3.79, 2.02 Hz, 2 H) 0.82 (dd, J=7.20, 2.15 Hz, 2 H) 1.93 (s, 1 H) 2.37 (s, 3 H) 2.68 (s, 3 H) 2.88 (td, J=7.20, 4.04 Hz, 1 H) 7.22 (d, J=7.58 Hz, 1 H) 7.50 (dd, J=7.58, 0.76 Hz, 1 H) 7.53-7.59 (m, 1 H) 7.66 (t, J=7.71 Hz, 1 H) 7.77 (dt, J=7.64, 1.48 Hz, 1 H) 7.91 (d, J=0.76 Hz, 1 H) 7.95 (dt, J=7.64, 0.98 Hz, 1 H) 8.05 (t, J=1.77 Hz, 1 H) 8.24 (br. s., 1 H) [M+H] calc'd for C$_{23}$H$_{21}$N$_3$O, 355; found, 355.

Compound 21: N-(4-(9H-pyrido[2,3-b]indol-5-ylthio)phenyl)acetamide

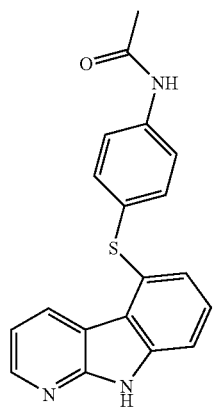

The title compound was synthesized by mixing Compound 4 (25 mg, 0.10 mmol, benzenethiol (21 µl, 0.20 mmol), caesium carbonate (33 mg, 0.10 mmol) and [1,1'-Bis(diphenylphosphino)-ferrocene]dichloropalladium(II) (7 mg, 0.01 mmol) in DMF and heating at 170° C. for 20 minutes in a microwave reactor. The product was purified by HPLC (Yield=42%). $^1$H NMR (400 MHz, CH$_3$OD) δ 8.97 (d, J=7.84 1 H) 8.41 (d, J=5.56 Hz 1 H) 7.55 (m, 3 H) 7.50 (t, 1 H) 7.40 (q, 1 H) 7.36 (d, J=8.84 Hz 2 H) 7.12 (d, J=7.36 Hz 1 H) 2.11 (s, 3 H). [M+H] calc'd for C$_{19}$H$_{15}$N$_3$OS 334; found, 334.

Compound 22: 5-(benzylthio)-9H-pyrido[2,3-b]indole

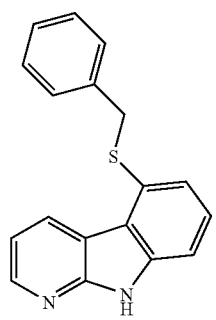

The title compound was synthesized using an analogous procedure to that described in the preparation of compound 21. Yield=39%. $^1$H NMR (400 MHz, CH$_3$OD) δ 8.40 (s, 1 H) 8.15 (s, 1 H) 8.10 (d, J=7.84 Hz 1 H) 8.01 (d, J=8.56 Hz 2 H) 7.87 (t, 1 H) 7.71 (t, 2 H) 7.32 (d, J=8.36 Hz 1 H) 7.24 (q, 1 H) 1.28 (t, 2 H). [M+H] calc'd for C$_{18}$H$_{14}$N$_2$S 291; found, 291.

Compound 23: 5-(phenylthio)-9H-pyrido[2,3-b]indole

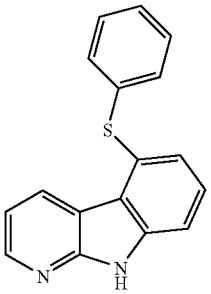

The title compound was synthesized using an analogous procedure to that described in the preparation of compound 21. Yield=18%. $^1$H NMR (400 MHz, CH$_3$OD) δ 8.66 (d, J=7.84 Hz 1 H) 8.33 (s, 1 H) 7.56 (d, J=8.32 Hz 1 H) 7.45 (t, 1 H) 7.25 (m, 3 H) 7.21 (d, J=7.93 Hz 2 H) 7.14 (q, 1 H) 1.30 (t, 2 H). [M+H] calc'd for C$_{17}$H$_{12}$N$_2$S 277; found, 277.

Compound 24: 5-(benzylthio)-8-methyl-9H-pyrido[2,3-b]indole

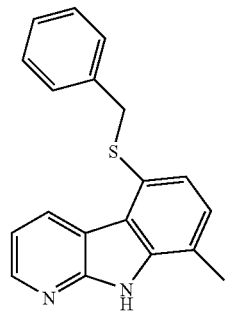

The title compound was synthesized using an analogous procedure to that described in the preparation of compound 21. Yield=14%. $^1$H NMR (400 MHz, CH$_3$OD) δ 8.88 (d, J=7.84 Hz 1 H) 8.34 (s, 1 H) 7.74 (s, 1 H) 7.19 (m, 6 H) 7.11 (d, J=7.56 Hz 1 H) 6.89 (s, 1 H) 2.28 (s, 3 H). [M+H] calc'd for C$_{19}$H$_{16}$N$_2$S 305; found, 305.

Compound 25: 5-(benzylthio)-3,8-dimethyl-9H-pyrido[2,3-b]indole

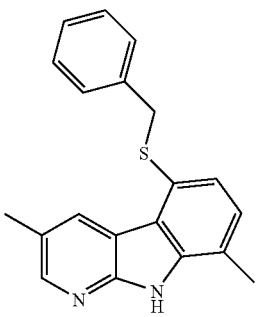

The title compound was synthesized using an analogous procedure to that described in the preparation of compound 21. $^1$H NMR (400 MHz, MeOD) δ ppm 2.54 (s, 4 H) 2.59 (s, 3 H) 4.27 (s, 2 H) 7.18 (dd, J=7.45, 1.39 Hz, 1 H) 7.16-7.19 (m, 1 H) 7.21 (dd, J=6.19, 1.39 Hz, 2 H) 7.25 (d, J=9.09 Hz, 1 H) 7.24 (s, 1 H) 7.87 (s, 1 H) 8.22 (br. s., 1 H) 8.91 (d, J=1.52 Hz, 1 H). [M+H] calc'd for $C_{20}H_{18}N_2S$, 319; found, 319.

Compound 26: 1-Benzyl-3-(3-bromo-5-methyl-pyridin-2-ylamino)-5-chloro-1H-pyrazin-2-one

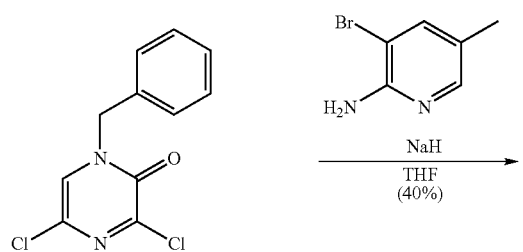

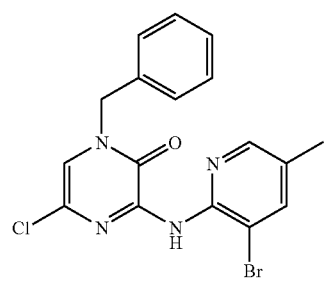

26

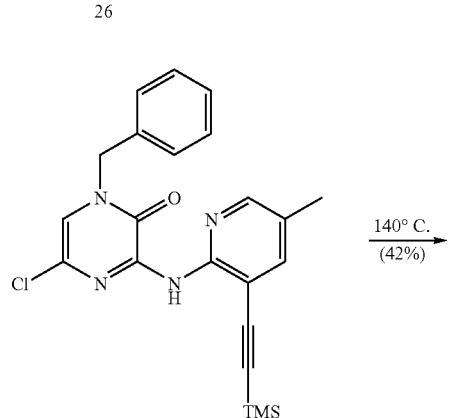

27

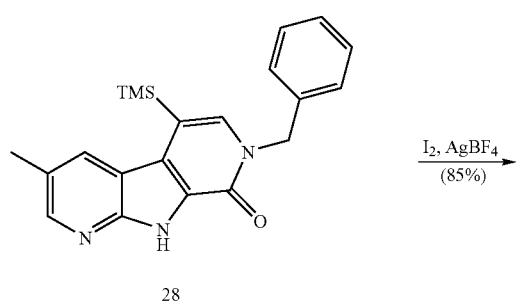

28

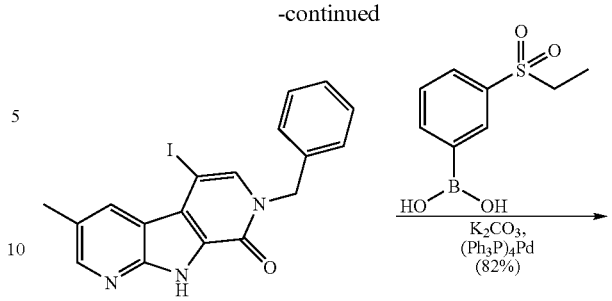

29

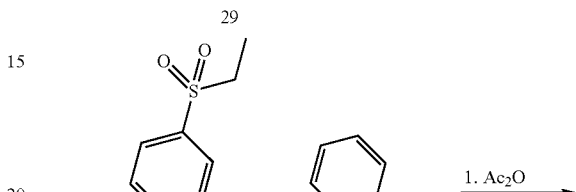

30

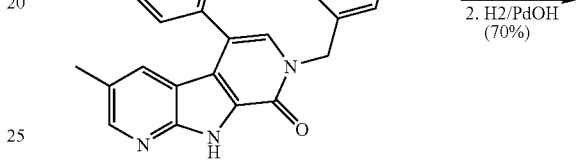

31

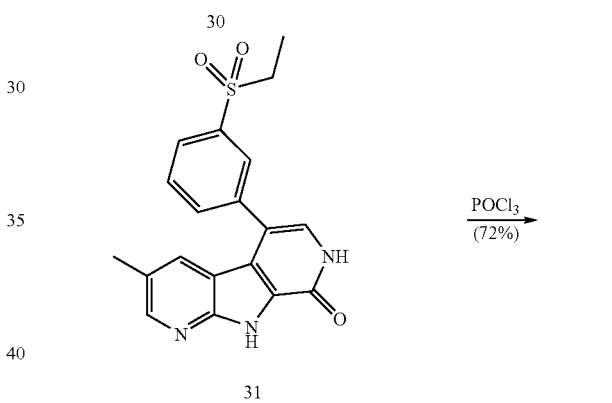

32

2-Amino-3-bromo-5-methyl-pyridine (1.0 g, 5.35 mmol) was added to a solution of sodium hydride (60%, 321 mg, 8.0 mmol) in dry THF (20 mL) at r.t. under nitrogen. After 30 minutes, 1-benzyl-3,5-dichloro-2(1H)-pyrazinone (see Vekemans, et. al., *J. Heterocyclic Chem.*, 20, (1983), 919-923) (1.36 g, 5.35 mmol) was added, and the reaction stirred at 72° C. for 4 h. The solution was concentrated in vacuo and the residue was dissolved in $CH_2Cl_2$. Organics were washed with $H_2O$ and brine, dried ($MgSO_4$), and concentrated. Purification by silica gel chromatography (2:1:1 hexanes/EtOAc/

CH$_2$Cl$_2$) gave 860 mg (40%) of the title compound as a pale yellow solid. $^1$H NMR (400 MHz, DMSO-d$_6$): δ 9.51 (s, 1H), 8.27 (s, 1H), 8.00 (s, 1H), 7.43 (s, 1H), 7.29-7.39 (m, 5H), 5.07 (s, 2H), 2.29 (s, 3H). MS (ES) [m+H] calc'd for C$_{17}$H$_{14}$BrClN$_4$O, 405, 407; found 405, 407.

Compound 27: 1-Benzyl-5-chloro-3-(5-methyl-3-trimethylsilanylethynyl-pyridin-2-ylamino)-1H-pyrazin-2-one

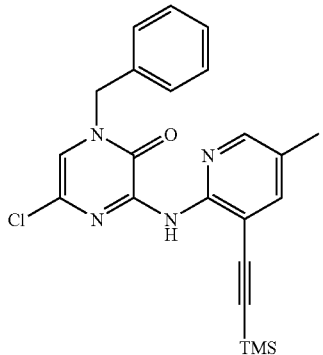

Compound 26 (2.0 g, 4.9 mmol), triphenylphosphine (52 mg, 0.2 mmol), dichlorobis(triphenylphosphine)palladium (II) (173 mg, 0.25 mmol), triethylamine (1.03 mL, 7.4 mmol), and TMS-acetylene (1.05 mL, 7.4 mmol) were combined in THF (20 mL) at r.t. under nitrogen. After stirring 10 min, copper iodide (40 mg) was added, and the reaction stirred for 8 h. The reaction was diluted with EtOAc, washed with brine, dried (MgSO$_4$), and concentrated in vacuo. Purification by silica gel chromatography (2:1:2 hexanes/EtOAc/CH$_2$Cl$_2$) gave 2.0 g (96%) of the title compound as a pale yellow solid. MS (ES) [m+H] calc'd for C$_{21}$H$_{23}$ClN$_4$OSi, 423, 425; found 423, 425.

Compound 28: 7-Benzyl-3-methyl-5-trimethylsilanyl-7,9-dihydro-dipyrido[2,3-b;4',3'-d]pyrrol-8-one

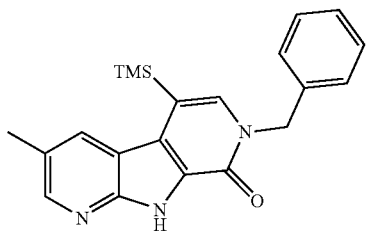

Compound 27 (3.5 g, 8.29 mmol) was dissolved in bromobenzene (150 mL). The solution was heated at 140° C. under N$_2$ and monitored by LC every hour. The reaction was complete after 7 hours. The solution was evaporated and purified by flash chromatography (3% MeOH/CH$_2$Cl$_2$) to give 2.5 g (83%) of intended product as a tan solid. $^1$H NMR (400 MHz, CDCl$_3$): δ 8.22 (s, 1H), 7.27-7.39 (m, 6H), 5.40 (s, 2H), 2.57 (s, 3H). MS (ES) [m+H] calc'd for C$_{21}$H$_{23}$N$_3$OSi, 362; found 362.

Compound 29: 7-Benzyl-5-iodo-3-methyl-7,9-dihydro-dipyrido[2,3-b;4',3'-d]pyrrol-8-one

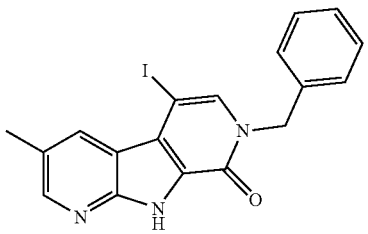

Compound 28 (2.5 g, 6.93 mmol) dissolved in dry ethanol (200 mL) and stirred under nitrogen at 0° C. Silver tetrafluoroborate (1.45 g, 7.45 mmol) was added, and the solution stirred for 10 minutes. Iodine (1.85 g, 7.3 mmol) was added, and the reaction stirred 1 h as a precipitate began to form. After evaporation of the solvent, the solid was taken up in CH$_2$Cl$_2$ and washed with water, which caused an insoluble precipitate to form. The solid was collected by filtration and washed with ethyl acetate to leave 2.5 g (87%) of intended product. $^1$H NMR (400 MHz, DMSO-d$_6$): δ 12.74 (s, 1H), 8.69 (s, 1H), 8.42 (s, 1H), 7.90 (s, 1H), 7.25-7.36 (m, 5H), 5.26 (s, 2H), 2.46 (s, 3H). MS (ES) [m+H] calc'd for C$_{18}$H$_{14}$IN$_3$O, 416; found 416.

Compound 30: 7-Benzyl-5-(3-ethanesulfonyl-phenyl)-3-methyl-7,9-dihydro-dipyrido[2,3-b;4',3'-d]pyrrol-8-one

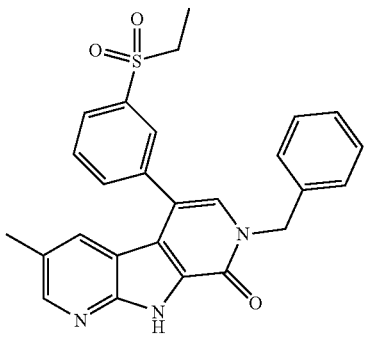

Compound 29 (2.82 g, 6.79 mmol), 3-ethansulfonylboronic acid (1.59 g, 7.46 mmol), and saturated potassium carbonate solution (2 mL) were combined in dioxane (8 mL) in a flask purged with nitrogen. Tetrakis(triphenylphosphine)palladium(0) (1.57 g, 1.36 mmol) was added, and the reaction stirred at 150° C. in the microwave for 20 min. The solution was filtered, and the solid was washed with water and then CH$_2$Cl$_2$ to leave 1.7 g (55%) of the title compound as an off-white solid. (A small amount of product remained in the organic layer.) $^1$H NMR (400 MHz, DMSO-d$_6$): δ 12.73 (s, 1H), 8.36 (s, 1H), 8.09 (s, 1H), 7.92-7.99 (m, 2H), 7.83 (t, 1H, J=7.6 Hz), 7.68 (s, 1H), 7.54 (s, 1H), 7.23-7.40 (m, 5H), 5.34 (s, 2H), 3.39 (q, 2H, J=7.2 Hz), 2.27 (s, 3H), 1.15 (t, 3H, J=7.2 Hz). MS (ES) [m+H] calc'd for C$_{26}$H$_{23}$N$_3$O$_3$S, 458; found 458.

Compound 31: 5-(3-Ethanesulfonyl-phenyl)-3-methyl-7,9-dihydro-dipyrido[2,3-b;4',3'-d]pyrrol-8-one

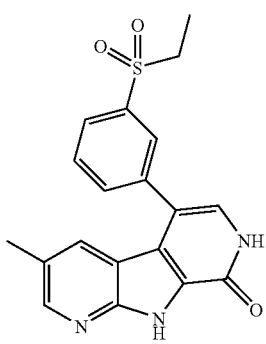

Compound 30 (24 mg, 0.053 mmol) was stirred in acetic anhydride (2 mL) at reflux overnight. Solvent was removed in vacuo, and the residue was subjected to hydrogenation with 20% palladium hydroxide on carbon (25 mg) in acetic acid (5 mL) under a balloon of hydrogen at 36° C. for 4 h. The reaction was filtered through Celite and concentrated in vacuo. Purification by prep HPLC gave 4.6 mg (24%) of the title compound as a white solid. $^1$H NMR (400 MHz, MeOD-d$_4$/CDCl$_3$): δ 8.41 (br s, 1H), 8.12 (s, 1H), 8.02 (d, 1H, J=8.0 Hz), 7.92 (d, 1H, J=8.0 Hz), 7.80 (t, 1H, J=8.0 Hz), 7.67 (s, 1H), 7.30 (br s, 1H), 7.14 (s, 1H), 3.25 (q, 2H, J=7.2 Hz), 2.35 (s, 3H), 1.31 (t, 3H, J=7.2 Hz). MS (ES) [m+H] calc'd for C$_{19}$H$_{17}$N$_3$O$_3$S, 368; found 368.

Compound 32: 8-Chloro-5-(3-ethanesulfonyl-phenyl)-3-methyl-9H-dipyrido[2,3-b;4',3'-d]pyrrole

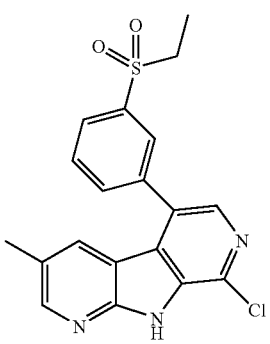

Compound 31 (50 mg, 0.136 mmol) stirred in POCl$_3$ (2 mL) with dimethylaniline (0.1 mL) at 108° C. under nitrogen for 16 h. The solution was concentrated and dissolved in CH$_2$Cl$_2$. Ice and saturated NaHCO$_3$ solution were added, and organics were extracted (2×) with CH$_2$Cl$_2$, dried (MgSO$_4$), and concentrated in vacuo. Purification by silica gel chromatography (3% MeOH/CH$_2$Cl$_2$) gave 36 mg (69%) of the title compound as a pale yellow solid. $^1$H NMR (400 MHz, MeOD-d$_4$/CDCl$_3$): δ 8.46 (s, 1H), 8.22 (s, 1H), 8.14 (s, 1H), 8.11 (d, 1H, J=8.0 Hz), 8.01 (d, 1H, J=8.0 Hz), 7.89 (t, 1H, J=8.0 Hz), 7.84 (s, 1H), 7.76 (s, 1H), 3.28 (q, 2H, J=7.2 Hz), 2.38 (s, 3H), 1.31 (t, 3H, J=7.2 Hz). MS (ES) [m+H] calc'd for C$_{19}$H$_{16}$ClN$_3$O$_2$S, 3.86, 388; found 386, 388.

Alternatively, Compound 32 was synthesized from Compound 33 as follows.

Compound 33: 2-(4-methoxybenzylamino)acetonitrile-HCl

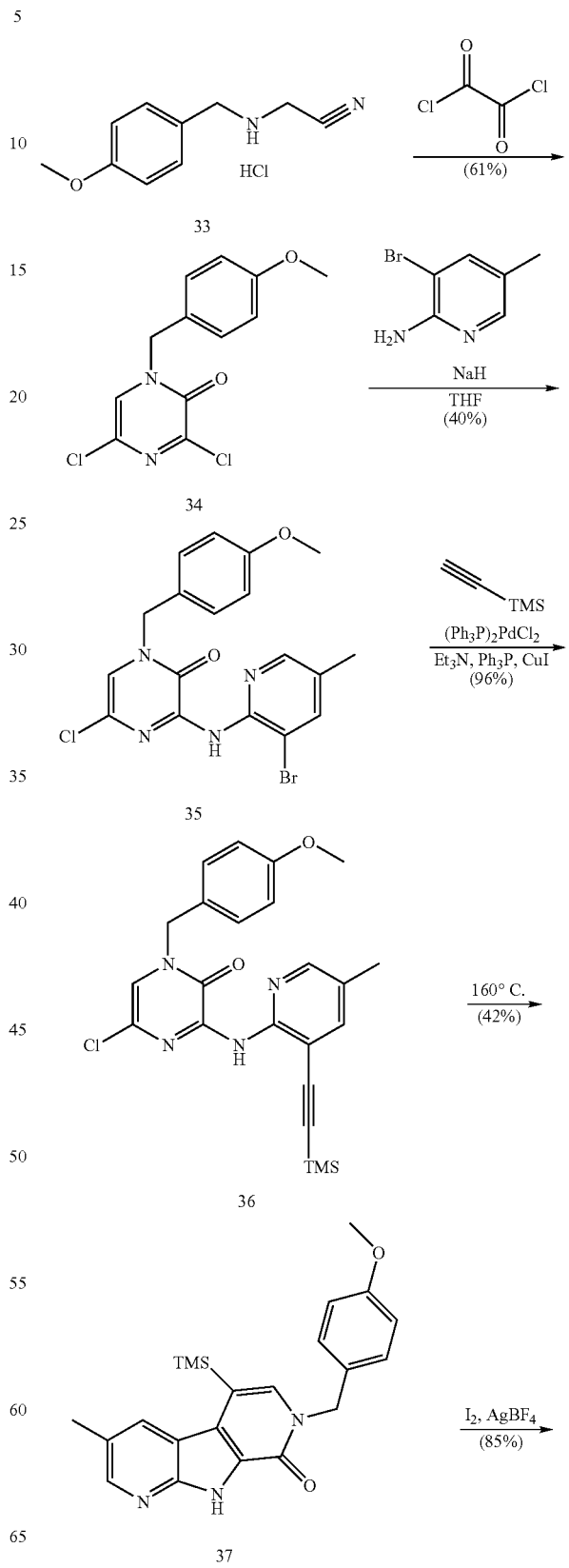

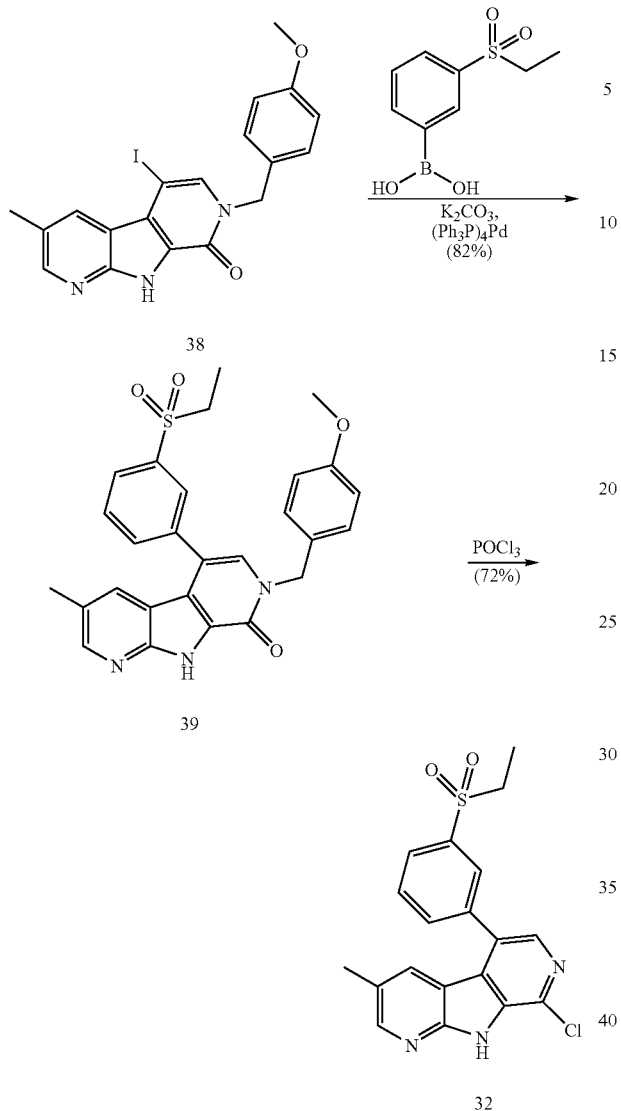

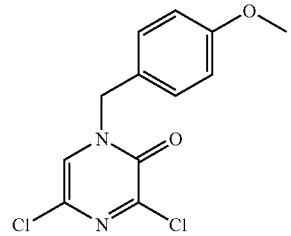

J=5.56 Hz, 2 H) 3.73 (s, 3 H) 6.88 (d, J=8.59 Hz, 2 H) 7.23 (d, J=8.59 Hz, 2 H). ESI-MS: m/z 177.3 (M+H)$^+$.

Compound 34:
3,5-dichloro-1-(4-methoxybenzyl)pyrazin-2(1H)-one

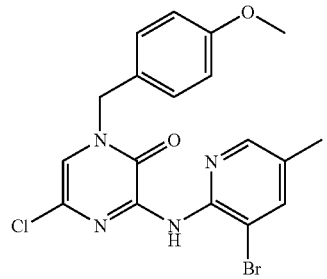

To the 1 L round bottom flask containing 2-(4-methoxybenzylamino) acetonitrile-HCl (55.6 g, 261.43 mmol), under N$_2$, was added chlorobenzene (414 mL) followed by oxalyl chloride (99.54 g, 784.27 mmol). After stirring at ambient temperature for 30 minutes, triethylamine-HCl (179.9 g, 1307.13 mmol) was added and mixture was allowed to stir overnight at ambient temperature. The reaction mixture was concentrated in vacuo, and the crude was taken up with DCM (700 mL) and transferred to a 2 L separatory funnel. The organic layer was then washed with water (2×600 mL) and brine (2×500 mL). After drying with MgSO$_4$, the organic layer was filtered and concentrated to a clear, brown oil. Chromatography on silica gel with ethyl acetate/DCM (3/97) afforded a light yellow crystalline solid (63.1 g, 84.6% yield). The desired product was verified by $^1$H-NMR and analytical LCMS and carried on as is. $^1$H NMR (400 MHz, DMSO-d$_6$) δ ppm 3.73 (s, 3 H) 5.02 (s, 2 H) 6.92 (d, J=8.59 Hz, 2 H) 7.36 (d, J=8.59 Hz, 2 H) 8.24 (s, 1 H). ESI-MS: m/z 307.2 (M+Na)$^+$.

Compound 35: 3-(3-bromo-5-methylpyridin-2-ylamino)-5-chloro-1-(4-methoxybenzyl)pyrazin-2(1H)-one In an appropriate round bottom flask, 4-Methoxyybenzylamine (50.57 g, 368.66 mmol) was first suspended in anhydrous THF (800 mL), treated with triethylamine (39.05 g, 385.89 mmol) and cooled in an ice/water bath. Bromoacetonitrile (41.33 g, 344.54 mmol) was added last and the reaction mixture was slowly warmed to ambient temperature, under N$_2$. After 3 h, the reaction was concentrated in vacuo, diluted with ethyl acetate (500 mL) and transferred to a 1 L separatory funnel containing 400 mL of water. After separating the two layers, the aqueous layer was washed with additional ethyl acetate (2×100 mL). The combined organic layers were washed with saturated brine (2×300 mL), dried with MgSO$_4$, filtered and concentrated in vacuo to afford a cloudy white solid. Chromatography on silica gel with ethyl acetate/hexanes (2/3) afforded clear oil (46.4 g=76% yield, confirmed by $^1$H-NMR and analytical LCMS). After suspending the clear oil in diethyl ether, 1.4 eqv of 4N HCl/dioxane (92.1 mL, 368.63 mmol) was added and the mixture was concentrated in vacuo affording a white solid that was carried on as is without further purification. $^1$H NMR (400 MHz, DMSO-d$_6$) δ ppm 2.94 (t, J=6.06 Hz, 1 H) 3.54 (d, J=7.07 Hz, 2 H) 3.67 (d, An oven dried, 2 L, three necked round bottom flask was charged with NaH (60% dispersion in oil, 11.9 g, 298.11 mmol), suspended in anhydrous tetrahydrofuran (500 mL) and cooled in an ice bath. To the cooled mixture, was added the solution of 2-amino-3-bromo-5-methyl pyridine (39.4 g, 210.433 mmol, 150 mL of anhydrous THF). The ice bath was removed and the reaction was allowed to warm to room temperature over a 1 h period. Via addition funnel, the solution of 3,5-dichloro-1-(4-methoxybenzyl)pyrazin-2(1H)-one (50.0 g, 175.36 mmol, 150 mL anhydrous tetrahydrofuran) was added in a rapid, drop-wise fashion, attached a reflux condenser and stirred in an oil bath heated at 72° C. (exothermic reaction occurred upon heating). After 3 h, the flask was removed from the oil bath, cooled to room temperature, quenched with isopropanol (15 mL) and BHT (0.075 g), and concentrated in vacuo to a dark crude. Chromatography on silica gel plug with ethyl acetate/DCM (3/97) afforded the desired product as a light tan solid. The mix fractions were combined, concentrated and the desired product was purified by recrystallization in ethyl acetate/diethyl ether and isolated by vacuum filtration. The two solid pools were combined (43 g, 56% yield) and verified by $^1$H-NMR and analytical LCMS. $^1$H NMR (400 MHz, DMSO-$d_6$) δ ppm 2.30 (s, 3 H) 3.74 (s, 3 H) 5.00 (s, 2 H) 6.93 (d, J=8.84 Hz, 2 H) 7.39 (s, 2 H) 7.42 (s, 1 H) 8.01 (s, 1 H) 8.28 (s, 1 H) 9.50 (s, 1 H). ESI-MS: m/z 437.2 (M+H)$^+$.

Compound 36: 5-chloro-1-(4-methoxybenzyl)-3-(5-methyl-3-((trimethylsilyl)ethynyl)pyridin-2-ylamino)pyrazin-2(1 H)-one

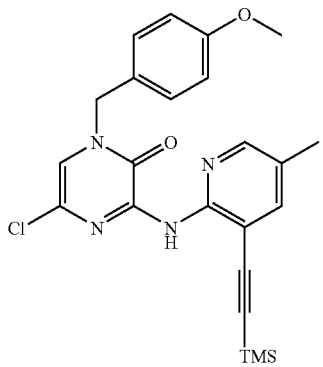

In a 1 L round bottom combined 3-(3-bromo-5-methylpyridin-2-ylamino)-5-chloro-1-(4-methoxybenzyl)pyrazin-2 (1H)-one (51.90 g, 119.12 mmol), triphenylphosphine (1.56 g, 5.96 mmol), (Ph$_3$P)PdCl$_2$ (4.18 g, 5.96 mmol) and suspended in anhydrous THF (450 mL). Triethylamine (18.08 g, 178.68 mmol) and trimethylsilyl acetylene (35.10 g, 357.36 mmol) were added next and mixture was stirred at ambient temperature, under N$_2$ for 10 minutes. Copper iodide (catalytic) was added last and reaction was stirred at ambient temperature. Reaction was monitored by analytical LCMS at one hour intervals and CuI was added until reaction is complete. The completed reaction was concentrated in vacuo, taken up with ethyl acetate (700 mL) and brine (300 mL) and filtered off undissolved solids before taking on to extraction. The organic layer was washed with additional brine (4×300 mL), dried with MgSO$_4$, filtered and concentrated in vacuo. Chromatography on silica gel plug with ethyl acetate/hexanes (1/9), two attempts, afforded the desired product (43.36 g. 81% yield). $^1$H NMR (400 MHz, DMSO-$d_6$) δ ppm 0.11 (s, 9 H) 2.26 (s, 3 H) 3.73 (s, 3 H) 5.00 (s, 2 H) 6.91 (d, J=8.59 Hz, 2 H) 7.38 (d, J=8.59 Hz, 2 H) 7.45 (s, 1 H) 7.74 (d, J=2.27 Hz, 1 H) 8.25 (d, J=2.27 Hz, 1 H) 9.51 (s, 1 H). ESI-MS: m/z 453.3 (M+H)$^+$.

Compound 37: 7-(4-methoxybenzyl)-3-methyl-5-trimethylsilyl-7,9-dihydro-8H-pyrido[4',3':4,5]pyrrolo[2,3-b]pyridin-8-one

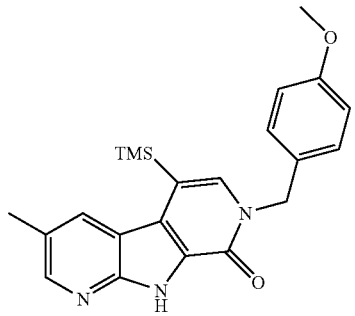

In a 2 L round bottom flask, 5-chloro-1-(4-methoxybenzyl)-3-(5-methyl-3-((trimethylsilyl)ethynyl)pyridin-2-ylamino)pyrazin-2(1H)-one (35.2 g, 77.85 mmol) was taken up with anhydrous toluene (880 mL), attached a reflux condenser and transferred to an oil bath that was heated to 130° C. The reaction was stirred in the oil bath for 94 h and concentrated in vacuo to afford a brown solid. The crude was suspended in ethyl acetate (200 mL) and heated to a mild boil. The product (pale yellow powder, 27.4 g, 89% yield) was collected by filtration, washed with additional ethyl acetate, diethyl ether and dried under high vacuum. $^1$H NMR (400 MHz, CHLOROFORM-d) δ ppm 0.43 (s, 9 H) 2.56 (s, 3 H) 3.80 (s, 3 H) 5.30 (s, 2 H) 6.89 (d, J=8.59 Hz, 2 H) 7.11 (s, 1 H) 7.35 (d, J=8.84 Hz, 2 H) 8.22 (s, 1 H) 8.52 (d, J=1.52 Hz, 1 H). ESI-MS: m/z 392.4 (M+H)$^+$.

Compound 38: 5-iodo-7-(4-methoxybenzyl)-3-methyl-7,9-dihydro-8H-pyrido [4',3':4,5]pyrrolo[2,3-b]pyridin-8-one

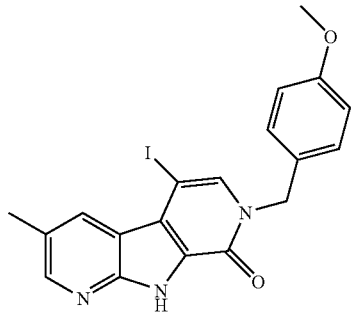

In a 2 L round bottom flask, 7-(4-methoxybenzyl)-3-methyl-5-trimethylsilyl-7,9-dihydro-8H-pyrido[4',3':4,5]pyrrolo[2,3-b]pyridin-8-one (18.6 g, 47.505 mmol) was suspended in ethanol (1 L) and DCM (150 mL), then cooled in an ice bath. To the cooled mixture was added silver tetrafluoroborate (AgBF$_4$, 10.17 g, 52.255 mmol) and after 15 minutes of stirring, iodine (18.08 g, 71.257 mmol) was added. The reaction was stirred at 0° C. for one hour followed by five hours at ambient temperature. The crude yellow solid was collected by filtration, suspended in 10% wt Na$_2$S$_2$O$_3$ (700 mL) and stirred for 1 h. The solid was collected by filtration and again washed with 10% wt Na$_2$S$_2$O$_3$. The product (light yellow solid) was collected by filtration, washed with water and diethyl ether and dried under high vacuum. The material was taken forward without further purification. $^1$H NMR (400 MHz, CHLOROFORM-d) δ ppm 2.59 (s, 3 H) 3.81 (s, 3 H 5.26 (s, 2 H) 6.90 (d, J=8.84 Hz, 2 H) 7.34 (d, J=8.59 Hz, 2 H) 7.44 (s, 1 H) 8.51 (s, 1 H) 8.92 (s, 1 H). ESI-MS: m/z 446.2 (M+H)⁺.

Compound 39: 5-[3-(ethylsulfonyl)phenyl]-7-(4-methoxybenzyl)-3-methyl-7,9-dihydro-8H-pyrido[4',3':4,5]pyrrolo [2,3-b]pyridin-8-one

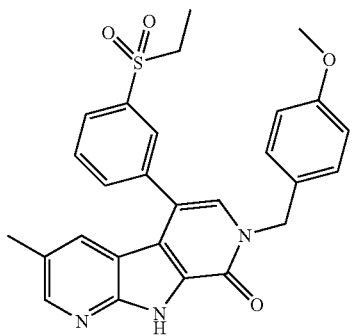

In an appropriate microwave reaction vessel was placed, 5-iodo-7-(4-methoxybenzyl)-3-methyl-7,9-dihydro-8H-pyrido[4',3':4,5]pyrrolo [2,3-b]pyridin-8-one (8.0 g, 17.967 mmol), 3-(ethylsulfonyl)phenyl boronic acid (4.62 g, 21.562 mmol), and Tetrakis(triphenylphosphine)Pd(0) (6.23 g, 5.390 mmol). The solids were then suspended in a dioxane/saturated K₂CO₃ solution (40.0 mL, 4/1) and the mixture was heated in a large scale CEM microwave for 20 minutes at 150° C. The reaction mixture was diluted with DCM (400 mL), then filtered off undissolved solids. The organic layer was washed with brine (300 mL), dried with MgSO₄, filtered and concentrated in vacuo affording an orange solid. The crude solid was washed with a hot ethyl acetate/hexanes solution (400 ml, 1/1) followed by a hot ethanol/DCM solution (400 mL, 4/1). The product was isolated by filtration, washed with ether and dried under vacuum affording an off-white solid. (6.83 g, 78%) ¹H NMR (400 MHz, CHLOROFORM-d) δ ppm 1.36 (t, J=7.45 Hz, 3 H) 2.44 (s, 3 H) 3.20 (q, J=7.33 Hz, 2 H) 3.80 (s, 3 H) 5.37 (s, 2 H) 6.90 (d, J=8.59 Hz, 2 H) 7.16 (s, 1 H) 7.37 (d, J=8.59 Hz, 3 H) 7.75 (t, J=7.71 Hz, 1 H) 7.78-7.87 (m, 2 H) 8.03 (d, J=7.58 Hz, 1 H) 8.12 (s, 1 H) 8.43 (s, 1 H). ESI-MS: m/z 488.3 (M+H)⁺.

Compound 32: 8-chloro-5-[3-(ethylsulfonyl)phenyl]-3-methyl-9H-pyrido[4',3':4,5]pyrrolo[2,3-b]pyridine

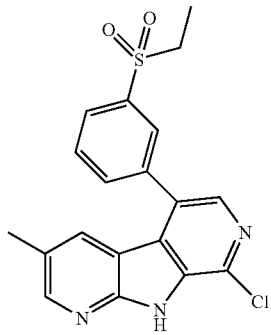

A 500 mL round bottom flask equipped with an N₂ inlet and reflux condenser was charged with 5-[3-(ethylsulfonyl)phenyl]-7-(4-methoxybenzyl)-3-methyl-7,9-dihydro-8H-pyrido [4',3':4,5]pyrrolo[2,3-b]pyridin-8-one (19.3 g, 39.584 mmol), tetramethylammonium chloride (4.77 g, 43.542 mmol), and POCl₃ (249.5 g, 1626.905 mmol) at room temperature, transferred to an oil bath and heated at 100° C. The reaction was monitored by HPLC, and determined to be complete after 2 h. The mixture was allowed to cool to ambient temperature. A separate 3 neck, 3 L flask was fitted with a cold thermometer, and two addition funnels. To this flask was added a solution of 33% by weight aqueous K₃PO₄ (1500 mL), cooled in a dry ice/acetone bath, followed by the dropwise addition of the aryl chloride suspension. The internal temperature was kept between 5 to 20° C. and the pH was carefully monitored and maintained at 11.5 during the quench using a slow addition of 10M KOH when necessary. The suspension was allowed to stir for 10 min at 5° C. after the addition was complete, and at ambient temperature for 2 h. The crude product was extracted from the aqueous layer with DCM (5×500 mL), dried with MgSO₄, filtered and concentrated in vacuo to a total volume of about 500 mL. The solution was allowed to sit at ambient temperature overnight. The precipitate was collected by filtration, washed with additional DCM and dried, affording a light grey solid (9.79 g) which was confirmed by analytical LCMS and ¹H-NMR as the free base. The DCM mother liquor was concentrated and taken up with a methanol/DCM mixture (300 mL, 15/85). To the light green solution was slowly added 30 mL 4N HCl in dioxane and the mixture were stirred for one hour at ambient temperature. 1200 mL of MTBE was slowly added and the resultant suspension was filtered. Chromatography on silica gel plug with methanol/DCM (3/97) afforded a yellow solid. The solid was washed with warm methanol (30 mL) and the resulting product was collected by filtration and washed with additional diethyl ether, affording an additional 1.7 g of the product as a free base. (9.79+1.7=11.49 g, 75% yield). ¹H NMR (400 MHz, DMSO-d₆) δ ppm 1.18 (t, J=7.33 Hz, 3 H) 2.32 (s, 3 H) 3.44 (q, J=7.33 Hz, 2 H) 7.70 (d, J=1.26 Hz, 1 H) 7.93 (t, J=7.71 Hz, 1 H) 8.04-8.15 (m, 2 H) 8.21 (d, J=10.61 Hz, 2 H) 8.53 (d, J=1.52 Hz, 1 H) 12.78 (br. s., 1 H). ESI-MS: m/z 386.3 (M+H)⁺.

Compound 40: N'-[5-(3-Ethanesulfonyl-phenyl)-3-methyl-9H-dipyrido[2,3-b;4',3'-d]pyrrol-8-yl]-N,N-dimethyl-propane-1,3-diamine

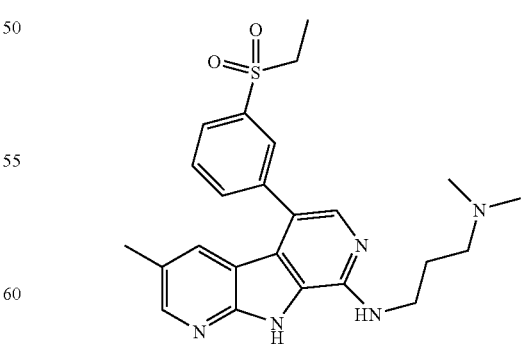

Compound 32 (16 mg, 0.041 mmol) was heated with 3-dimethylamino-1-propylamine (1 mL) at 206° C. in the microwave for 30 min. Purification by prep-HPLC gave 10.2 (55%) of the title compound as a pale yellow solid. ¹H NMR (400 MHz, MeOD-$d_4$): δ 8.65 (br s, 1H), 8.17 (s, 1H), 8.12 (d, 1H, J=7.6 Hz), 7.98 (d, 1H, J=7.6 Hz), 7.91 (t, 1H, J=7.6 Hz), 7.67 (s, 1H), 7.66 (s, 1H), 3.80 (t, 2H, J=6.8 Hz), 3.28-3.43 (m, 4H), 2.96 (s, 6H), 2.29-2.38 (m, 5H), 1.28 (t, 3H, J=7.2 Hz). MS (ES) [m+H] calc'd for $C_{24}H_{29}N_5O_2S$, 452; found 452.

Compound 41: N'-[5-(3-Ethanesulfonyl-phenyl)-3-methyl-9H-dipyrido[2,3-b;4',3'-d]pyrrol-8-yl]-N,N-dimethyl-ethane-1,2-diamine

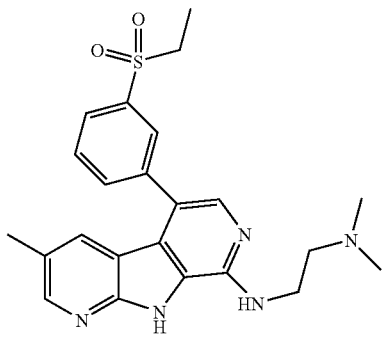

The title compound was prepared in 77% yield using N,N-dimethylethylenediamine in the procedure outlined for the preparation of compound 40. $^1$H NMR (400 MHz, MeOD-$d_4$): δ 8.53 (br s, 1H), 8.15 (s, 1H), 8.12 (d, 1H, J=7.6 Hz), 7.97 (d, 1H, J=7.6 Hz), 7.88 (t, 1H, J=7.6 Hz), 7.73 (s, 1H), 7.72 (s, 1H), 4.11 (t, 2H, J=5.6 Hz), 3.66 (t, 2H, J=5.6 Hz), 3.32 (q, 2H, J=7.2 Hz), 3.06 (s, 6H), 2.37 (s, 3H), 1.29 (t, 3H, J=7.6 Hz). MS (ES) [m+H] calc'd for $C_{23}H_{27}N_5O_2S$, 438; found 438.

Compound 42: [5-(3-Ethanesulfonyl-phenyl)-3-methyl-9H-dipyrido[2,3-b;4',3'-d]pyrrol-8-yl]-(3-morpholin-4-yl-propyl)-amine

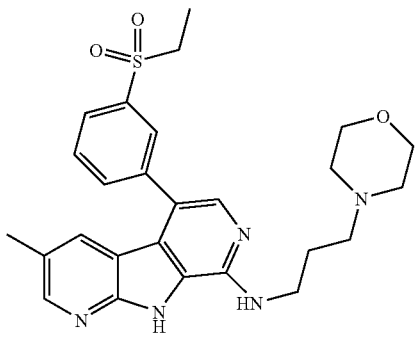

The title compound was prepared in 81% yield using 1-(3-aminopropyl)-morpholine in the procedure outlined for the preparation of compound 40. $^1$H NMR (400 MHz, MeOD-$d_4$): δ 8.52 (s, 1H), 8.18 (s, 1H), 8.14 (d, 1H, J=7.6 Hz), 7.99 (d, 1H, J=7.6 Hz), 7.66 (s, 1H), 7.65 (s, 1H), 3.82-4.03 (m, 4H), 3.81 (t, 2H, J=6.4 Hz), 3.20-3.55 (m, 8H), 2.32-2.40 (m, 5H), 1.29 (t, 3H, J=7.2 Hz). MS (ES) [m+H] calc'd for $C_{26}H_{31}N_5O_3S$, 494; found 494.

Compound 43: [5-(3-Ethanesulfonyl-phenyl)-3-methyl-9H-dipyrido[2,3-b;4',3'-d]pyrrol-8-yl]-(1-methyl-piperidin-4-yl)-amine

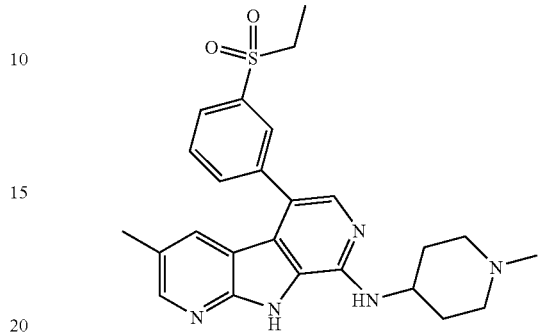

The title compound was prepared in 31% yield using 4-amino-1-methyl-piperidine in the procedure outlined for the preparation of compound 40. $^1$H NMR (400 MHz, MeOD-$d_4$): δ 8.53 (br s, 1H), 8.19 (s, 1H), 8.13 (d, 1H, J=7.6 Hz), 8.01 (d, 1H, J=7.6 Hz), 7.90 (t, 1H, J=7.6 Hz), 7.72 (s, 1H), 7.67 (s, 1H), 4.23-4.31 (m, 1H), 3.69-3.77 (m, 2H), 3.20-3.38 (m, 4H), 2.97 (s, 3H), 2.46-2.54 (m, 2H), 2.36 (s, 3H), 2.01-2.15 (m, 2H), 1.29 (t, 3H, J=7.2 Hz). MS (ES) [m+H] calc'd for $C_{25}H_{29}N_5O_2S$, 464; found 464.

Compound 44: 2-[5-(3-Ethanesulfonyl-phenyl)-3-methyl-9H-dipyrido[2,3-b;4',3'-d]pyrrol-8-ylamino]-ethanol

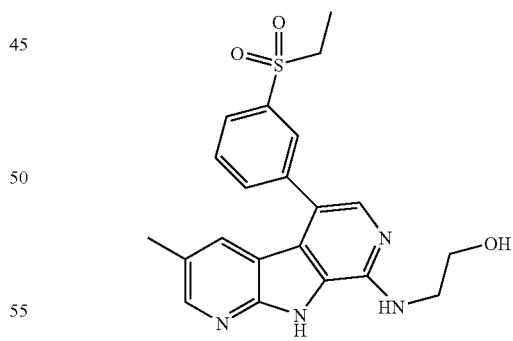

The title compound was prepared in 88% yield using ethanolamine in the procedure outlined for the preparation of compound 40. $^1$H NMR (400 MHz, MeOD-$d_4$): δ 8.51 (s, 1H), 8.20 (s, 1H), 8.13 (d, 1H, J=7.6 Hz), 8.00 (d, 1H, J=7.6 Hz), 7.90 (t, 1H, J=7.6 Hz), 7.64 (s, 1H), 7.63 (s, 1H), 3.99 (t, 2H, J=4.8 Hz), 3.82 (t, 2H, J=4.8 Hz), 3.33 (q, 2H, J=7.2 Hz), 2.35 (s, 3H), 1.29 (t, 3H, J=7.2 Hz). MS (ES) [m+H] calc'd for $C_{21}H_{22}N_4O_3S$, 411; found 411.

Compound 45: [5-(3-Ethanesulfonyl-phenyl)-3-methyl-9H-dipyrido[2,3-b;4',3'-d]pyrrol-8-yl]-(1-methyl-piperidin-4-ylmethyl)-amine

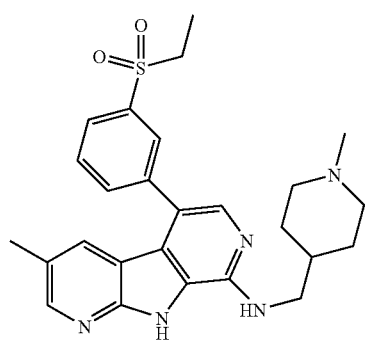

The title compound was prepared in 55% yield using 4-aminomethyl-1-methyl-piperidine in the procedure outlined for the preparation of compound 40. $^1$H NMR (400 MHz, MeOD-d$_4$): δ 8.55 (s, 1H), 8.22 (s, 1H), 8.16 (d, 1H, J=7.6 Hz), 8.03 (d, 1H, J=7.6 Hz), 7.94 (t, 1H, J=7.6 Hz), 7.69 (s, 1H), 7.68 (s, 1H), 3.60-3.70 (m, 4H), 3.33 (q, 2H, J=7.2 Hz), 3.03-3.12 (m, 2H), 2.92 (s, 3H), 2.39 (s, 3H), 2.21-2.30 (m, 3H), 1.69-1.79 (m, 2H), 1.31 (t, 3H, J=7.2 Hz). MS (ES) [m+H] calc'd for C$_{26}$H$_{31}$N$_5$O$_2$S, 478; found 478.

Compound 46: 5-(3-Ethanesulfonyl-phenyl)-3,8-dimethyl-9H-dipyrido[2,3-b;4',3'-d]pyrrole

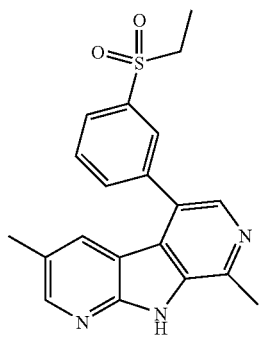

Trimethylaluminum (2.0 M, 70 μL, 0.14 mmol) was added to a solution of compound 32 (9.0 mg, 0.023 mmol) and tetrakis(triphenylphosphine)palladium (0) (13.3 mg, 0.012 mmol) in dioxane (1 mL) under nitrogen in sealed tube. The reaction was heated at 120° C. in the microwave for 20 min and then concentrated in vacuo. Purification by prep-HPLC gave 8.2 mg (96%) of the title compound as a pale yellow solid. $^1$H NMR (400 MHz, MeOD-d$_4$): δ 8.68 (s, 1H), 8.43 (s, 1H), 8.32 (s, 1H), 8.21 (d, 1H, J=7.6 Hz), 8.11 (d, 1H, J=7.6 Hz), 7.97 (t, 1H, J=7.6 Hz), 7.81 (s, 1H), 3.34 (q, 2H, J=7.2 Hz), 3.14 (s, 3H), 2.39 (s, 3H), 1.29 (t, 3H, J=7.2 Hz). MS (ES) [m+H] calc'd for C$_{20}$H$_{19}$N$_3$O$_2$S, 366; found 366.

Compound 47: 5-(3-Ethanesulfonyl-phenyl)-8-ethyl-3-methyl-9H-dipyrido[2,3-b;4',3'-d]pyrrole

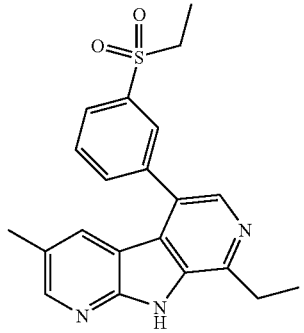

The title compound was prepared in 68% yield using triethylaluminum in the procedure outlined for the preparation of compound 46. $^1$H NMR (400 MHz, MeOD-d$_4$): δ 8.69 (s, 1H), 8.42 (s, 1H), 8.31 (s, 1H), 8.21 (d, 1H, J=7.6 Hz), 8.12 (d, 1H, J=7.6 Hz), 7.98 (t, 1H, J=7.6 Hz), 7.80 (s, 1H), 3.51 (q, 2H, J=7.6 Hz), 3.33 (q, 2H, J=7.2 Hz), 2.39 (s, 3H), 1.57 (t, 3H, J=7.6 Hz), 1.29 (t, 3H, J=7.2 Hz). MS (ES) [m+H] calc'd for C$_{21}$H$_{21}$N$_3$O$_2$S, 380; found 380.

Compound 48: 5-(3-Ethanesulfonyl-phenyl)-3-methyl-9H-dipyrido[2,3-b;4',3'-d]pyrrole-8-carbonitrile

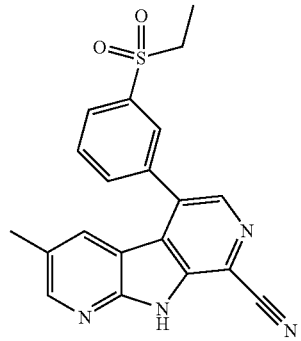

Zinc cyanide (5.0 mg, 0.037 mmol) was added to a solution of compound 32 (12.0 mg, 0.031 mmol) and tetrakis(triphenylphosphine)palladium(0) (11 mg, 0.009 mmol) in DMF (1 mL) under nitrogen in sealed tube. The reaction was heated at 160° C. in the microwave for 30 min and then concentrated in vacuo. Purification by prep-HPLC gave 10 mg (86%) of the title compound as a pale yellow solid. $^1$H NMR (400 MHz, MeOD-d$_4$): δ 8.76 (br s, 1H), 8.48 (s, 1H), 8.26 (s, 1H), 8.16 (d, 1H, J=7.6 Hz), 8.02 (d, 1H, J=7.6 Hz), 7.91 (t, 1H, J=7.6 Hz), 7.81 (s, 1H), 3.29 (q, 2H, J=7.2 Hz), 2.40 (s, 3H), 1.35 (t, 3H, J=7.2 Hz). MS (ES) [m+H] calc'd for C$_{20}$H$_{16}$N$_4$O$_2$S, 377; found 377.

Compound 49: 5-(3-Ethanesulfonyl-phenyl)-3-methyl-9H-dipyrido[2,3-b;4',3'-d]pyrrole-8-carboxylic acid amide

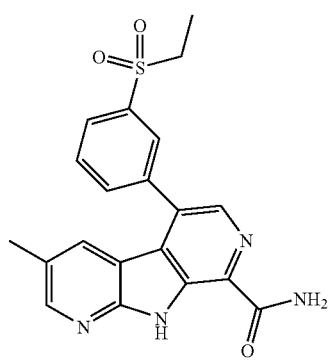

Compound 48 (10 mg, 0.027 mmol) stirred in THF (1 mL). A solution of KOH (25 mg, 0.44 mmol) in 30% $H_2O_2$ (0.5 mL) was added, and the reaction stirred for 3 h at r.t. Purification by prep-HPLC gave 8.2 mg (77%) of the title compound as an off-white solid. $^1$H NMR (400 MHz, MeOD-$d_4$): δ 8.49 (br s, 1H), 8.41 (s, 1H), 8.26 (s, 1H), 8.15 (d, 1H, J=7.6 Hz), 8.06 (d, 1H, J=7.6 Hz), 7.92 (t, 1H, J=7.6 Hz), 7.85 (s, 1H), 3.32 (q, 2H, J=7.2 Hz), 2.39 (s, 3H), 1.31 (t, 3H, J=7.6 Hz). MS (ES) [m+H] calc'd for $C_{20}H_{18}N_4O_3S$, 395; found 395.

Compound 50: 5-(3-Ethanesulfonyl-phenyl)-8-ethoxy-3-methyl-9H-dipyrido[2,3-b;4',3'-d]pyrrole

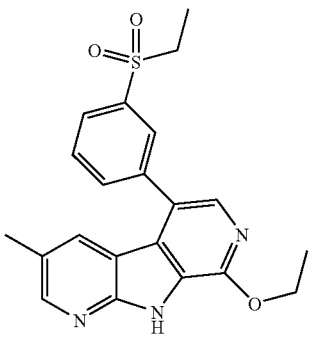

Compound 32 (4 mg, 0.01 mmol) was heated in a solution of sodium ethoxide in ethanol (21 wt. %, 0.5 mL) at 200° C. in the microwave for 30 min. Purification by prep-HPLC gave 3.2 mg (78%) of the title compound as a pale yellow solid. $^1$H NMR (400 MHz, MeOD-$d_4$): δ 8.47 (br s, 1H), 8.18 (s, 1H), 8.03 (d, 1H, J=7.6 Hz), 7.96 (d, 1H, J=7.6 Hz), 7.81-7.89 (m, 3H), 4.63 (q, 2H, J=7.2 Hz), 3.26 (q, 2H, J=7.2 Hz), 2.38 (s, 3H), 1.56 (t, 3H, J=7.6 Hz), 1.32 (t, 3H, J=7.6 Hz). MS (ES) [m+H] calc'd for $C_{21}H_{21}N_3O_3S$, 396; found 396.

Compound 51: {3-[5-(3-Ethanesulfonyl-phenyl)-3-methyl-9H-dipyrido[2,3-b;4',3'-d]pyrrol-8-yloxy]-propyl}-dimethyl-amine

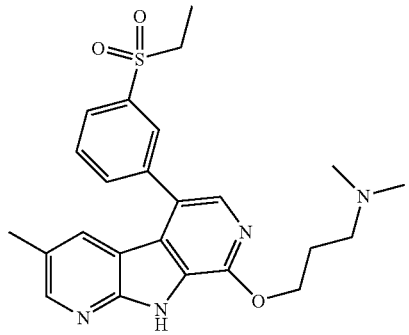

3-Dimethylamino-1-propanol (100 mL, 0.84 mmol) was added to a solution of sodium hydride (60%, 34 mg, 0.84 mmol) in dry dioxane (1 mL) under nitrogen. After stirring for 20 min, compound 32 (30 mg, 0.11 mmol) was added, and the reaction stirred at 180° C. in the microwave for 1 h. The solution was concentrated at purified by prep-HPLC to give 30 mg (69%) of the title compound as a pale yellow solid. $^1$H NMR (400 MHz, MeOD-$d_4$): δ 8.42 (br s, 1H), 8.24 (s, 1H), 8.10 (d, 1H, J=7.6 Hz), 8.03 (d, 1H, J=7.6 Hz), 7.90 (t, 1H, J=7.6 Hz), 7.89 (s, 1H), 7.82 (s, 1H), 4.75 (t, 2H, J=5.6 Hz), 3.46-3.54 (m, 2H), 3.34 (q, 2H, J=7.2 Hz), 3.01 (s, 6H), 2.38-2.46 (m, 2H), 2.38 (s, 3H), 1.32 (t, 3H, J=7.6 Hz). MS (ES) [m+H] calc'd for $C_{24}H_{28}N_4O_3S$, 453; found 453.

Compound 52: 2-[5-(3-Ethanesulfonyl-phenyl)-3-methyl-9H-dipyrido[2,3-b;4',3'-d]pyrrol-8-yloxy]-ethanol

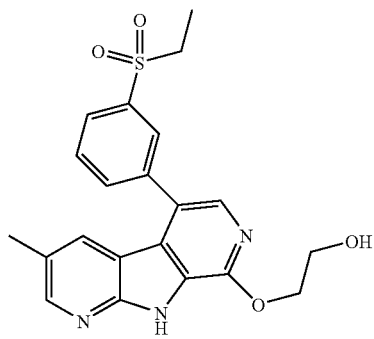

The title compound was prepared in 18% yield using ethylene glycol in the procedure outlined for the preparation of compound 51. $^1$H NMR (400 MHz, MeOD-$d_4$): δ 8.47 (br s, 1H), 8.19 (s, 1H), 8.02-8.09 (m, 2H), 7.97 (d, 1H, J=7.6 Hz), 7.94 (s, 1H), 7.88 (t, 1H, J=7.6 Hz), 4.68 (t, 2H, J=4.8 Hz), 4.05 (t, 2H, J=4.8 Hz), 3.31 (q, 2H, J=7.2 Hz), 2.41 (s, 3H), 1.29 (t, 3H, J=7.6 Hz). MS (ES) [m+H] calc'd for $C_{21}H_{21}N_3O_4S$, 412; found 412.

Compound 53: 5-(3-Ethanesulfonyl-phenyl)-3-methyl-8-(1-methyl-piperidin-4-ylmethoxy)-9H-dipyrido[2,3-b;4',3'-d]pyrrole

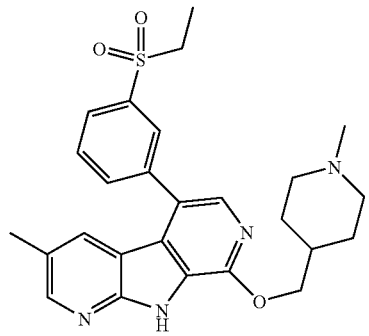

The title compound was prepared in 78% yield using 1-methyl-piperidine-3-methanol in the procedure outlined for the preparation of compound 51. $^1$H NMR (400 MHz, MeOD-d$_4$): δ 8.42 (br s, 1H), 8.20 (s, 1H), 8.06 (d, 1H, J=7.6 Hz), 7.99 (d, 1H, J=7.6 Hz), 7.81-7.89 (m, 3H), 4.51 (d, 2H, J=6.4 Hz), 3.57-3.63 (m, 2H), 3.32 (q, 2H, J=7.2 Hz), 3.02-3.13 (m, 2H), 2.90 (s, 3H), 2.36 (s, 3H), 2.24-2.32 (m, 3H), 1.61-1.73 (m, 2H), 1.29 (t, 3H, J=7.2 Hz). MS (ES) [m+H] calc'd for C$_{26}$H$_{30}$N$_4$O$_3$S, 479; found 479.

Compound 54: 3-[5-(3-Ethanesulfonyl-phenyl)-3-methyl-9H-dipyrido[2,3-b;4',3'-d]pyrrol-8-yloxy]-propan-1-ol

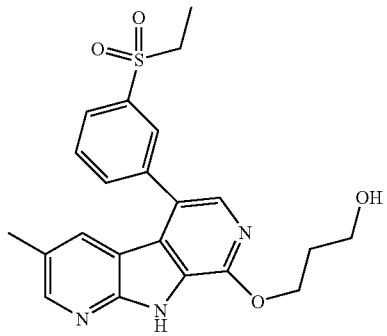

The title compound was prepared in 30% yield using 1,3-propanediol in the procedure outlined for the preparation of compound 51. $^1$H NMR (400 MHz, MeOD-d$_4$): δ 8.52 (br s, 1H), 8.23 (s, 1H), 8.09 (d, 1H, J=7.6 Hz), 7.96-8.03 (m, 2H), 7.93 (s, 1H), 7.89 (t, 1H, J=7.6 Hz), 4.75 (t, 2H, J=6.4 Hz), 3.88 (t, 2H, J=6.4 Hz), 3.34 (q, 2H, J=7.2 Hz), 2.41 (s, 3H), 2.16-2.22 (m, 2H), 1.32 (t, 3H, J=7.2 Hz). MS (ES) [m+H] calc'd for C$_{22}$H$_{23}$N$_3$O$_4$S, 426; found 426.

Compound 55: (R)-2-[5-(3-Ethanesulfonyl-phenyl)-3-methyl-9H-dipyrido[2,3-b;4',3'-d]pyrrol-8-yloxymethyl]-propane-1,3-diol

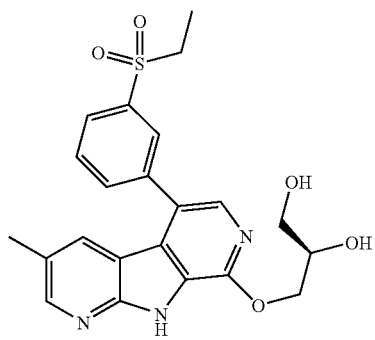

The title compound was prepared in 68% yield using (S)-2,2-dimethyl-1,3-dioxolane-4-methanol in the procedure outlined for the preparation of compound 51, followed by deprotection in TFA/H$_2$O/THF (1:1:5) for 3h. $^1$H NMR (400 MHz, DMSO-d$_6$): δ 12.37 (s, 1H), 8.42 (s, 1H), 8.14 (s, 1H), 7.96-8.04 (m, 2H), 7.80-7.88 (m, 2H), 7.69 (s, 1H), 4.40-4.90 (m, 4H), 3.91-3.99 (m, 1H), 3.52-3.60 (m, 2H), 3.55 (q, 2H, J=7.2 Hz), 2.29 (s, 3H), 1.18 (t, 3H, J=7.2 Hz). MS (ES) [m+H] calc'd for C$_{22}$H$_{23}$N$_3$O$_5$S, 442; found 442.

Compound 56: (S)-2-[5-(3-Ethanesulfonyl-phenyl)-3-methyl-9H-dipyrido[2,3-b;4',3'-d]pyrrol-8-yloxymethyl]-propane-1,3-diol

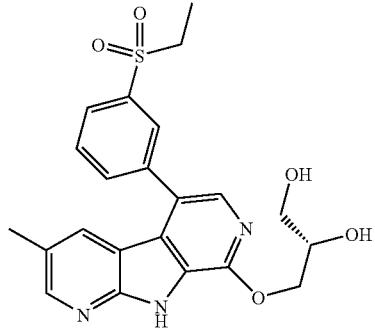

The title compound was prepared in 65% yield using (R)-2,2-dimethyl-1,3-dioxolane-4-methanol in the procedure outlined for the preparation of compound 51, followed by deprotection in TFA/H$_2$O/THF (1:1:5) for 3 h. $^1$H NMR (400 MHz, DMSO-d$_6$): δ 12.37 (s, 1H), 8.42 (s, 1H), 8.14 (s, 1H), 7.96-8.04 (m, 2H), 7.80-7.88 (m, 2H), 7.69 (s, 1H), 4.40-4.90 (m, 4H), 3.91-3.99 (m, 1H), 3.52-3.60 (m, 2H), 3.55 (q, 2H, J=7.2 Hz), 2.29 (s, 3H), 1.18 (t, 3H, J=7.2 Hz). MS (ES) [m+H] calc'd for C$_{22}$H$_{23}$N$_3$O$_5$S, 442; found 442.

Compound 57: 1-[5-(3-Ethanesulfonyl-phenyl)-3-methyl-9H-dipyrido[2,3-b;4',3'-d]pyrrol-8-yloxy]-2-methyl-propan-2-ol

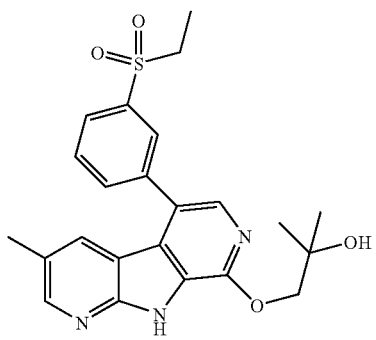

The title compound was prepared in 16% yield using 2-benzyloxy-2-methyl-1-propanol (see Fleming, et. al., *Can. J. Chem.*, 52, (1974), 888-892) in the procedure outlined for the preparation of compound 51, followed by benzyl deprotection by hydrogenation at 1 atm with 10% Pd/C in MeOH for 1 h. $^1$H NMR (400 MHz, DMSO-d$_6$): δ 12.40 (s, 1H), 8.45 (s, 1H), 8.15 (s, 1H), 7.98-8.05 (m, 2H), 7.82-7.89 (m, 2H), 7.71 (s, 1H), 4.27 (s, 2H), 3.40 (q, 2H, J=7.2 Hz), 2.31 (s, 3H), 1.30 (s, 6H), 1.17 (t, 3H, J=7.2 Hz). MS (ES) [m+H] calc'd for C$_{23}$H$_{25}$N$_3$O$_4$S, 440; found 440.

Compound 58: 5-(3-Ethanesulfonyl-phenyl)-3-methyl-8-phenoxy-9H-dipyrido[2,3-b;4',3'-d]pyrrole

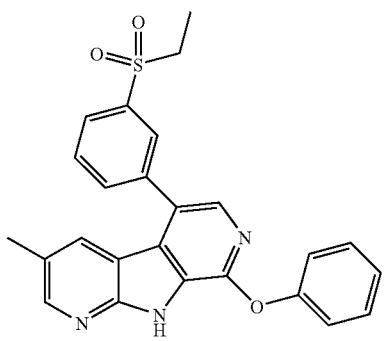

The title compound was prepared in 30% yield using phenol in the procedure outlined for the preparation of compound 51. $^1$H NMR (400 MHz, MeOD-d$_4$): δ 8.40 (br s, 1H), 8.18 (s, 1H), 8.03 (d, 1H, J=7.6 Hz), 7.92 (d, 1H, J=7.6 Hz), 7.77-7.85 (m, 3H), 7.40-7.48 (m, 2H), 7.21-7.29 (m, 3H), 3.21 (q, 2H, J=7.2 Hz), 2.38 (s, 3H), 1.31 (t, 3H, J=7.2 Hz). MS (ES) [m+H] calc'd for C$_{25}$H$_{21}$N$_3$O$_3$S, 444; found 444.

Compound 59: 5-(3-Ethanesulfonyl-phenyl)-3-methyl-8-(thiazol-5-ylmethoxy)-9H-dipyrido[2,3-b;4',3'-d]pyrrole

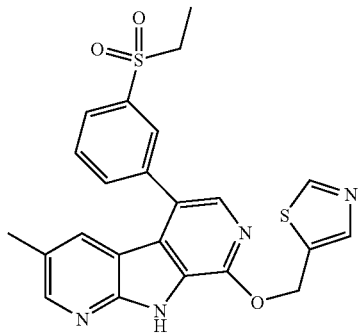

The title compound was prepared in 20% yield using thiazole-5-methanol in the procedure outlined for the preparation of compound 51. $^1$H NMR (400 MHz, MeOD-d$_4$): δ 8.98 (br s, 1H), 8.34 (br s, 1H), 8.19 (s, 1H), 7.96-8.07 (m, 3H), 7.90 (s, 1H), 7.80-7.87 (m, 2H), 5.91 (s, 2H), 3.26 (q, 2H, J=7.2 Hz), 2.35 (s, 3H), 1.32 (t, 3H, J=7.2 Hz). MS (ES) [m+H] calc'd for C$_{23}$H$_{20}$N$_4$O$_3$S$_2$, 465; found 465.

Compound 60: 5-(3-Ethanesulfonyl-phenyl)-8-(1-ethyl-piperidin-4-ylmethoxy)-3-methyl-9H-dipyrido[2,3-b;4',3'-d]pyrrole

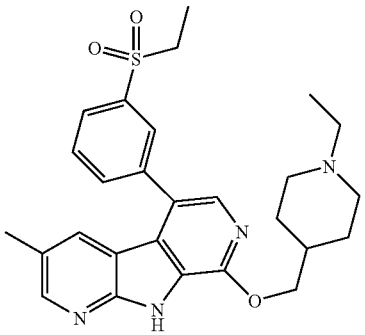

The title compound was prepared in 24% yield using 1-ethyl-piperidine-3-methanol in the procedure outlined for the preparation of compound 51. $^1$H NMR (400 MHz, MeOD-d$_4$): δ 8.49 (br s, 1H), 8.20 (s, 1H), 8.03-8.10 (m, 2H), 7.99 (d, 1H, J=7.6 Hz), 7.95 (s, 1H), 7.89 (t, 1H, J=7.6 Hz), 4.56 (d, 2H, J=6.4 Hz), 3.65-3.73 (m, 2H), 3.21-3.36 (m, 4H), 3.02-3.12 (m, 2H), 2.43 (s, 3H), 2.24-2.40 (m, 3H), 1.80-1.90 (m, 2H), 1.43 (t, 3H, J=7.2 Hz), 1.31 (t, 3H, J=7.2 Hz). MS (ES) [m+H] calc'd for C$_{27}$H$_{32}$N$_4$O$_3$S, 493; found 493.

Compound 61: (S)-1-[5-(3-Ethanesulfonyl-phenyl)-3-methyl-9H-dipyrido[2,3-b;4',3'-d]pyrrol-8-yloxy]-propan-2-ol

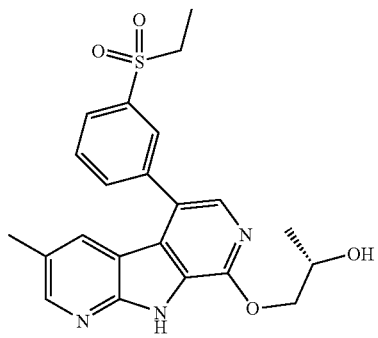

The title compound was prepared in 13% yield using (S)-2-benzyloxy-1-propanol (see Mislow, et. al., *J. Am. Chem. Soc.*, 82, (1960), 5512-5513) in the procedure outlined for the preparation of compound 51, followed by benzyl deprotection by hydrogenation at 1 atm with 10% Pd/C in MeOH for 1 h. $^1$H NMR (400 MHz, MeOD-d$_4$): δ 8.43 (br s, 1H), 8.21 (s, 1H), 8.09 (d, 1H, J=7.6 Hz), 8.02 (d, 1H, J=7.6 Hz), 7.82-7.90 (m, 3H), 4.29-4.59 (m, 3H), 3.36 (q, 2H, J=7.6 Hz), 2.39 (s, 3H), 1.38 (d, 3H, J=6.4 Hz), 1.30 (t, 3H, J=7.6 Hz). MS (ES) [m+H] calc'd for C$_{22}$H$_{23}$N$_3$O$_4$S, 426; found 426.

Compound 62: (R)-1-[5-(3-Ethanesulfonyl-phenyl)-3-methyl-9H-dipyrido[2,3-b;4',3'-d]pyrrol-8-yloxy]-propan-2-ol

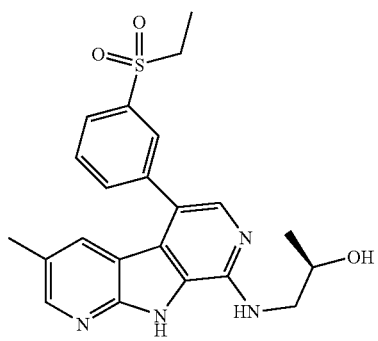

The title compound was prepared in 56% yield using (S)-2-benzyloxy-1-propanol (see Mulzer, et. al., *Tetrahedron Lett.*, 24, (1983), 2843-2846) in the procedure outlined for the preparation of compound 51, followed by benzyl deprotection by hydrogenation at 1 atm with 10% Pd/C in MeOH for 1 h. $^1$H NMR (400 MHz, DMSO-d$_6$): δ 12.40 (s, 1H), 8.44 (s, 1H), 8.16 (s, 1H), 8.00-8.07 (m, 2H), 7.85-7.92 (m, 2H), 7.71 (s, 1H), 4.30-4.40 (m, 2H), 4.08-4.15 (m, 1H), 3.43 (q, 2H, J=7.2 Hz), 2.31 (s, 3H), 1.26 (d, 3H, J=6.4 Hz), 1.18 (t, 3H, J=7.2 Hz). MS (ES) [m+H] calc'd for C$_{22}$H$_{23}$N$_3$O$_4$S, 426; found 426.

Compound 63: L-Valine-2-[5-(3-ethanesulfonyl-phenyl)-3-methyl-9H-dipyrido[2,3-b;4',3'-d]pyrrol-8-yloxy]-ethyl ester

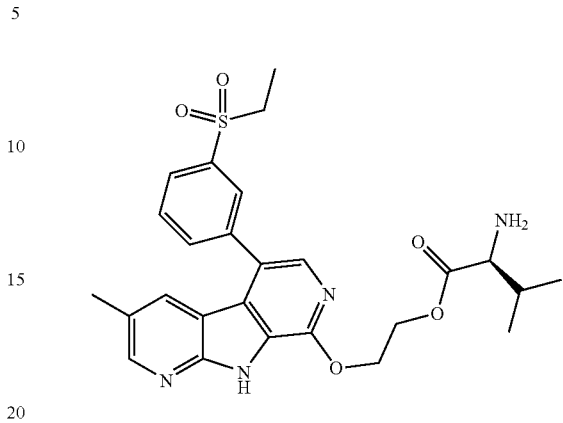

BOC-L-valine (51 mg, 0.23 mmol) and compound 52 (80 mg, 0.19 mmol) were stirred in CH$_2$Cl$_2$ (6 mL) at r.t. DIEA (51 µL, 0.29 mmol) and HATU (110 mg, 0.29 mmol) were added, and the reaction stirred for 6 h. Organics were washed with 0.1 N HCl and brine, dried (Na$_2$SO$_4$) and concentrated in vacuo. The residue was stirred in 33% TFA/CH$_2$Cl$_2$ (3 mL) for 1 h, concentrated, and purified by prep-HPLC to give 68 mg (68%) of the title compound as a pale yellow powder. $^1$H NMR (400 MHz, MeOD-d$_4$): δ 8.40 (br s, 1H), 8.19 (s, 1H), 8.06 (d, 1H, J=7.6 Hz), 7.97 (d, 1H, J=7.6 Hz), 7.81-7.88 (m, 3H), 4.69-4.96 (m, 4H), 3.97 (d, 1H, J=4.8 Hz), 3.33 (q, 2H, J=7.2 Hz), 2.35 (s, 3H), 2.20-2.30 (m, 1H), 1.29 (t, 3H, J=7.2 Hz), 0.93-1.02 (m, 6H). MS (ES) [m+H] calc'd for C$_{26}$H$_{30}$N$_4$O$_5$S, 511; found 511.

Compound 64: L-Alanine-(R)-2-[5-(3-ethanesulfonyl-phenyl)-3-methyl-9H-dipyrido[2,3-b;4',3'-d]pyrrol-8-yloxy]-1-methyl-ethyl ester

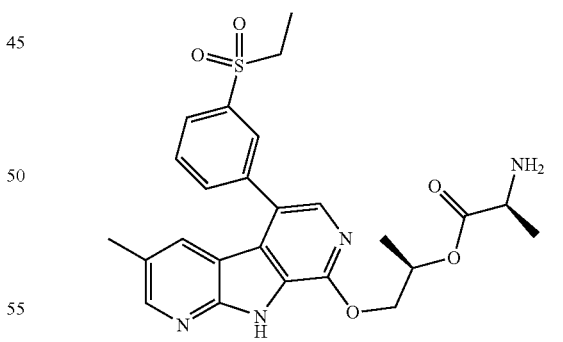

The title compound was prepared in 79% yield using BOC-L-alanine and example 62 in the procedure outlined for the preparation of compound 63. $^1$H NMR (400 MHz, MeOD-d$_4$): δ 8.46 (br s, 1H), 8.19 (s, 1H), 8.05 (d, 1H, J=7.6 Hz), 7.98 (d, 1H, J=7.6 Hz), 7.79-7.88 (m, 3H), 5.51-5.59 (m, 1H), 4.60-4.85 (m, 2H), 4.12 (q, 1H, J=7.2 Hz), 3.33 (q, 2H, J=7.2 Hz), 2.34 (s, 3H), 1.55 (d, 3H, J=7.2 Hz), 1.51 (d, 3H, J=6.4 Hz), 1.29 (t, 3H, J=7.2 Hz). MS (ES) [m+H] calc'd for C$_{25}$H$_{28}$N$_4$O$_5$S, 497; found 497.

Compound 65: 3-(3-Bromo-5-chloro-pyridin-2-ylamino)-5-chloro-1-(4-methoxy-benzyl)-1H-pyrazin-2-one

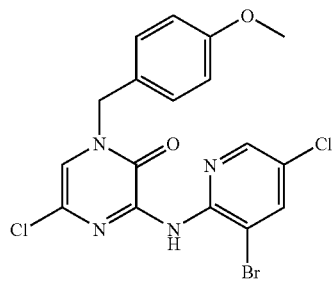

The title compound was prepared in 58% yield from 2-amino-3-bromo-5-chloropyridine and 3,5-dichloro-1-(4-methoxy-benzyl)-1H-pyrazin-2-one in a manner analogous to that for the preparation of example 26. $^1$H NMR (400 MHz, DMSO-d$_6$): δ 9.58 (s, 1H), 8.51 (d, 1H, J=2.4 Hz), 8.40 (d, 1H, J=2.4 Hz), 7.51 (s, 1H), 7.36 (d, 2H, J=8.8 Hz), 6.92 (d, 2H, J=8.8 Hz), 5.00 (s, 2H), 3.73 (s, 3H). MS (ES) [m+H] calc'd for C$_{17}$H$_{13}$BrCl$_2$N$_4$O$_2$, 455, 457, 459; found 455, 457, 459.

Compound 66: 5-Chloro-3-(5-chloro-3-trimethylsilanylethynyl-pyridin-2-ylamino)-1-(4-methoxy-benzyl)-1H-pyrazin-2-one

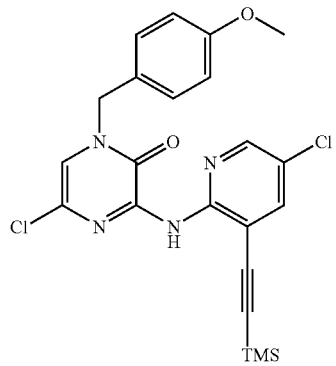

The title compound was prepared in 89% yield from compound 65 according to the procedure outline for the preparation of compound 27. $^1$H NMR (400 MHz, DMSO-d$_6$): δ 9.68 (s, 1H), 8.46 (d, 1H, J=2.8 Hz), 8.07 (d, 1H, J=2.8 Hz), 7.54 (s, 1H), 7.37 (d, 2H, J=8.8 Hz), 6.90 (d, 2H, J=8.8 Hz), 5.00 (s, 2H), 3.72 (s, 3H), 0.16 (s, 9H). MS (ES) [m+H] calc'd for C$_{22}$H$_{22}$Cl$_2$N$_4$O$_2$Si, 473, 475; found 473, 475.

Compound 67: 3-Chloro-7-(4-methoxy-benzyl)-5-trimethylsilanyl-7,9-dihydro-dipyrido[2,3-b;4',3'-d]pyrrol-8-one

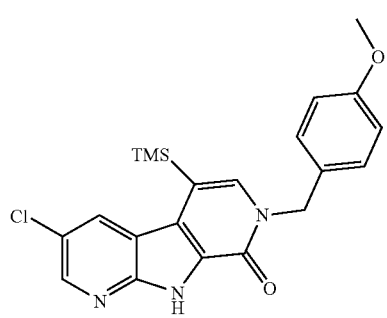

Compound 66 (5.8 g, 12.3 mmol) and DIEA (3.2 mL, 18.4 mmol) were dissolved in toluene (600 mL), and the solution was heated at reflux under N$_2$ for four days. The solution was concentrated and purified by flash chromatography (30% EtOAc/CH$_2$Cl$_2$) to give 4.4 g (87%) of the title compound as a tan solid. $^1$H NMR (400 MHz, DMSO-d$_6$): δ 12.98 (s, 1H), 8.54 (d, 1H, J=2.4 Hz), 8.20 (d, 1H, J=2.4 Hz), 7.37 (s, 1H), 7.32 (d, 2H, J=8.8 Hz), 6.90 (d, 2H, J=8.8 Hz), 5.25 (s, 2H), 3.71 (s, 3H), 0.39 (s, 9H). MS (ES) [m+H] calc'd for C$_{21}$H$_{22}$ClN$_3$O$_2$Si, 412, 414; found 412, 414.

Compound 68: 3-Chloro-5-iodo-7-(4-methoxy-benzyl)-7,9-dihydro-dipyrido[2,3-b;4',3'-d]pyrrol-8-one

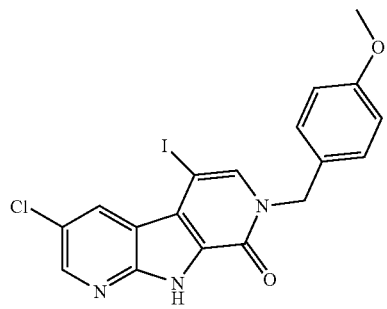

The title compound was prepared in quantitative yield from compound 67 according to the procedure outline for the preparation of compound 29. $^1$H NMR (400 MHz, DMSO-d$_6$): δ 13.12 (s, 1H), 8.84 (d, 1H, J=2.4 Hz), 8.59 (d, 1H, J=2.4 Hz), 7.94 (s, 1H), 7.34 (d, 2H, J=8.8 Hz), 6.89 (d, 2H, J=8.8 Hz), 5.19 (s, 2H), 3.71 (s, 3H). MS (ES) [m+H] calc'd for C$_{18}$H$_{13}$ClIN$_3$O$_2$, 466, 468; found 466, 468.

Compound 69: 3-Chloro-5-(3-ethanesulfonyl-phenyl)-7-(4-methoxy-benzyl)-7,9-dihydro-dipyrido[2,3-b;4',3'-d]pyrrol-8-one

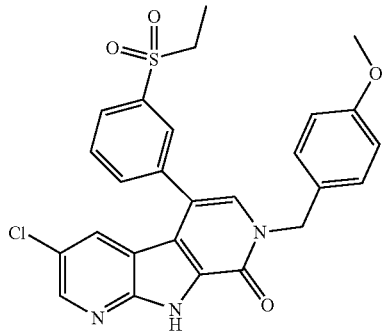

The title compound was prepared in 48% yield from compound 68 according to the procedure outline for the preparation of example 30. $^1$H NMR (400 MHz, DMSO-d$_6$): δ 13.12 (s, 1H), 8.52 (d, 1H, J=2.4 Hz), 8.06 (d, 1H, J=2.4 Hz), 7.80-7.99 (m, 3H), 7.73 (s, 1H), 7.65 (s, 1H), 7.39 (d, 2H, J=8.8 Hz), 6.89 (d, 2H, J=8.8 Hz), 5.27 (s, 2H), 3.70 (s, 3H), 3.39 (q, 2H, J=7.2 Hz), 1.15 (t, 3H, J=7.2 Hz). MS (ES) [m+H] calc'd for C$_{26}$H$_{22}$ClN$_3$O$_4$S, 508, 510; found 508, 510.

Compound 70: 3,8-Dichloro-5-(3-ethanesulfonyl-phenyl)-9H-dipyrido[2,3-b;4',3'-d]pyrrole

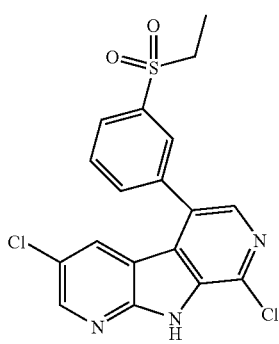

Phosphorous oxychloride (8 mL) was added to a mixture of compound 69 (1.05 g, 2.07 mmol) and ammonium chloride (380 mg, 2.28 mmol), and the reaction was heated at 108° C. for 4 h. The reaction was concentrated in vacuo and quenched with ice. The precipitated was collected by filtration and washed with H$_2$O and cold MeOH to give 660 mg (79%) of the title compound as a pale yellow solid. $^1$H NMR (400 MHz, DMSO-d$_6$): δ 13.12 (s, 1H), 8.69 (d, 1H, J=2.4 Hz), 8.25 (s, 1H), 8.20 (d, 1H, J=2.4 Hz), 8.04-8.10 (m, 2H), 7.93 (t, 1H, J=7.6 Hz), 7.80 (s, 1H), 3.42 (q, 2H, J=7.2 Hz), 1.17 (t, 3H, J=7.2 Hz). MS (ES) [m+H] calc'd for C$_{18}$H$_{13}$Cl$_2$N$_3$O$_2$S, 406, 408; found 406, 408.

Compound 71: 3-Chloro-5-(3-ethanesulfonyl-phenyl)-8-(1-methyl-piperidin-4-ylmethoxy)-9H-dipyrido[2,3-b;4',3'-d]pyrrole

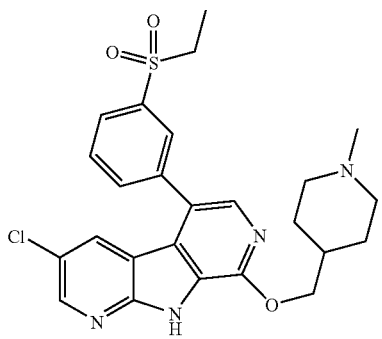

The title compound was prepared in 14% yield using compound 70 and 1-methyl-piperidine-3-methanol in the procedure outlined for the preparation of compound 51. $^1$H NMR (400 MHz, MeOD-d$_4$): δ 8.49 (s, 1H), 8.17 (d, 1H, J=1.6 Hz), 8.08 (d, 1H, J=7.6 Hz), 7.99 (d, 1H, J=7.6 Hz), 7.82-7.90 (m, 2H), 7.80 (s, 1H), 4.52 (d, 2H, J=6.0 Hz), 3.56-3.62 (m, 2H), 3.33 (q, 2H, J=7.2 Hz), 3.02-3.11 (m, 2H), 2.90 (s, 3H), 2.25-2.33 (m, 3H), 1.60-1.72 (m, 2H), 1.31 (t, 3H, J=7.2 Hz). MS (ES) [m+H] calc'd for C$_{25}$H$_{27}$ClN$_4$O$_3$S, 499, 501; found 499, 501.

Compound 72: (R)-1-[3-Chloro-5-(3-ethanesulfonyl-phenyl)-9H-dipyrido[2,3-b;4',3'-d]pyrrol-8-yloxy]-propan-2-ol

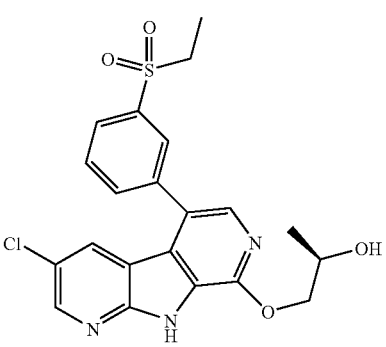

The title compound was prepared in 15% yield using (S)-2-benzyloxy-1-propanol (see Mulzer, et. al., *Tetrahedron Lett.*, 24, (1983), 2843-2846) and compound 70 in the procedure outlined for the preparation of example 51, followed by benzyl deprotection by hydrogenation at 1 atm with 10% Pd/C in MeOH for 1 h. $^1$H NMR (400 MHz, MeOD-d$_4$): δ 8.49 (s, 1H), 8.17 (s, 1H), 8.06 (d, 1H, J=7.6 Hz), 7.97 (d, 1H, J=7.6 Hz), 7.80-7.89 (m, 3H), 4.30-4.59 (m, 3H), 3.32 (q, 2H, J=7.2 Hz), 1.32-1.40 (m, 6H). MS (ES) [m+H] calc'd for C$_{21}$H$_{20}$ClN$_3$O$_4$S, 446, 448; found 446, 448.

Compound 73: 2-[5-(3-Ethanesulfonyl-phenyl)-3-methyl-9H-dipyrido[2,3-b;4',3'-d]pyrrol-8-yl]methyl amine

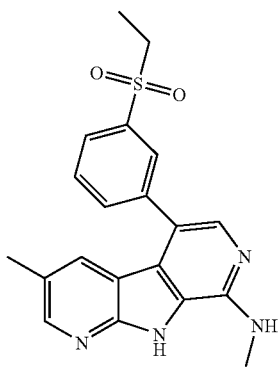

The title compound was prepared using methyl amine in the procedure outlined for the preparation of compound 40. $^1$H NMR (400 MHz, MeOD) δ ppm 1.30 (s, 3 H) 2.37 (s, 3 H) 7.64 (s, 1 H) 7.66 (dd, J=2.02, 0.76 Hz, 1 H) 7.91 (t, J=7.71 Hz, 1 H) 8.01-8.04 (m, J=7.71, 1.14, 0.88, 0.88 Hz, 1 H) 8.15 (ddd, J=7.89, 1.83, 1.14 Hz, 1 H) 8.22 (t, J=1.64 Hz, 1 H) 8.53 (s, 1 H) [M+H] calc'd for $C_{20}H_{20}N_4O_2S$, 381; found, 381.

Compound 74: 2-[5-(3-Ethanesulfonyl-phenyl)-3-methyl-9H-dipyrido[2,3-b;4',3'-d]pyrrol-8-yl]methanethiol

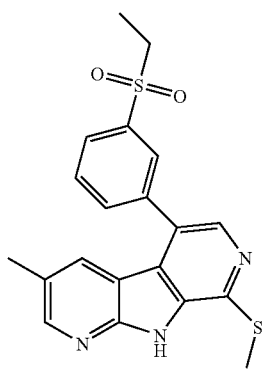

The title compound was prepared using methanethiol in the procedure outlined for the preparation of compound 40. $^1$H NMR (400 MHz, MeOD) δ ppm 1.28-1.31 (m, 3 H) 2.38 (s, 3 H) 2.85 (s, 3 H) 7.82 (s, 1 H) 7.92 (t, J=7.45 Hz, 1 H) 8.05-8.08 (m, J=7.71, 1.14, 0.88, 0.88 Hz, 1 H) 8.14 (ddd, J=7.64, 1.20, 1.01 Hz, 1 H) 8.27 (dd, J=3.66, 0.63 Hz, 1 H) 8.30 (s, 1 H) 8.49 (s, 1 H) [M+H] calc'd for $C_{20}H_{19}N_3O_2S_2$, 398; found, 398.

Compound 75: 2-[5-(3-Ethanesulfonyl-phenyl)-3-methyl-9H-dipyrido[2,3-b;4',3'-d]pyrrol-8-yl] ethanethiol

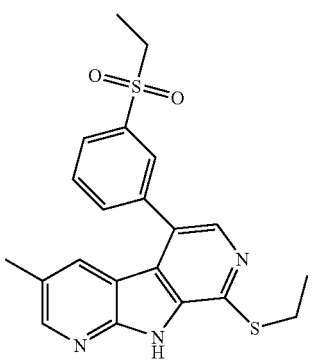

The title compound was prepared using ethanethiol in the procedure outlined for the preparation of compound 40. $^1$H NMR (400 MHz, MeOD) δ ppm 1.30 (t, J=7.33 Hz, 3 H) 1.45 (t, J=7.33 Hz, 3 H) 1.93 (s, 3 H) 2.37 (s, 2 H) 3.44 (d, J=7.33 Hz, 2 H) 7.82 (s, 1 H) 7.92 (t, J=7.71 Hz, 1 H) 8.07 (dt, J=7.77, 1.42 Hz, 1 H) 8.13 (dt, J=7.83, 1.52 Hz, 1 H) 8.27 (t, J=1.77 Hz, 1 H) 8.31 (s, 1 H) 8.50 (br. s., 1 H) [M+H] calc'd for $C_{21}H_{21}N_3O_2S_2$, 412; found 412.

Compound 76: 5-[3-(cyclopropylcarboxamide)phenyl]-7-(4-methoxybenzyl)-3-methyl-7,9-dihydro-8H-pyrido [4',3':4,5]pyrrolo[2,3-b]pyridin-8-one

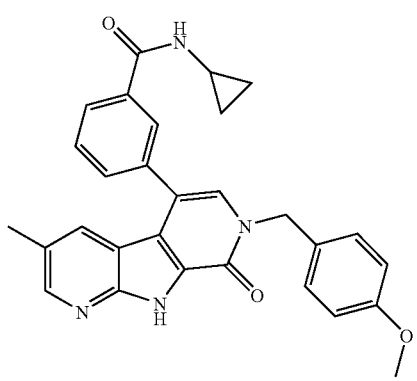

The title compound was prepared using the similar procedure outlined for the preparation of compound 39. $^1$H NMR (400 MHz, CHLOROFORM-d) δ ppm 0.63 (ddd, J=3.79, 1.77, 1.52 Hz, 2 H) 0.81 (dd, J=7.33, 2.02 Hz, 2 H) 2.31 (s, 2 H) 2.66 (s, 3 H) 3.76 (s, 3 H) 5.34 (s, 2 H) 6.89 (d, J=8.84 Hz, 2 H) 7.35 (d, J=8.84 Hz, 2 H) 7.40 (s, 1 H) 7.64 (d, J=7.83 Hz, 1 H) 7.60 (t, J=2.02 Hz, 1 H) 7.75 (d, J=2.78 Hz, 1 H) 7.92 (dd, J=7.96, 1.14 Hz, 1 H) 8.00 (t, J=1.64 Hz, 1 H) 8.34 (d, J=2.02 Hz, 1 H) [M+H] calc'd for $C_{29}H_{26}N_4O_3$, 479; found 479.

133

Compound 77: 8-Chloro-5-[3-(cyclopropylcarboxamide)phenyl]-3-methyl-9H-dipyrido[2,3-b;4',3'-d]pyrrole

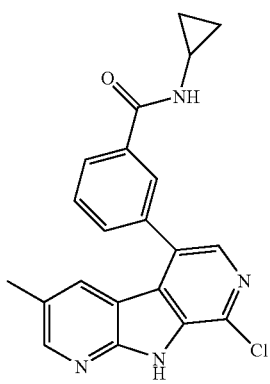

The title compound was prepared from compound 76 using the similar procedure outlined for the preparation of compound 32. [M+H] calc'd for $C_{21}H_{17}ClN_4O$, 377.1; found, 377.2.

Compound 78: 2-[5-(3-cyclopropylcarbonylaminophenyl)-3-methyl-9H-dipyrido[2,3-b;4',3'-d]pyrrol-8-yl]ethanethiol

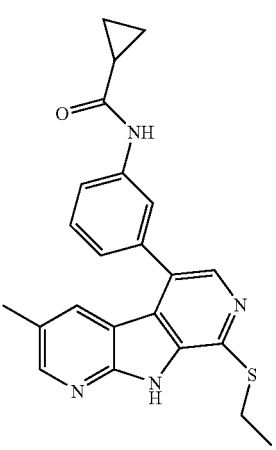

The title compound was prepared using ethanethiol in the procedure outlined for the preparation of compound 40. $^1$H NMR (400 MHz, MeOD) δ ppm 0.88 (d, J=7.83 Hz, 2 H) 0.97 (t, J=2.40 Hz, 2 H) 1.44 (t, J=7.33 Hz, 3 H) 2.38 (s, 3 H) 3.41 (d, J=7.33 Hz, 2 H) 7.39 (d, J=7.83 Hz, 1 H) 7.56 (t, J=7.83 Hz, 1 H) 7.66 (d, J=8.84 Hz, 1 H) 7.85 (s, 1 H) 8.26 (s, 1 H) 8.48 (br. s., 1 H) 10.26 (s, 1 H) ) [M+H] calc'd for $C_{23}H_{22}N_4OS$, 403; found, 403.

134

Compound 79: 1-Acetyl-4-bromo-1,2-dihydro-indol-3-one

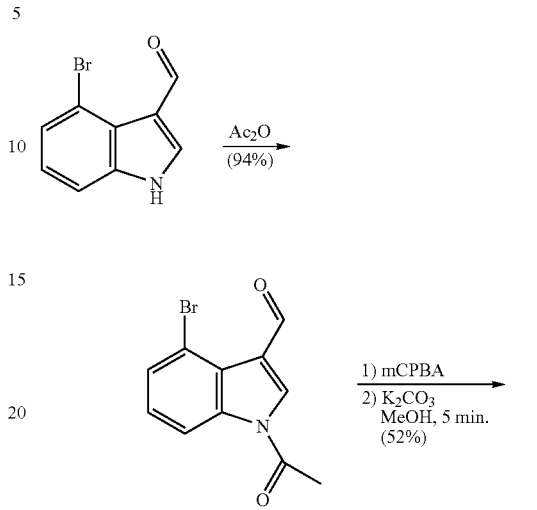

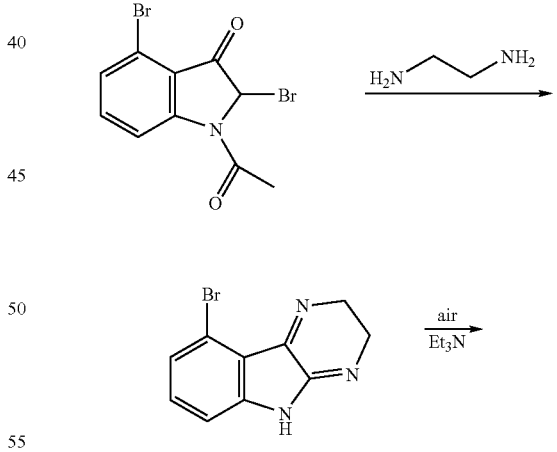

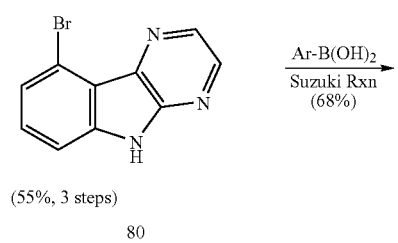

Compound 81: 9-(3-Ethanesulfonyl-phenyl)-5H-pyrazino[2,3-b]indole

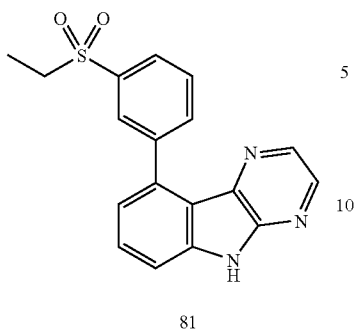

81

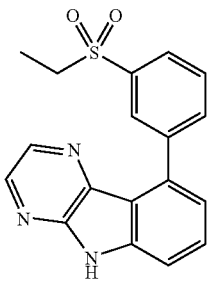

4-Bromo-1H-indole-3-carbaldehyde (4.0 g, 17.8 mmol) was stirred in acetic anhydride (20 mL) at reflux for 4 h. The reaction was cooled and concentrated in vacuo. Cold MeOH was added to precipitate a white solid, which was collected by filtration to give 3.5 g (74%) of 1-acetyl-4-bromo-1H-indole-3-carbaldehyde. MS (ES) [m+H] calc'd for $C_{11}H_8BrNO_2$, 266, 268; found 266, 268.

1-Acetyl-4-bromo-1H-indole-3-carbaldehyde (3.5 g, 13.2 mmol) was dissolved in $CH_2Cl_2$ (50 mL). 3-Chloroperbenzoic acid (3.9 g, 15.8 mmol) was added, and the reaction stirred 16 h at r.t. The solution was washed with sat. $NaHCO_3$ and brine, dried ($MgSO_4$), and concentrated. The residue was stirred with $K_2CO_3$ (100 mg) in MeOH (50 mL) for 2 min. The solution was concentrated and purified by silica gel chromatography (100% $CH_2Cl_2$) to give 880 mg (26%) of the title compound as a faintly blue solid. MS (ES) [m+H] calc'd for $C_{10}H_8BrNO_2$, 254, 256; found 254, 256.

Compound 80: 9-Bromo-5H-pyrazino[2,3-b]indole

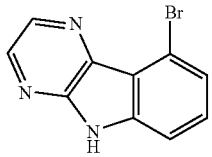

1-Acetyl-4-bromo-1,2-dihydro-indol-3-one (460 mg, 1.81 mmol) was dissolved in $CH_2Cl_2$ (8 mL). Bromine (111 μL, 2.2 mmol) was added slowly, and the reaction stirred for 20 min and then was concentrated in vacuo. The residue was dissolved in THF (8 mL). Ethylenediamine (244 μL, 3.6 mmol) was added, and the reaction stirred for 16 h at r.t. Triethylamine (2 mL) and MeOH (4 mL) were added, and the reaction stirred while left open to air for 24 h. The solution was concentrated in vacuo and purified by silica gel chromatography (8% MeOH/$CH_2Cl_2$) to give 248 mg (55%) of the title compound as a red solid. MS (ES) [m+H] calc'd for $C_{10}H_6BrN_3$, 248, 250; found 248, 250.

Compound 80 (50 mg, 0.2 mmol), 3-ethanesulfonyl-phenylboronic acid (65 mg, 0.3 mmol), tetrakis(triphenylphosphine)palladium (0) (116 mg, 0.1 mmol), and potassium carbonate (83 mg, 0.6 mmol), were combined in dioxane (2 mL) and $H_2O$ (0.2 mL) in a sealed tube under nitrogen. The reaction was heated at 150° C. in the microwave for 20 min and then concentrated in vacuo. Purification by silica gel chromatography (5% MeOH/$CH_2Cl_2$) gave 46 mg (68%) of the title compound as a light orange solid. $^1$H NMR (400 MHz, $CH_3OD$) δ 8.42 (t, 1H, J=2.8 Hz), 8.31 (d, 1H, J=2.8 Hz), 8.24 (d, 1H, J=2.8 Hz), 8.06 (d, 1H, J=7.6 Hz), 7.96 (d, 1H, J=7.6 Hz), 7.60-7.75 (m, 3H), 7.31 (dd, 1H, J=7.2, 1.2 Hz), 3.33 (q, 2H, J=7.2 Hz), 1.37 (t, 3H, J=7.2 Hz). MS (ES) [m+H] calc'd for $C_{18}H_{15}N_3O_2S$, 338; found 338.

Compound 82: 3-(6-chloro-3-methyl-2-nitro-4-(trifluoromethyl)phenyl)-2-fluoro-5-methylpyridine

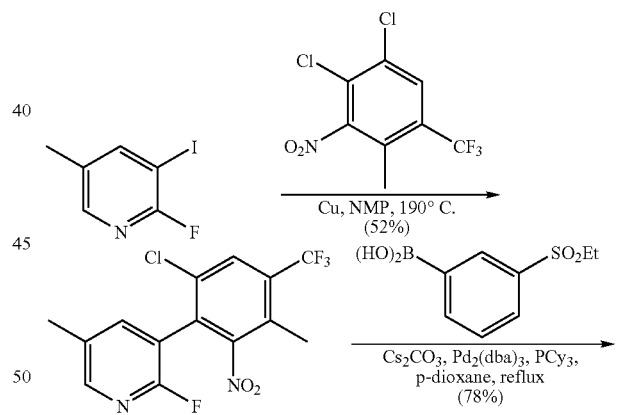

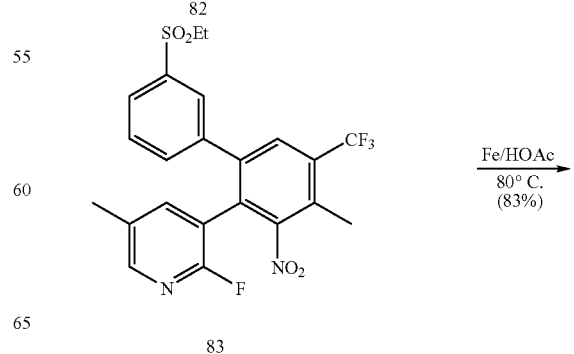

82

83

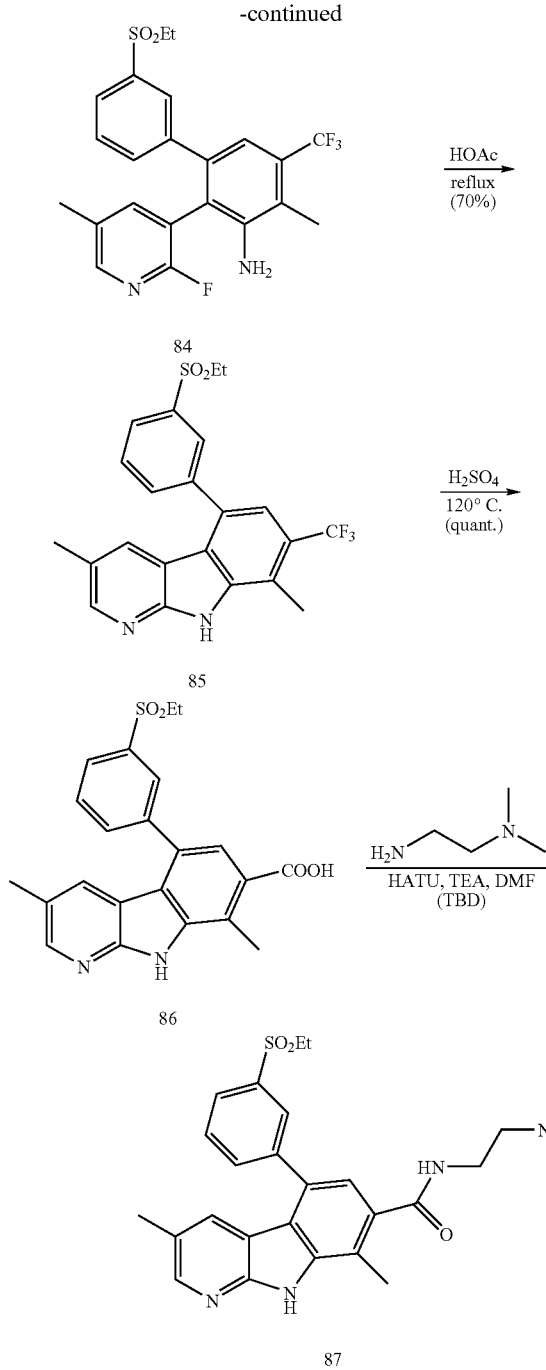

phy (98:2 Toluene:EtOAc) gave 11.4 g (52%) of the title compound as a tan solid. $^1$H NMR (400 MHz, DMSO-$d_6$): δ 8.34 (s, 1H), 8.26 (s, 1H), 7.86-7.89 (m, 1H), 2.4 (s, 3H), 2.34 (s, 3H). MS (ES) [m+H] calc'd for $C_{14}H_9ClF_4N_2O_2$, 349; found 349.2.

Compound 83: 3-(3'-(ethylsulfonyl)-4-methyl-3-nitro-5-(trifluoromethyl)biphenyl-2-yl)-2-fluoro-5-methylpyridine A mixture of 3-(6-chloro-3-methyl-2-nitro-4-(trifluoromethyl)phenyl)-2-fluoro-5-methylpyridine (6.0 g, 17.2 mmol), 3-ethylsulfonylphenylboronic acid (4.79 g, 22.4 mmol), bis(dibenzylidineacetone)Pd(0) (1.48 g, 2.6 mmol), tricyclohexylphosphine (1.45 g, 5.2 mmol), $Cs_2CO_3$ (14.0 g, 43 mmol), and dioxane (60 mL) was heated at reflux for 4.5 hr. After completion the reaction was cooled to room temperature, filtered, rinsed with dioxane, and concentrated in vacuo. The resulting oil was reconstituted in EtOAc (75 mL) washed with $H_2O$ (1×30 mL) and brine (1×30 mL), dried ($MgSO_4$), and concentrated in vacuo. Purification by silica gel chromatography (4:1 hexanes/EtOAc) gave 6.5 g (78%) of the title compound as a tan solid. $^1$H NMR (400 MHz, DMSO-$d_6$): δ 8.15 (s, 1H), 8.04 (s, 1H), 7.90-7.93 (m, 1H), 7.80-7.82 (m, 1H), 7.60-7.70 (m, 3H), 3.1-3.2 (m, 2H), 2.49 (s, 3H), 2.25 (s, 3H), 0.85 (t, 3H). MS (ES) [m+H] calc'd for $C_{22}H_{18}F_4N_2O_4S$, 483; found 483.3.

Compound 84: 3'-(ethylsulfonyl)-2-(2-fluoro-5-methylpyridin-3-yl)-4-methyl-5-(trifluoromethyl)biphenyl-3-amine A mixture of 3-(3'-(ethylsulfonyl)-4-methyl-3-nitro-5-(trifluoromethyl)biphenyl-2-yl)-2-fluoro-5-methylpyridine (6.4 g, 13.3 mmol), iron (3.7 g, 66.3 mmol), HOAc, (32 mL), and $H_2O$ (11 mL) was heated at 80° C. for 2 h. After completion the reaction was concentrated in vacuo. The residue was reconstituted in dichloromethane (100 mL), filtered, and rinsed with dichloromethane (3×30 mL). The organic phase 2-Fluoro-3-iodo-5-picoline (15.0 g, 63 mmol) was added drop wise during 2 h as a solution in NMP (20 mL) to a stirred suspension of 3,4-dichlororo-2-nitro-6-(trifluoromethyl)-toluene (52.1 g, 190 mmol) and copper (12.1 g, 190 mmol) in NMP (115 mL) at 190° C. After completion of the reaction (2.5 h), the mixture was cooled to room temperature, filtered, rinsed with NMP (3×5 mL) followed by EtOAc (100 mL). The filtrate was diluted with EtOAc (400 mL) affording a turbid solution. The organic layer was partitioned with sat. $NaHCO_3$ (150 mL) affording a suspension/emulsion. $H_2O$ (50 mL) and MeOH (50 mL) were added to aid solubility. The aqueous layer was washed with EtOAc (5×150 mL). The organic layers were combined, dried ($MgSO_4$), and concentrated in vacuo. Two purifications by silica gel chromatograwas washed with sat. NaHCO₃ (1×100 mL) and brine (1×50 mL), dried (MgSO₄), filtered, and concentrated in vacuo. Purification by silica gel chromatography (1:1 hexanes/EtOAc) gave 5.0 g (83%) of the title compound as a tan solid. ¹H NMR (400 MHz, DMSO-d₆): δ 7.93 (s, 1H), 7.67-7.7.71 (m, 2H), 7.53 (t, 1H), 7.46-7.48 (m, 1H), 7.42 (s, 1H), 6.93 (s, 1H), 5.09 (s, 2H), 3.11 (q, 2H), 2.27 (s, 3H), 2.21 (s, 3H), 0.85 (t, 3H). MS (ES) [m+H] calc'd for C₂₂H₂₀F₄N₂O₂S, 453; found 453.3.

Compound 85: 5-(3-(ethylsulfonyl)phenyl)-3,8-dimethyl-7-(trifluoromethyl)-9H-pyrido[2,3-b]indole acetate

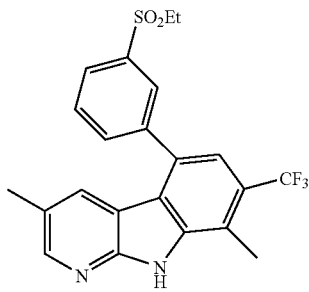

3'-(ethylsulfonyl)-2-(2-fluoro-5-methylpyridin-3-yl)-4-methyl-5-(trifluoromethyl)biphenyl-3-amine (4.9 g, 10.8 mmol) was dissolved in HOAc (35 mL) and heated at reflux for 3 h. The reaction mixture was cooled to room temperature affording a crystalline product. The resulting suspension was filtered, rinsed with HOAc (3×5 mL) followed by H₂O (3×10 mL) and the solids dried in vacuo to give 3.73 g (70%) of the title compound as a white solid. NMR analysis confirmed that the product was isolated as the mono-acetate salt. ¹H NMR (400 MHz, DMSO-d₆): δ 12.35 (s, 1H), 12.0 (s, 1H), 8.39 (s, 1H), 8.15 (s, 1H), 8.04-8.09 (m, 2H), 7.90 (t, 1H), 7.51 (s, 1H), 7.42 (s, 1H), 3.43 (q, 2H), 2.76 (s, 3H), 2.28 (s, 3H), 1.91 (s, 3H), 1.18 (t, 3H). MS (ES) [m+H] calc'd for C₂₂H₁₉F₃N₂O₂S, 433; found 433.3.

Compound 86: 5-(3-(ethylsulfonyl)phenyl)-3,8-dimethyl-9H-pyrido[2,3-b]indole-7-carboxylic acid

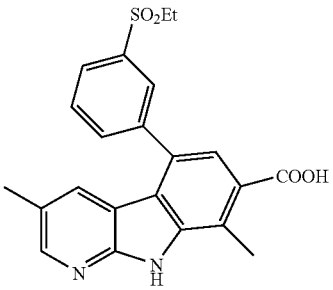

5-(3-(ethylsulfonyl)phenyl)-3,8-dimethyl-7-(trifluoromethyl)-9H-pyrido[2,3-b]indole acetate (3.6 g, 7.3 mmol) was dissolved in concentrated H₂SO₄ (30 mL) and heated at 120° C. for 30 min. The reaction was cooled to room temperature and poured over ice affording a white precipitate. The resulting suspension was filtered, rinsed with H₂O (3×30 mL) followed by IPA (3×10 mL) and dried in vacuo to 3.2 g (quant.) to give the title compound as a white solid. ¹H NMR (400 MHz, DMSO-d₆): δ 12.20 (s, 1H), 8.36 (s, 1H), 8.12 (s, 1H), 8.02-8.07 (m, 2H), 7.89 (t, 1H), 7.61 (s, 1H), 7.54 (s, 1H), 3.43 (q, 2H), 2.85 (s, 3H), 2.28 (s, 3H), 1.18 (t, 3H). MS (ES) [m+H] calc'd for C₂₂H₂₀N₂O₄S, 409; found 409.3.

Compound 87: N-(2-(dimethylamino)ethyl)-5-(3-(ethylsulfonyl)phenyl)-3,8-dimethyl-9H-pyrido[2,3-b]indole-7-carboxamide

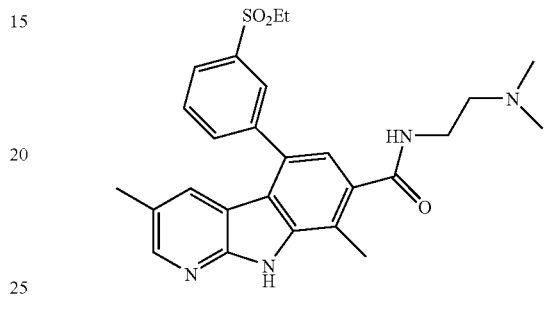

A mixture of 5-(3-(ethylsulfonyl)phenyl)-3,8-dimethyl-9H-pyrido[2,3-b]indole-7-carboxylic acid (3.0 g, 73 mmol), N,N-Dimethylethylene diamine (g, mmol), HATU (g, mmol), triethylamine (g, mmol) and DMF (mL) was stirred at room temperature for two days. The reaction mixture was poured over ice affording a precipitate, The resulting suspension was filtered, rinsed with H₂O and dried in vacuo to g (%). ¹H NMR (400 MHz, DMSO-d₆): δ 12.04 (s, 1H), 8.28-8.31 (m, 2H), 8.12 (s, 1H), 8.01-8.05 (m, 2H), 7.89 (t, 1H), 7.52 (s, 1H), 7.12 (s, 1H), 3.43 (q, 2H), 2.63 (s, 3H), 2.27 (s, 3H), 2.20 (s, 6H), 1.17 (t, 3H). MS (ES) [m+H] calc'd for C₂₆H₃₀N₄O₃S, 479; found 479.4.

Compound 88: N-(2-(methylamino)ethyl)-5-(3-(ethylsulfonyl)phenyl)-3,8-dimethyl-9H-pyrido[2,3-b]indole-7-carboxamide

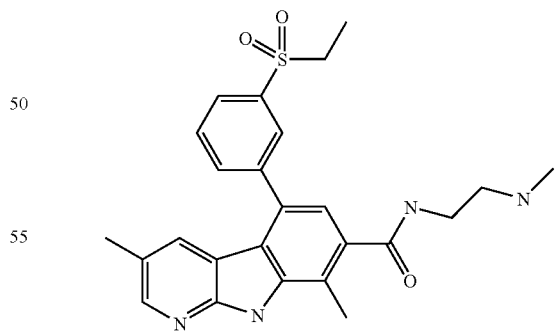

The title compound was synthesized using an analogous procedure to that described in the preparation of compound 87. ¹H NMR (400 MHz, DMSO-d₆) δ ppm 1.17 (t, J=7.33 Hz, 3 H) 2.27 (s, 3 H) 2.63 (t, J=5.31 Hz, 3 H) 2.67 (s, 3 H) 3.12 (ddd, J=11.87, 6.32, 6.06 Hz, 2 H) 3.42 (q, J=7.41 Hz, 2 H) 3.56 (q, J=6.15 Hz, 2 H) 7.28 (s, 1 H) 7.51 (s, 1 H) 7.91 (t, J=7.83 Hz, 1 H) 8.04 (ddd, J=16.36, 7.77, 1.14 Hz, 2 H) 8.12

(s, 1 H) 8.33 (s, 1 H) 8.43 (br. s., 1 H) 8.57 (t, J=5.68 Hz, 1 H) 12.09 (s, 1 H) ESI-MS: m/z 465 (m+H)+

Compound 89: N-(2-(methoxy)ethyl)-5-(3-(ethylsulfonyl)phenyl)-3,8-dimethyl-9H-pyrido[2,3-b]indole-7-carboxamide

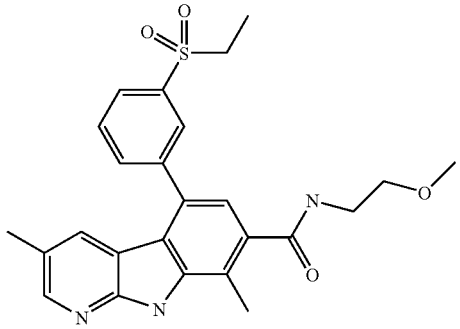

The title compound was synthesized using an analogous procedure to that described in the preparation of compound 87. ¹H NMR (400 MHz, , DMSO-d₆) δ ppm 1.17 (t, J=7.33 Hz, 3 H) 2.27 (s, 3 H) 2.63 (s, 3 H) 3.29 (s, 3 H) 3.37-3.51 (m, 6 H) 7.12 (s, 1 H) 7.53 (d, J=1.26 Hz, 1 H) 7.89 (t, J=7.71 Hz, 1 H) 7.99-8.06 (m, 2 H) 8.12 (s, 1 H) 8.31 (s, 1 H) 8.43 (t, J=5.31 Hz, 1 H) 12.05 (s, 1 H) ESI-MS: m/z 466 (m+H)+

Compound 90: N-(2-(dimethylamino)ethyl)-N-methyl-5-(3-(ethylsulfonyl)phenyl)-3,8-dimethyl-9H-pyrido[2,3-b]indole-7-carboxamide

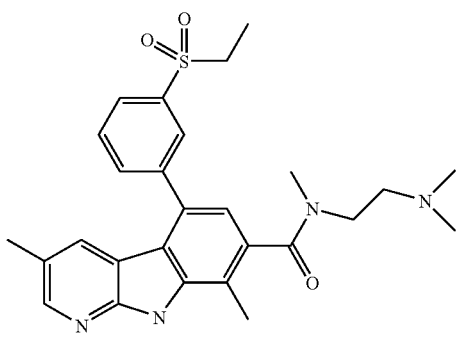

The title compound was synthesized using an analogous procedure to that described in the preparation of compound 87. ¹H NMR (400 MHz, DMSO-d₆) δ ppm 1.17 (t, J=7.20 Hz, 3 H) 2.26 (s, 3 H) 2.64 (br. s., 3 H) 2.86 (s, 3 H) 2.91 (s, 3 H) 3.35-3.45 (m, 6 H) 7.06 (s, 1 H) 7.47 (s, 1 H) 7.89 (t,J=7.71 Hz, 1 H) 8.00-8.09 (m, 3 H) 8.31 (s, 1 H) 9.49 (br. s., 1 H) 12.11 (s, 1 H). ESI-MS: m/z 493 (m+H)+

Compound 91: N,N-dimethyl-5-(3-(ethylsulfonyl)phenyl)-3,8-dimethyl-9H-pyrido[2,3-b]indole-7-methylcarboxamide

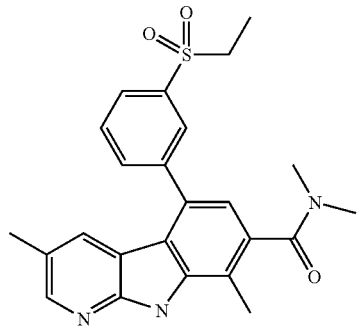

The title compound was synthesized using an analogous procedure to that described in the preparation of compound 87. ¹H NMR (400 MHz, DMSO-d₆) δ ppm 1.17 (t, J=7.33 Hz, 3 H) 2.27 (s, 3 H) 2.46 (br. s., 3 H) 2.84 (s, 3 H) 3.05 (br. s., 3 H) 3.33-3.50 (m, 2 H) 6.97 (s, 1 H) 7.52 (d, J=1.52 Hz, 1 H) 7.87 (t, J=7.71 Hz, 1 H) 8.02 (t, J=7.33 Hz, 2 H) 8.10 (s, 1 H) 8.30 (d, J=1.52 Hz, 1 H) 12.08 (s, 1 H). ESI-MS: m/z 436 (m+H)+

Compound 92: 5-(3-(ethylsulfonyl)phenyl)-3,8-dimethyl-9H-pyrido[2,3-b]indole-7-yl)(4-methylpiperazin-1-yl)methanone

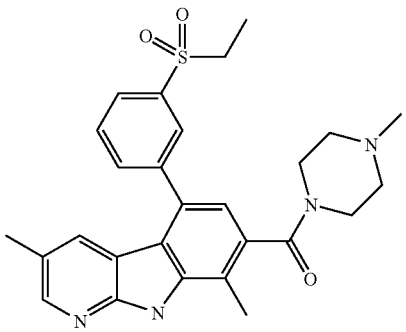

The title compound was synthesized using an analogous procedure to that described in the preparation of compound 87. ¹H NMR (400 MHz, DMSO-d₆) δ ppm 1.18 (t, J=7.33 Hz, 3 H) 2.27 (s, 3 H) 2.57 (br. s., 3 H) 2.82-2.85 (br, 3 H) 3.10-3.68 (m, 9 H) 4.77 (m, 1H) 7.10 (br. d., 1 H) 7.51 (br. d, J=7.83 Hz, 1 H) 7.90 (t, J=7.33 Hz, 1 H) 7.99-8.13 (m, 3 H) 8.32 (s, 1 H) 9.96 (br. s., 1 H) 12.15 (s, 1 H). ESI-MS: m/z 491 (m+H)+

Compound 93: 5-(3-(ethylsulfonyl)phenyl)-3,8-dimethyl-N-(2-piperazin-1-yl)ethyl)-9H-pyrido[2,3-b]indole-7-carboxamide

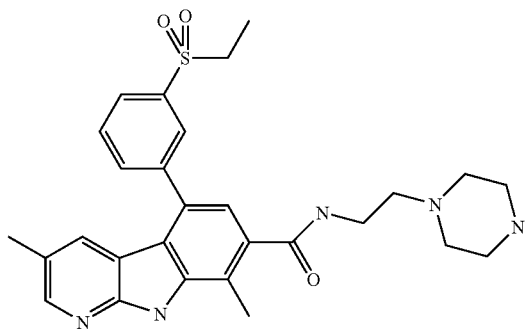

The title compound was synthesized using an analogous procedure to that described in the preparation of compound 87. $^1$H NMR (400 MHz, DMSO-d$_6$) δ ppm 1.17 (t, J=7.33 Hz, 3 H) 2.27 (s, 3 H) 2.66 (s, 3 H) 3.17-3.45 (m, 12 H) 3.59 (q, J=5.64 Hz, 2 H) 7.20 (s, 1 H) 7.52 (s, 1 H) 7.90 (t, J=7.71 Hz, 1 H) 8.04 (m, 2 H) 8.12 (s, 1 H) 8.33 (d, J=2.02 Hz, 1 H) 8.56 (t, J=5.68 Hz, 1 H) 8.99 (br. s., 1 H) 12.10 (s, 1 H). ESI-MS: m/z 520 (m+H)$^+$

Compound 94: 5-(3-(ethylsulfonyl)phenyl)-3,8-dimethyl-N-(3-(4-methylpiperazin-1-yl)propyl)-9H-pyrido[2,3-b]indole-7-carboxamide

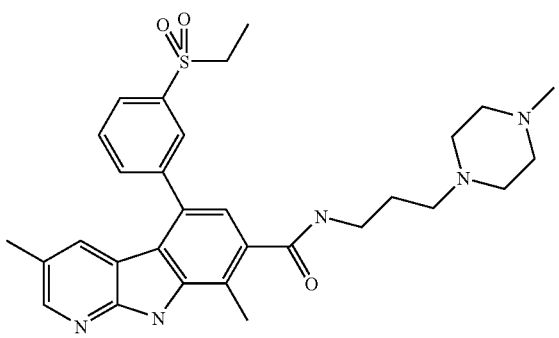

The title compound was synthesized using an analogous procedure to that described in the preparation of compound 87. $^1$H NMR (400 MHz, DMSO-d$_6$) δ ppm 1.17 (t, J=7.83 Hz, 3 H) 1.87 (br. s., 2 H) 2.27 (s, 3 H) 2.64 (s, 3 H) 2.82 (br. s., 3 H) 3.03 (br. s., 4 H) 3.31-3.49 (m, 8 H) 7.15 (s, 1 H) 7.52 (s, 1 H) 7.90 (t, J=7.71 Hz, 1 H) 8.00-8.07 (m, 2 H) 8.11 (s, 1 H) 8.32 (d, J=2.02 Hz, 1 H) 8.49-8.53 (m, 1 H) 12.08 (s, 1 H) ESI-MS: m/z 548 (m+H)$^+$

Compound 95: 5-(3-(ethylsulfonyl)phenyl)-3,8-dimethyl-9H-pyrido[2,3-b]indole-7-yl)(morpholino)methanone

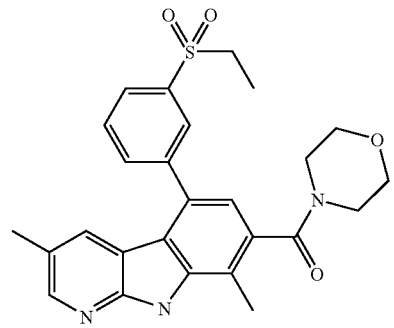

The title compound was synthesized using an analogous procedure to that described in the preparation of compound 87. $^1$H NMR (400 MHz, CHLOROFORM-d) δ ppm 1.38 (t, J=7.33 Hz, 3 H) 2.37 (s, 3 H) 2.71 (s, 3 H) 3.23 (q, J=7.33 Hz, 2 H) 3.39 (m, 2 H) 3.64 (d, J=13.14 Hz, 1 H) 3.64 (d, J=5.05 Hz, 1 H) 3.80-4.01 (m, 4 H) 7.04 (s, 1 H) 7.62 (s, 1 H) 7.78 (t, J=7.71 Hz, 1 H) 7.93 (dt, J=7.77, 1.42 Hz, 1 H) 8.07 (ddd, J=7.71, 1.64, 1.52 Hz, 1 H) 8.24 (t, J=1.64 Hz, 1 H) 8.34 (d, J=1.77 Hz, 1 H) 10.97 (br. s., 1 H) ESI-MS: m/z 478 (m+H)$^+$

Compound 96: azetidin-1-yl(5-(3-(ethylsulfonyl)phenyl)-3,8-dimethyl-9H-pyrido[2,3-b]indol-7-yl)methanone

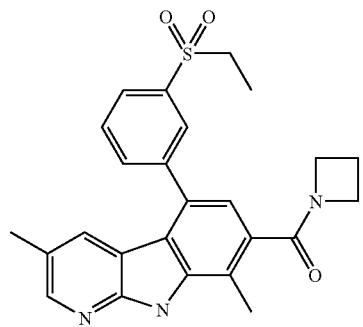

The title compound was synthesized using an analogous procedure to that described in the preparation of compound 87. $^1$H NMR (400 MHz, CHLOROFORM-d) δ ppm 1.37 (t, J=7.45 Hz, 3 H) 2.28-2.41 (m, 5 H) 2.75 (s, 3 H) 3.23 (q, J=7.58 Hz, 2 H) 4.03 (t, J=7.58 Hz, 2 H) 4.30 (t, J=7.96 Hz, 2 H) 7.12 (s, 1 H) 7.61 (s, 1 H) 7.77 (t, J=7.96 Hz, 1 H) 7.94 (ddd, J=7.89, 1.45, 1.26 Hz, 1 H) 8.06 (dd, J=8.21, 1.39 Hz, 1 H) 8.22 (t, J=1.52 Hz, 1 H) 8.33 (d, J=1.26 Hz, 1 H) 10.25 (br. s., 1 H). ESI-MS: m/z 448 (m+H)$^+$ Compound 97: (5-(3-(ethylsulfonyl)phenyl)-3,8-dimethyl-9H-pyrido[2,3-b]indol-7-yl)(thaiazolidin-3-yl)methanone

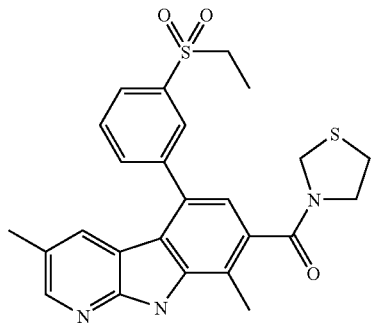

The title compound was synthesized using an analogous procedure to that described in the preparation of compound 87. ¹H NMR (400 MHz, DICHLOROMETHANE-d₂) δ ppm 1.18 (t, J=7.33 Hz, 3 H) 2.27 (s, 3 H) 2.56 (s, 3H) 2.99 (m, 1 H) 3.12 (m, 1 H) 3.43-3.51 m, 3H) 3.89 (m, 1 H) 4.32 (s, 1 H) 4.71 (s, 1 H) 7.06 (d, J=3.03 Hz, 1 H) 7.52 (br. s., 1 H) 7.88 (t, J=7.83 Hz, 1 H) 7.98-8.07 (m, 2 H) 8.12 (d, J=1.52 Hz, 1 H) 8.32 (d, J=1.77 Hz, 1 H) 12.11 (br. s., 1 H). ESI-MS: m/z 480 (m+H)⁺

Compound 98: (R)-5-(3-(ethylsulfonyl)phenyl)-N-(2-hydroxypropyl)-3,8-dimethyl-9H-pyrido[2,3-b]indole-7-carboxamide

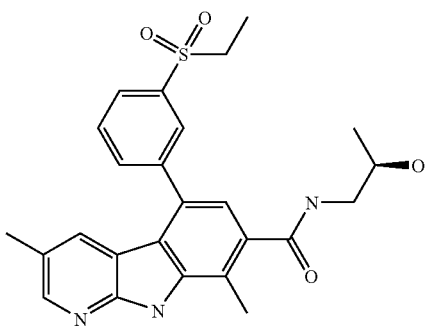

The title compound was synthesized using an analogous procedure to that described in the preparation of compound 87. ¹H NMR (400 MHz, DMSO-d₆) δ ppm 1.13 (d, J=6.82 Hz, 3 H) 1.17 (t, J=7.33 Hz, 3 H) 2.26 (s, 3 H) 2.62 (s, 3 H) 3.30-3.45 (m, 2 H) 3.41 (q, J=7.33 Hz, 2 H) 4.00-4.06 (m, 1 H) 7.12 (s, 1 H) 7.51 (d, J=1.26 Hz, 1 H) 7.89 (t, J=7.71 Hz, 1 H) 7.99-8.05 (m, 2 H) 8.11 (m, 2 H) 8.30 (s, 1 H) 12.04 (s, 1 H). ESI-MS: m/z 466 (m+H)⁺

Compound 99: (S)-5-(3-(ethylsulfonyl)phenyl)-N-(2-hydroxypropyl)-3,8-dimethyl-9H-pyrido[2,3-b]indole-7-carboxamide

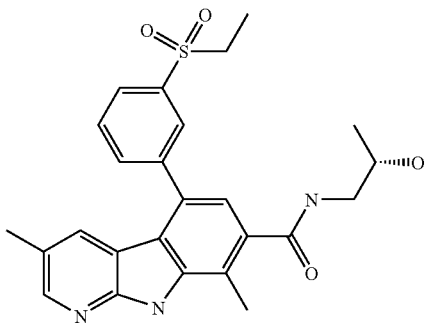

The title compound was synthesized using an analogous procedure to that described in the preparation of compound 87. ¹H NMR (400 MHz, DMSO-d₆) δ ppm 1.10 (d, J=6.32 Hz, 3 H) 1.17 (t, J=7.33 Hz, 3 H) 2.27 (s, 3 H) 2.64 (s, 3 H) 3.22 (t, J=6.06 Hz, 2 H) 3.42 (q, J=7.33 Hz, 2 H) 3.72-3.88 (m, 1 H) 7.17 (s, 1 H) 7.55 (d, J=1.52 Hz, 1 H) 7.89 (t, J=7.71 Hz, 1 H) 8.03 (m, 2 H) 8.13 (t, J=1.64 Hz, 1 H) 8.31 (d, J=1.52 Hz, 1 H) 8.34 (t, J=5.94 Hz, 1 H) 12.09 (s, 1 H). ESI-MS: m/z 466 (m+H)⁺

Compound 100: 5-(3-(ethylsulfonyl)phenyl)-N-(2-hydroxyethyl)-3,8-dimethyl-9H-pyrido[2,3-b]indole-7-carboxamide

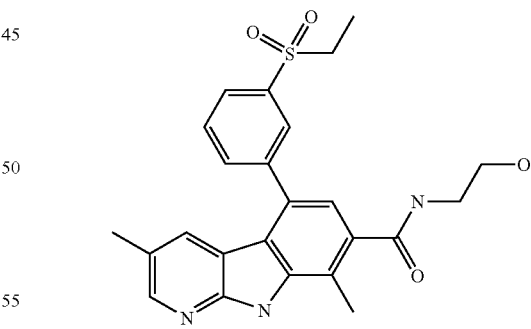

The title compound was synthesized using an analogous procedure to that described in the preparation of compound 87. ¹H NMR (400 MHz, DMSO-d₆) δ ppm 1.17 (t, J=7.33 Hz, 3 H) 2.27 (s, 3 H) 2.63 (s, 3 H) 3.34 (q, J=6.23 Hz, 2 H) 3.42 (q, J=7.33 Hz, 2 H) 3.53 (t, J=6.19 Hz, 2 H) 7.17 (s, 1 H) 7.53 (d, J=1.77 Hz, 1 H) 7.89 (t, J=7.71 Hz, 1 H) 8.03 (m, 2 H) 8.13 (t, J=1.64 Hz, 1 H) 8.34 (t, J=5.68 Hz, 1 H) 8.31 (d, J=1.52 Hz, 1 H) 12.05 (s, 1 H). ESI-MS: m/z 452 (m+H)⁺

Compound 101: N-(2,3-dihydroxypropyl)-5-(3-(ethylsulfonyl)phenyl)-3,8-dimethyl-9H-pyrido[2,3-b]indole-7-carboxamide

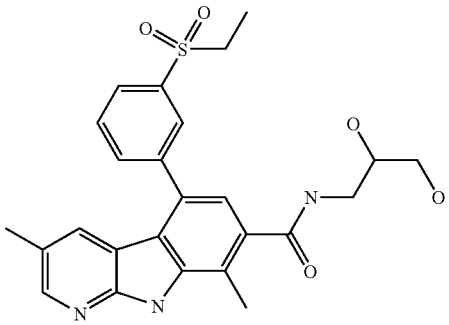

The title compound was synthesized using an analogous procedure to that described in the preparation of compound 87. $^1$H NMR (400 MHz, DMSO-d$_6$) δ ppm 1.17 (t, J=7.33 Hz, 3 H) 2.27 (s, 3 H) 2.64 (s, 3 H) 3.22 (ddd, J=13.14, 6.44, 6.19 Hz, 1 H) 3.35-3.45 (m, 5 H) 3.66 (qd, J=5.60, 5.43 Hz, 1 H) 7.18 (s, 1 H) 7.54 (s, 1 H) 7.89 (t, J=7.83 Hz, 1 H) 8.03 (m, 2 H) 8.13 (s, 1 H) 8.29-8.35 (m, 2 H) 12.09 (s, 1 H). ESI-MS: m/z 482(m+H)$^+$

Compound 102: 5-(3-(ethylsulfonyl)phenyl)-N-(2-hydroxy-2methylpropyl)-3,8-dimethyl-9H-pyrido[2,3-b]indole-7-carboxamide

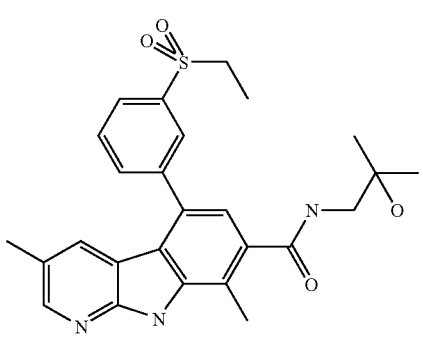

The title compound was synthesized using an analogous procedure to that described in the preparation of compound 87. $^1$H NMR (400 MHz, DMSO-d$_6$) δ ppm 1.17-1.14 (m, 9 H) 2.27 (s, 3 H) 2.64 (s, 3 H) 3.26 (d, J=6.32 Hz, 2 H) 3.41 (q, J=7.33 Hz, 2 H) 7.16 (s, 1 H) 7.54 (s, 1 H) 7.89 (t, J=7.71 Hz, 1 H) 8.04 (d, J=7.58 Hz, 2 H) 8.13 (t, J=1.64 Hz, 1 H) 8.25 (t, J=5.94 Hz, 1 H) 8.31 (d, J=1.26 Hz, 1 H) 12.07 (s, 1 H). ESI-MS: m/z 480 (m+H)$^+$

Compound 103: 5-(3-(ethylsulfonyl)phenyl)-N-(1-isopropylpiperidin-4-yl)-3,8-dimethyl-9H-pyrido[2,3-b]indole-7-carboxamide

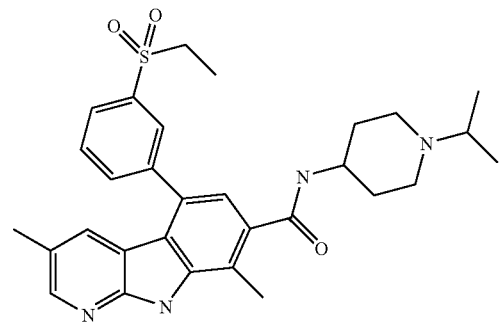

The title compound was synthesized using an analogous procedure to that described in the preparation of compound 87. $^1$H NMR (400 MHz, DMSO-d$_6$) δ ppm 1.13-1.27 (m, 9 H) 1.72-1.84 (m, 2 H) 2.05-2.17 (m, 2 H) 2.27 (s, 3 H) 2.63 (s, 3 H) 3.13 (m, 3 H) 3.42 (m, 4 H) 4.08 (m, 1H) 7.12 (s, 1 H) 7.53 (d, J=1.77 Hz, 1 H) 7.89 (t, J=7.71 Hz, 1 H) 8.04 (m, 2 H) 8.09-8.14 (s, 1 H) 8.32 (d, J=1.52 Hz, 1 H) 8.55 (d, J=7.58 Hz, 1 H) 9.11 (br. s., 1 H) 12.11 (s, 1 H). ESI-MS: m/z 533 (m+H)$^+$

Compound 104: N-(1-ethylpiperidin-4-yl)-5-(3-(ethylsulfonyl)phenyl)-3,8-dimethyl-9H-pyrido[2,3-b]indole-7-carboxamide

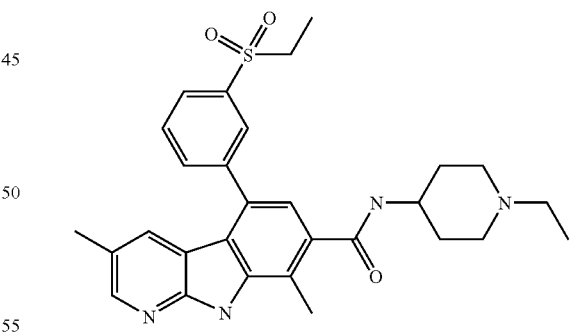

The title compound was synthesized using an analogous procedure to that described in the preparation of compound 87. $^1$H NMR (400 MHz, DMSO-d$_6$) δ ppm 1.14-1.25 (m, 6 H) 1.73 (m, 2 H) 2.00-2.12 (m, 2 H) 2.27 (s, 3 H) 2.63 (s, 3 H) 3.00-3.17 (m, 4 H) 3.42 (q, J=7.33 Hz, 2 H) 3.53 (m, 2 H) 7.12 (s, 1 H) 7.52 (d, J=1.26 Hz, 1 H) 7.89 (t, J=7.71 Hz, 1 H) 7.99-8.07 (m, 2 H) 8.11 (s, 1 H) 8.31 (s, 1 H) 8.53 (d, J=7.58 Hz, 1 H) 9.17 (br. s., 1 H) 12.08 (s, 1 H). ESI-MS: m/z 519 (m+H)$^+$

Compound 105: 5-(3-(ethylsulfonyl)phenyl)-3,8-dimethyl- N-thiazol-2-yl)-9H-pyrido[2,3-b]indole-7-carboxamide

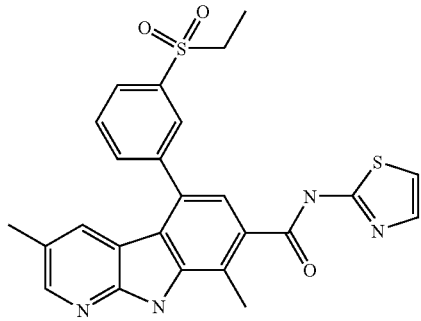

The title compound was synthesized using an analogous procedure to that described in the preparation of compound 87. $^1$H NMR (400 MHz, DMSO-d$_6$) δ ppm 1.18 (t, J=7.33 Hz, 3 H) 2.30 (s, 3 H) 2.72 (s, 3 H) 3.42 (q, J=7.41 Hz, 2 H) 7.30 (d, J=3.54 Hz, 1 H) 7.41 (s, 1 H) 7.56 (d, J=3.79 Hz, 1 H) 7.63 (s, 1 H) 7.90 (t, J=7.83 Hz, 1 H) 8.04 (d, J=7.59 Hz, 1 H) 8.12 (d, J=7.58 Hz, 1 H) 8.21 (s, 1 H) 8.36 (s, 1 H) 12.25 (s, 1 H) 12.66 (br. s., 1 H). ESI-MS: m/z 491 (m+H)$^+$

Compound 106: 5-(3-(ethylsulfonyl)phenyl)-3,8-dimethyl- N-(2-(2,2,2-trifluoroethoxy)ethyl-9H-pyrido[2,3-b]indole-7-carboxamide

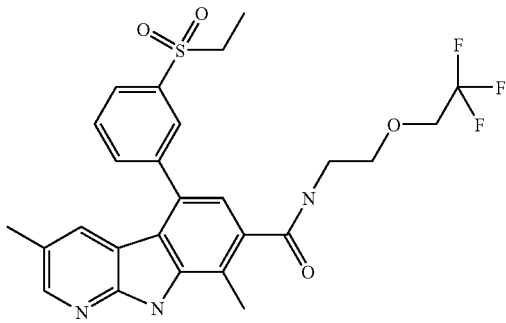

The title compound was synthesized using an analogous procedure to that described in the preparation of compound 87. $^1$H NMR (400 MHz, DMSO-d$_6$) δ ppm 1.17 (t, J=7.33 Hz, 3 H) 2.27 (s, 3 H) 2.63 (s, 3 H) 3.41 (q, J=7.33 Hz, 2 H) 3.47 (q, J=5.56 Hz, 2 H) 3.75 (t, J=5.68 Hz, 2 H) 4.11 (q, J=9.52 Hz, 2 H) 7.14 (s, 1 H) 7.56 (s, 1 H) 7.91 (t, J=7.83 Hz, 1 H) 7.99-8.06 (m, 2 H) 8.12 (s, 1 H) 8.32 (s, 1 H) 8.49 (t, J=5.68 Hz, 1 H) 12.10 (s, 1 H). ESI-MS: m/z 534 (m+H)$^+$

Compound 107: 5-(3-(ethylsulfonyl)phenyl)-3,8-dimethyl- N-(piperidin-3-yl)-9H-pyrido[2,3-b]indole-7-carboxamide

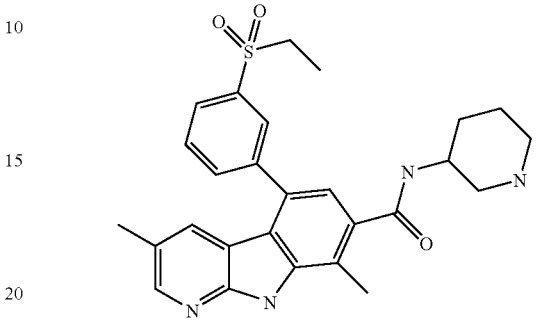

The title compound was synthesized using an analogous procedure to that described in the preparation of compound 87. $^1$H NMR (400 MHz, DMSO-d$_6$) δ ppm 1.17 (t, J=7.33 Hz, 3 H) 1.56-1.69 (m, 2 H) 1.96-1.88 (m, 2 H) 2.27 (s, 3 H) 2.63 (s, 3 H) 2.82 (m, 2 H) 3.22 (m, 1 H) 3.42 (m, 3 H) 4.16 (m, 1 H) 7.16 (s, 1 H) 7.51 (s, 1 H) 7.90 (t, J=7.71 Hz, 1 H) 7.99-8.08 (m, 2H) 8.11 (t, J=1.64 Hz, 1 H) 8.32 (d, J=2.02 Hz, 1 H) 8.51 (d, J=7.58 Hz, 1 H) 8.58-8.74 (m, 2 H) 12.09 (s, 1 H). ESI-MS: m/z 491 (m+H)$^+$

Compound 108: 5-(3-(ethylsulfonyl)phenyl)-3,8-dimethyl- N-(piperidin-4-yl)-9H-pyrido[2,3-b]indole-7-carboxamide

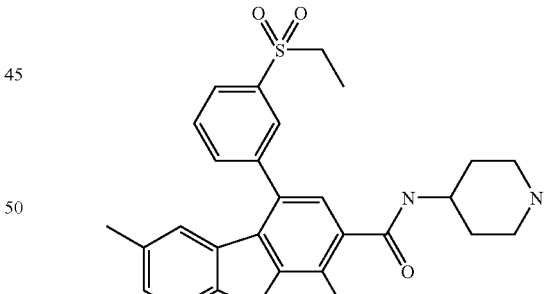

The title compound was synthesized using an analogous procedure to that described in the preparation of compound 87. $^1$H NMR (400 MHz, DMSO-d$_6$) δ ppm 1.18 (t, J=7.33 Hz, 3 H) 1.60-1.77 (m, 2 H) 2.05-2.03 (m, 2H) 2.27 (s, 3 H) 2.62 (s, 3 H) 3.04 (q, J=9.85 Hz, 2 H) 3.33-3.29 (m, 2H) 3.42 (q, J=7.49 Hz, 2 H) 4.10 (m, 1 H) 7.12 (s, 1 H) 7.51 (d, J=1.52 Hz, 1 H) 7.89 (t, J=7.71 Hz, 1 H) 7.99-8.08 (m, 2 H) 8.11 (s, 1 H) 8.32 (d, J=1.52 Hz, 1 H) 8.34-8.42 (m, 1H) 8.51 (d, J=7.58 Hz, 1 H) 8.60-8.66 (m, 1H) 12.08 (s, 1 H). ESI-MS: m/z 491 (m+H)$^+$

Compound 109: 5-(3-(ethylsulfonyl)phenyl)-3,8-dimethyl-N-(piperidin-3-yl)-9H-pyrido[2,3-b]indole-7-carboxamide

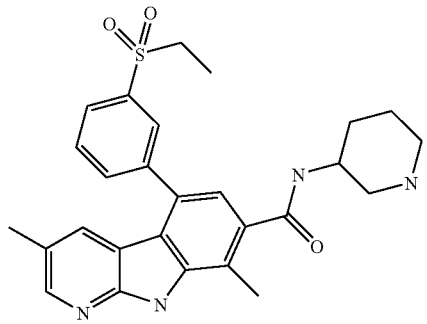

The title compound was synthesized using an analogous procedure to that described in the preparation of compound 87. $^1$H NMR (400 MHz, DMSO-$d_6$) δ ppm 1.17 (t, J=7.45 Hz, 3 H) 1.57-1.69 (m, 2 H) 1.83-2.01 (m, 2 H) 2.27 (s, 3 H) 2.63 (s, 3 H) 2.74-2.90 (m, 2 H) 3.21 (m, 1 H) 3.42 ((m, 3 H)) 4.17 (m, 1 H) 7.16 (s, 1 H) 7.51 (s, 1 H) 7.90 (t, J=7.58 Hz, 1 H) 8.03 (m, 2 H) 8.11 (s, 1 H) 8.32 (s, 1 H) 8.50 (d, J=7.58 Hz, 1 H) 8.58-8.71 (m, 2 H) 12.09 (s, 1 H). ESI-MS: m/z 491 (m+H)$^+$

Compound 110: 5-(3-(ethylsulfonyl)phenyl)-N-(2-(2-hydroxyethoxy)ethyl-3,8-dimethyl-9H-pyrido[2,3-b]indole-7-carboxamide

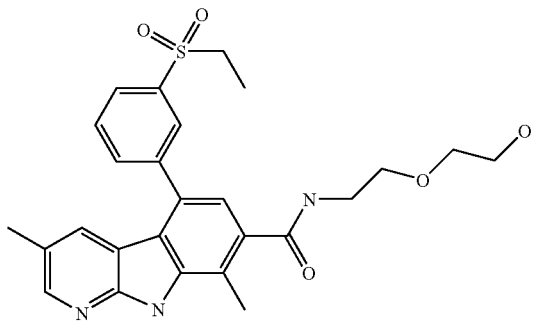

The title compound was synthesized using an analogous procedure to that described in the preparation of compound 87. $^1$H NMR (400 MHz, DMSO-$d_6$) δ ppm 1.17 (t, J=7.20 Hz, 3 H) 2.27 (s, 3 H) 2.63 (s, 3 H) 3.37-3.58 (m, 11 H) 7.14 (s, 1 H) 7.55 (s, 1 H) 7.88 (t, J=7.82 Hz, 1 H) 8.04-8.03 (m, 2H) 8.12 (s, 1 H) 8.31 (s, 1 H) 8.41 (t, J=5.68 Hz, 1 H) 12.08 (s, 1 H) ESI-MS: m/z 496 (m+H)$^+$

Compound 111: 5-(3-(cyclopropanecarboxamido)phenyl)-N-(2-(dimethylamino)ethyl)-3,8-dimethyl-9H-pyrido[2,3-b]indole-7-carboxamide

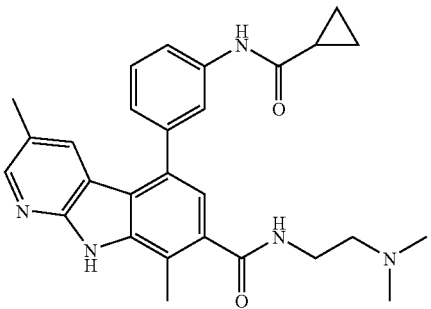

The title compound was synthesized using an analogous procedure to that described in the preparation of compound 87. $^1$H NMR (400 MHz, DMSO-$d_6$) δ ppm 0.75-0.84 (m, 4 H) 1.80 (t, J=4.93 Hz, 1 H) 2.27 (s, 3 H) 2.64 (s, 3 H) 2.87 (d, J=4.55 Hz, 6 H) 3.29 (q, J=5.56 Hz, 2 H) 3.61 (q, J=5.64 Hz, 2 H) 7.16 (s, 1 H) 7.27 (d, J=7.33 Hz, 1 H) 7.50 (t, J=7.71 Hz, 1 H) 7.63 (d, J=8.34 Hz, 1 H) 7.68 (s, 1 H) 7.99 (s, 1 H) 8.29 (s, 1 H) 8.58 (t, J=5.43 Hz, 1 H) 9.39 (br. s., 1 H) 10.38 (s, 1 H) 11.99 (s, 1 H); ESI-MS: m/z calc'd for C28H31N5O2 469.25; found 470.4 (M+H)$^+$

Compound 112: 5-(3-(ethylsulfonyl)phenyl)-3,8-dimethyl-N-(1-methylpiperidin-4-yl)-9H-pyrido[2,3-b]indole-7-carboxamide

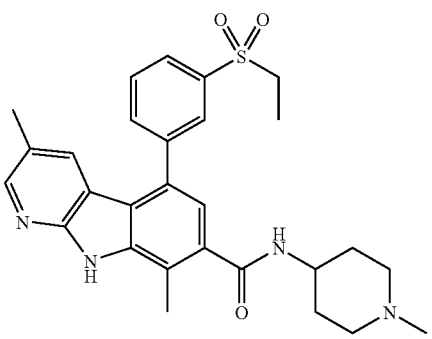

The title compound was synthesized using an analogous procedure to that described in the preparation of compound 87. $^1$H NMR (400 MHz, DMSO-$d_6$) δ ppm 1.18 (t, J=7.45 Hz, 3 H) 1.72-1.75 (m, 2 H) 1.98 (m, 1 H) 2.10 (d, J=14.65 Hz, 2 H) 2.27 (s, 3 H) 2.62 (s, 3 H) 2.77 (d, J=4.55 Hz, 3 H) 3.06-3.17 (m, 2 H) 3.39-3.48 (m, 4 H) 7.11 (s, 1 H) 7.51 (s, 1 H) 7.89 (t, J=7.71 Hz, 1 H) 8.03 (dd, J=14.91, 7.83 Hz, 2 H) 8.11 (s, 1 H) 8.32 (d, J=1.52 Hz, 1 H) 8.50 (d, J=7.58 Hz, 1 H) 9.28 (br. s., 1 H) 12.08 (s, 1 H); ESI-MS: m/z calc'd for C28H32N4O3S 504.22; found 505.4 (M+H)$^+$ Compound 113: 5-(3-(ethylsulfonyl)phenyl)-3,8-dimethyl-N-((1-methylpiperidin-4-yl)methyl)-9H-pyrido[2,3-b]indole-7-carboxamide

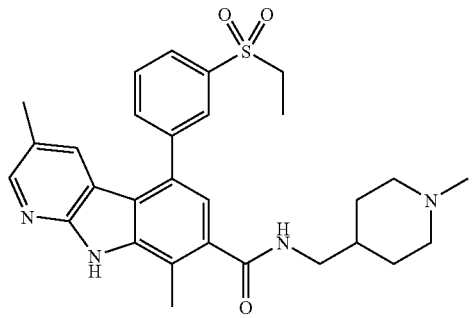

The title compound was synthesized using an analogous procedure to that described in the preparation of compound 87. $^1$H NMR (400 MHz, DMSO-d$_6$) δ ppm 1.18 (t, J=7.33 Hz, 3 H) 1.38 (d, J=10.86 Hz, 2 H) 1.78 (br. s., 1 H) 1.91 (d, J=13.39 Hz, 2 H) 2.27 (s, 3 H) 2.63 (s, 3 H) 2.75 (d, J=4.80 Hz, 3 H) 2.86-2.97 (m, 2 H) 3.20 (t, J=6.19 Hz, 2 H) 3.42 (q, J=7.33 Hz, 4 H) 7.14 (s, 1 H) 7.51 (d, J=1.26 Hz, 1 H) 7.89 (t, J=7.71 Hz, 1 H) 8.03 (dd, J=10.61, 8.59 Hz, 2 H) 8.12 (s, 1 H) 8.32 (d, J=1.52 Hz, 1 H) 8.50 (q, J=6.06 Hz, 1 H) 9.18 (br. s., 1 H) 12.08 (s, 1 H); ESI-MS: m/z calc'd for C29H34N4O3S 518.24; found 519.4 (M+H)$^+$ Compound 114: N-(3-(dimethylamino)propyl)-5-(3-(ethylsulfonyl)phenyl)-3,8-dimethyl-9H-pyrido[2,3-b]indole-7-carboxamide

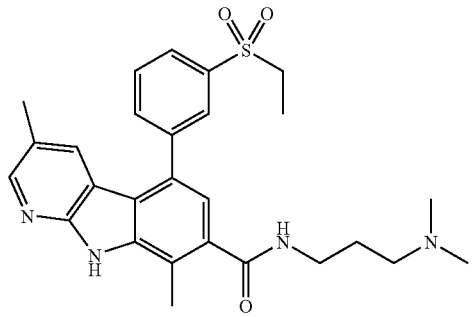

The title compound was synthesized using an analogous procedure to that described in the preparation of compound 87. $^1$H NMR (400 MHz, DMSO-d$_6$) δ ppm 1.18 (t, J=7.33 Hz, 3 H) 1.85-1.95 (m, 1 H) 1.91 (d, J=7.83 Hz, 1 H) 2.27 (s, 3 H) 2.65 (s, 3 H) 2.80 (d, J=4.80 Hz, 6 H) 3.13 (dt, J=10.36, 5.18 Hz, 2 H) 3.34 (q, J=6.32 Hz, 2 H) 3.42 (q, J=7.41 Hz, 2 H) 7.17 (s, 1 H) 7.52 (s, 1 H) 7.90 (t, J=7.71 Hz, 1 H) 8.04 (t, J=9.09 Hz, 2 H) 8.12 (s, 1 H) 8.32 (d, J=1.52 Hz, 1 H) 8.53 (t, J=5.81 Hz, 1 H) 9.35 (br. s., 1 H) 12.08 (s, 1 H); ESI-MS: m/z calc'd for C27H32N4O3S 492.22; found 493.4 (M+H)$^+$ Compound 115: 5-(3-(ethylsulfonyl)phenyl)-3,8-dimethyl-N-(2-(pyrrolidin-1-yl)ethyl)-9H-pyrido[2,3-b]indole-7-carboxamide

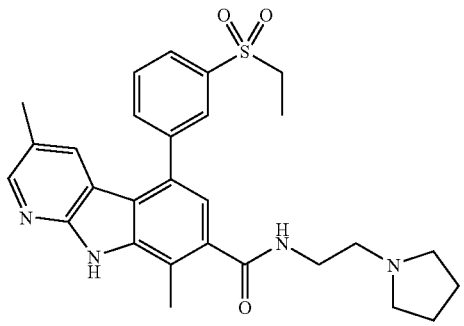

The title compound was synthesized using an analogous procedure to that described in the preparation of compound 87. $^1$H NMR (400 MHz, DMSO-d$_6$) δ ppm 1.17 (t, J=7.33 Hz, 3 H) 1.87 (dd, J=7.20, 4.93 Hz, 2 H) 2.03 (t, J=6.82 Hz, 2 H) 2.27 (s, 3 H) 3.08 (dd, J=10.48, 7.45 Hz, 2 H) 3.36 (q, J=5.89 Hz, 2 H) 3.42 (q, J=7.33 Hz, 2 H) 3.63 (td, J=12.88, 5.56 Hz, 4 H) 7.24 (s, 1 H) 7.52 (s, 1 H) 7.90 (t, J=7.71 Hz, 1 H) 8.04 (dd, J=14.27, 7.71 Hz, 2 H) 8.12 (s, 1 H) 8.33 (d, J=1.52 Hz, 1 H) 8.62 (t, J=5.68 Hz, 1 H) 9.53 (br. s., 1 H) 12.10 (s, 1 H); ESI-MS: m/z calc'd for C28H32N4O3S 504.22; found 505.4 (M+H)$^+$ Compound 116: (S)-5-(3-(ethylsulfonyl)phenyl)-3,8-dimethyl-N-(1-methylpiperidin-3-yl)-9H-pyrido[2,3-b]indole-7-carboxamide

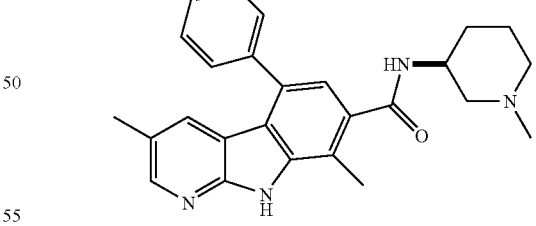

The title compound was synthesized using an analogous procedure to that described in the preparation of compound 87. $^1$H NMR (400 MHz, DMSO-d$_6$) δ ppm 1.18 (t, J=7.45 Hz, 3 H) 1.20-2.0 (m, 6 H) 2.27 (s, 3 H) 2.62 (s, 3 H) 2.70-4.4 (m, 8 H) 7.12 (s, 1 H) 7.52 (s, 1 H) 7.91 (d, J=7.58 Hz, 1 H) 8.01 (d, J=8.84 Hz, 1 H) 8.06 (d, J=8.84 Hz, 1 H) 8.11 (d, J=1.52 Hz, 1 H) 8.33 (s, 1 H) 8.62 (d, J=7.83 Hz, 1 H). [M+H] calc'd for C$_{28}$H$_{32}$N$_2$O$_2$S 505; found 505.4.

Compound 117: (R)-5-(3-(ethylsulfonyl)phenyl)-3,8-dimethyl-N-(1-methylpiperidin-3-yl)-9H-pyrido[2,3-b]indole-7-carboxamide

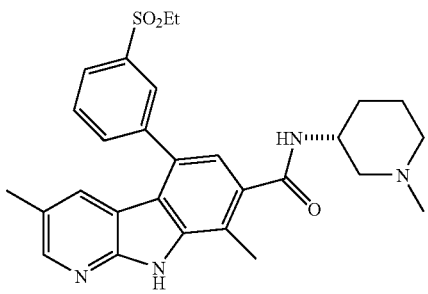

The title compound was synthesized using an analogous procedure to that described in the preparation of compound 87. $^1$H NMR (400 MHz, DMSO-$d_6$) δ ppm 1.18 (t, J=7.45 Hz, 3 H) 1.20-2.0 (m, 6 H) 2.27 (s, 3 H) 2.62 (s, 3 H) 2.70-4.40 (m, 8 H) 7.13 (s, 1 H) 7.53 (d, J=1.01 Hz, 1 H) 7.90 (t, J=7.83 Hz, 1 H) 8.04 (dd, J=17.43, 8.34 Hz, 2 H) 8.11 (d, J=1.52 Hz, 1 H) 8.33 (s, 1 H) 8.62 (d, J=7.83 Hz, 1 H) 12.11 (s, 1 H). [M+H] calc'd for $C_{28}H_{32}N_2O_2S$ 505; found, 505.4.

Compound 118: 5-chloro-3,8-dimethyl-N-(1-methylpiperidin-4-yl)-9H-pyrido[2,3-b]indole-7-carboxamide

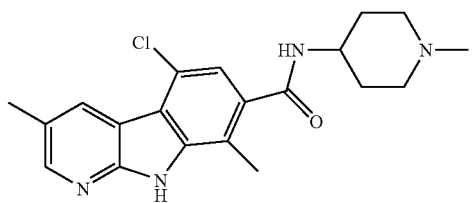

The title compound was synthesized from 5-chloro-3,8-dimethyl-9H-pyrido[2,3-b]indole-7-carboxalic acid and 1-methylpiperidin-4-amine using an analogous procedure to that described in the preparation of compound 87. $^1$H NMR (400 MHz, DMSO-$d_6$ with TFD) δ ppm 1.70-2.2 (m, 4 H) 2.53 (br. s., 3 H) 2.58 (s, 3 H) 2.74-2.82 (m, 3 H) 2.80-4.10 (m, 5 H) 7.29 (s, 1 H) 8.47 (s, 1 H) 8.70 (s, 1 H). [M+H] calc'd for $C_{20}H_{18}N_2O_2S$ 371; found 371.4.

Compound 119: 5-(3-(cyclopropanecarboxamido)phenyl)-3,8-dimethyl-N-(1-methyl-piperidin-4-yl)-9H-pyrido[2,3-b]indole-7-carboxamide

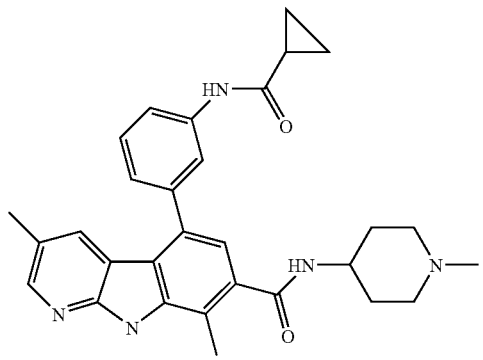

The title compound was synthesized from 5-chloro-3,8-dimethyl-N-(1-methylpiperidin-4-yl)-9H-pyrido[2,3-b]indole-7-carboxamide and 3-(cyclopropanecarboxamido)phenyl boronic acid using an analogous procedure to that described in the preparation of compound 83. $^1$H NMR (400 MHz, DMSO-$d_6$) δ ppm 0.77-0.82 (m, 4 H) 1.53 (qd, J=11.66, 3.41 Hz, 2 H) 1.79-1.82 (m, 3 H) 1.95 (t, J=10.86 Hz, 2 H) 2.15 (s, 3 H) 2.27 (s, 3 H) 2.59 (s, 3 H) 2.74 (d, J=11.12 Hz, 2 H) 3.75 (m, 1 H) 6.98 (s, 1 H) 7.27 (d, J=7.58 Hz, 1 H) 7.49 (t, J=7.96 Hz, 1 H) 7.69 (d, J=2.02 Hz, 2 H) 7.91 (s, 1 H) 8.25-8.30 (m, 2 H) 10.37 (s, 1 H) 11.92 (br. s., 1 H); [M+H] calc'd for $C_{30}H_{34}N_5O_2$, 496.3.; found, 496.4.

Compound 120: 5-chloro-N-(2-(dimethylamino)ethyl)-3,8-dimethyl-9H-pyrido[2,3-b]indole-7-carboxamide

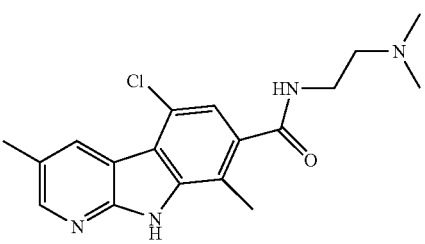

The title compound was synthesized from 5-chloro-3,8-dimethyl-9H-pyrido[2,3-b]indole-7-carboxalic acid and N,N-dimethylethane-1,2-diamine using an analogous procedure to that described in the preparation of compound 87. $^1$H NMR (400 MHz, DMSO-$d_6$) δ ppm 2.20 (s, 6 H) 2.42 (t, J=6.69 Hz, 2 H) 2.49 (br. s., 3 H) 2.55 (s, 3 H) 3.35 (d, J=6.57 Hz, 2 H) 7.18 (s, 1 H) 8.31 (t, J=5.56 Hz, 1 H) 8.40 (d, J=2.02 Hz, 1 H) 8.53 (s, 1 H) 12.14 (s, 1 H). [M+H] calc'd for $C_{18}H_{21}ClN_4O$ 345; found, 345.4.

Compound 121: 5-(3-(cyclopropylcarbamoyl)phenyl)-N-(2-(dimethylamino)ethyl)-3,8-dimethyl-9H-pyrido[2,3-b]indole-7-carboxamide

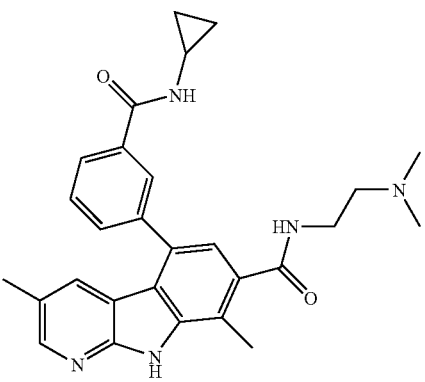

The title compound was synthesized from 5-chloro-N-(2-(dimethylamino)ethyl)-3,8-dimethyl-9H-pyrido[2,3-b]indole-7-carboxamide and 3-(cyclopropylcarbamoyl)phenyl boronic acid using an analogous procedure to that described in the preparation of compound 83. $^1$H NMR (400 MHz, DMSO-$d_6$) δ ppm 0.57 (dd, J=3.92, 2.40 Hz, 2 H) 0.71 (dd, J=6.95, 2.40 Hz, 2 H) 1.23 (s, 1 H) 2.26 (s, 3 H) 2.65 (s, 3 H) 2.87 (d, J=5.05 Hz, 6 H) 3.29 (q, J=5.98 Hz, 2 H) 3.61 (q, J=6.15 Hz, 2 H) 7.20 (s, 1 H) 7.50 (s, 1 H) 7.66 (t, J=7.83 Hz, 1 H) 7.77 (d, J=7.83 Hz, 1 H) 7.98 (d, J=7.83 Hz, 1 H) 8.08 (s, 1 H) 8.31 (d, J=1.77 Hz, 1 H) 8.57-8.61 (m, 1 H) 8.59 (d, J=4.55 Hz, 1 H) 12.05 (s, 1 H). [M+H] calc'd for $C_{28}H_{31}N_5O_2$ 470; found, 470.4.

Compound 122: 4-(2-Fluoro-5-methyl-pyridin-3-yl)-3,5-dinitro-benzonitrile

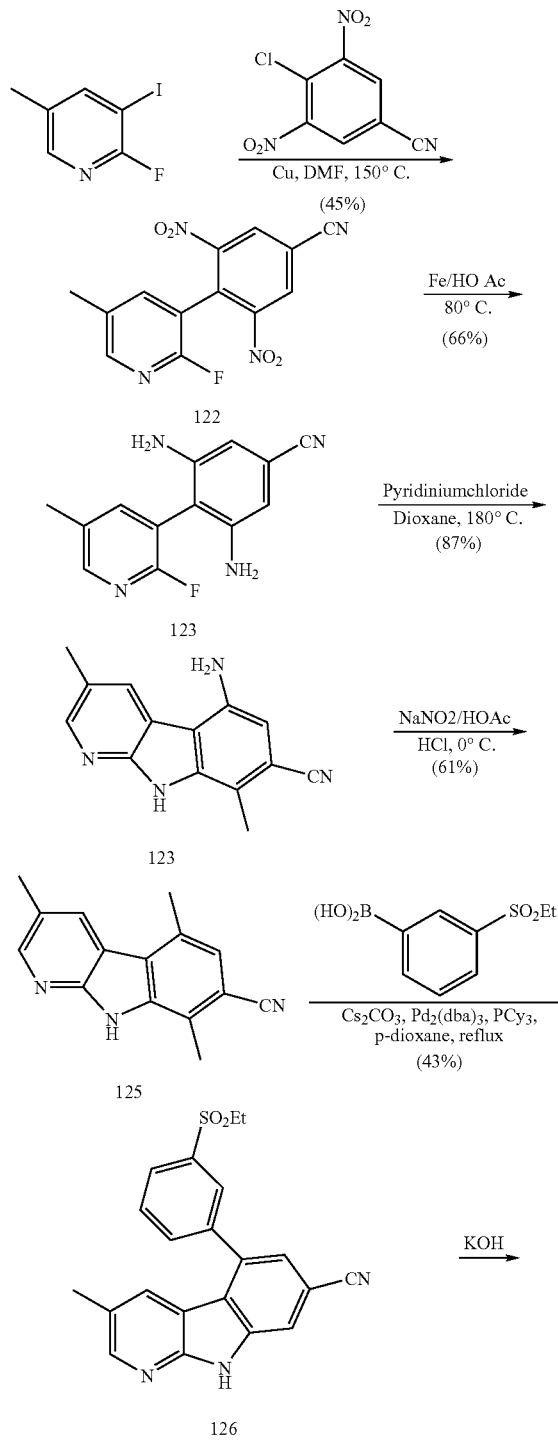

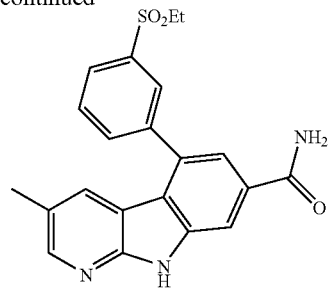

127

4-Chloro-3,5-dinitro-benzonitrile (200 mg, 0.88 mmol), 2-fluoro-3-iodo-5-picoliene (208 mg, 0.88 mmol), and copper (45 µm powder, 168 mg, 2.6 mmol) were combined in DMF (2 mL) in a sealed tube purged with nitrogen. The reaction was heated at 150° C. for 30 min in the microwave. The reaction was diluted with acetone and the solids were removed by filtration. The solution was concentrated in vacuo. Purification by silica gel chromatography (80% $CH_2Cl_2$/hexanes) gave 119 mg (45%) of the title compound as a faintly yellow solid, which was slow to crystallize. $^1$H NMR (400 MHz, CDCl$_3$): δ 8.50 (s, 2H), 8.16 (d, 1H, J=1.2 Hz), 7.42 (dd, 1H, J=8.8, 2.0 Hz), 2.38 (s, 3H). MS (ES) [m+H] calc'd for $C_{13}H_7FN_4O_4$, 303; found 303.

Compound 123: 3,5-Diamino-4-(2-fluoro-5-methyl-pyridin-3-yl)-benzonitrile

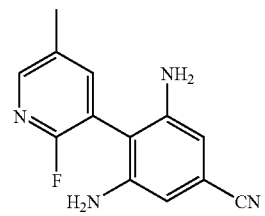

Compound 122 (119 mg, 0.39 mmol) was stirred in HOAc (3 mL) with H$_2$O (0.5 mL) and stirred at 76° C. Iron powder (~325 mesh, 88 mg, 1.56 mmol) was added, and the reaction stirred for 4 h. The solution was concentrated in vacuo, diluted with EtOAc (30 mL), and made basic with sat. NaHCO$_3$. The material was then filtered through Celite, and the organics were separated, dried (MgSO$_4$), and concentrated in vacuo to give 148 mg (66%) of the title compound as a brown oil. MS (ES) [m+H] calc'd for $C_{13}H_{11}FN_4$, 243; found 243.

Compound 124: 5-Amino-3-methyl-9H-pyrido[2,3-b]indole-7-carbonitrile

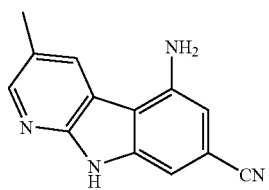

Compound 123 (148 mg, 0.61 mmol) was dissolved in dioxane (2 mL) with pyridinium chloride (80 mg), and the solution was heated at 180° C. in the microwave for 15 minutes. The solution was concentrated in vacuo. Purification by flash chromatography (20% acetone/CH$_2$Cl$_2$) gave 118 mg (87%) of the title compound as an off-white solid. MS (ES) [m+H] calc'd for C$_{13}$H$_{10}$N$_4$, 223; found 223.

Compound 125: 5-Iodo-3-methyl-9H-pyrido[2,3-b]indole-7-carbonitrile

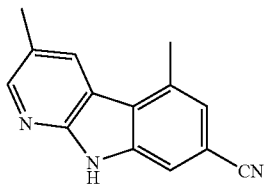

Compound 124 (118 mg, 0.53 mmol) was dissolved in HOAc (2 mL) with H$_2$O (1 mL), and the solution stirred at 0° C. Concentrated HCl (120 µL) in H$_2$O (120 mL) was added, and the reaction stirred for 5 min. Sodium nitrite (54 mg, 0.78 mmol) in H$_2$O (120 µL) was added dropwise, and the red solution stirred for 10 min. A solution of iodine (10 mg) and potassium iodide (129 mg, 0.78 mmol) in H$_2$O (300 µL) was added dropwise, and the brown frothy solution stirred for 30 min at 0° C. and then 30 min while warming to r.t. The reaction was diluted with H$_2$O (5 mL) and extracted with CHCl$_3$. Organics were dried (MgSO$_4$) and concentrated in vacuo. Purification by silica gel chromatography gave 108 mg (61%) of the title compound as a faintly yellow solid. MS (ES) [m+H] calc'd for C$_{13}$H$_8$IN$_3$, 334; found 334.

Compound 126: 5-(3-Ethanesulfonyl-phenyl)-3-methyl-9H-pyrido[2,3-b]indole-7-carbonitrile

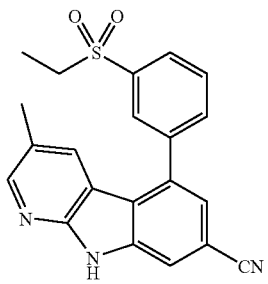

The title compound was prepared in 43% yield from Compound 125 according to the procedure outlined in the preparation of compound 81. $^1$H NMR (400 MHz, CD$_3$OD) δ 8.34 (s, 1H), 8.21 (s, 1H), 8.13 (d, 1H, J=7.6 Hz), 8.00 (t, 1H, J=7.6 Hz), 7.89-7.98 (m, 2H), 7.59 (s, 1H), 7.49 (s, 1H), 3.35 (q, 2H, J=7.2 Hz), 2.33 (s, 3H), 1.29 (t, 3H, J=7.2 Hz). MS (ES) [m+H] calc'd for C$_{21}$H$_{17}$N$_3$O$_2$S, 376; found 376.

Compound 127: 5-(3-Ethanesulfonyl-phenyl)-3-methyl-9H-pyrido[2,3-b]indole-7-carboxylic acid amide

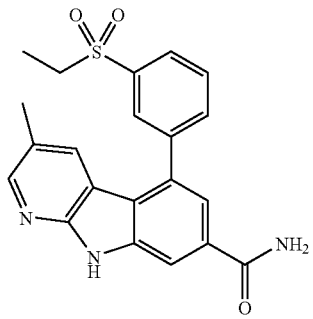

Compound 126 (30 mg, 0.08 mmol) stirred in dioxane (2 mL) at r.t. A solution of potassium hydroxide (25 mg, 0.44 mmol) in 30% H$_2$O$_2$ solution (1 mL) was added, and the reaction stirred for 18 h. The solution was neutralized with 1N HCl and concentrated in vacuo. Purification by silica gel chromatography (5 to 8% MeOH/CH$_2$Cl$_2$ gave 14.8 mg (47%) of the title compound as a white solid. $^1$H NMR (400 MHz, CD$_3$OD) δ 8.28 (s, 1H), 8.22 (s, 1H), 8.12 (s, 1H), 8.10 (d, 1H, J=7.6 Hz), 8.02 (d, 1H, J=7.6 Hz), 7.88 (t, 1H, J=7.68 (s, 1H), 7.62 (s, 1H), 3.34 (q, 2H, J=7.2 Hz), 2.31 (s, 3H), 1.29 (t, 3H, J=7.2 Hz). MS (ES) [m+H] calc'd for C$_{21}$H$_{19}$N$_3$O$_3$S, 394; found 394.

Compound 128: 4-(2-Fluoro-5-methyl-pyridin-3-yl)-3,5-dinitro-benzoic acid methyl ester

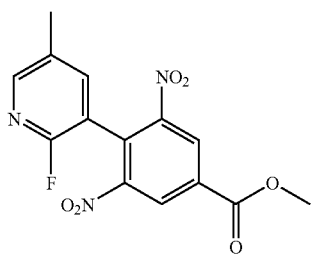

The title compound was prepared from 4-chloro-3,5-dinitro-benzoic acid methyl ester in 94% yield according to the procedure outline for the preparation of Compound 122. MS (ES) [m+H] calc'd for C$_{14}$H$_{10}$FN$_3$O$_6$, 336; found 336.

Compound 129: 3,5-Diamino-4-(2-fluoro-5-methyl-pyridin-3-yl)-benzoic acid methyl ester

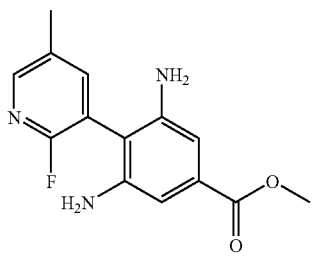

Compound 128 (2.02, 6.03 mmol) was stirred in MeOH (150 mL) with 10% Pd/C (200 mg) under a balloon of hydrogen for 1.5 h. The reaction was filtered through Celite and concentrated to give 1.64 g (99%) of the title compound as a brown solid. MS (ES) [m+H] calc'd for $C_{14}H_{14}FN_3O_2$, 276; found 276.

Compound 130: 5-Amino-3-methyl-9H-pyrido[2,3-b]indole-7-carboxylic acid methyl ester

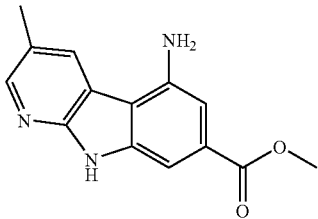

The title compound was prepared in 88% yield from example Compound 128 according to the procedure outlined for the preparation of Compound 124. MS (ES) [m+H] calc'd for $C_{14}H_{13}N_3O_2$, 256; found 256.

Compound 131: 5-Todo-3-methyl-9H-pyrido[2,3-b]indole-7-carboxylic acid methyl ester

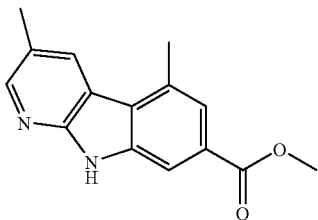

The title compound was prepared in 69% yield from Compound 130 according to the procedure outlined for the preparation of Compound 125. MS (ES) [m+H] calc'd for $C_{14}H_{11}IN_2O_2$, 367; found 367.

Compound 132: 5-(3-Ethanesulfonyl-phenyl)-3-methyl-9H-pyrido[2,3-b]indole-7-carboxylic acid methyl ester

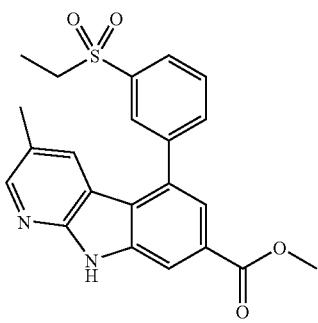

The title compound was prepared in 65% yield from Compound 131 according to the procedure outlined in the preparation of Compound 81. MS (ES) [m+H] calc'd for $C_{22}H_{20}N_2O_4S$, 409; found 409.

Compound 133: [5-(3-Ethanesulfonyl-phenyl)-3-methyl-9H-pyrido[2,3-b]indol-7-yl]-methanol

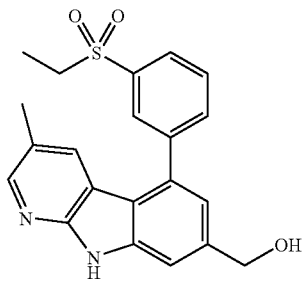

LAH reduction of Compound 132 provided the title compound. $^1$H NMR (400 MHz, MeOD) δ ppm 1.29 (t, J=7.45 Hz, 5 H) 2.40 (s, 4 H) 7.34 (s, 1 H) 7.74 (d, J=0.51 Hz, 1 H) 7.90 (t, J=7.83 Hz, 2 H) 7.99 (s, 1 H) 8.03 (ddd, J=7.71, 1.39, 1.26 Hz, 2 H) 8.11 (d, J=7.07 Hz, 1 H) 8.22 (t, J=1.52 Hz, 1 H) 8.27 (br. s., 1 H) [M+H] calc'd for $C_{21}H_{20}N_2O_3S$, 381; found, 381.

Compound 134: [5-(3-Ethanesulfonyl-phenyl)-3-methyl-9H-pyrido[2,3-b]indol-7-ylmethyl]-dimethyl-amine

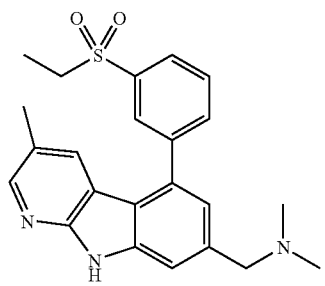

Methanesulfonyl chloride (18 μL, 0.24 mmol) was added to a solution of Compound 133 (46 mg, 0.12 mmol) and diisopropylethylamine (43 μL, 0.25 mmol) in THF (1 mL) at 0° C. After stirring for 3 h, dimethylamine (2M, 1 mL, 2 mmol) was added, and the reaction stirred for 16 h. The solution was concentrated in vacuo and purified by prep-HPLC to give 32 mg (65%) of the title compound as a pale yellow oil. $^1$H NMR (400 MHz, CD$_3$OD) δ 8.36 (br s, 1H), 8.22 (s, 1H), 8.13 (d, 1H, J=7.6 Hz), 8.05 (d, 1H, J=7.6 Hz), 7.88-7.94 (m, 2H), 7.85 (s, 1H), 7.44 (s, 1H), 4.57 (s, 2H), 3.33 (q, 2H, J=7.2Hz), 2.94 (s, 6H), 2.39 (s, 3H), 1.30 (t, 3H, J=7.2 Hz). MS (ES) [m+H] calc'd for $C_{23}H_{25}N_3O_2S$, 408; found 408.

Compound 135: 5-(3-Ethanesulfonyl-phenyl)-3-methyl-7-morpholin-4-ylmethyl-9H-pyrido[2,3-b]indole

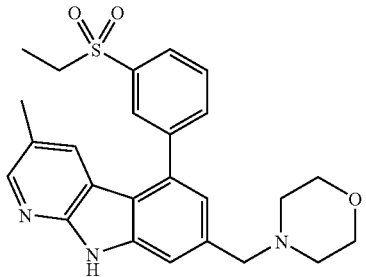

The title compound was prepared from Compound 133 and morpholine according to the procedure outline for the preparation of Compound 134. $^1$H NMR (400 MHz, CD$_3$OD) δ 8.42 (br s, 1H), 8.24 (s, 1H), 8.14 (d, 1H, J=7.6 Hz), 8.03 (d, 1H, J=7.6 Hz), 7.97 (s, 1H), 7.90 (t, 1H, J=7.6 Hz), 7.87 (s, 1H), 7.48 (s, 1H), 4.62 (s, 2H), 4.00-4.09 (m, 2H), 3.71-3.80 (m, 2H), 3.41-3.50 (m, 2H), 3.27-3.32 (m, 4H), 2.39 (s, 3H), 1.29 (t, 3H, J=7.2 Hz). MS (ES) [m+H] calc'd for C$_{25}$H$_{27}$N$_3$O$_3$S, 450; found 450.

Compound 136: 5-(3-Ethanesulfonyl-phenyl)-3-methyl-7-(4-methyl-piperazin-1-ylmethyl)-9H-pyrido[2,3-b]indole

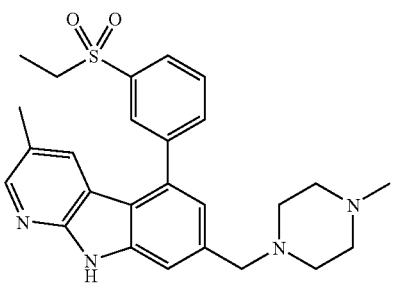

The title compound was prepared from Compound 133 and morpholine according to the procedure outline for the preparation of Compound 134. $^1$H NMR (400 MHz, CD$_3$OD) δ 8.39 (br s, 1H), 8.23 (s, 1H), 8.12 (d, 1H, J=7.6 Hz), 8.05 (s, 1H), 8.03 (d, 1H, J=7.6 Hz), 7.90 (t, 1H, J=7.6 Hz), 7.83 (s, 1H), 7.49 (s, 1H), 4.38 (s, 2H), 3.48-3.56 (m, 2H), 3.26-3.40 (m, 6H), 2.95 (s, 3H), 2.41 (s, 3H), 1.29 (t, 3H, J=7.2 Hz). MS (ES) [m+H] calc'd for C$_{26}$H$_{30}$N$_4$O$_2$S, 463; found 463.

Compound 137: 5-(3-Ethanesulfonyl-phenyl)-3-methyl-7-pyrrolidin-1-ylmethyl-9H-pyrido[2,3-b]indole

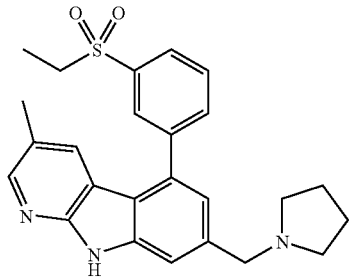

The title compound was prepared from Compound 133 and morpholine according to the procedure outline for the preparation of Compound 134. $^1$H NMR (400 MHz, CD$_3$OD) δ 8.36 (br s, 1H), 8.23 (s, 1H), 8.13 (d, 1H, J=7.6 Hz), 8.04 (d, 1H, J=7.6 Hz), 7.96 (s, 1H), 7.91 (t, 1H, J=7.6 Hz), 7.87 (s, 1H), 7.47 (s, 1H), 4.62 (s, 2H), 3.51-3.60 (m, 2H), 3.20-3.36 (m, 4H), 2.39 (s, 3H), 2.15-2.23 (m, 2H), 1.99-2.07 (m, 2H), 1.29 (t, 3H, J=7.2 Hz). MS (ES) [m+H] calc'd for C$_{25}$H$_{27}$N$_3$O$_2$S, 434; found 434.

Compound 138: [5-(3-Ethanesulfonyl-phenyl)-3-methyl-9H-pyrido[2,3-b]indol-7-ylmethyl]-ethyl-amine

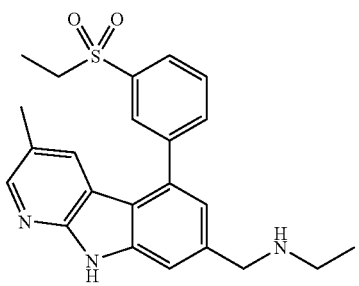

The title compound was prepared from Compound 133 and morpholine according to the procedure outline for the preparation of Compound 134. $^1$H NMR (400 MHz, CD$_3$OD) δ 8.19 (s, 1H), 8.13 (s, 1H), 8.04 (d, 1H, J=7.6 Hz), 7.97 (d, 1H, J=7.6 Hz), 7.84 (t, 1H, J=7.6 Hz), 7.64 (s, 1H), 7.54 (s, 1H), 7.22 (s, 1H), 4.25 (s, 2H), 3.34 (q, 2H, J=7.2 Hz), 2.99-3.07 (m, 2H), 2.25 (s, 3H), 1.20-1.29 (m, 6H). MS (ES) [m+H] calc'd for C$_{23}$H$_{25}$N$_3$O$_2$S, 408; found 408.

Compound 139: 5-(3-Ethanesulfonyl-phenyl)-3-methyl-9H-pyrido[2,3-b]indole-7-carboxylic acid

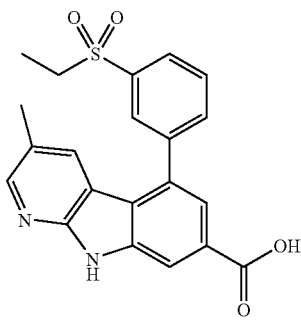

Compound 132 (260 mg, 0.64 mmol) was stirred 1N NaOH (1 mL) in MeOH (2 mL) at 60° C. for 2 h. The reaction was allowed to cool, and was acidified with 1 N HCl and extracted with CHCl$_3$. Organics were dried (MgSO$_4$) and concentrated to give 228 mg (90%) of the title compound as a white solid. $^1$H NMR (400 MHz, CD$_3$OD) δ 8.34 (br s, 1H), 8.29 (s, 1H), 8.21 (s, 1H), 8.11 (d, 1H, J=7.6 Hz), 8.01 (d, 1H, J=7.6 Hz), 7.90 (t, 1H, J=7.6 Hz), 7.87 (s, 1H), 7.79 (s, 1H), 3.31 (q, 2H, J=7.2 Hz), 2.35 (s, 3H), 1.29 (t, 3H, J=7.2 Hz). MS (ES) [m+H] calc'd for C$_{21}$H$_{18}$N$_2$O$_4$S, 395; found 395.

Compound 140: [5-(3-Ethanesulfonyl-phenyl)-3-methyl-9H-pyrido[2,3-b]indol-7-yl]-(4-methyl-piperazin-1-yl)-methanone

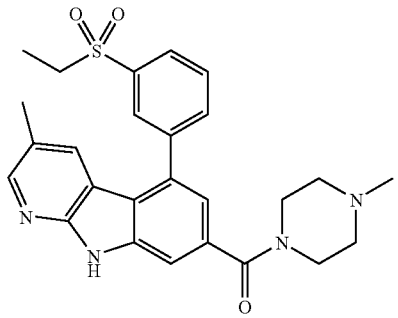

Compound 139 (40 mg, 0.1 mmol) and HOBT (17 mg, 0.11 mmol) stirred in $CH_2Cl_2$ (2 mL) at r.t. EDC (29 mt, 0.15 mmol) and 1-methylpiperazine (45 mL, 0.4 mmol) were added, and the reaction stirred for 3 h. Organics were washed with brine, dried ($Na_2SO_4$), and concentrated in vacuo. Purification by prep-HPLC gave 32 mg (67%) of the title compound as a pale yellow solid. $^1H$ NMR (400 MHz, $CD_3OD$) δ 8.36 (s, 1H), 8.22 (s, 1H), 8.12 (d, 1H, J=7.6 Hz), 8.03 (d, 1H, J=7.6 Hz), 7.87-7.95 (m, 2H), 7.80 (s, 1H), 7.40 (s, 1H), 3.39-3.62 (m, 4H), 3.31 (q, 2H, J=7.2 Hz), 3.16-3.30 (m, 4H), 2.95 (s, 3H), 2.38 (s, 3H), 1.29 (t, 3H, J=7.2 Hz). MS (ES) [m+H] calc'd for $C_{26}H_{28}N_4O_3S$, 477; found 477.

Compound 141: 5-(3-Ethanesulfonyl-phenyl)-3-methyl-9H-pyrido[2,3-b]indole-7-carboxylic acid (2-dimethylamino-ethyl)-amide

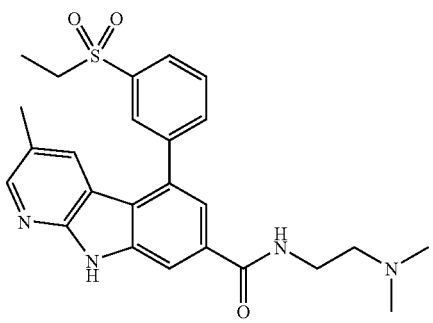

The title compound was prepared in 65% yield according to the procedure outlined for the preparation of Compound 140. $^1H$ NMR (400 MHz, $CD_3OD$) δ 8.38 (br s, 1H), 8.23 (s, 1H), 8.20 (s, 1H), 8.12 (d, 1H, J=7.6 Hz), 8.04 (d, 1H, J=7.6 Hz), 7.91 (t, 1H, J=7.6 Hz), 7.84 (s, 1H), 7.75 (s, 1H), 3.80-3.86 (m, 2H), 3.42 (t, 2H, J=5.6 Hz), 3.34 (q, 2H, J=7.2 Hz), 3.01 (s, 6H), 2.38 (s, 3H), 1.30 (t, 3H, J=7.2 Hz). MS (ES) [m+H] calc'd for $C_{25}H_{28}N_4O_3S$, 465; found 465.

Compound 142: 5-(3-Ethanesulfonyl-phenyl)-3-methyl-9H-pyrido[2,3-b]indole-7-carboxylic acid (3-dimethylamino-propyl)-amide

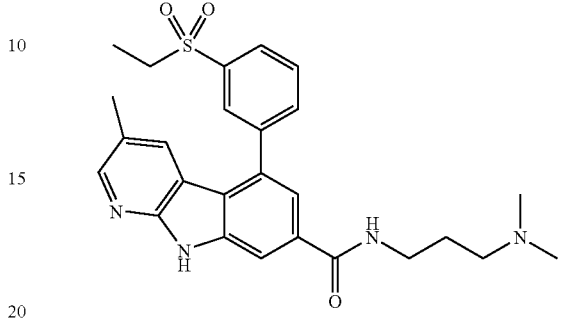

The title compound was prepared in 63% yield according to the procedure outlined for the preparation of Compound 140. $^1H$ NMR (400 MHz, $CD_3OD$) δ 8.39 (br s, 1H), 8.24 (s, 1H), 8.19 (s, 1H), 8.13 (d, 1H, J=7.6 Hz), 8.04 (d, 1H, J=7.6 Hz), 7.88-7.96 (m, 2H), 7.78 (s, 1H), 3.56 (t, 2H, J=6.4 Hz), 3.20-3.35 (m, 4H), 2.93 (s, 6H), 2.39 (s, 3H), 2.02-2.11 (m, 2H), 1.30 (t, 3H, J=7.2 Hz). MS (ES) [m+H] calc'd for $C_{26}H_{30}N_4O_3S$, 478; found 478.

Compound 143: 5-(3-Ethanesulfonyl-phenyl)-3-methyl-7-(2H-tetrazol-5-yl)-9H-pyrido[2,3-b]indole Compound 126 (14 mg, 0.037 mmol), sodium azide (9.7 mg, 0.15 mmol), and ammonium chloride (8.0 mg, 0.15 mmol) were combined in DMF (1 mL) and heated at 158° C. in the microwave for 1 h. Purification by prep-HPLC gave 12 mg (77%) of the title compound as a white solid. $^1H$ NMR (400 MHz, DMSO-$d_6$) δ 12.35 (s, 1H), 8.35 (s, 1H), 8.26 (s, 1H), 8.20 (s, 1H), 8.02-8.11 (m, 2H), 7.94 (t, 1H, J=5.6 Hz), 7.83 (s, 1H), 7.54 (s, 1H), 3.44 (q, 2H, J=7.2 Hz), 2.27 (s, 3H), 1.17 (t, 3H, J=7.2 Hz). MS (ES) [m+H] calc'd for $C_{21}H_{18}N_6O_2S$, 419; found 419.

Compound 144: (3-Dimethylamino-pyrrolidin-1-yl)-[5-(3-ethanesulfonyl-phenyl)-3-methyl-9H-pyrido[2,3-b]indol-7-yl]-methanone

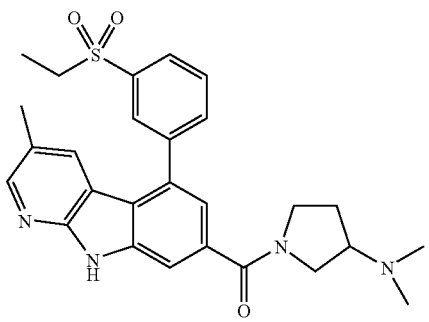

The title compound was prepared in 71% yield according to the procedure outlined for the preparation of Compound 140. $^1$H NMR (400 MHz, CD$_3$OD) δ 8.33 (br s, 1H), 8.21 (s, 1H), 8.11 (d, 1H, J=7.6 Hz), 8.03 (d, 1H, J=7.6 Hz), 7.90 (t, 1H, J=7.6 Hz), 7.81 (s, 1H), 7.76 (s, 1H), 7.40 (s, 1H), 3.71-4.16 (m, 5H), 3.32 (q, 2H, J=7.2 Hz), 2.85-3.05 (m, 6H), 2.45-2.55 (m, 1H), 2.35 (s, 3H), 2.16-2.24 (m, 1H), 1.29 (t, 3H, J=7.2 Hz). MS (ES) [m+H] calc'd for C$_{27}$H$_{30}$N$_4$O$_3$S, 491; found 491.

Compound 145: N-ethyl-5-(3-(ethylsulfonyl)phenyl)-3-methyl-9H-pyrido[2,3-b]indole-7-carboxamide

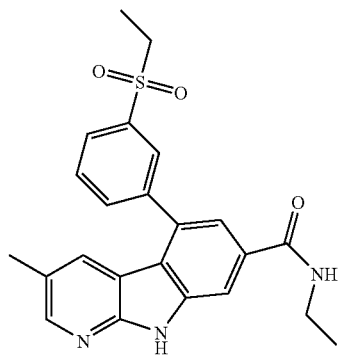

The title compound was synthesized using an analogous procedure to that described in the preparation of Compound 140. $^1$H NMR (400 MHz, MeOD) δ ppm 1.28 (dt, J=10.29, 7.23 Hz, 7 H) 2.37 (s, 3 H) 3.32-3.36 (m, 2 H) 3.48 (q, J=7.33 Hz, 2 H) 7.71 (d, J=1.52 Hz, 1 H) 7.85 (s, 1 H) 7.91 (t, J=7.83 Hz, 1 H) 8.06 (ddd, J=7.70, 1.39, 1.26 Hz, 1 H) 8.11-8.14 (m, 1 H) 8.12 (d, J=1.52 Hz, 1 H) 8.24 (t, J=1.77 Hz, 1 H) 8.33 (s, 1 H) [M+H] calc'd for C$_{23}$H$_{23}$N$_3$O$_3$S, 422; found, 422.

Compound 146: 6-Bromo-5-(3-ethanesulfonyl-phenyl)-3-methyl-9H-pyrido[2,3-b]indole-7-carboxylic acid methyl ester

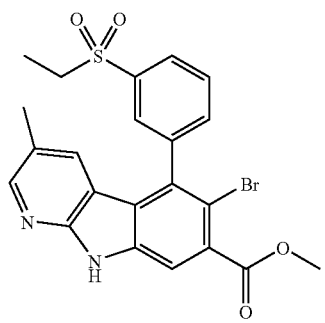

N-Bromosuccinimide (59 mg, 0.33 mmol) was added to a solution of Compound 132 (128 mg, 0.31 mmol) in CH$_2$Cl$_2$ (3 mL) at r.t. The reaction was stirred for 18 h at 30° C and was then concentrated in vacuo. Purification by prep-HPLC gave 36 mg (24%) of the title compound as a white solid. $^1$H NMR (400 MHz, CDCl$_3$) δ 12.28 (br s, 1H), 8.23 (s, 1H), 8.15-8.19 (m, 2H), 7.98 (s, 1H), 7.87 (t, 1H, J=7.6 Hz), 7.72 (d, 1H, J=7.6 Hz), 7.08 (s, 1H), 4.03 (s, 3H), 3.22 (q, 2H, J=7.2 Hz), 2.34 (s, 3H), 1.33 (t, 3H, J=7.2 Hz). MS (ES) [m+H] calc'd for C$_{22}$H$_{19}$BrN$_2$O$_4$S, 487, 489; found 487, 489.

Compound 147: 8-Bromo-5-(3-ethanesulfonyl-phenyl)-3-methyl-9H-pyrido[2,3-b]indole-7-carboxylic acid methyl ester

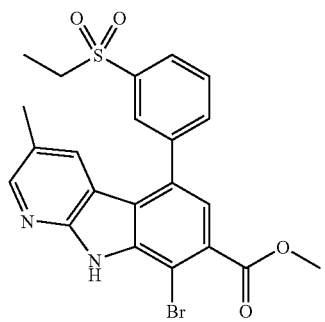

The title compound was isolated in 8% yield from the above reaction for the preparation of Compound 146. $^1$H NMR (400 MHz, CDCl$_3$) δ 13.32 (br s, 1H), 8.23 (s, 1H), 8.10-8.20 (m, 3H), 7.94 (d, 1H, J=7.6 Hz), 7.79-7.88 (m, 2H), 4.02 (s, 3H), 3.22 (q, 2H, J=7.2 Hz), 2.49 (s, 3H), 1.35 (t, 3H, J=7.2 Hz). MS (ES) [m+H] calc'd for C$_{22}$H$_{19}$BrN$_2$O$_4$S, 487, 489; found 487, 489.

Compound 148: 6-Chloro-5-(3-ethanesulfonyl-phenyl)-3-methyl-9H-pyrido[2,3-b]indole-7-carboxylic acid methyl ester

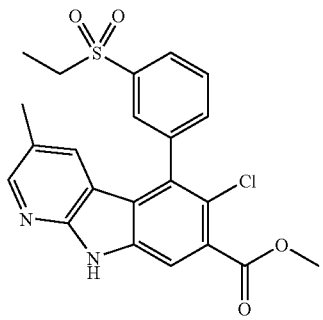

N-Chlorosuccinimide (79 mg, 0.59 mmol) was added to a solution of Compound 132 (220 mg, 0.54 mmol) in CH$_2$Cl$_2$ (3 mL) with HOAc (1 mL) at r.t. The reaction was stirred for 18 h at 32° C. and was then concentrated in vacuo. Purification by prep-HPLC gave 88 mg (37%) of the title compound as a white solid. $^1$H NMR (400 MHz, CDCl$_3$) δ 14.20 (br s, 1H), 8.23 (s, 1H), 8.11-8.19 (m, 2H), 8.00 (s, 1H), 7.87 (t, 1H, J=7.6 Hz), 7.74 (d, 1H, J=7.6 Hz), 7.28 (s, 1H), 4.01 (s, 3H), 3.23 (q, 2H, J=7.2 Hz), 2.37 (s, 3H), 1.34 (t, 3H, J=7.2 Hz). MS (ES) [m+H] calc'd for C$_{22}$H$_{19}$ClN$_2$O$_4$S, 443, 445; found 443, 445.

Compound 149: 8-Chloro-5-(3-ethanesulfonyl-phenyl)-3-methyl-9H-pyrido[2,3-b]indole-7-carboxylic acid methyl ester

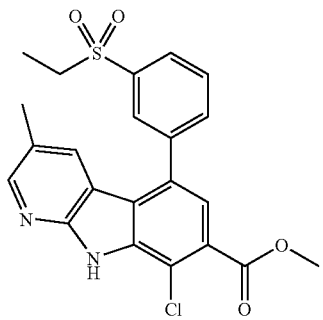

The title compound was isolated in 5% yield from the above reaction for the preparation of Compound 146. $^1$H NMR (400 MHz, CDCl$_3$) δ 13.70 (br s, 1H), 8.30 (s, 1H), 8.11-8.26 (m, 3H), 7.94 (d, 1H, J=7.6 Hz), 7.80-7.88 (m, 2H), 4.03 (s, 3H), 3.23 (q, 2H, J=7.2 Hz), 2.50 (s, 3H), 1.36 (t, 3H, J=7.2 Hz). MS (ES) [m+H] calc'd for C$_{22}$H$_{19}$ClN$_2$O$_4$S, 443, 445; found 443, 445.

Compound 150: 5-(benzylthio)-3-methyl-9H-pyrido[2,3-b]indole-7-carboxylic acid

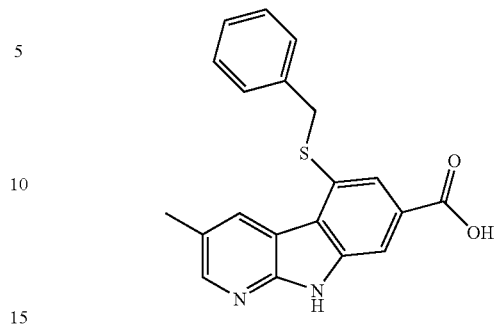

The title compound was synthesized using an analogous procedure to that described in the preparation of Compound 21. $^1$H NMR (400 MHz, MeOD) δ ppm 2.52 (s, 3 H) 4.39 (s, 2 H) 7.15-7.29 (m, 3 H) 7.34 (d, J=7.83 Hz, 2 H) 7.87 (s, 2 H) 7.92 (s, 1 H) 8.07 (s, 1 H) 8.30 (s, 1 H) 8.75 (br. s., 1 H) [M+H] calc'd for C$_{20}$H$_{16}$N$_2$O$_2$S, 349; found, 349.

Compound 151: 5-(benzylthio)-N-(2-(dimethylamino)ethyl)-3-methyl-9H-pyrido[2,3-b]indole-7-carboxamide

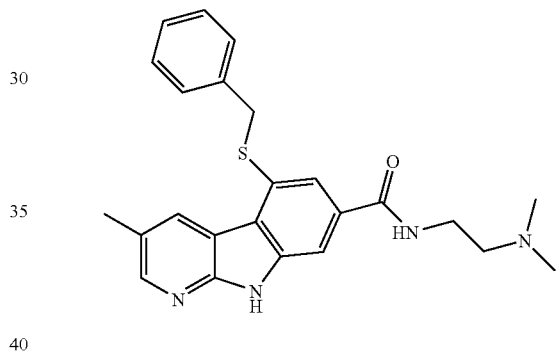

The title compound was synthesized from Compound 150 using an analogous procedure to that described in the preparation of Compound 140. $^1$H NMR (400 MHz, MeOD) δ ppm 2.53 (s, 3 H) 3.02 (s, 6 H) 3.43 (t, J=5.81 Hz, 2 H) 3.82 (t, J=5.81 Hz, 2 H) 4.42 (s, 2 H) 7.16-7.26 (m, 3 H) 7.31 (d, J=7.83 Hz, 2 H) 7.82 (d, J=1.26 Hz, 1 H) 7.96 (s, 1 H) 8.30 (s, 1 H) 8.80 (s, 1 H) [M+H] calc'd for C$_{24}$H$_{26}$N$_4$OS, 419; found, 419.

Compound 152: 5-(3-(N-ethylsulfamoyl)phenyl)-8-methoxy-3-methyl-N-(1-methylpiperidin-4-yl)-9H-pyrido[2,3-b]indole-7-carboxamide

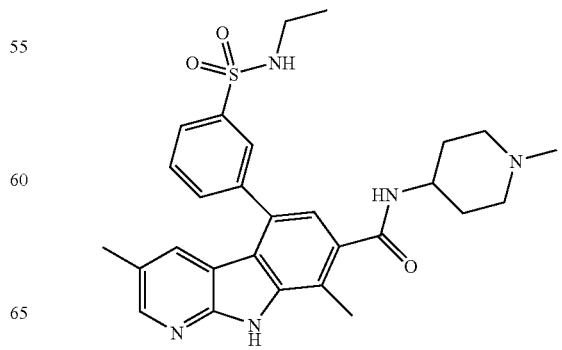

The title compound was synthesized using an analogous procedure to that described in the preparation of Compound 87. $^1$H NMR (400 MHz, Methanol-d$_4$) δ 8.28 (s, 1 H) 8.13 (s, 1 H) 8.04 (m, 1 H) 7.88 (m, 1 H) 7.75 (m, 1 H) 7.81 (t, J=7.84 Hz, 1 H) 7.24 (s, 1 H) 4.22 (m, 1 H) 3.62 (m, br, 2 H) 3.22 (m, 2 H) 3.01 (q, J=7.32 Hz, 2 H) 2.92 (s, 3 H) 2.72 (s, 3 H) 2.36 (m, 5 H) 1.93 (m, 2 H) 1.11 (t, J=7.32 Hz, 3 H). [M+H] calc'd for C$_{28}$H$_{34}$N$_5$O$_3$S, 520; found, 520.

Compound 153: 5-(3-(cyclopropylsulfonyl)phenyl)-3,8-dimethyl-N-(1-methylpiperidin-4-yl)-9H-pyrido[2,3-b]indole-7-carboxamide

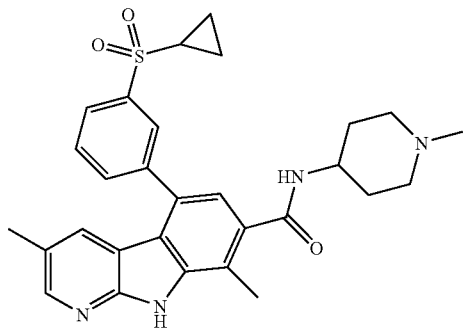

The title compound was synthesized using an analogous procedure to that described in the preparation of Compound 87. $^1$H NMR (400 MHz, Methanol-d$_4$) δ 8.32 (s, 1 H) 8.19 (s, 1 H) 8.11 (m, 1 H) 7.99 (m, 1 H) 7.89 (m, 2 H) 7.3 (s, 1 H) 4.22 (m, 1 H) 3.74 (m, 1 H) 3.64 (m, 2 H) 3.65 (m, 2 H) 3.22 (m, 2 H) 2.93 (s, 3 H) 2.72 (s, 3 H) 2.36 (m, 5 H) 1.93 (m, 2 H) 1.28 (m, 2 H) 1.14 (m, 2 H). [M+H] calc'd for C$_{29}$H$_{33}$N$_4$O$_3$S, 517; found, 517.

Compound 154: 3-bromo-N-(5-chloro-2-methoxyphenyl)-5-methylpyridin-amine

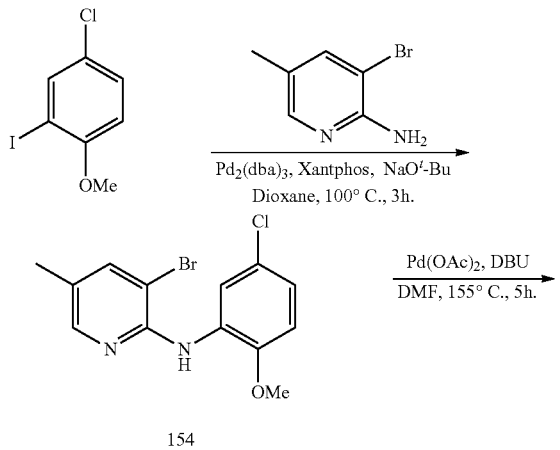

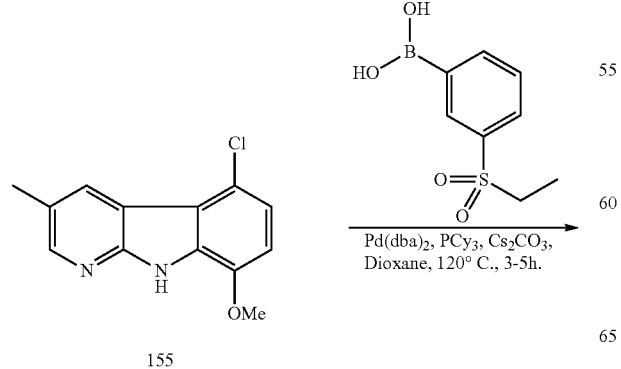

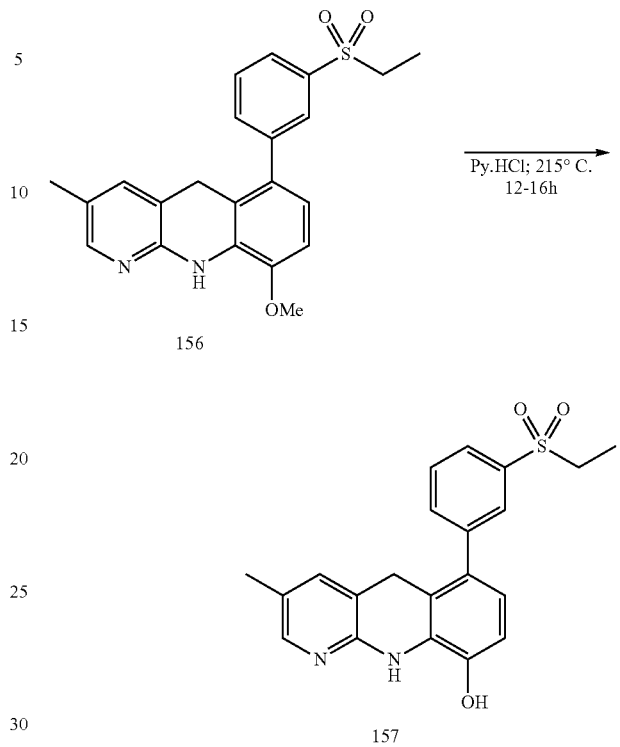

In a oven dried 50 mL round bottom flask were sequentially added 4-chloro-2-iodo-1-methoxybenzen (1.13 g, 4.2 mmol), 3-bromo-5-methylpyridin-2-amine (945 mg, 5.05 mmol), Pd$_2$(dba)$_3$ (192 mg, 0.21 mmol), xantphos (146 mg, 0.06 mmol) and Na$^t$BuO (605 mg, 6.3 mmol) at room temperature. The solid materials were kept under vacuum for 5 min. and then refilled with nitrogen. This process was repeated thrice before adding dry, degassed dioxane (10 mL). The heterogeneous mixture was stirred at room temperature for 15 min. and then at 100° C. for 1 h. Finally upon completion of the reaction, it was diluted with ether and filtered through a small pad of silica gel with several washings. All the washings and filtrate concentrated in vacuum and the crude residue was further purified by flash chromatography to provide title compound (1.16 g, 84%).

Compound 155:
5-choloro-8-methoxy-9H-pyrido[2,3-b]indole

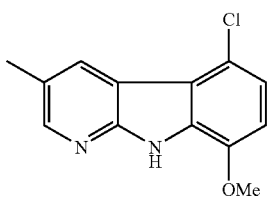

To a stirred solution of Compound 154 (1.0 g, 3.05 mmol) in anhydrous and degassed DMF (10 mL), were added Pd(OAc)$_2$ (69 mg, 3.1 mmol) and DBU (1.37 mL, 9.15 mmol), under nitrogen. After being stirred for 6 h. at 155° C. the reaction was quenched by addition of water (20 mL). The solid precipitates out was filtered and washed thoroughly with water. The residue was dried under vacuum and purified by flash chromatography to furnish the title compound (488 mg, 65%).

Compound 156: 5-(3-(ethylsulfonyl)phenyl-8-methoxy-3-methyl-9H-pyrido[2,3-b]indole

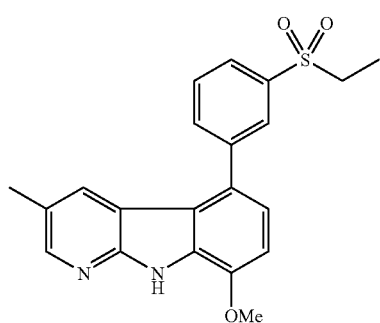

To a stirred solution of Compound 155 (400 mg, 1.62 mmol) and 3-(ethylsulfonyl)phenylboronic acid (694 mg, 3.24 mmol) in anhydrous and degassed dioxane (8 mL), were added Pd(dba)$_2$ (140 mg, 0.24 mmol), PCy$_3$ (0.68 mL, 20% wt solution in toluene, 0.49 mmol) and Cs$_2$CO$_3$ (1.32 g, 4.05 mmol), under nitrogen. After being stirred for 6 h. under reflux (oil bath temperature 125° C.) the reaction was diluted with EtOAc and filtered through a small pad of celite. The residue was washed thoroughly with EtOAc and 10% MeOH in CH$_2$Cl$_2$. All the washings and filtrate were concentrated in vacuum and the crude residue was triturated with ether and then with MeOH. The crude mass was dried under vacuum to give title compound (493 mg, 80%) which was used directly for next step without further purification.

Compound 157: 5-(3-(ethylsulfonyl)phenyl)-3-methyl-9H-pyrido[2,3-b]indol-8-ol

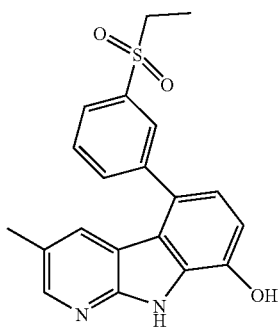

Compound 156 (450 mg, 1.18 mmol) and pyridine hydrochloride (2.73 g, 23.6 mmol) was taken in a sealed tube and heated at 215° C. for 12 h. The black mass was dissolved in water and extracted twice with 5% EtOH in CH$_2$Cl$_2$. The combined organic extracts were concentrated and the residual mass was purified by flash chromatography to provide the title compound (259 mg, 60%). $^1$H NMR (400 MHz, DMSO-d$_6$) δ ppm 1.17 (t, J=7.33 Hz, 3 H) 2.25 (s, 3 H) 3.40 (q, J=7.49 Hz, 2 H) 6.97 (s, 2 H) 7.54 (d, J=1.77 Hz, 1 H) 7.83 (t, J=7.71 Hz, 1 H) 7.94-7.98 (m, 2 H) 8.06 (t, J=1.64 Hz, 1 H) 8.24 (d, J=1.77 Hz, 1 H) 10.08 (s, 1 H) 11.73 (s, 1 H). [M+H] calc'd for C$_{20}$H$_{18}$N$_2$O$_3$S 367; found, 367.1.

Compound 158: 8-methoxy-3-methyl-5-(3-(pyrrolidin-1-ylsulfonyl)phenyl)-9H-pyrido[2,3-b]indole

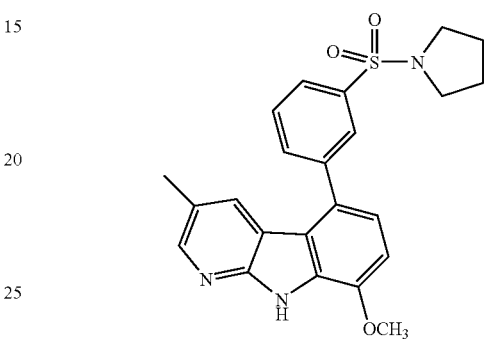

The title compound was synthesized from Compound 155 using an analogous procedure to that outlined in the preparation of Compound 156. $^1$H NMR (400 MHz, DMSO-d$_6$) δ ppm 1.72-1.68 (m, 4 H) 2.25 (s, 3 H) 3.23-3.19 (m, 4 H) 4.02 (s, 3 H) 7.07 (d, J=8.4 Hz, 1 H) 7.15 (d, J=8.0 Hz, 1 H) 7.47 (d, J=1.26 Hz, 1 H) 7.83 (d, J=7.58 Hz, 1 H) 7.90-7.94 (m, 3 H) 8.26 (d, J=1.77 Hz, 1 H) 12.03 (s, 1 H); [M+H] calc'd for C$_{23}$H$_{24}$N$_3$O$_3$S, 422.2; found 422.3.

Compound 159: (R)-8-methoxy-3-methyl-5-(3-(pyrrolidin-3-ylsulfonyl)phenyl)-9H-pyrido[2,3-b]indole

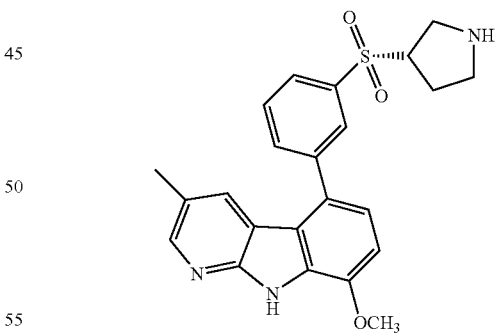

The title compound was synthesized from Compound 155 using an analogous procedure to that outlined in the preparation of Compound 156. $^1$H NMR (400 MHz, DMSO-d$_6$) δ ppm 1.92-2.02 (m, 2 H) 2.26 (s, 3 H) 2.74-2.87 (m, 2 H) 3.03 (dd, J=8.0, 8.1, Hz, 1 H) 3.11 (dd, J=5.31, 8.0 Hz, 1 H) 3.17 (d, J=5.31 Hz, 1 H) 4.02 (s, 3 H) 7.09 (d, J=8.1 Hz, 1 H) 7.15 (d, J=8.0 Hz, 1 H) 7.51 (d, J=1.26 Hz, 1 H) 7.85 (t, J=7.71 Hz, 1 H) 7.97 (d, J=7.96 Hz, 1 H) 8.01 (d, J=8.0 Hz, 1 H) 8.07 (d, J=1.52 Hz, 1 H) 8.26 (d, J=1.52 Hz, 1 H) 12.04 (s, 1 H); [M+H] calc'd for C$_{23}$H$_{23}$N$_3$O$_3$S, 422.2; found, 422.3.

175

Compound 160: N-cyclopropyl-4-(8-methoxy-3-methyl-9H-pyrido[2,3-b]indol-5-yl)picolinamide

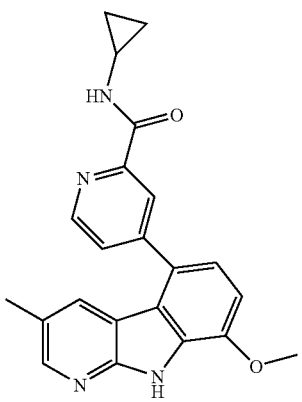

The title compound was synthesized from Compound 155 using an analogous procedure to that outlined in the preparation of Compound 156. $^1$H NMR (400 MHz, MeOD) δ ppm 0.74 (br. s., 2 H) 0.88 (d, J=9.35 Hz, 2 H) 2.37 (s, 3 H) 4.11 (s, 3 H) 7.22 (s, 2 H) 7.82 (br. s., 1 H) 7.94 (s, 1 H) 8.26 (br. s., 1 H) 8.36 (br. s., 1 H) 8.76 (br. s., 1 H) [M+H] calc'd for $C_{22}H_{20}N_4O_2$, 373; found, 373.

Compound 161: N-(3-(8-methoxy-3-methyl-9H-pyrido[2,3-b]indol-5-yl)phenyl)acetamide

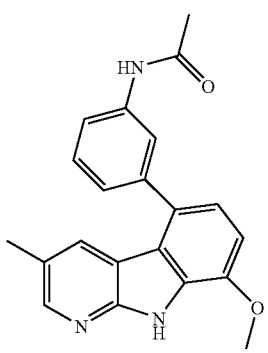

The title compound was synthesized from Compound 155 using an analogous procedure to that outlined in the preparation of Compound 156. $^1$H NMR (400 MHz, Methanol-d$_4$) δ 8.24 (s, 1 H) 8.18 (s, 1 H) 7.93 (s, 1 H) 7.56 (m, 1 H) 7.52 (t, J=7.56 Hz, 1 H) 7.34 (m, 1 H) 7.22 (d, J=8.08 Hz, 1 H) 7.18 (d, J=8.08 Hz, 1 H) 4.11 (s, 3 H) 2.40 (s, 3 H) 2.17 (s, 3 H). [M+H] calc'd for $C_{21}H_{20}N_3O_2$, 346; found, 346.

176

Compound 162: N-(3-(8-methoxy-3-methyl-9H-pyrido[2,3-b]indol-5-yl)phenyl)cyclopropanecarboxamide

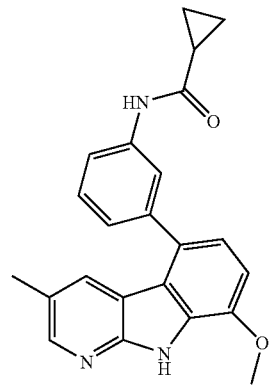

The title compound was synthesized from Compound 155 using an analogous procedure to that outlined in the preparation of Compound 156. $^1$H NMR (400 MHz, Methanol-d$_4$) δ 8.44 (s, 1 H) 8.25 (s, 1 H) 8.00 (s, 1 H) 7.52 (m, 2 H) 7.27 (m, 3 H) 4.11 (s, 3 H) 2.43 (s, 3 H) 1.80 (m, 1 H) 0.95 (m, 2 H) 0.88 (m, 2 H). [M+H] calc'd for $C_{23}H_{22}N_3O_2$, 372; found, 372.

Compound 163: N-cyclopropyl-3-(8-methoxy-3-methyl-9H-pyrido[2,3-b]indol-5-yl)benzamide

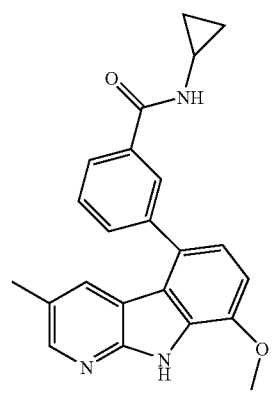

The title compound was synthesized from Compound 155 using an analogous procedure to that outlined in the preparation of Compound 156. $^1$H NMR (400 MHz, Methanol-d$_4$) δ 8.26 (s, 1 H) 8.07 (s, 1 H) 7.91 (m, 2 H) 7.77 (m, 1 H) 7.66 (t, J=7.56 Hz, 1 H) 7.24 (m, 2 H) 4.12 (s, 3 H) 2.80 (m, 1 H) 2.38 (s, 3 H) 0.82 (m, 2 H) 0.66 (m, 2 H). [M+H] calc'd for $C_{23}H_{22}N_3O_2$, 372; found, 372.

Compound 164: N,N-diethyl-3-(8-methoxy-3-methyl-9H-pyrido[2,3-b]indol-5-yl)benzamide

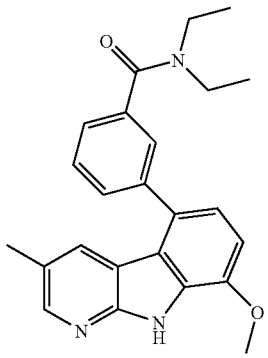

The title compound was synthesized from Compound 155 using an analogous procedure to that outlined in the preparation of Compound 156. $^1$H NMR (400 MHz, Methanol-$d_4$) δ 8.26 (s, 1 H) 8.07 (s, 1 H) 7.91 (m, 2 H) 7.77 (m, 1 H) 7.66 (t, J=7.56 Hz, 1 H) 7.24 (m, 2 H) 4.12 (s, 3 H) 3.99 (q, J=7.52 Hz 1 H) 2.38 (s, 3 H) 1.35 (t, J=7.52 Hz, 6 H). [M+H] calc'd for $C_{24}H_{25}N_3O_2$, 387; found, 387.2

Compound 165: 5-(benzo[d][1,3]dioxol-5-yl)-8-methoxy-3-methyl-9H-pyrido[2,3-b]indole

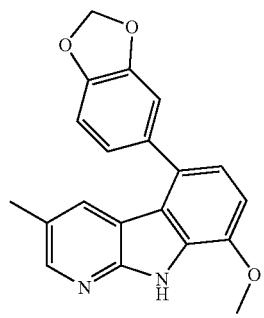

The title compound was synthesized from Compound 155 using an analogous procedure to that outlined in the preparation of Compound 156. $^1$H NMR (400 MHz, Methanol-$d_4$) δ 8.14 (s, 1 H) 7.20 (d, J=8.36 Hz, 1 H) 7.18 (d, J=8.36 Hz, 1 H) 7.04 (m, 4 H) 6.10 (s, 2 H) 4.11 (s, 3 H) 2.42 (s, 3 H). [M+H] calc'd for $C_{20}H_{17}N_2O_3$, 333; found, 333; found, 333.

Compound 166: 6-(8-methoxy-3-methyl-9H-pyrido[2,3-b]indol-5-yl)-4H-chromen-4-one

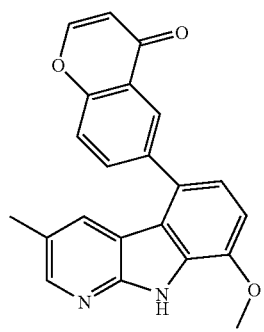

The title compound was synthesized from Compound 155 using an analogous procedure to that outlined in the preparation of Compound 156. $^1$H NMR (400 MHz, Methanol-$d_4$) δ 8.37 (s, 1 H) 8.29 (m, 2 H) 8.07 (m, 2 H) 7.84 (d, J=8.84 Hz, 1 H) 7.31 (m, 2 H) 6.48 (d, J=5.8 Hz, 1 H) 4.15 (s, 3 H) 2.40 (s, 3 H). [M+H] calc'd for $C_{22}H_{17}N_2O_3$, 357; found, 357.

Compound 167: N-(2-hydroxyethyl)-3-(8-methoxy-3-methyl-9H-pyrido[2,3-b]indol-5-yl)benzamide

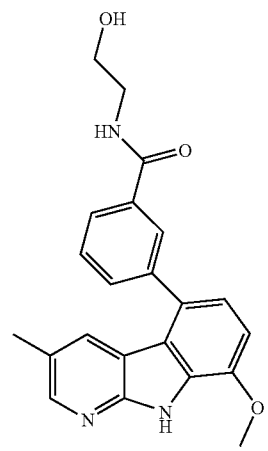

The title compound was synthesized from Compound 155 using an analogous procedure to that outlined in the preparation of Compound 156. $^1$H NMR (400 MHz, Methanol-$d_4$) δ 8.30 (s, 1 H) 8.12 (m, 2 H) 8.00 (m, 1 H) 7.72 (m, 1 H) 7.70 (t, J=7.34 (m, 2 H) 4.14 (s, 3 H) 3.75 (t, J=5.8 Hz, 2 H) 3.56 (t, J=5.8 Hz, 2 H) 2.43 (s, 3 H). [M+H] calc'd for $C_{22}H_{22}N_3O_3$, 376; found, 376.

Compound 168: (3-(8-methoxy-3-methyl-9H-pyrido[2,3-b]indol-5-yl)phenyl)(pyrrolidin-1-yl)methanone

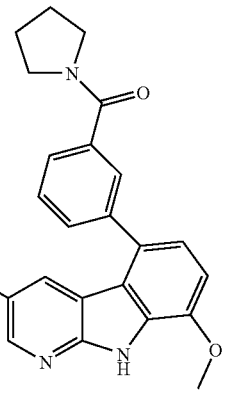

The title compound was synthesized from Compound 155 using an analogous procedure to that outlined in the preparation of Compound 156. $^1$H NMR (400 MHz, Methanol-$d_4$) δ 8.27 (s, 1 H) 8.03 (s, 1 H) 7.70 (m, 4 H) 7.26 (d, J=8.32 Hz, 1 H) 7.21 (d, J=8.32 Hz, 1 H) 4.12 (s, 3 H) 3.64 (t, J=6.84 Hz, 2 H) 3.58 (t, J=6.84 Hz, 2 H) 2.41 (s, 3 H) 1.95 (m, 4 H). [M+H] calc'd for $C_{22}H_{22}N_3O_3$, 376; found, 376.

Compound 169: N-ethyl-3-(8-methoxy-3-methyl-9H-pyrido[2,3-b]indol-5-yl)benzenesulfonamide

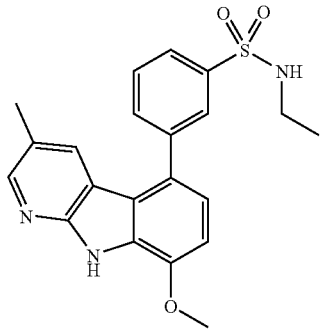

The title compound was synthesized from Compound 155 using an analogous procedure to that outlined in the preparation of Compound 156. $^1$H NMR (400 MHz, DMSO-$d_6$) δ ppm 1.00 (t, J=7.20 Hz, 3 H) 2.26 (s, 3 H) 2.86 (dd, J=7.33, 5.81 Hz, 2 H) 4.02 (s, 3 H) 7.07 (d, J=8.08 Hz, 1 H) 7.12-7.18 (m, 1 H) 7.52 (s, 1 H) 7.69 (t, J=5.81 Hz, 1 H) 7.79 (d, J=7.58 Hz, 1 H) 7.84 (d, J=1.52 Hz, 1 H) 7.89 (d, J=7.58 Hz, 1 H) 8.00 (d, J=1.77 Hz, 1 H) 8.26 (d, J=1.77 Hz, 1 H) 12.06 (s, 1 H); ESI-MS: m/z calc'd for C21H21N3O3S 395.13; found 396.3 (M+H)$^+$

Compound 170: 8-ethoxy-5-(3-(ethylsulfonyl)phenyl)-3-methyl-9H-pyrido[2,3-b]indole

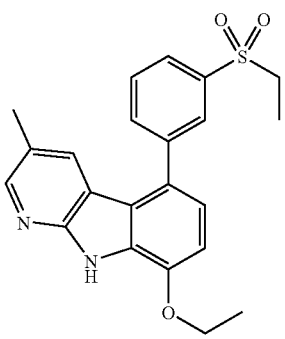

The title compound was synthesized by using an analogous synthetic sequence to that outlined in the preparation of Compound 156. $^1$H NMR (400 MHz, DMSO-$d_6$) δ ppm 1.17 (t, J=7.33 Hz, 3 H) 1.48 (t, J=6.95 Hz, 3 H) 2.26 (s, 3 H) 3.41 (q, J=7.49 Hz, 2 H) 4.31 (q, J=7.24 Hz, 2 H) 7.07-7.11 (m, 1 H) 7.09 (d, J=6.32 Hz, 1 H) 7.12-7.17 (m, 1 H) 7.56 (s, 1 H) 7.85 (t, J=7.71 Hz, 1 H) 8.00 (d, J=1.26 Hz, 1 H) 7.97 (dd, J=3.41, 1.64 Hz, 1 H) 8.08 (s, 1 H) 8.28 (br. s., 1 H) 12.03 (br. s., 1 H); ESI-MS: m/z calc'd for C22H22N2O3S 394.14; found 395.3 (M+H)$^+$

Compound 171: 8-(difluoromethoxy)-5-(3-(ethylsulfonyl)phenyl)-3-methyl-9H-pyrido[2,3-b]indole

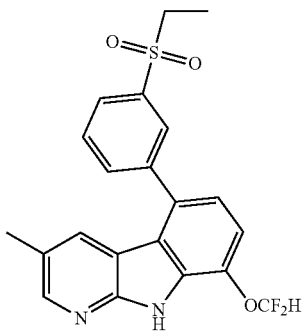

The title compound was synthesized by using an analogous synthetic sequence to that outlined in the preparation of Compound 156. $^1$H NMR (400 MHz, DMSO-$d_6$) δ ppm 1.17 (t, J=7.33 Hz, 3 H) 2.27 (s, 3 H) 3.42 (d, J=7.33 Hz, 2 H) 7.17 (d, J=8.08 Hz, 1 H) 7.40 (t, J=73.6 Hz, 1 H) 7.42 (s, 1 H) 7.50 (s, 1 H) 7.89 (t, J=7.71 Hz, 1 H) 8.0-8.1 (m, 2 H) 8.11 (t, J=1.77 Hz, 1 H) 8.33 (br. s., 1 H) 12.36 (s, 1 H). [M+H] calc'd for C$_{21}$H$_{18}$F$_2$N$_2$O$_3$S 417; found, 417.3.

Compound 172: 5-(3-(ethylsulfonyl)phenyl)-3-methyl-8-(2,2,2-trifluoroethoxy)-9H-pyrido[2,3-b]indole

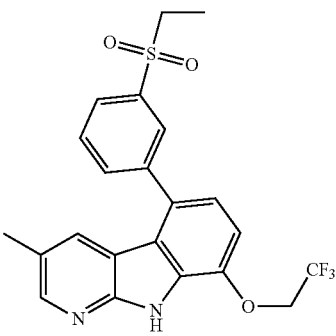

The title compound was synthesized by using an analogous synthetic sequence to that outlined in the preparation of Compound 156. $^1$H NMR (400 MHz, DMSO-$d_6$) δ ppm 1.17 (t, J=7.45 Hz, 3 H) 2.27 (s, 3 H) 3.42 (q, J=7.33 Hz, 2 H) 5.03 (q, J=9.01 Hz, 2 H) 7.13 (d, J=8.34 Hz, 1 H) 7.32 (d, J=8.34 Hz, 1 H) 7.54 (d, J=1.26 Hz, 1 H) 7.87 (t, J=7.71 Hz, 1 H) 8.00 (td, J=8.72, 1.26 Hz, 2 H) 8.09 (t, J=1.64 Hz, 1 H) 8.31 (d, J=1.77 Hz, 1 H) 12.23 (s, 1 H). [M+H] calc'd for C$_{22}$H$_{19}$F$_3$N$_2$O$_3$S 449; found, 449.3.

Compound 173: 4-((4-chloro-2-iodophenoxy)methyl)-1-methylpiperidine

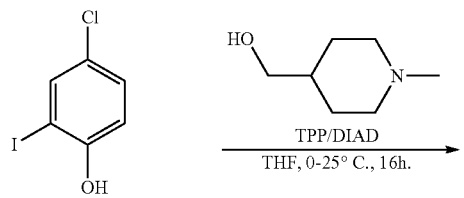

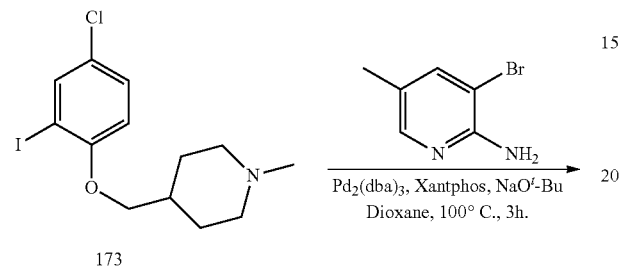

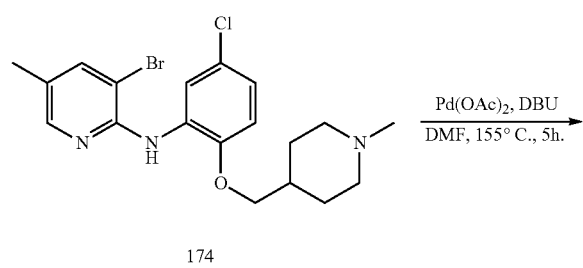

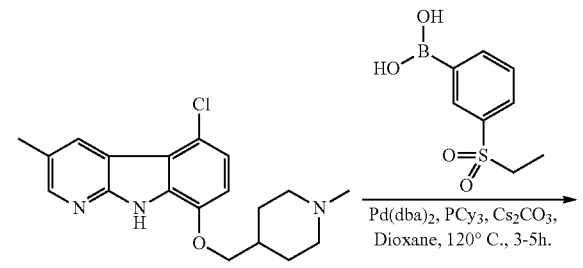

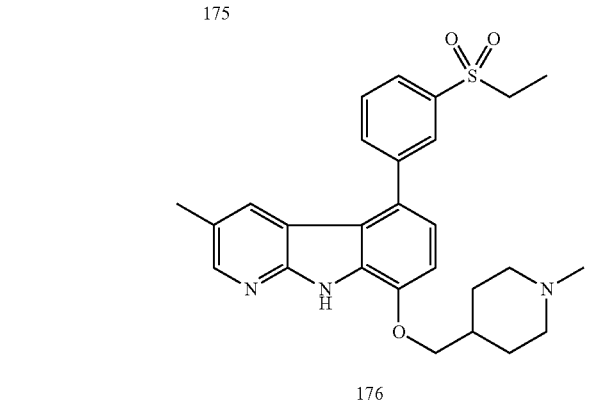

To a stirred solution of 4-chloro-2-iodophenol (1.72 g, 6.75 mmol) in anhydrous THF (10.0 mL) were sequentially added (1-methylpiperidin-4-yl)methanol (1.31 g, 10.14 mmol) and triphenyl phosphine (2.66 g, 10.14 mmoL). The reaction mixture was cooled to 0° C., and to it diisopropyl-azodicarboxylate (1.96 mL, 10.14 mmol) was added in drop wise manner. After the addition was over, stirring continued for another 0.5 h at 0° C. and then for 12 h at room temperature. Solvents were removed in vacuum and the residue was purified by silica gel column chromatography, providing Compound 173 (1.85 g, 75%).

Compound 174: 3-bromo-N-(5-chloro-2-((1-methylpiperidin-4-yl)methoxy)phenyl)-5-methylpyridin-2-amine

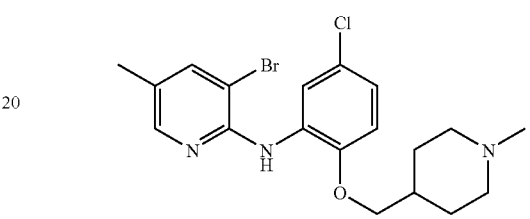

In a oven dried 50 mL round bottom flask were sequentially added Compound 173 (620 mg, 1.69 mmol), 3-bromo-5-methylpyridin-2-amine (381 mg, 2.03 mmol), $Pd_2(dba)_3$ (77 mg, 0.08 mmol), xantphos (59 mg, 0.10 mmol) and $Na^tBuO$ (244 mg, 2.53 mmol) at room temperature. The solid materials were kept under vacuum for 5 min. and then refilled with nitrogen. This process was repeated thrice before adding dry, degassed dioxane (8 mL). The heterogeneous mixture was stirred at room temperature for 15 min. and then at 100° C. for 2 h. Finally upon completion of the reaction, it was diluted with EtOAc and filtered through a small pad of silica gel with several washings. All the washings and filtrate concentrated in vacuum and the crude residue was further purified by flash chromatography to provide pure Compound 174 (574 mg, 80%).

Compound 175: 5-chloro-3-methyl-8-((1-methylpiperidin-4-yl)methoxy)-9H-pyrido[2,3-b]indole

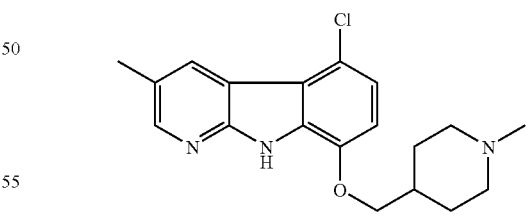

To a stirred solution of Compound 174 (450 mg, 1.06 mmol) in anhydrous and degassed DMF (3 mL), were added $Pd(OAc)_2$ (59 mg, 0.26 mmol) and DBU (0.48 mL, 3.18 mmol), under nitrogen. After being stirred for 6 h. at 155° C. the reaction was quenched by addition of water (5 mL). The solid precipitates out was filtered and washed thoroughly with water. The residue was dried under vacuum and purified by flash chromatography to furnish Compound 175 (237 mg, 65%).

Compound 176: 5-(3-(ethylsulfonyl)phenyl)-3-methyl-8-((1-methylpiperidin-4-yl)methoxy)-9H-pyrido[2,3-b]indole

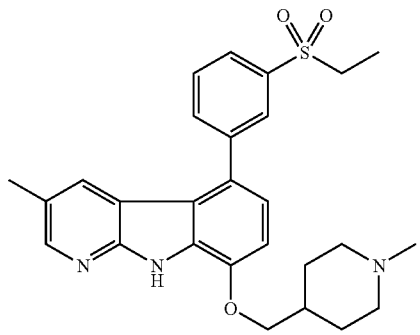

To a stirred solution of Compound 175 (170 mg, 0.49 mmol) and 3-(ethylsulfonyl)phenylboronic acid (265 mg, 1.24 mmol) in anhydrous and degassed dioxane (5 mL), were added Pd(dba)$_2$ (70 mg, 0.12 mmol), PCy$_3$ (0.34 mL, 20% wt solution in toluene, 0.24 mmol) and Cs$_2$CO$_3$ (479 mg, 1.47 mmol), under nitrogen. After being stirred for 6 h. under reflux (oil bath temperature 125° C.) the reaction was diluted with EtOAc and filtered through a small pad of celite. The residue was washed thoroughly with EtOAc and 10% MeOH in CH$_2$Cl$_2$. All the washings and filtrate were concentrated in vacuum and the crude residue was triturated with ether and then with MeOH and then purified through preparative HPLC to give Compound 176 (176 mg, 75%). $^1$H NMR (400 MHz, DMSO-d$_6$) δ ppm 1.20 (t, J=7.34 Hz, 3 H) 1.50-1.61 (m, 2 H) 2.18 (br. s., 1 H) 2.13-2.20 (m, 1 H) 2.23-2.31 (m, 5 H) 2.82 (s, 3 H) 2.98-3.09 (m, 2 H) 3.39 (q, J=7.34 Hz, 2 H) 3.54 (d, J=10.60 Hz, 2 H) 4.12 (d, J=6.52 Hz, 2 H) 7.06-7.17 (m, 2 H) 7.53 (s, 1 H) 7.85 (t, J=7.74 Hz, 1 H) 7.96 (d, J=7.66 Hz, 1 H) 8.00 (d, J=7.66 Hz, 1 H) 8.06 (s, 1 H) 8.28 (d, J=1.47 Hz, 1 H) 11.83 (br. s., 1 H), [M+H] calc'd for C$_{27}$H$_{32}$N$_3$O$_3$S, 478.2; found, 478.4; [M+H+TFA] calc'd for C$_{29}$H$_{33}$N$_3$O$_5$F$_3$S, 592.2; found, 592.4.

Compound 177: N-cyclopropyl-3-(3-methyl-8-((1-methylpiperidin-4-yl)methoxy)-9H-pyrido[2,3-b]indol-5-yl)benzamide

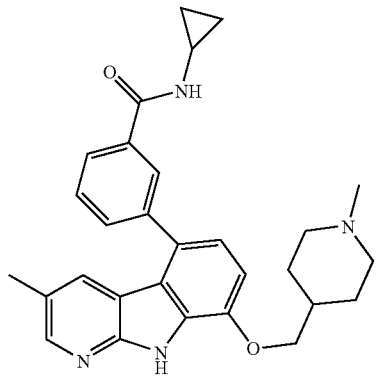

The title compound was synthesized using an analogous procedure to that outlined in the preparation of Compound 176. $^1$H NMR (400 MHz, Methanol-d$_4$) δ 8.28 (s, 1 H) 8.07 (s, 1 H) 7.92 (m, 3 H) 7.79 (m, 1 H) 7.67 (t, J=7.56 Hz, 1 H) 7.25 (d, J=8.36 Hz, 1 H) 7.21 (d, J=8.36 Hz, 1 H) 4.24 (d, J=6.08 Hz, 2 H) 3.65 (m, br, 2 H) 3.14 (m, 2 H) 2.94(m, 4 H) 2.38 (m, 6 H) 1.75 (m, 2 H) 0.83 (m, 2 H) 0.66 (m, 2 H). [M+H] calc'd for C$_{29}$H$_{33}$N$_4$O$_2$, 469; found, 469.

Compound 178: 5-(3-(cyclopropylsulfonyl)phenyl)-3-methyl-8-((1-methylpiperidin-4-yl)methoxy)-9H-pyrido[2,3-b]indole

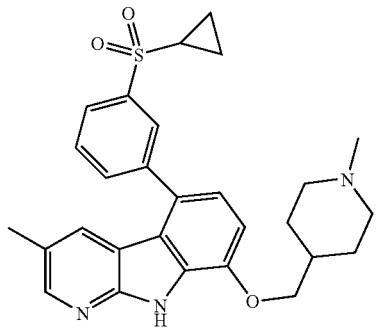

The title compound was synthesized using an analogous procedure to that outlined in the preparation of Compound 176. $^1$H NMR (400 MHz, Methanol-d$_4$) δ 8.28 (s, 1 H) 8.18 (s, 1 H) 8.05 (m, 2 H) 7.93 (m, 1 H) 7.85 (t, J=7.56 Hz, 1 H) 7.27 (m, 2 H) 4.21 (d, J=5.8 Hz, 2 H) 3.65 (m, br, 2 H) 3.14 (m, 2 H) 2.94(s, 3 H) 2.85 (m, 1 H) 2.40 (m, 6 H) 1.75 (m, 2 H) 1.29 (m, 2 H) 1.14 (m, 2 H). [M+H] calc'd for C$_{28}$H$_{32}$N$_3$O$_3$S, 490; found, 490.

Compound 179: N-methyl-3-(3-methyl-8-((1-methylpiperidin-4-yl)methoxy)-9H-pyrido[2,3-b]indole-5-yl)benzenesulfonamide

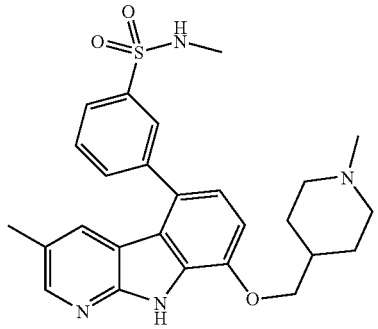

The title compound was synthesized using an analogous procedure to that outlined in the preparation of Compound 176. $^1$H NMR (400 MHz, Methanol-d$_4$) δ 8.28 (s, 1 H) 8.18 (s, 1 H) 8.05 (m, 2 H) 7.93 (m, 1 H) 7.85 (t, J=7.56 Hz, 1 H) 7.27 (m, 2 H) 4.21 (d, J=5.8 Hz, 2 H) 3.65 (m, br, 2 H) 3.14 (m, 2 H) 2.94(s, 3 H) 2.85 (m, 1 H) 2.47 (d, J=6.2 Hz 3 H) 1.75 (m, 2 H) 1.29 (m, 2 H) 1.14 (m, 2 H). [M+H] calc'd for C$_{26}$H$_{30}$N$_4$O$_3$S, 479; found, 479.2.

Compound 180: N,N-dimethyl-3-(3-methyl-8-((1-methylpiperidin-4-yl)methoxy)-9H-pyrido[2,3-b]indole-5-yl)benzenesulfonamide

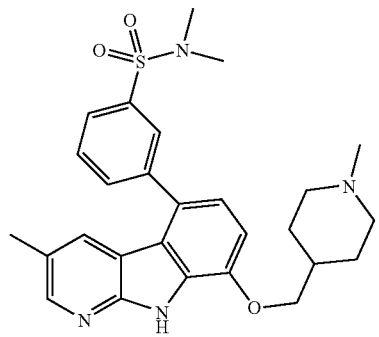

The title compound was synthesized using an analogous procedure to that outlined in the preparation of Compound 176. $^1$H NMR (400 MHz, Methanol-$d_4$) δ 8.28 (s, 1 H) 8.18 (s, 1 H) 8.05 (m, 2 H) 7.93 (m, 1 H) 7.85 (t, J=7.56 Hz, 1 H) 7.27 (m, 2 H) 4.21 (d, J=5.8 Hz, 2 H) 3.65 (m, br, 2 H) 3.14 (m, 2 H) 2.94(s, 3 H) 2.85 (m, 1 H) 2.66 (s, 3 H) 1.75 (m, 2 H) 1.29 (m, 2 H) 1.14 (m, 2 H). [M+H] calc'd for $C_{27}H_{32}N_4O_3S$, 493; found, 493.2

Compound 181: N-(3-(3-methyl-8-((1-methylpiperidin-4-yl)methoxy)-9H-pyrido[2,3-b]indol-5-yl)phenyl)cyclopropanecarboxamide

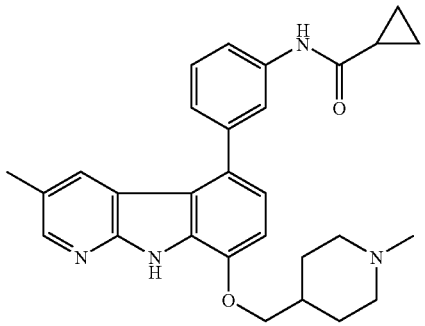

The title compound was synthesized using an analogous procedure to that outlined in the preparation of Compound 176. $^1$H NMR (400 MHz, DMSO-$d_6$) δ ppm 0.78-0.80 (m, 4 H) 1.45-1.55 (m, 2 H) 1.75-1.84 (m, 1 H) 2.09-2.18 (m, 1 H) 2.27 (s, 3 H) 2.54 (s, 3 H) 2.80 (d, J=4.80 Hz, 2 H) 2.96-3.08 (m, 2 H) 3.53 (d, J=11.37 Hz, 2 H) 4.08 (d, J=6.82 Hz, 2 H) 6.98 (d, J=8.08 Hz, 1 H) 7.09 (d, J=8.34 Hz, 1 H) 7.22 (d, J=7.83 Hz, 1 H) 7.46 (t, J=7.83 Hz, 1 H) 7.61 (d, J=8.08 Hz, 1 H) 7.72 (d, J=1.26 Hz, 1 H) 7.91 (s, 1 H) 8.25 (d, J=1.77 Hz, 1 H) 9.23 (br. s., 1 H) 10.33 (s, 1 H) 11.89 (s, 1 H); [M+H] calc'd for $C_{29}H_{33}N_4O_2$, 469.3; found, 469.5; [M+H+TFA] calc'd for $C_{31}H_{34}N_4O_4F_3$, 583.3; found, 583.5.

Compound 182: 5-(3-(ethylthio)phenyl)-3-methyl-8-((1-methylpiperidin-4-yl)methoxy)-9H-pyrido[2,3-b]indole

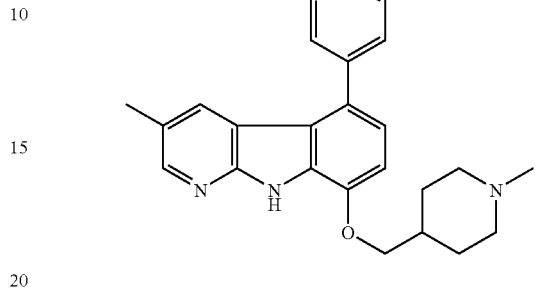

The title compound was synthesized using an analogous procedure to that outlined in the preparation of Compound 176. $^1$H NMR (400 MHz, DMSO-$d_6$) δ ppm 1.28 (t, J=7.20 Hz, 3 H) 1.48-1.56 (m, 2 H) 2.09-2.20 (m, 1 H) 2.25 (br. s., 2 H) 2.27 (s, 3 H) 2.80 (d, J=4.55 Hz, 3 H) 3.03 (q, J=7.16 Hz, 4 H) 3.53 (d, J=11.37 Hz, 2 H) 4.08 (d, J=6.82 Hz, 2 H) 7.00 (d, J=8.08 Hz, 1 H) 7.10 (d, J=8.34 Hz, 1 H) 7.36-7.52 (m, 4 H) 7.59 (s, 1 H) 8.27 (s, 1 H) 9.41 (br. s., 1 H) 11.95 (s, 1 H); [M+H] calc'd for $C_{27}H_{32}N_3OS$, 446.2; found, 446.4; [M+H+TFA] calc'd for $C_{29}H_{33}N_3O_3F_3S$, 560.2; found, 560.4.

Compound 183: 5-(3-ethoxyphenyl)-3-methyl-8-((1-methylpiperidin-4-yl)methoxy)-9H-pyrido[2,3-b]indole

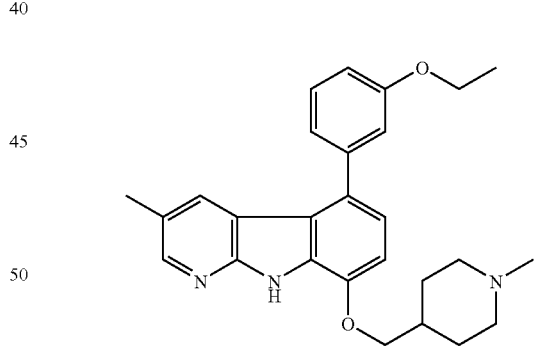

The title compound was synthesized using an analogous procedure to that outlined in the preparation of Compound 176. $^1$H NMR (400 MHz, DMSO-$d_6$) δ ppm 1.35 (t, J=6.95 Hz, 3 H) 1.44-1.56 (m, 2 H) 2.10-2.18 (m, 1 H) 2.25 (br. s., 5 H) 2.80 (d, J=4.80 Hz, 3 H) 2.97-3.07 (m, 2 H) 3.52 (d, J=11.62 Hz, 2 H) 4.06-4.09 (m, 4 H) 6.98-7.14 (m, 5 H) 7.44 (t, J=7.71 Hz, 1 H) 7.64 (s, 1 H) 8.25 (s, 1 H) 9.28 (br. s., 1 H) 11.87 (s, 1 H); [M+H] calc'd for $C_{27}H_{32}N_3O_2$, 430.2; found, 430.5; [M+H+TFA] calc'd for $C_{29}H_{33}N_3O_4F_3$, 544.2; found, 544.4.

Compound 184: 5-(3-(ethylsulfonyl)phenyl)-3-methyl-8-(piperidin-4-ylmethoxy)-9H-pyrido[2,3-b]indole

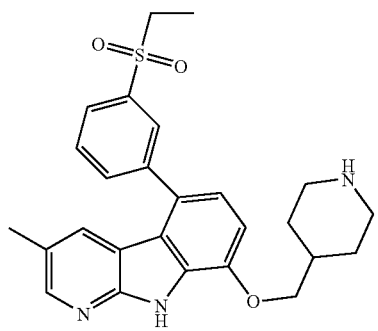

The title compound was synthesized by using an analogous synthetic sequence to that outlined in the preparation of Compound 176. $^1$H NMR (400 MHz, MeOD) δ ppm 1.29 (t, J=7.33 Hz, 3 H) 1.71 (d, J=11.37 Hz, 2 H) 2.27-2.40 (m, 6 H) 3.11 (t, J=12.25 Hz, 2 H) 3.51 (d, J=12.88 Hz, 2 H) 4.20 (br. s., 2 H) 7.28 (br. s., 2 H) 7.86 (t, J=7.70 Hz, 1 H) 7.92-8.00 (m, 1 H) 8.00-8.08 (m, 2 H) 8.18 (br. s., 1 H) 8.29 (br. s., 1 H) [M+H] calc'd for $C_{26}H_{29}N_3O_3S$, 464; found, 464.

Compound 185: (S)-5-(3-(ethylsulfonyl)phenyl)-3-methyl-8-((1-methylpyrrolidin-3-yl)methoxy)-9H-pyrido[2,3-b]indole

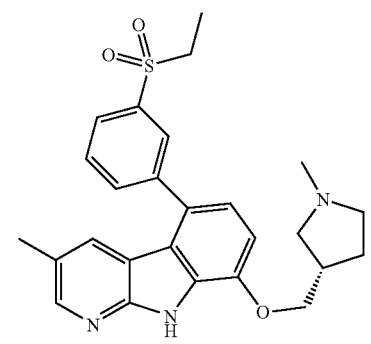

The title compound was synthesized by using an analogous synthetic sequence to that outlined in the preparation of Compound 176. $^1$H NMR (400 MHz, Methanol-d$_4$) δ 8.31 (s, br, 1 H) 8.19 (s, 1 H) 8.06 (m, 1 H) 8.00 (m, 1 H) 7.89 (m, 2 H) 7.27 (m, 2 H) 4.38 (m, 2 H) 3.91 (m, 2 H) 3.50 (m, 1 H) 3.35 (t, J=7.32 Hz, 2 H) 3.19 (m, 1 H) 3.07 (s, 3H) 2.6-2.25 (m, 6 H) 1.31 (t, J=7.32 Hz, 3 H). [M+H] calc'd for $C_{26}H_{30}N_3O_3S$, 464; found, 464.

Compound 186: (R)-5-(3-(ethylsulfonyl)phenyl)-3-methyl-8-((1-methylpyrrolidin-3-yl)methoxy)-9H-pyrido[2,3-b]indole

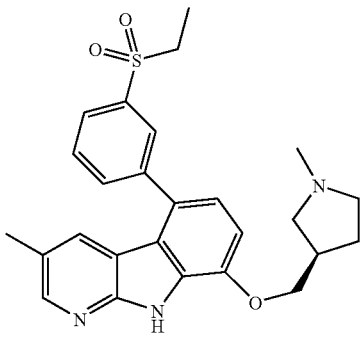

The title compound was synthesized by using an analogous synthetic sequence to that outlined in the preparation of Compound 176. $^1$H NMR (400 MHz, Methanol-d$_4$) δ 8.31 (s, br, 1 H) 8.19 (s, 1 H) 8.06 (m, 1 H) 8.00 (m, 1 H) 7.89 (m, 2 H) 7.27 (m, 2 H) 4.38 (m, 2 H) 3.91 (m, 2 H) 3.50 (m, 1 H) 3.35 (t, J=7.32 Hz, 2 H) 3.19 (m, 1 H) 3.07 (s, 3H) 2.6-2.25 (m, 6 H) 1.31 (t, J=7.32 Hz, 3 H). [M+H] calc'd for $C_{26}H_{30}N_3O_3S$, 464; found, 464.

Compound 187: (S)-5-(3-(ethylsulfonyl)phenyl)-3-methyl-8-((1-methylpyrrolidin-2-yl)methoxy)-9H-pyrido[2,3-b]indole

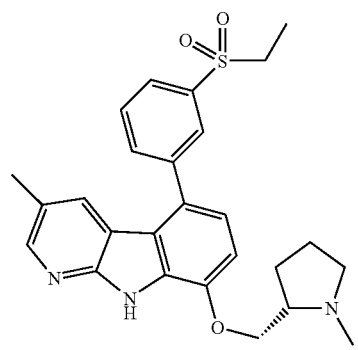

The title compound was synthesized by using an analogous synthetic sequence to that outlined in the preparation of Compound 176. $^1$H NMR (400 MHz, DMSO-d$_6$) δ ppm 1.17 (t, J=7.33 Hz, 3 H) 1.71-1.77 (m, 4 H) 2.12 (m, 1 H) 2.26 (s, 3 H) 2.45 (s, 3 H) 2.78 (br. s., 1 H) 3.03 (m, 1 H) 3.41 (q, J=7.33 Hz, 2 H) 4.07 (dd, J=9.60, 6.32 Hz, 1 H) 4.28 (dd, J=9.85, 5.05 Hz, 1 H) 7.06 (d, J=8.01 Hz, 1 H) 7.16 (d, J=8.08 Hz, 1 H) 7.54 (s, 1 H) 7.84 (t, J=7.71 Hz, 1 H) 7.98 (t, J=7.58 Hz, 2 H) 8.08 (s, 1 H) 8.28 (s, 1 H) 12.06 (s, 1 H); [M+H] calc'd for $C_{26}H_{30}N_3O_3S$, 464.2.; found, 464.4.

Compound 188: (S)-5-(3-(ethylsulfonyl)phenyl)-3-methyl-8-(pyrrolidin-3-ylmethoxy)-9H-pyrido[2,3-b]indole

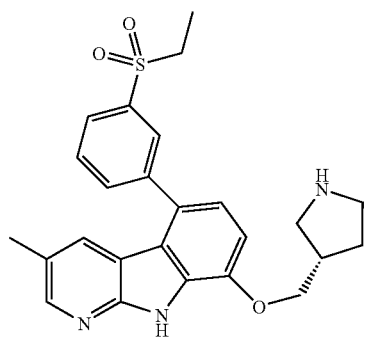

The title compound was synthesized by using an analogous synthetic sequence to that outlined in the preparation of Compound 176. $^1$H NMR (400 MHz, Methanol-d$_4$) δ 8.29-8.21 (m, 2 H) 8.07 (m, 1 H) 8.00-7.92 (m, 2 H) 7.86 (m, 1 H) 7.27 (m, 2 H) 4.50-4.12 (m, 4 H) 3.70-3.48 (m, 1 H) 3.35 (t, J=7.32 Hz, 2 H) 3.19 (m, 1 H) 2.58 (m, 3 H) 2.37 (s, 3 H) 1.31 (t, J=7.32 Hz, 3 H). [M+H] calc'd for C$_{25}$H$_{28}$N$_3$O$_3$S, 450; found, 450.

Compound 189: (R)-5-(3-(ethylsulfonyl)phenyl)-3-methyl-8-(pyrrolidin-3-ylmethoxy)-9H-pyrido[2,3-b]indole

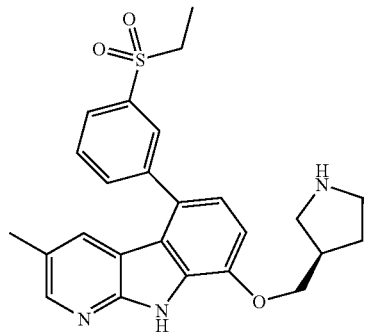

The title compound was synthesized by using an analogous synthetic sequence to that outlined in the preparation of Compound 176. $^1$H NMR (400 MHz, Methanol-d$_4$) δ 8.29-8.21 (m, 2 H) 8.07 (m, 1 H) 8.00-7.92 (m, 2 H) 7.86 (m, 1 H) 7.27 (m, 2 H) 4.50-4.12 (m, 4 H) 3.70-3.48 (m, 1 H) 3.35 (t, J=7.32 Hz, 2 H) 3.19 (m, 1 H) 2.58 (m, 3 H) 2.37 (s, 3 H) 1.31 (t, J=7.32 Hz, 3 H). [M+H] calc'd for C$_{25}$H$_{28}$N$_3$O$_3$S, 450; found, 450.

Compound 190: 3-(5-chloro-3-methyl-9H-pyrido[2,3-b]indol-8-yloxy)-N,N-dimethylpropan-1-amine

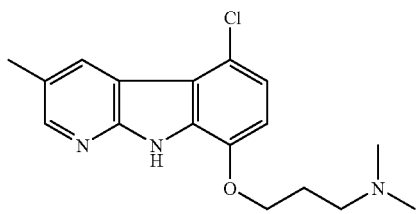

The title compound was synthesized by using an analogous synthetic sequence to that outlined in the preparation of Compound 175. $^1$H NMR (400 MHz, DMSO-d$_6$) δ ppm 0.75-0.81 (m, 4 H) 1.80 (m, 1 H) 2.22 (dd, J=9.98, 5.43 Hz, 2 H) 2.27 (s, 3 H) 2.88 (s, 3 H) 2.89 (s, 3 H) 3.46-3.51 (m, 2 H) 4.28 (t, J=5.56 Hz, 2 H) 6.99 (d, J=8.08 Hz, 1 H) 7.10 (d, J=8.08 Hz, 1 H) 7.23 (d, J=7.83 Hz, 1 H) 7.46 (t, J=7.83 Hz, 1 H) 7.61 (d, J=9.09 Hz, 1 H) 7.74 (d, J=1.26 Hz, 1 H) 7.92 (s, 1 H) 8.27 (d, J=1.52 Hz, 1 H) 9.63 (br. s., 1 H) 10.34 (s, 1 H) 11.90 (s, 1 H); [M+H] calc'd for C$_{17}$H$_{20}$ClN$_3$O, 317; found, 317.2

Compound 191: N-(3-(8-(3-(dimethylamino)propoxy)-3-methyl-9H-pyrido[2,3-b]indol-5-yl)phenyl)cyclopropanecarboxamide

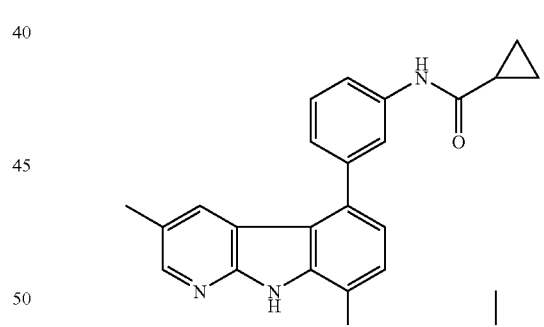

The title compound was synthesized from Compound 190 using an analogous procedure to that outlined in the preparation of Compound 176. $^1$H NMR (400 MHz, DMSO-d$_6$) δ ppm 0.75-0.81 (m, 4 H) 1.80 (m, 1 H) 2.22 (dd, J=9.98, 5.43 Hz, 2 H) 2.27 (s, 3 H) 2.88 (s, 3 H) 2.89 (s, 3 H) 3.46-3.51 (m, 2 H) 4.28 (t, J=5.56 Hz, 2 H) 6.99 (d, J=8.08 Hz, 1 H) 7.10 (d, J=8.08 Hz, 1 H) 7.23 (d, J=7.83 Hz, 1 H) 7.46 (t, J=7.83 Hz, 1 H) 7.61 (d, J=9.09 Hz, 1 H) 7.74 (d, J=1.26 Hz, 1 H) 7.92 (s, 1 H) 8.27 (d, J=1.52 Hz, 1 H) 9.63 (br. s., 1 H) 10.34 (s, 1 H) 11.90 (s, 1 H); [M+H] calc'd for C$_{27}$H$_{31}$N$_4$O$_2$, 443.2; found, 443.3.

191

Compound 192: N-cyclopropyl-3-(8-(3-(dimethylamino)propoxy)-3-methyl-9H-pyrido[2,3-b]indol-5-yl)benzamide

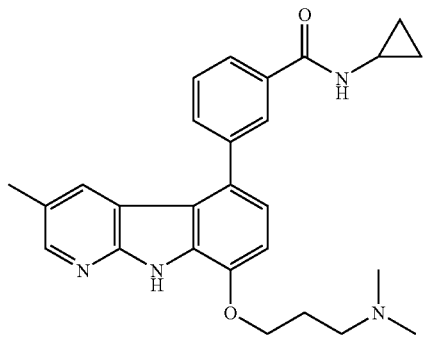

The title compound was synthesized from Compound 190 using an analogous procedure to that outlined in the preparation of Compound 176. $^1$H NMR (400 MHz, DMSO-d$_6$) δ ppm 0.54-0.58 (m, 2 H) 0.66-0.73 (m, 2 H) 2.21-2.24 (m, 2 H) 2.26 (s, 3 H) 2.85 (m, 1 H) 2.88 (s, 3 H) 2.89 (s, 3 H) 3.47-3.52 (m, 2 H) 4.29 (t, J=5.43 Hz, 2 H) 7.05 (d, J=8.08 Hz, 1 H) 7.13 (d, J=8.08 Hz, 1 H) 7.54 (s, 1 H) 7.62 (t, J=7.71 Hz, 1 H) 7.72 (d, J=7.58 Hz, 1 H) 7.93 (d, J=7.83 Hz, 1 H) 8.03 (s, 1 H) 8.28 (s, 1 H) 8.55 (d, J=4.04 Hz, 1 H) 9.60 (br. s., 1 H) 11.93 (s, 1 H); [M+H] calc'd for C$_{27}$H$_{31}$N$_4$O$_2$, 443.2; found, 443.3.

Compound 193: 3-(8-(3-(dimethylamino)propoxy)-3-methyl-9H-pyrido[2,3-b]indol-5-yl)-N-methylbenzenesulfonamide

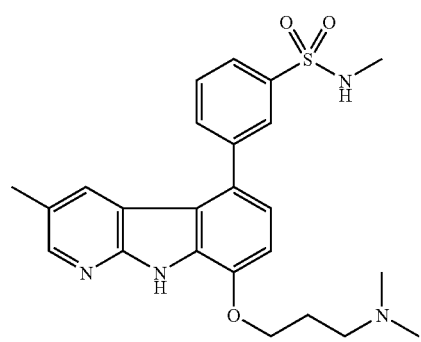

The title compound was synthesized from Compound 190 using an analogous procedure to that outlined in the preparation of Compound 176. $^1$H NMR (400 MHz, DMSO-d$_6$) δ ppm 2.21-2.24 (m, 2 H) 2.26 (s, 3 H) (m, 2 H) 2.47 (s, 3 H) 2.88 (s, 3 H) 3.47-3.52 (m, 2 H) 4.29 (t, J=5.43 Hz, 2 H) 7.05 (d, J=8.08 Hz, 1 H) 7.13 (d, J=8.08 Hz, 1 H) 7.54 (s, 1 H) 7.62 (t, J=7.71 Hz, 1 H) 7.72 (d, J=7.58 Hz, 1 H) 7.93 (d, J=7.83 Hz, 1 H) 8.03 (s, 1 H) 8.28 (s, 1 H) 8.55 (d, J=4.04 Hz, 1 H) 9.60 (br. s., 1 H) 11.93 (s, 1 H); [M+H] calc'd for C$_{24}$H$_{28}$N$_4$O$_3$S, 453.2; found, 453.4.

192

Compound 194: 3-(8-(3-(dimethylamino)propoxy)-3-methyl-9H-pyrido[2,3-b]indol-5-yl)-N,N-dimethylbenzenesulfonamide

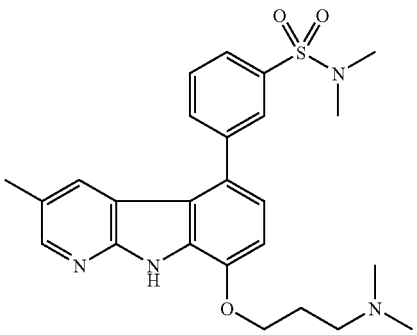

The title compound was synthesized from Compound 190 using an analogous procedure to that outlined in the preparation of Compound 176. $^1$H NMR (400 MHz, DMSO-d$_6$) δ ppm 2.21-2.24 (m, 2 H) 2.26 (s, 3 H) (m, 2 H) 2.66 (s, 6 H) 2.88 (s, 3 H) 2.89 (s, 3 H) 3.47-3.52 (m, 2 H) 4.29 (t, J=5.43 Hz, 2 H) 7.05 (d, J=8.08 Hz, 1 H) 7.13 (d, J=8.08 Hz, 1 H) 7.54 (s, 1 H) 7.62 (t, J=7.71 Hz, 1 H) 7.72 (d, J=7.58 Hz, 1 H) 7.93 (d, J=7.83 Hz, 1 H) 8.03 (s, 1 H) 8.28 (s, 1 H) 8.55 (d, J=4.04 Hz, 1 H) 9.60 (br. s., 1 H) 11.93 (s, 1 H); [M+H] calc'd for C$_{25}$H$_{30}$N$_4$O$_3$S, 467.2; found, 467.2.

Compound 195: 3'-(ethylsulfonyl)biphenyl-4-ol

Compound 196: 3'-(ethylsulfonyl)-3-iodobiphenyl-4-ol

Compound 197: 4-((3'-(ethylsulfonyl)-3-iodobiphenyl-4-yloxy)methyl)-1-methylpiperidine

Compound 198: 3-bromo-5-chloro-N-(3'-(ethylsulfonyl)-4-((1-methylpiperidin-4-yl)methoxy)biphenyl-3-yl)pyridin-2-amine

Compound 199: 3-chloro-5-(3-(ethylsulfonyl)phenyl)-8-((1-methylpiperidin-4-yl)methoxy)-9H-pyrido[2,3-b]indole

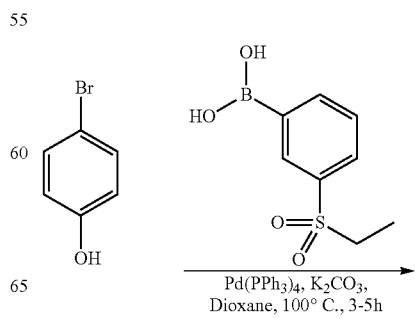

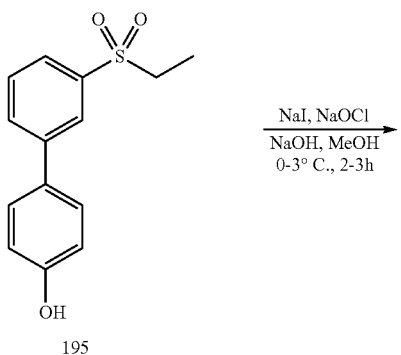

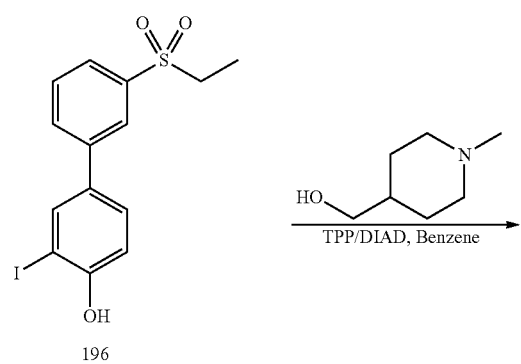

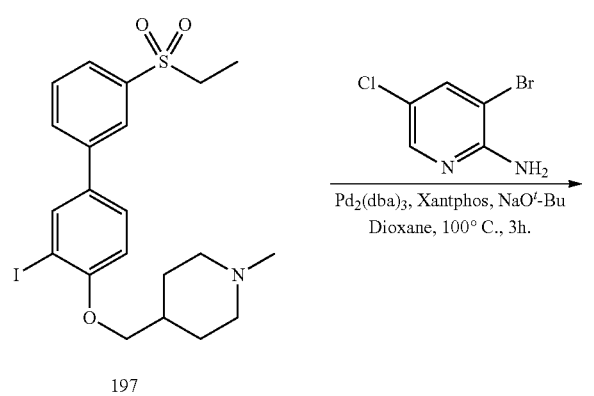

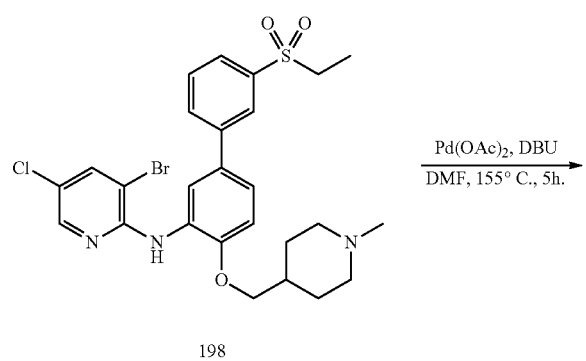

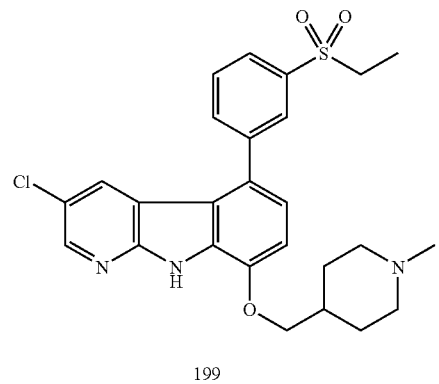

¹H NMR (400 MHz, DMSO-d₆) δ ppm 1.17 (t, J=7.33 Hz, 3 H) 1.41 (qd, J=11.62, 3.03 Hz, 2 H) 1.86-1.96 (m, 5 H) 2.19 (s, 3 H) 2.84 (br. d, J=10.86 Hz, 2 H) 3.41 (q, J=7.49 Hz, 2 H) 4.09 (d, J=6.32 Hz, 2 H) 7.11-7.21 (m, 2 H) 7.62 (d, J=2.53 Hz, 1 H) 7.87 (t, J=7.71 Hz, 1 H) 8.00 (t, J=7.83 Hz, 2 H) 8.05 (s, 1 H) 8.45 (d, J=2.53 Hz, 1 H) 12.45 (s, 1 H); [M+H] calc'd for $C_{26}H_{29}ClN_3O_3S$, 498.2; found, 498.2; [M+H+TFA] calc'd for $C_{28}H_{30}ClN_3O_5F_3S$, 612.2; found, 612.1.

Compound 200: 3-chloro-5-(3-(ethylsulfonyl)phenyl)-8-(piperidin-4-ylmethoxy)-9H-pyrido[2,3-b]indole

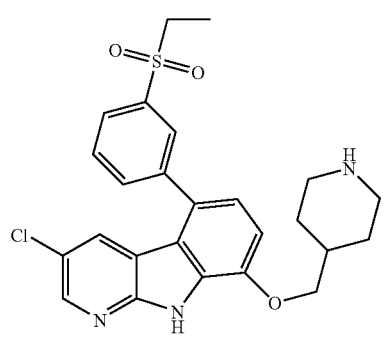

The title compound was synthesized by using an analogous synthetic sequence to that outlined in the preparation of Compound 199. ¹H NMR (400 MHz, MeOD) δ ppm 1.32 (t, J=7.33 Hz, 4 H) 1.60-1.72 (m, 1 H) 2.31 (d, J=13.89 Hz, 2 H) 3.11 (td, J=12.82, 2.40 Hz, 2 H) 3.51 (d, J=12.63 Hz, 2 H) 4.19 (d, J=6.57 Hz, 2 H) 7.11-7.15 (m, 1 H) 7.16-7.20 (m, 1 H) 7.64 (d, J=2.27 Hz, 1 H) 7.85 (t, J=7.71 Hz, 1 H) 7.95 (ddd, J=7.71, 1.39, 1.26 Hz, 1 H) 8.05 (ddd, J=8.08, 1.52, 1.26 Hz, 1 H) 8.13 (t, J=1.52 Hz, 1 H) 8.31 (s, 1 H)

Compound 201: 5-(3-(ethylsulfonyl)phenyl)-8-((1-methylpiperidin-4-yl)methoxy)-3-(trifluoromethyl)-9H-pyrido[2,3-b]indole

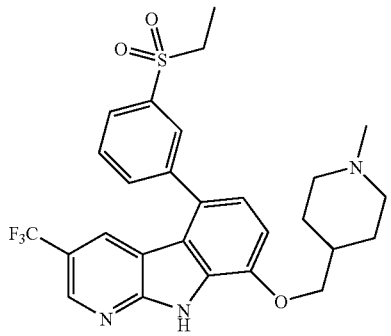

The title compound was synthesized by using an analogous synthetic sequence to that outlined in the preparation of Compound 199. $^1$H NMR (400 MHz, Methanol-d$_4$) δ 8.72 (s, 1 H) 8.15 (s, 1 H) 8.10 (m, 1 H) 7.99 (m, 1 H) 7.93 (s, 1 H) 7.88 (t, J=7.6 Hz, 1 H) 7.28 (d, J=8.08 Hz, 1 H) 7.23 (d, J=8.08 Hz, 1 H) 4.24 (d, J=6.32 Hz, 2 H) 3.65 (m, br, 2 H) 3.43 (q, J=7.32 Hz, 2 H) 3.14 (m, br, 2 H) 2.95 (s, 3 H) 2.38 (m, br, 3 H) 1.68 (m, br, 2 H) 1.31 (t, J=7.32 Hz, 3 H). [M+H] calc'd for $C_{27}H_{29}F_3N_3O_3S$, 532; found, 532.

Compound 202: 5-(3-(ethylsulfonyl)phenyl)-8-((1-methylpiperidin-4-yl)methoxy)-9H-pyrido[2,3-b]indole-3-carbonitrile

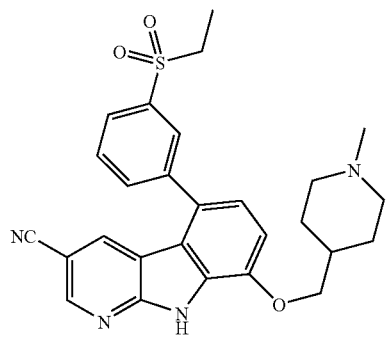

The title compound was synthesized by using an analogous synthetic sequence to that outlined in the preparation of Compound 199. $^1$H NMR (400 MHz, Methanol-d$_4$) δ 8.63 (s, 1 H) 8.22 (s, 1 H) 8.09 (m, 1 H) 7.98 (m, 1 H) 7.94 (m, 2 H) 7.89 (t, J=7.84 Hz, 1 H) 7.26 (d, J=8.08 Hz, 1 H) 7.23 (d, J=8.08 Hz, 1 H) 4.24 (d, J=6.28 Hz, 2 H) 3.65 (m, br, 2 H) 3.38 (q, J=7.32 Hz, 2 H) 3.15 (m, br, 2 H) 2.95 (s, 3 H) 2.42 (m, br, 3 H) 1.72 (m, br, 2 H) 1.31 (t, J=7.32 Hz, 3 H). [M+H] calc'd for $C_{27}H_{29}N_4O_3S$, 489; found, 489.

Compound 203: 2-(5-(3-(ethylsulfonyl)phenyl)-7-fluoro-3-methyl-9H-pyrido[2,3-b]indol-8-yloxy)-N,N-dimethylethanamine

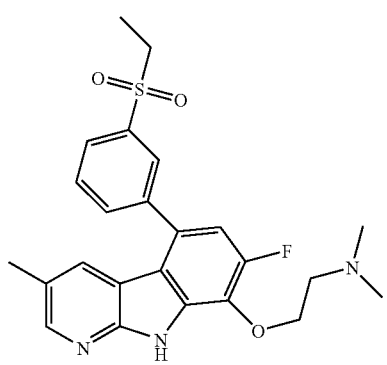

The title compound was synthesized by using an analogous synthetic sequence to that outlined in the preparation of Compound 199. $^1$H NMR (400 MHz, MeOD) δ ppm 1.29 (t, J=7.45 Hz, 3 H) 2.32 (s, 3 H) 3.13 (s, 6 H) 3.74 (t, 2 H) 4.64 (t, J=4.80 Hz, 2 H) 7.11 (d, J=12.63 Hz, 1 H) 7.59 (s, 1 H) 7.88 (t, J=7.71 Hz, 1 H) 7.98 (dd, J=6.82, 2.02 Hz, 1 H) 8.10 (dd, J=7.45, 1.64 Hz, 1 H) 8.16 (t, J=1.64 Hz, 1 H) 8.26 (s, 1 H) [M+H] calc'd for $C_{24}H_{26}FN_3O_3S$, 456; found, 456.

Compound 204: 3-(3-chloro-5-(3-(ethylsulfonyl)phenyl)-7-fluoro-9H-pyrido[2,3-b]indol-8-yloxy)-N,N-dimethylpropan-1-amine

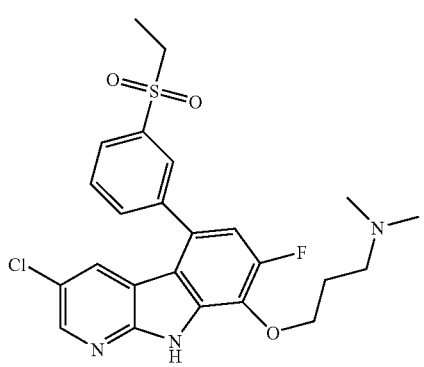

The title compound was synthesized by using an analogous synthetic sequence to that outlined in the preparation of Compound 199. $^1$H NMR (400 MHz, MeOD) δ ppm 1.31 (t, J=7.45 Hz, 3 H) 2.34 (br. s., 2 H) 3.00 (s, 6 H) 3.54 (d, J=8.08 Hz, 2 H) 4.46 (t, J=6.19 Hz, 2 H) 7.09 (d, J=12.63 Hz, 1 H) 7.57 (d, J=2.27 Hz, 1 H) 7.89 (d, J=7.07 Hz, 1 H) 7.97 (d, J=9.35 Hz, 1 H) 8.09-8.14 (m, 2 H) 8.35 (s, 1 H) [M+H] calc'd for $C_{24}H_{25}ClFN_3O_3S$, 490; found, 490.

Compound 205: 3-(5-(3-(ethylsulfonyl)phenyl)-3-methyl-9H-pyrido[2,3-b]indol-8-yloxy)-N,N-dimethylpropan-1-amine Compound 206: 2-(5-(3-(ethylsulfonyl)phenyl)-3-methyl-9H-pyrido[2,3-b]indol-8-yloxy)-N,N-dimethylethanamine

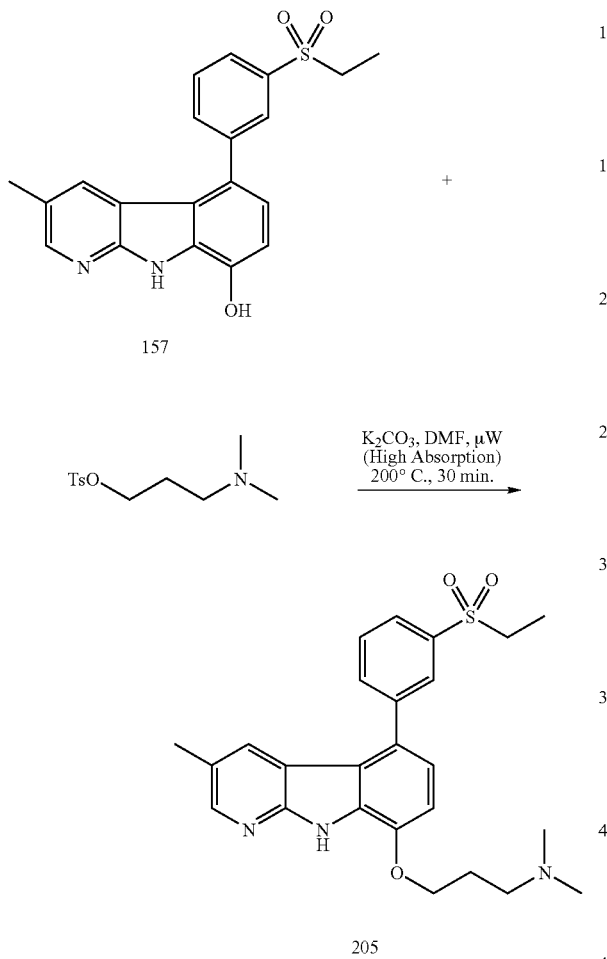

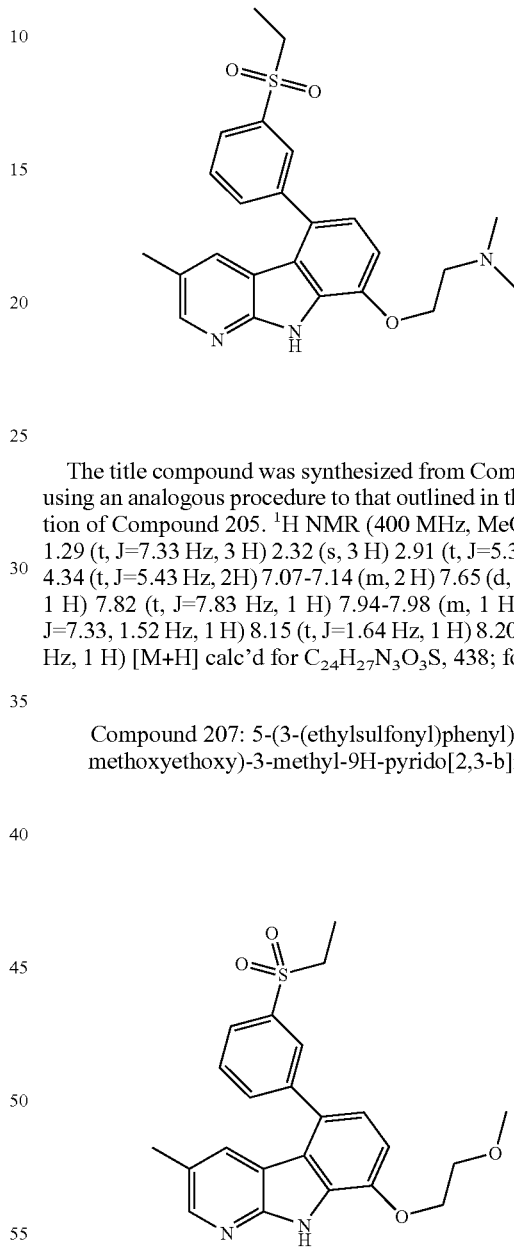

A 5 mL microwave vial was charged with Compound 157 (290 mg, 0.79 mmol), 3-(dimethylamino)propyl-4-methylbenzenesulfonate (224 mg, 0.87 mmol), potassium carbonate (218 mg, 1.58 mmol) and 2 mL of anhydrous DMF, under nitrogen atmosphere. The reaction mixture was heated at 200° C. for 30 min. in microwave with high absorption. The reaction was quenched with addition of water, and the solid precipitate out was collected by filtration and purified through preparative HPLC to provide title compound (1438 mg, 40%). $^1$H NMR (400 MHz, DMSO-$d_6$) δ ppm 1.17 (t, J=7.33 Hz, 3 H) 1.99 (qd, J=6.61, 6.44 Hz, 2 H) 2.20 (s, 6 H) 2.26 (s, 3 H) 2.53-2.56 (m, 2 H) 3.41 (q, J=7.33 Hz, 2 H) 4.25 (t, J=6.19 Hz, 2H) 7.05-7.09 (m, 1 H) 7.11-7.14 (m, 1 H) 7.54 (d, J=1.52 Hz, 1 H) 7.85 (t, J=7.83 Hz, 1 H) 7.98 (t, J=6.95 Hz, 2 H) 8.06-8.08 (m, 1 H) 8.27 (d, J=1.77 Hz, 1 H) 12.13 (s, 1 H); [M+H] calc'd for $C_{25}H_{30}N_3O_3S$, 452.2; found, 452.4.

The title compound was synthesized from Compound 157 using an analogous procedure to that outlined in the preparation of Compound 205. $^1$H NMR (400 MHz, MeOD) δ ppm 1.29 (t, J=7.33 Hz, 3 H) 2.32 (s, 3 H) 2.91 (t, J=5.31 Hz, 2 H) 4.34 (t, J=5.43 Hz, 2H) 7.07-7.14 (m, 2 H) 7.65 (d, J=2.02 Hz, 1 H) 7.82 (t, J=7.83 Hz, 1 H) 7.94-7.98 (m, 1 H) 8.02 (dd, J=7.33, 1.52 Hz, 1 H) 8.15 (t, J=1.64 Hz, 1 H) 8.20 (d, J=2.02 Hz, 1 H) [M+H] calc'd for $C_{24}H_{27}N_3O_3S$, 438; found, 438.

Compound 207: 5-(3-(ethylsulfonyl)phenyl)-8-(2-methoxyethoxy)-3-methyl-9H-pyrido[2,3-b]indole The title compound was synthesized from Compound 157 using an analogous procedure to that outlined in the preparation of Compound 205. $^1$H NMR (400 MHz, CDCl$_3$) δ 8.22 (s, 1 H) 8.19 (s, 1 H) 8.14 (m, 1 H) 8.06 (m, 1 H) 7.91 (m, 1 H) 7.81 (m, 1 H) 7.28 (d, J=8.32 Hz, 1 H) 7.22 (d, J=8.32 Hz, 1 H) 4.44 (m, 2 H) 3.95 (m, 2 H) 3.58 (s, 3 H) 3.23 (q, J=7.32 Hz, 2 H) 2.49 (s, 3 H) 1.37 (t, J=7.32 Hz, 3 H). [M+H] calc'd for $C_{23}H_{25}N_2O_4S$, 425; found, 425.

Compound 208: 2-(5-(3-(ethylsulfonyl)phenyl)-3-methyl-9H-pyrido[2,3-b]indol-8-yloxy)acetonitrile

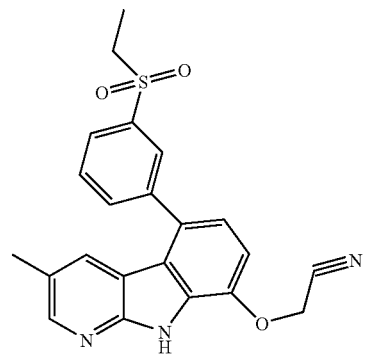

The title compound was synthesized from Compound 157 and 2-bromoacetonitrile using an analogous procedure to that outlined in the preparation of Compound 205. $^1$H NMR (400 MHz, CHLOROFORM-d) δ ppm 1.36 (t, J=7.33 Hz, 3 H) 3.22 (q, J=7.33 Hz, 3 H) 5.14 (s, 2 H) 7.31-7.37 (m, 2 H) 7.82 (t, J=7.71 Hz, 1 H) 7.91 (d, J=7.83 Hz, 1 H) 8.09 (d, J=7.83 Hz, 1 H) 8.11-8.15 (m, 2 H) 8.22 (s, 1 H) 14.04 (br. s., 1 H) [M+H] calc'd for $C_{22}H_{19}N_3O_3S$, 406; found, 406.

Compound 209: 3-(5-(3-(ethylsulfonyl)phenyl)-3-methyl-9H-pyrido[2,3-b]indol-8-yloxy)propanenitrile

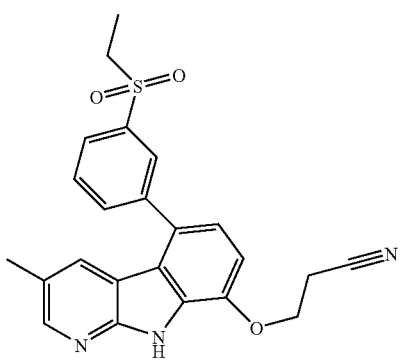

The title compound was synthesized from Compound 157 and 3-bromopropionitrile using an analogous procedure to that outlined in the preparation of Compound 205. $^1$H NMR (400 MHz, MeOD) δ ppm 1.28 (d, J=14.65 Hz, 2 H) 1.28 (s, 2 H) 2.30 (s, 3 H) 3.10 (t, J=6.69 Hz, 2 H) 5.12 (t, J=6.82 Hz, 2 H) 7.00-7.05 (m, 2 H) 7.53 (dd, J=2.02, 0.76 Hz, 1 H) 7.81 (t, J=7.45 Hz, 1 H) 7.92 (ddd, J=7.89, 1.45, 1.26 Hz, 1 H) 8.02 (dt, J=7.83, 1.52 Hz, 1 H) 8.10 (t, J=1.89 Hz, 1 H) 8.26 (d, J=2.02 Hz, 1 H) [M+H] calc'd for $C_{23}H_{21}N_3O_3S$, 421; found, 421.

Compound 210: (R)-8-(1-tert-butyldiphenylsilyloxy)propan-2-yloxy)-(5-(3-(ethylsulfonyl)phenyl)-3-methyl-9H-pyrido[2,3-b]indole

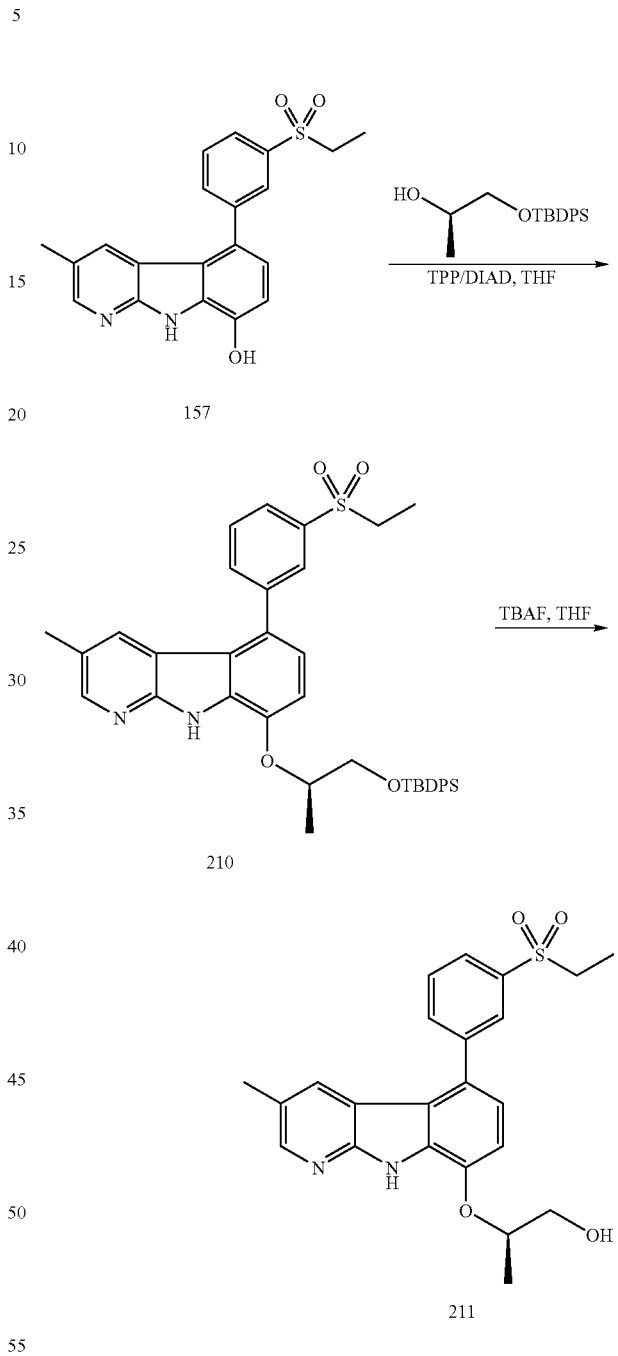

To a stirred solution of Compound 157 (75 mg, 0.204 mmol) in anhydrous THF (3.0 mL) were sequentially added (R)-(tert-butyldiphenylsilyloxy)propan-2-ol (77 mg, 0.245 mmol) and triphenyl phosphine (81 mg, 0.31 mmoL). The reaction mixture was cooled to 0° C., and to it diisopropylazodicarboxylate (60 µL, 0.31 mmol) was added in drop wise manner. After the addition was over, stirring continued for another 0.5 h at 0° C. and then for 12 h at room temperature. Solvents were removed in vacuum and the residue was purified by silica gel column chromatography, provided the title compound (108 mg, 80%).

Compound 211: (R)-2-(5-(3-(ethylsulfonyl)phenyl)-3-methyl-9H-pyrido[2,3-b]indol-8-yloxy)propan-1-ol

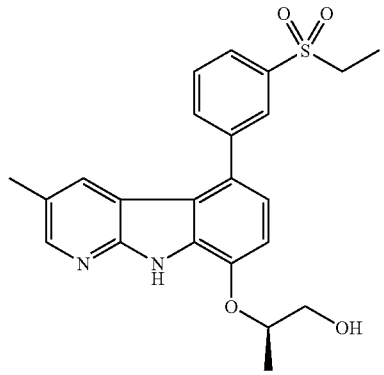

Compound 210 (100 mg, 0.15 mmol) was taken in a THF (3 mL) and stirred for 12 h at room temperature with TBAF (0.19 mL, 0.19 mmol, 1 M solution in THF). The reaction mixture was diluted with EtOAc and washed with aqueous NH$_4$Cl and brine. The organic extract was dried over Na$_2$SO$_4$, concentrated and purified by preparative HPLC to provide the title compound (50 mg, 73%). $^1$H NMR (400 MHz, DMSO-d$_6$) δ ppm 1.17 (t, J=7.45 Hz, 3 H) 1.36 (d, J=6.06 Hz, 3 H) 2.26 (s, 3 H) 3.40 (q, J=7.41 Hz, 2 H) 3.63-3.72 (m, 2 H) 4.63 (m, 1 H) 4.90 (t, J=6.19 Hz, 1 H) 7.07 (d, J=8.08 Hz, 1 H) 7.15-7.19 (m, 1 H) 7.56 (s, 1 H) 7.85 (t, J=7.71 Hz, 1 H) 7.97-7.99 (m, 2 H) 8.07-8.10 (m, 1 H) 8.27 (d, J=2.02 Hz, 1 H) 11.82 (s, 1 H); [M+H] calc'd for C$_{23}$H$_{25}$N$_2$O$_4$S, 425.2.; found, 425.3.

Compound 212: (S)-2-(5-(3-(ethylsulfonyl)phenyl)-3-methyl-9H-pyrido[2,3-b]indol-8-yloxy)propan-1-ol

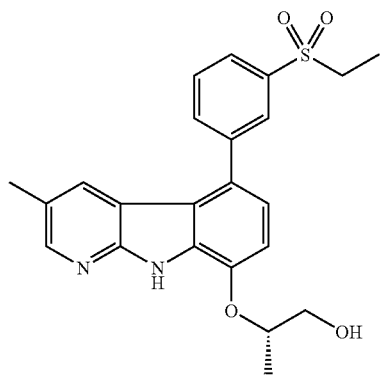

The title compound was synthesized from Compound 157 using an analogous procedure to that outlined in the preparation of Compound 211. $^1$H NMR (400 MHz, DMSO-d$_6$) δ ppm 1.17 (t, J=7.45 Hz, 3 H) 1.36 (d, J=6.06 Hz, 3 H) 2.26 (s, 3 H) 3.40 (q, J=7.41 Hz, 2 H) 3.63-3.72 (m, 2 H) 4.63 (m, 1 H) 4.90 (t, J=6.19 Hz, 1 H) 7.07 (d, J=8.08 Hz, 1 H) 7.15-7.19 (m, 1 H) 7.56 (s, 1 H) 7.85 (t, J=7.71 Hz, 1 H) 7.97-7.99 (m, 2 H) 8.07-8.10 (m, 1 H) 8.27 (d, J=2.02 Hz, 1 H) 11.82 (s, 1 H); [M+H] calc'd for C$_{23}$H$_{25}$N$_2$O$_4$S, 425.2.; found, 425.3.

Compound 213: 1-(5-(3-(ethylsulfonyl)phenyl)-3-methyl-9H-pyrido[2,3-b]indol-8-yloxy)propan-2-ol

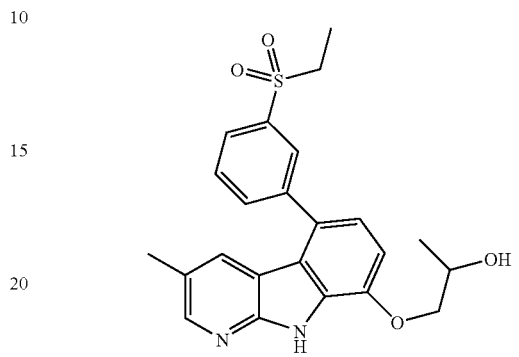

The title compound was synthesized from Compound 157 using an analogous procedure to that outlined in the preparation of Compound 211. $^1$H NMR (400 MHz, Methanol-d$_4$) δ 8.28 (s, 1 H) 8.19 (m, 1 H) 8.06 (m, 1 H) 8.00 (m, 1 H) 7.92 (s, 1 H) 7.87 (t, J=8.0 Hz, 1 H) 7.26 (m, 2 H) 4.31 (m, 2 H) 4.10 (m, 1 H) 3.30 (q, J=7.5 Hz, 2 H) 2.40 (s, 3 H) 1.40 (d, J=8 Hz, 3 H) 1.31 (t, J=7.5 Hz, 3 H). [M+H] calc'd for C$_{23}$H$_{25}$N$_2$O$_4$S, 425; found, 425.

Compound 214: (S)-4-(5-(3-(ethylsulfonyl)phenyl)-3-methyl-9H-pyrido[2,3-b]indol-8-yloxy)-2-methyl-pentan-2-ol

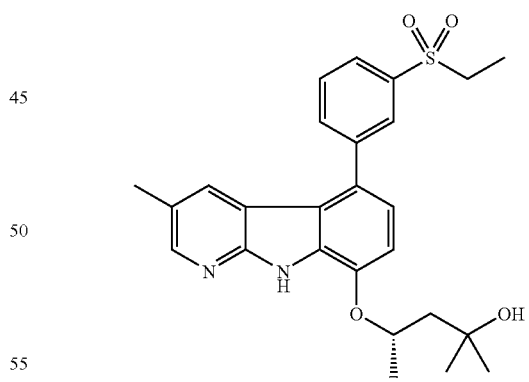

The title compound was synthesized from Compound 157 using an analogous procedure to that outlined in the preparation of Compound 211. $^1$H NMR (400 MHz, DMSO-d$_6$) δ ppm 1.16 (t, J=7.33 Hz, 3 H) 1.17 (d, J=6.2 Hz, 3 H) 1.43 (s, 3 H) 1.46 (s, 3H) 1.93 (d, J=5.81 Hz, 2 H) 2.26 (s, 3 H) 3.41 (q, J=6.33 Hz, 2 H) 4.05 (m, 1 H) 7.07 (d, J=8.08 Hz, 1 H) 7.23 (d, J=8.08 Hz, 1 H) 7.53 (s, 1 H) 7.86 (t, J=7.58 Hz, 1 H) 8.00 (dd, J=7.71, 1.64 Hz, 2 H) 8.09-8.11 (m, 1 H) 8.28 (s, 1 H) 11.95 (s, 1 H); [M+H] calc'd for C$_{26}$H$_{31}$N$_2$O$_4$S, 467.2; found 467.3.

Compound 215: 2-(5-(3-(ethylsulfonyl)phenyl)-3-methyl-9H-pyrido[2,3-b]indol-8-yloxy)ethanol

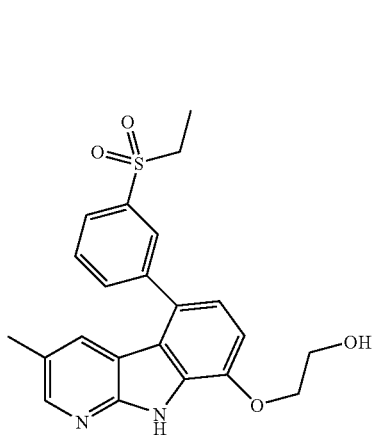

The title compound was synthesized from Compound 157 and 2-(benzyloxy)ethanol using an analogous procedure to that outlined in the preparation of Compound 210 followed by debenzylation using Pd/C—H$_2$. $^1$H NMR (400 MHz, Methanol-d$_4$) δ 8.30 (s, 1 H) 8.19 (m, 1 H) 8.06 (m, 1 H) 8.00 (m, 2 H) 7.87 (t, J=8.0 Hz, 1 H) 7.26 (m, 2 H) 4.38 (t, J=4 Hz, 2 H) 4.08 (t, J=4 Hz, 2 H) 3.30 (q, J=7.5 Hz, 2 H) 2.41 (s, 3 H) 1.31 (t, J=7.5 Hz, 3 H). [M+H] calc'd for C$_{22}$H$_{23}$N$_2$O$_4$S, 411; found, 411.

Compound 216: 3-(5-(3-(ethylsulfonyl)phenyl)-3-methyl-9H-pyrido[2,3-b]indol-8-yloxy)propan-1-ol

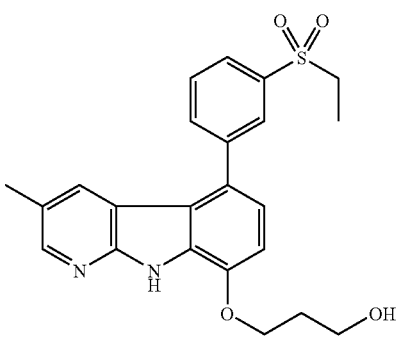

The title compound was synthesized from Compound 157 and 3-(benzyloxy)propan-1-ol using an analogous procedure to that outlined in the preparation of Compound 210 followed by debenzylation using Pd/C—H$_2$. $^1$H NMR (400 MHz, DMSO-d$_6$) δ ppm 1.18 (t, J=7.33 Hz, 3 H) 2.01 (t, J=6.19 Hz, 2 H) 2.27 (s, 3 H) 3.41 (q, J=7.33 Hz, 2 H) 3.72 (q, J=5.98 Hz, 2 H) 4.30 (t, J=6.19 Hz, 2 H) 4.57 (t, J=5.18 Hz, 1 H) 7.06-7.17 (m, 2 H) 7.55 (s, 1 H) 7.85 (t, J=7.71 Hz, 1 H) 8.00 (br. s., 1 H) 7.98 (d, J=5.05 Hz, 2 H) 8.08 (s, 1 H) 8.28 (s, 1 H) 11.99 (s, 1 H); ESI-MS: m/z calc'd for C23H24N2O4S 424.15; found 425.3 (M+H)$^+$ Compound 217: 3-(3-chloro-5-(3-(ethylsulfonyl)phenyl)-8-methoxy-9H-pyrido[2,3-b]indol-8-ol

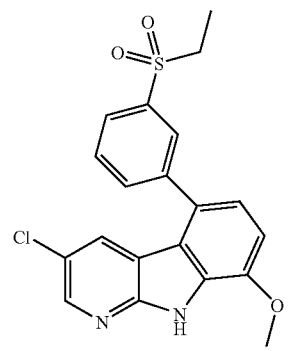

The title compound was synthesized by using an analogous synthetic sequence to that outlined in the preparation of Compound 199. [M+H] calc'd for C$_{20}$H$_{17}$ClN$_2$O$_3$S, 400; found, 400.2.

Compound 218: (3-chloro-5-(3-(ethylsulfonyl)phenyl)-9H-pyrido[2,3-b]indol-8-ol

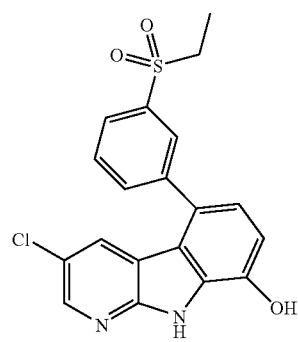

The title compound was prepared from Compound 217 by using an analogous procedure to that outlined in the preparation of Compound 157. $^1$H NMR (400 MHz, Methanol-d$_4$) δ 8.35 (s, 1 H) 8.15 (m, 1 H) 8.07 (m, 1 H) 7.97 (m, 1 H) 7.88 (t, J=8.0 Hz, 1 H) 7.66 (s, 1 H) 7.23 (d, J=8.36 Hz, 1 H) 7.16 (d, J=8.36 Hz, 1 H) 4.44 (t, J=5.8 Hz, 2 H) 3.72 (t, J=8.0 Hz, 2 H) 3.43 (q, J=7.32 Hz, 2 H) 3.03 (s, 6 H) 2.41 (m, 2 H) 1.34 (t, J=7.32 Hz, 3 H) [M+H] calc'd for C$_{24}$H$_{27}$ClN$_3$O$_3$S, 472; found, 472.

Compound 219: 3-(3-chloro-5-(3-(ethylsulfonyl)phenyl)-9H-pyrido[2,3-b]indol-8-yloxy)-N,N-dimethylpropan-1-amine

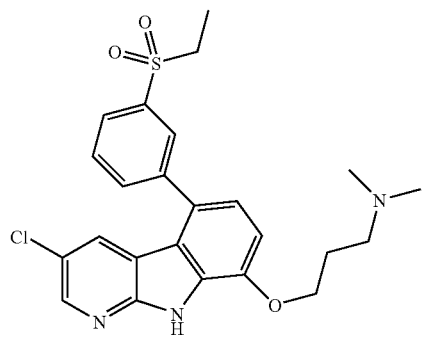

The title compound was prepared from Compound 218 by using an analogous procedure to that outlined in the preparation of Compound 205. $^1$H NMR (400 MHz, Methanol-d$_4$) δ 8.35 (s, 1 H) 8.15(m, 1 H) 8.07 (m, 1 H) 7.97 (m, 1 H) 7.88 (t, J=8.0 Hz, 1 H) 7.66 (s, 1 H) 7.23 (d, J=8.36 Hz, 1 H) 7.16 (d, J=8.36 Hz, 1 H) 4.44 (t, J=5.8 Hz, 2 H) 3.72 (t, J=8.0 Hz, 2 H) 3.43 (q, J=7.32 Hz, 2 H) 3.03 (s, 6 H) 2.41 (m, 2 H) 1.34 (t, J=7.32 Hz, 3 H). [M+H] calc'd for C$_{24}$H$_{27}$ClN$_3$O$_3$S, 472; found, 472.

Compound 220: 2-(3-chloro-5-(3-(ethylsulfonyl)phenyl)-9H-pyrido[2,3-b]indol-8-yloxy)-N,N-diethylethanamine

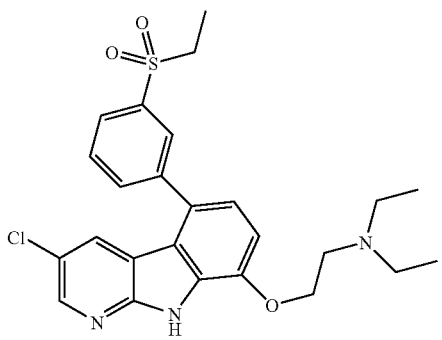

The title compound was prepared from Compound 218 by using an analogous procedure to that outlined in the preparation of Compound 205. $^1$H NMR (400 MHz, Methanol-d$_4$) δ 8.37 (s, 1 H) 8.15 (m, 1 H) 8.07 (m, 1 H) 7.97 (m, 1 H) 7.88 (t, J=8.0 Hz, 1 H) 7.67 (s, 1 H) 7.30 (d, J=8.08 Hz, 1 H) 7.20 (d, J=8.08 Hz, 1 H) 4.67 (t, J=4.0 Hz, 2 H) 3.80 (t, J=4.0 Hz, 2 H) 3.51 (m, 4 H) 3.41 (q, J=8.0 Hz, 2 H) 1.45 (t, J=7.36 Hz, 6 H) 1.33 (t, J=8.0 Hz, 3 H). [M+H] calc'd for C$_{25}$H$_{29}$ClN$_3$O$_3$S, 486; found, 486.

Compound 221: 2-(3-chloro-5-(3-(ethylsulfonyl)phenyl)-9H-pyrido[2,3-b]indol-8-yloxy)-N,N-dimethylethanamine

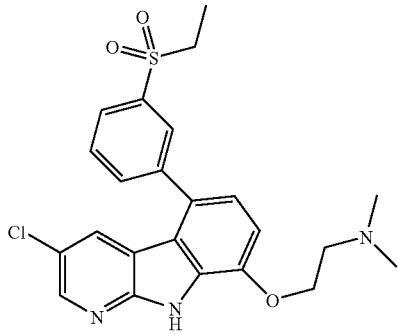

The title compound was prepared from Compound 218 by using an analogous procedure to that outlined in the preparation of Compound 205. $^1$H NMR (400 MHz, Methanol-d$_4$) δ 8.40 (s, 1 H) 8.14 (m, 1 H) 8.10 (m, 1 H) 8.00 (m, 1 H) 7.89 (t, J=8.0 Hz, 1 H) 7.69 (s, 1 H) 7.28 (d, J=8.08 Hz, 1 H) 7.20 (d, J=8.08 Hz, 1 H) 4.68 (t, J=5.0 Hz, 2 H) 3.80 (t, J=5.0 Hz, 2 H) 3.43 (q, J=7.32 Hz, 2 H) 3.13 (s, 6 H) 1.33 (t, J=7.32 Hz, 3 H). [M+H] calc'd for C$_{23}$H$_{25}$ClN$_3$O$_3$S, 458; found, 458.

Compound 222: 3-chloro-5-(3-(ethylsulfonyl)phenyl)-8-(2-(pyrrolidin-1-yl)ethoxy)-9H-pyrido[2,3-b]indole

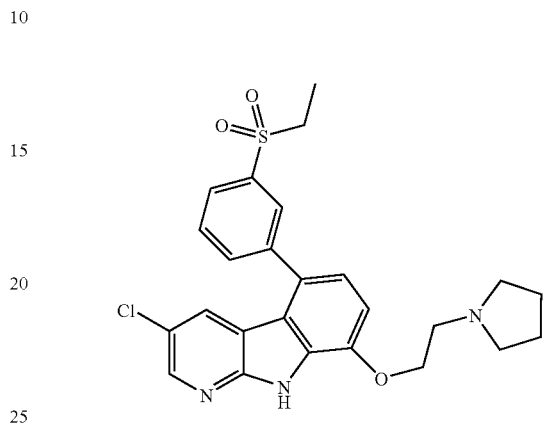

The title compound was prepared from Compound 218 by using an analogous procedure to that outlined in the preparation of Compound 205. $^1$H NMR (400 MHz, Methanol-d$_4$) δ 8.40 (s, 1 H) 8.13 (m, 1 H) 8.10 (m, 1 H) 7.98 (m, 1 H) 7.90 (t, J=8.0 Hz, 1 H) 7.89 (s, 1 H) 7.28 (d, J=8.32 Hz, 1 H) 7.20 (d, J=8.32 Hz, 1 H) 4.65 (t, J=5.0 Hz, 2 H) 3.87 (t, J=5.0 Hz, 2 H) 3.40 (q, J=7.32 Hz, 2 H) 3.25 (br, 4 H) 2.25 (br, 4H) 1.33 (t, J=7.32 Hz, 3 H). [M+H] calc'd for C$_{25}$H$_{27}$ClN$_3$O$_3$S, 484; found, 484.

Compound 223: 3-chloro-5-(3-(ethylsulfonyl)phenyl)-8-(2-(4-methylpiperazin-1-yl)ethoxy)-9H-pyrido[2,3-b]indole

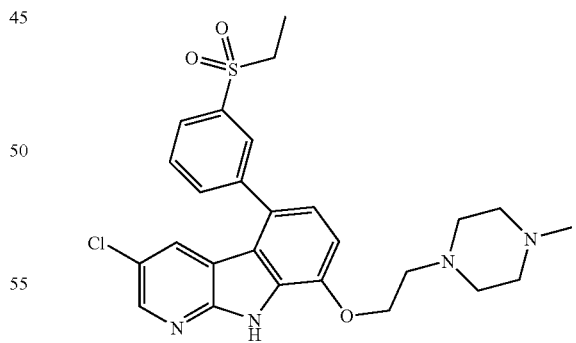

The title compound was prepared from Compound 218 by using an analogous procedure to that outlined in the preparation of Compound 205. $^1$H NMR (400 MHz, DMSO-d$_6$) δ 8.47 (s, 1 H) 7.90 (m, 3 H) 7.88 (t, J=8.0 Hz, 1 H) 7.64 (s, 1 H) 7.28 (d, J=8.08 Hz, 1 H) 7.20 (d, J=8.08 Hz, 1 H) 4.46 (t, J=5.0 Hz, 2 H) 3.75-3.0 (m, br, 10 H) 2.80 (s, 3 H) 1.18 (t, J=7.6 Hz, 3 H). [M+H] calc'd for C$_{26}$H$_{30}$ClN$_4$O$_3$S, 513; found, 513.

Compound 224: 2-(3-chloro-5-(3-(ethylsulfonyl)phenyl)-9H-pyrido[2,3-b]indol-8-yloxy)ethanol

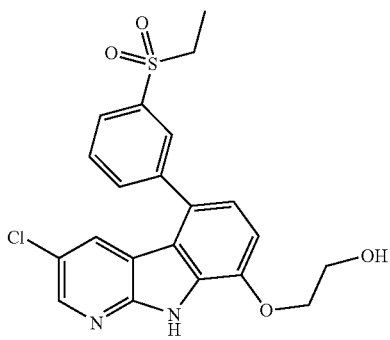

The title compound was prepared from Compound 218 by using an analogous procedure to that outlined in the preparation of Compound 215. $^1$H NMR (400 MHz, Methanol-$d_4$) δ 8.39 (s, 1 H) 8.14 (m, 1 H) 8.06 (m, 1 H) 8.00 (m, 1 H) 7.87 (t, J=8.0 Hz, 1 H) 7.71 (d, J=4.0 Hz, 1 H) 7.21 (d, J=8.0 Hz, 1 H) 7.16 (d, J=8.0 Hz, 1 H) 4.36 (t, J=4 Hz, 2 H) 4.07 (t, J=4 Hz, 2 H) 3.30 (q, J=7.5 Hz, 2 H) 1.31 (t, J=7.5 Hz, 3 H). [M+H] calc'd for $C_{21}H_{20}ClN_2O_4S$, 431; found, 431.

Compound 225: 3-(3-chloro-5-(3-(ethylsulfonyl)phenyl)-9H-pyrido[2,3-b]indol-8-yloxy)propan-1-ol

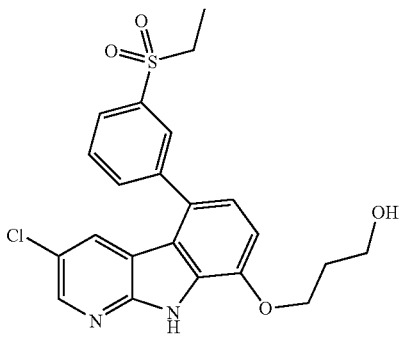

The title compound was prepared from Compound 218 by using an analogous procedure to that outlined in the preparation of Compound 215. $^1$H NMR (400 MHz, Methanol-$d_4$) δ 8.45 (s, 1 H) 8.06 (m, 1 H) 8.01 (m, 2 H) 7.87 (t, J=8.0 Hz, 1 H) 7.63 (s, 1 H) 7.23 (d, J=8.32 Hz, 1 H) 7.16 (d, J=8.32 Hz, 1 H) 4.34 (t, J=6.32 Hz, 2 H) 3.72 (t, J=6.32 Hz, 2 H) 3.43 (q, J=7.32 Hz, 2 H) 2.02 (m, 2 H) 1.18 (t, J=7.32 Hz, 3 H). [M+H] calc'd for $C_{22}H_{22}ClN_2O_4S$, 445; found, 445.

Compound 226: (S)-2-(5-(3-(ethylsulfonyl)phenyl)-3-methyl-9H-pyrido[2,3-b]indol-8-yloxy)ethyl 2-aminopropanoate

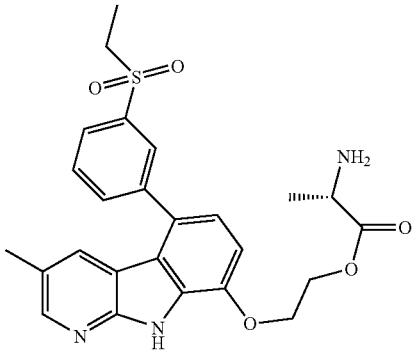

The title compound was prepared from Compound 215 by using an analogous procedure to that outlined in the preparation of Compound 64. $^1$H NMR (400 MHz, DMSO) δ ppm 1.18 (t, J=7.33 Hz, 3 H) 1.40 (d, J=7.33 Hz, 3 H) 2.27 (s, 3 H) 3.42 (q, J=7.33 Hz, 2 H) 4.20 (d, J=5.05 Hz, 1 H) 4.53 (t, J=4.42 Hz, 2 H) 4.58-4.69 (m, 2 H) 7.12 (d, J=8.08 Hz, 1 H) 7.23 (d, J=8.08 Hz, 1 H) 7.55 (s, 1 H) 7.87 (t, J=7.83 Hz, 1 H) 8.00 (dd, J=12.63, 7.58 Hz, 2 H) 8.08 (s, 1 H) 8.29 (s, 1 H) 8.33 (br. s., 2 H) 11.95 (s, 1 H) [M+H] calc'd for $C_{25}H_{27}N_3O_5S$, 482; found, 482.

Compound 227: (S)-3-(5-(3-(ethylsulfonyl)phenyl)-3-methyl-9H-pyrido[2,3-b]indol-8-yloxy)propyl 2-aminopropanoate The title compound was prepared from Compound 216 by using an analogous procedure to that outlined in the preparation of Compound 64. $^1$H NMR (400 MHz, DMSO-$d_6$) δ ppm 1.17 (t, J=7.33 Hz, 3 H) 1.39 (d, J=7.07 Hz, 3 H) 2.20-2.24 (m, 2 H) 2.26 (s, 3 H) 4.14 (m, 1 H) 4.32 (t, J=5.68 Hz, 2 H) 4.56 (m., 2 H) 7.08-7.11 (m, 1 H) 7.12-7.16 (m, 1 H) 7.55 (s, 1 H) 7.85 (t, J=7.83 Hz, 1 H) 7.98 (dd, J=10.23, 8.46 Hz, 2 H) 8.06 (s, 1 H) 8.28 (br. s., 3 H) 12.07 (s, 1 H); [M+H] calc'd for $C_{26}H_{30}N_3O_5S$, 496.2.; found, 496.4.

Compound 228: (S)-3-(3-chloro-5-(3-(ethylsulfonyl)phenyl)-9H-pyrido[2,3-b]indol-8-yloxy)propyl 2-aminopropanoate

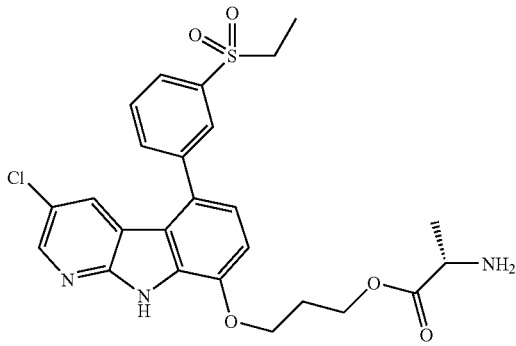

The title compound was prepared from Compound 225 by using an analogous procedure to that outlined in the preparation of Compound 64. $^1$H NMR (400 MHz, Methanol-$d_4$) δ 8.36 (s, 1 H) 8.12 (s, 1 H) 8.08 (m, 1 H) 7.97 (m, 1 H) 7.88 (t, J=7.84 Hz, 1 H) 7.69 (s, 1 H) 7.21 (d, J=8.32 Hz, 1 H) 7.16 (d, J=8.32 Hz, 1 H) 4.65 (m, 2 H) 4.42 (t, J=6.08 Hz, 2 H) 4.14 (q, J=7.32Hz, H) 3.36 (q, J=7.6 Hz, 2 H) 2.39 (m, 2 H) 1.55 (d, J=7.32 Hz, 3 H) 1.33 (t, J=7.6 Hz, 3 H). [M+H] calc'd for $C_{25}H_{27}ClN_3O_5S$, 516; found, 516.

Compound 229: (R)-8-((2,2-dimethyl-1,3-dioxolan-4-yl)methoxy-5-(3-ethylsulfonyl)phenyl)-3-methyl-9H-pyrido[2,3-b]indole

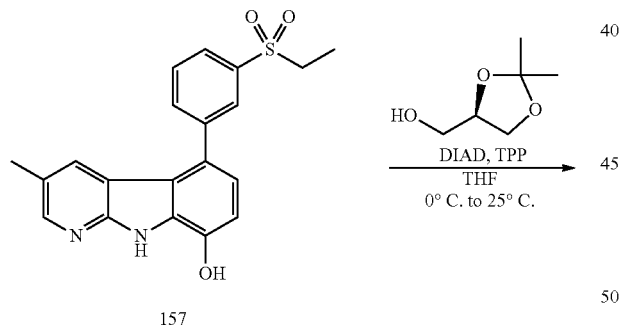

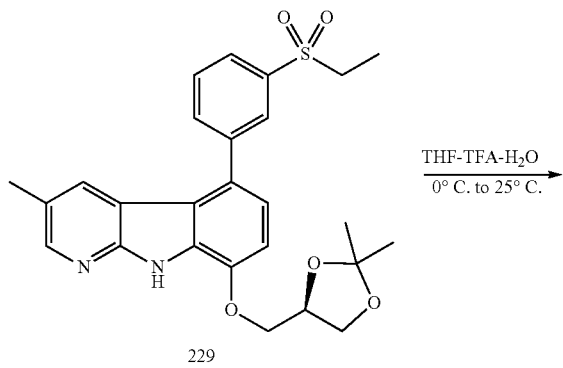

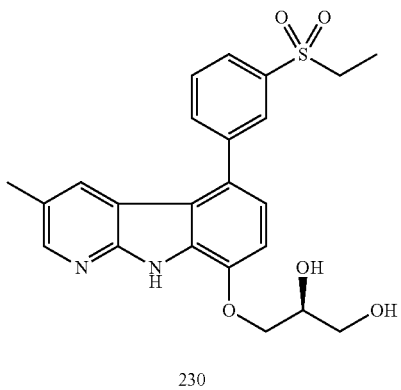

To a stirred solution of Compound 157 (160 mg, 0.44 mmol) in anhydrous THF (2.5 mL) were sequentially added (R)-(2,2-dimethyl-1,3-dioxolan-4-yl)methanol (82 µL, 0.66 mmol) and triphenyl phosphine (173 mg, 0.66 mmoL). The reaction mixture was cooled to 0° C., and to it diisopropylazodicarboxylate (128 µL, 0.66 mmol) was added in drop wise manner. After the addition was over, stirring continued for another 0.5 h at 0° C. and then for 12 h at room temperature. Solvents were removed in vacuum and the residue was purified by silica gel column chromatography, providing the title compound (148 mg, 70%). [M+H] calc'd for $C_{26}H_{28}N_2O_5S$, 481.1; found, 481.3.

Compound 230: (S)-3-(5-(3-(ethylsulfonyl)phenyl)-3-methyl-9H-pyrido[2,3-b]indol-8-yloxy)propane-1,2-diol

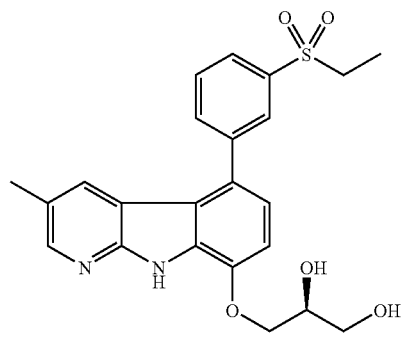

Compound 229 (120 mg, 0.25 mmol) was taken in a mixture of THF-TFA-H$_2$O (3:1:1, 5 mL) and stirred for 6 h at room temperature. The reaction mixture was diluted with methylene chloride and washed with aqueous NaHCO$_3$ and brine. The organic extract was dried over Na$_2$SO$_4$, concentrated and purified to afford the title compound. $^1$H NMR (400 MHz, DMSO-$d_6$) δ ppm 1.17 (t, J=7.33 Hz, 3 H) 2.27 (s, 3 H) 3.41 (q, J=7.41 Hz, 2 H) 3.60 (t, J=5.81 Hz, 2 H) 3.96 (m, 1 H) 4.11 (dd, J=9.60, 6.06 Hz, 1 H) 4.27 (dd, J=9.60, 4.29 Hz, 1 H) 4.73 (t, J=5.68 Hz, 1 H) 4.99 (d, J=5.31 Hz, 1 H) 7.07-7.15 (m, 2 H) 7.57 (d, J=1.77 Hz, 1 H) 7.85 (t, J=7.71 Hz, 1 H) 7.97 (t, J=1.64 Hz, 1 H) 7.99 (m, 1 H) 8.09 (t, J=1.64 Hz, 1 H) 8.28 (d, J=2.02 Hz, 1 H) 11.93 (s, 1 H); [M+H] calc'd for $C_{23}H_{25}N_2O_5S$, 441.1; found, 441.3.

Compound 231: (R)-3-(5-(3-(ethylsulfonyl)phenyl)-3-methyl-9H-pyrido[2,3-b]indol-8-yloxy)propane-1,2-diol

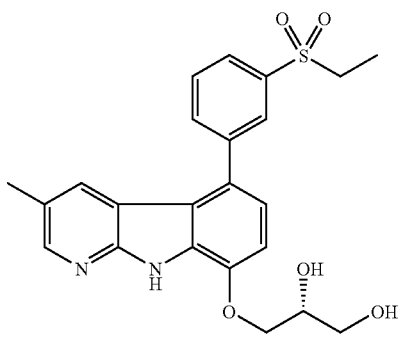

The title compound was prepared from Compound 157 using an analogous procedure to the procedure described for the preparation of Compound 230. $^1$H NMR (400 MHz, DMSO-$d_6$) δ ppm 1.17 (t, J=7.33 Hz, 3 H) 2.27 (s, 3 H) 3.41 (q, J=7.41 Hz, 2 H) 3.60 (t, J=5.81 Hz, 2 H) 3.96 (m, 1 H) 4.11 (dd, J=9.60, 6.06 Hz, 1 H) 4.27 (dd, J=9.60, 4.29 Hz, 1 H) 4.73 (t, J=5.68 Hz, 1 H) 4.99 (d, J=5.31 Hz, 1 H) 7.07-7.15 (m, 2 H) 7.57 (d, J=1.77 Hz, 1 H) 7.85 (t, J=7.71 Hz, 1 H) 7.97 (t, J=1.64 Hz, 1 H) 7.99 (m, 1 H) 8.09 (t, J=1.64 Hz, 1 H) 8.28 (d, J=2.02 Hz, 1 H) 11.93 (s, 1 H); [M+H] calc'd for $C_{23}H_{25}N_2O_5S$, 441.1; found, 441.4.

Compound 232: (R)-1-(dimethylamino)-3-(5-(3-(ethylsulfonyl)phenyl)-3-methyl-9H-pyrido[2,3-b]indol-8-yloxy)propan-2-ol

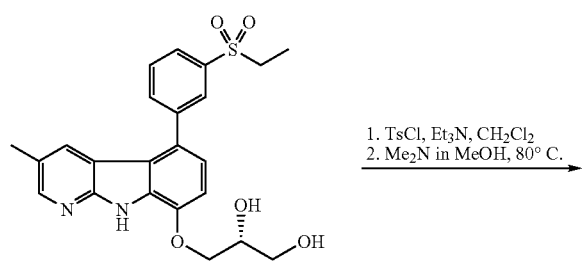

1. TsCl, Et₃N, CH₂Cl₂
2. Me₂N in MeOH, 80° C.

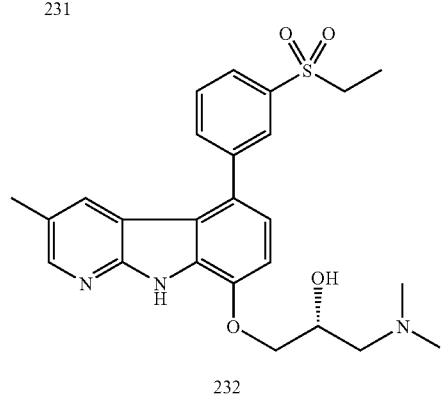

To a solution of Compound 231 (75 mg, 0.17 mmol) in a mixture of DMF and CH₂Cl₂ (5 mL, 2:3) were sequentially added triethyl amine (5 μL, 0.34 mmol) and p-toluenesulfonyl chloride (50 mg, 0.26 mmol) at 0° C. Slowly the reaction temperature was raised to room temperature and stirred for 12 h. The reaction was diluted with CH₂Cl₂ and the organic layer was successively washed with NH₄Cl and brine solution. Solvents were dried over Na₂SO₄ and removed under vacuum. The residual mass was directly used for next step.

The crude mass was taken in 1 mL of MeOH and treated with 0.5 mL of dimethyl amine in a sealed tube, at 80° C. for 6 h. Solvents were removed and directly subjected to preparative HPLC purification to give the title compound (22 mg, 27% for two steps). $^1$H NMR (400 MHz, DMSO-$d_6$) δ ppm 1.17 (t, J=7.45 Hz, 3 H) 2.26 (s, 3 H) 2.32 (s, 6 H) 2.66-2.73 (m, 2 H) 4.05-4.16 (m, 2 H) 4.25 (dd, J=9.09, 3.28 Hz, 1 H) 7.07-7.16 (m, 4 H) 7.57 (s, 1 H) 7.85 (t, J=7.71 Hz, 1 H) 7.98 (dt, J=7.77, 1.80 Hz, 2 H) 8.09 (s, 1 H) 8.29 (d, J=1.77 Hz, 1 H) 12.02 (s, 1 H); [M+H] calc'd for $C_{25}H_{30}N_3O_4S$, 468.2; found, 468.3.

Compound 233: (R)-1-(5-(3-(ethylsulfonyl)phenyl)-3-methyl-9H-pyrido[2,3-b]indol-8-yloxy)propan-2-ol

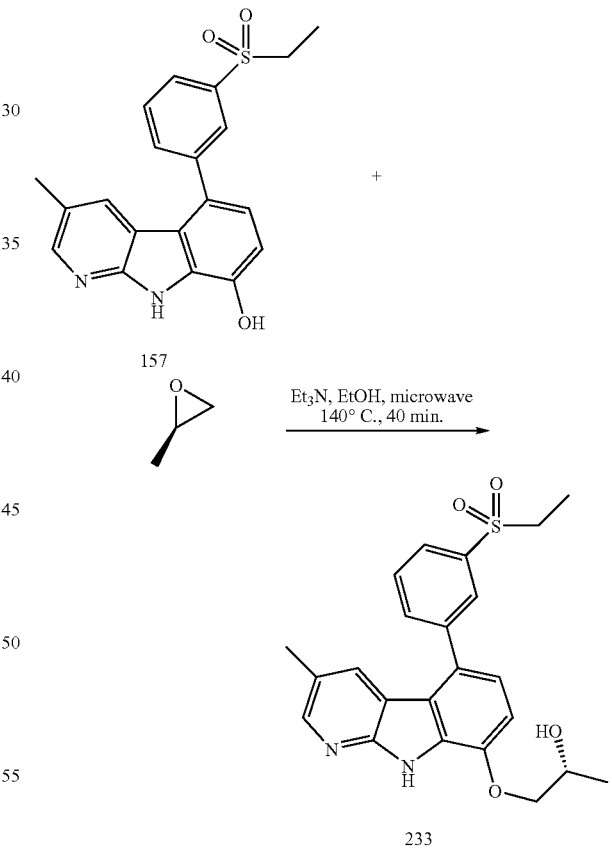

A 5 mL microwave vial was charged with Compound 157 (200 mg, 0.545 mmol), (R)-2-methyloxirane (191 μL, 2.72 mmol), triethyl amine (8 μL, 0.054 mmol) and 2 mL of EtOH. The reaction mixture was heated at 140° C. for 30 min. in microwave. Solvents were removed in vacuum and the residue was purified by preparative HPLC to yield the title compound (46 mg, 20%). $^1$H NMR (400 MHz, DMSO-$d_6$) δ ppm 1.17 (t, J=7.33 Hz, 3 H) 1.25 (d, J=6.06 Hz, 3 H) 2.27 (s, 3 H)

3.41 (q, J=7.33 Hz, 2 H) 3.94 (m, 1 H) 4.09-4.16 (m, 2 H) 4.97 (d, J=4.04 Hz, 1 H) 7.07-7.14 (m, 2 H) 7.57 (s, 1 H) 7.85 (t, J=7.71 Hz, 1 H) 7.96-8.00 (m, 2 H) 8.09 (s, 1 H) 8.28 (d, J=1.52 Hz, 1 H) 11.94 (s, 1 H); [M+H] calc'd for $C_{23}H_{25}N_2O_4S$, 425.2.; found, 425.3.

Compound 234: (S)-1-(5-(3-(ethylsulfonyl)phenyl)-3-methyl-9H-pyrido[2,3-b]indol-8-yloxy)propan-2-ol

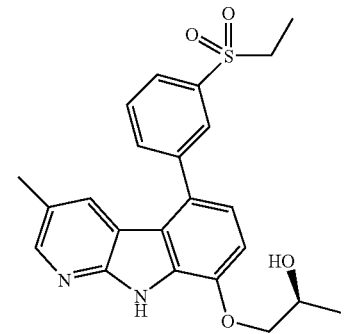

The title compound was prepared from Compound 157 using an analogous procedure to the procedure described for the preparation of Compound 233. $^1$H NMR (400 MHz, DMSO-$d_6$) δ ppm 1.17 (t, J=7.33 Hz, 3 H) 1.25 (d, J=6.06 Hz, 3 H) 2.27 (s, 3 H) 3.41 (q, J=7.33 Hz, 2 H) 3.94 (m, 1 H) 4.09-4.16 (m, 2 H) 4.97 (d, J=4.04 Hz, 1 H) 7.07-7.14 (m, 2 H) 7.57 (s, 1 H) 7.85 (t, J=7.71 Hz, 1 H) 7.96-8.00 (m, 2 H) 8.09 (s, 1 H) 8.28 (d, J=1.52 Hz, 1 H) 11.94 (s, 1 H); [M+H] calc'd for $C_{23}H_{25}N_2O_4S$, 425.2; found, 425.3.

Compound 235: 3-2(-bromo-5-methoxyphenyl)-2-fluoro-5-methyl-pyridne

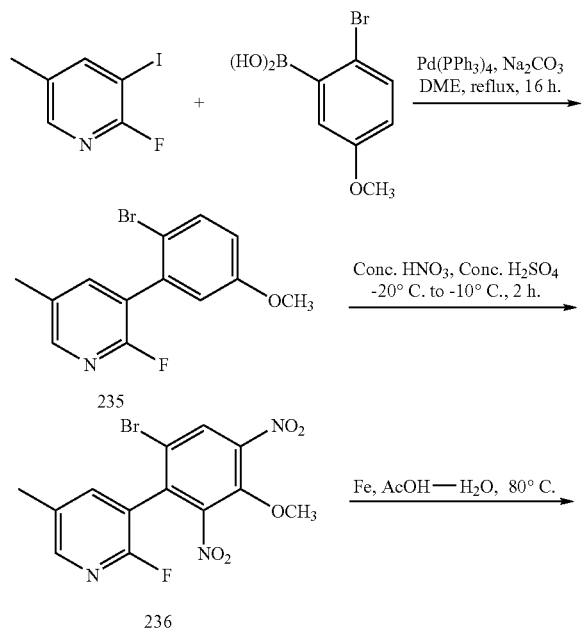

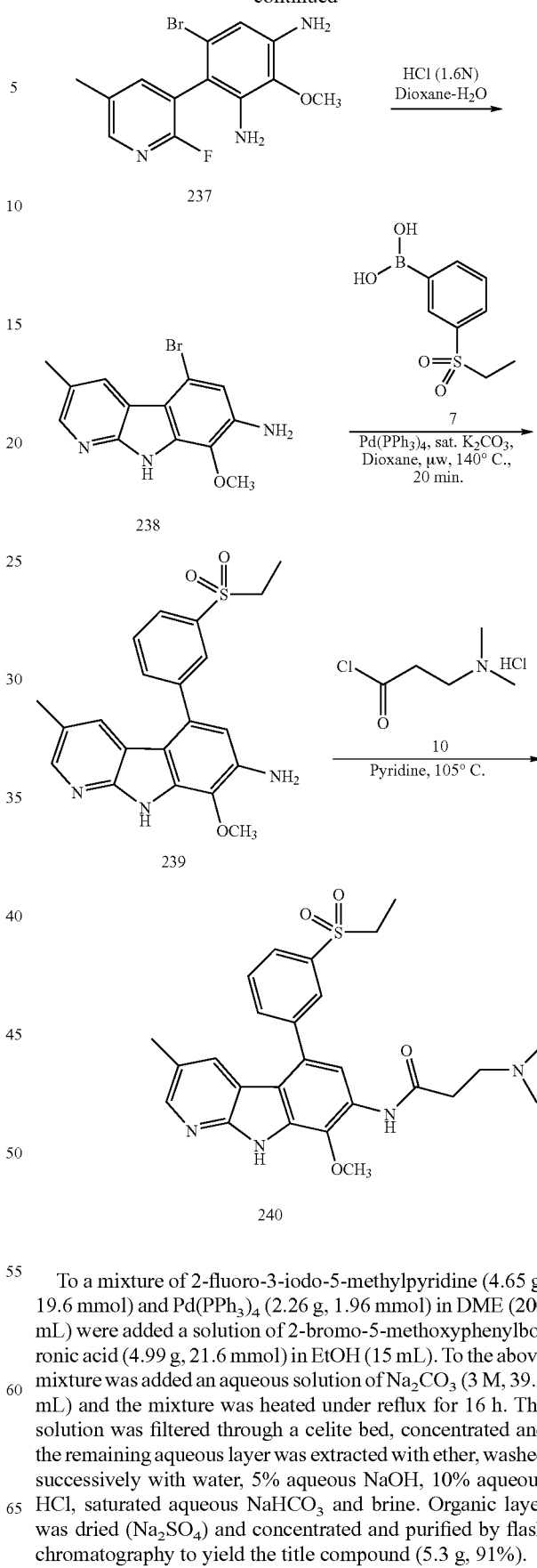

To a mixture of 2-fluoro-3-iodo-5-methylpyridine (4.65 g, 19.6 mmol) and Pd(PPh$_3$)$_4$ (2.26 g, 1.96 mmol) in DME (200 mL) were added a solution of 2-bromo-5-methoxyphenylboronic acid (4.99 g, 21.6 mmol) in EtOH (15 mL). To the above mixture was added an aqueous solution of Na$_2$CO$_3$ (3 M, 39.2 mL) and the mixture was heated under reflux for 16 h. The solution was filtered through a celite bed, concentrated and the remaining aqueous layer was extracted with ether, washed successively with water, 5% aqueous NaOH, 10% aqueous HCl, saturated aqueous NaHCO$_3$ and brine. Organic layer was dried (Na$_2$SO$_4$) and concentrated and purified by flash chromatography to yield the title compound (5.3 g, 91%).

Compound 236: 3-(6-bromo-3-methoxy-2,4-dinitro-phenyl)-2-fluoro-5-methylpyridne

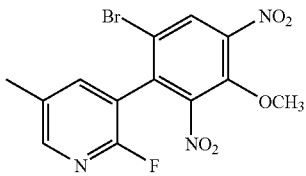

Compound 235 (2.0 g, 6.75 mmol) was added to a mixture of conc. HNO₃ (90%) and conc. H₂SO₄ (95-98%) (20 mL, 2:3) at −20° C. Slowly the reaction was warmed to −5° C. and stirred for another 1.5 h. The crude mixture was poured into ice-water, solid precipitates out and collected by filtration, washed thoroughly with water and dried under vacuum to provide the title compound (2.08 g, 80%).

Compound 237: 5 -4-(2-fluoro-5-methylpyridne-3-yl)-methoxybenzene-1,3-diamine

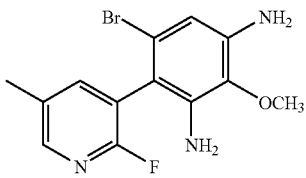

To Compound 236 (1.02 g, 2.65 mmol) in AcOH—H₂O (8 mL, 3:1) at 80° C. was added iron powder (1.48 g, 26.5 mmol) and stirred for 2.0 h. Solvents were removed under vacuum and the residue was dissolved in CH₂Cl₂, and washed with aqueous NaHCO₃ and brine. The organic extracts were dried (Na₂SO₄) and concentrated and purified by flash chromatography to yield the title compound (830 mg, 96%).

Compound 238: 5-bromo-8-methoxy-3-methyl-9H-pyrido[2,3-b]indol-7-amine

Compound 237 (5.0 g, 15.32 mmol) was taken into a mixture of dioxane-H₂O (100 mL, 1:4) and to it was added aqueous HCl (9.6 mL, 1.6 N in water). The reaction mixture was heated reflux for 6 h. Reaction was diluted with EtOAc and washed with aqueous NaHCO₃ and brine. The organic extracts were dried (Na₂SO₄) and concentrated and purified by flash chromatography to yield the title compound (4.2 g, 89%). ¹H NMR (400 MHz, DMSO-d₆) δ ppm 2.41 (s, 3 H) 3.77 (s, 3 H) 5.36 (s, 2 H) 6.81 (s, 1 H) 8.12 (d, J=2.27 Hz, 1 H) 8.33 (d, J=2.02 Hz, 1 H) 11.65 (s, 1 H); [M+H] calc'd for C₁₃H₁₃BrN₃O, 306.02; found, 306.2.

Compound 239: (5-(3-(ethylsulfonyl)phenyl)-8-methoxy-3-methyl-9H-pyrido[2,3-b]indol-7-amine

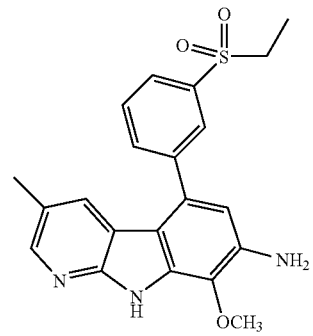

A 5 mL microwave vial was charged with Compound 238 (500 mg, 1.63 mmol), 3-(ethylsulfonyl)phenylboronic acid (419 mg, 1.96 mmol) and Pd(PPh₃)₄ (188 mg, 0.16 mmol). To the mixture was added dioxane (5 mL) and a saturated aqueous solution of K₂CO₃ (2.5 mL). The reaction mixture was heated at 140° C. for 20 min. in microwave. The reaction was diluted with EtOAc and washed with aqueous water and brine. The organic extracts were dried (Na₂SO₄) and concentrated and purified by flash chromatography to yield the title compound (528 mg, 82%).
¹H NMR (400 MHz, DMSO-d₆) δ ppm 1.16 (t, J=7.33 Hz, 3 H) 2.25 (s, 3 H) 3.95 (s, 3 H) 7.44 (br. s., 1 H) 7.78 (br. s., 1 H) 7.87 (d, J=7.58 Hz, 1 H) 7.96 (d, J=3.28 Hz, 1 H) 8.01 (d, J=7.33 Hz, 1 H) 8.07 (br. s., 1 H) 8.23 (br. s., 1 H) 9.88 (br. s., 1 H) 12.07 (br. s., 1 H); [M+H] calc'd for C₂₁H₂₁N₃O₄S, 396.2; found, 396.3.

Compound 240: 3-(dimethylamino)-N-(5-(3-(ethylsulfonyl)phenyl)-8-methoxy-3-methyl-9H-pyrido[2,3-b]indol-7-yl)propanamide

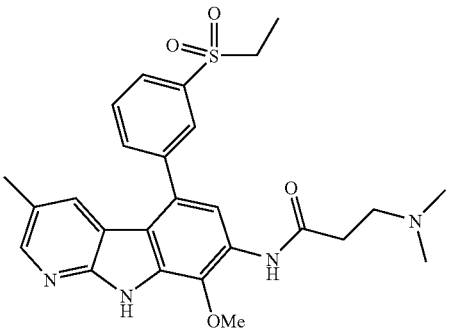

To a suspension of Compound 239 (150 mg, 0.38 mmol) in pyridine (2.0 mL) was added 3-(dimethylamino)propanoyl chloride (71 mg, 0.38 mmol) and the reaction mixture was heated at 105° C. for 5 h. and quenched with aqueous NH₄Cl solution. Organic matter was extracted with CH₂Cl₂ (with 10% EtOH) and washed with brine. The organic extracts were dried (Na₂SO₄) and concentrated and purified by preparative HPLC to yield the title compound (103 mg, 55%). ¹H NMR (400 MHz, DMSO-d$_6$) δ ppm 1.16 (t, J=7.33 Hz, 3 H) 2.24 (s, 3 H) 2.33 (s, 6 H) 2.56 (t, J=5.81 Hz, 2 H) 2.62 (t, J=5.31 Hz, 2 H) 3.41 (d, J=7.33 Hz, 2 H) 3.93 (s, 3 H) 7.41 (d, J=1.26 Hz, 1 H) 7.87 (t, J=7.71 Hz, 1 H) 7.93-7.97 (m, 1 H) 8.03 (d, J=8.84 Hz, 1 H) 8.06 (s, 2 H) 8.22 (d, J=2.02 Hz, 1 H) 10.99 (br. s., 1 H) 12.07 (s, 1 H); [M+H] calc'd for C$_{26}$H$_{31}$N$_4$O—$_4$S, 495.2; found, 495.4.

Compound 241: N-(3-(7-amino-8-methoxy-3-methyl-9H-pyrido[2,3-b]indol-5-yl)phenyl)-cyclopropanecarboxamide

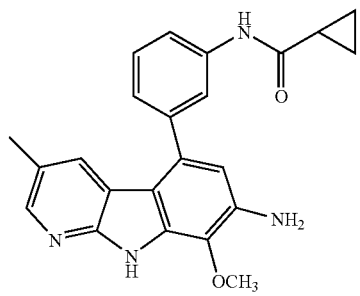

The title compound was prepared from Compound 238 by using an analogous procedure to that outlined in the preparation of Compound 239. $^1$H NMR (400 MHz, DMSO-d$_6$) δ ppm 0.77-0.81 (m, 4 H) 1.79 (p, J=6.06 Hz, 1 H) 2.20 (s, 3 H) 3.82 (s, 3 H) 5.21 (s, 2 H) 6.48 (s, 1 H) 7.18 (d, J=7.58 Hz, 1 H) 7.45-7.41 (m, 2 H) 7.63 (d, J=8.34 Hz, 1 H) 7.83 (s, 1 H) 8.00 (s, 1 H) 10.31 (s, 1 H) 11.47 (s, 1 H); [M+H] calc'd for C$_{23}$H$_{22}$N$_4$O$_2$, 387.17; found, 387.13.

Compound 242: N-(5-(3-(ethylsulfonyl)phenyl)-8-methoxy-3-methyl-9H-pyrido[2,3-b]indol-7-yl)-cyclopropanecarboxamide

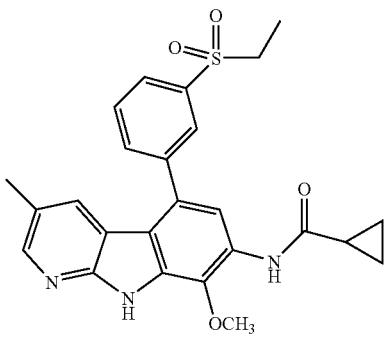

The title compound was prepared from Compound 239 by using an analogous procedure to that outlined in the preparation of Compound 241. $^1$H NMR (400 MHz, DMSO-d$_6$) δ ppm 0.82 (br. s., 4 H) 1.16 (t, J=7.33 Hz, 3 H) 2.17 (m., 1 H) 2.25 (s, 3 H) 3.95 (s, 3 H) 7.44 (br. s., 1 H) 7.78 (br. s., 1 H) 7.87 (d, J=7.58 Hz, 1 H) 7.96 (d, J=3.28 Hz, 1 H) 8.01 (d, J=7.33 Hz, 1 H) 8.07 (br. s., 1 H) 8.23 (br. s., 1 H) 9.88 (br. s., 1 H) 12.07 (br. s., 1 H); [M+H] calc'd for C$_{25}$H$_{26}$N$_3$O$_4$S, 464.2; found, 464.3.

Compound 243: 1-acetyl-N-(5-(3-(ethylsulfonyl)phenyl)-8-methoxy-3-methyl-9H-pyrido[2,3-b]indol-7-yl)piperidine-4-carboxamide

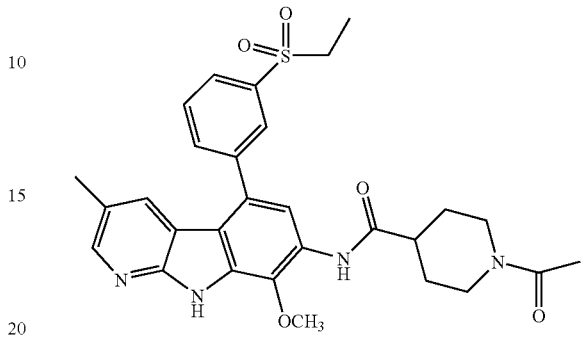

The title compound was prepared from Compound 239 by using an analogous procedure to that outlined in the preparation of Compound 241. $^1$H NMR (400 MHz, DMSO-d$_6$) δ ppm 1.16 (t, J=7.33 Hz, 3 H) 1.45 (qd, J=12.25, 3.92 Hz, 1 H) 1.60 (qd, J=12.08, 3.92 Hz, 1 H) 1.86 (t, J=12.13 Hz, 1 H) 1.85 (d, J=1.77 Hz, 1 H) 2.01 (s, 3 H) 2.25 (s, 3 H) 2.57-2.65 (m, 1 H) 2.87 (m, 1 H) 3.08 (t, J=13.89 Hz, 1 H) 3.41 (q, J=7.33 Hz, 2 H) 3.88 (d, J=13.89 Hz, 1 H) 3.93 (s, 3 H) 4.42 (d, J=13.39 Hz, 1 H) 7.44 (d, J=1.26 Hz, 1 H) 7.70 (s, 1 H) 7.87 (t, J=7.71 Hz, 1 H) 7.96 (d, J=7.83 Hz, 1 H) 8.02 (d, J=7.83 Hz, 1 H) 8.06 (d, J=1.52 Hz, 1 H) 8.24 (d, J=1.77 Hz, 1 H) 9.62 (s, 1 H) 12.09 (s, 1 H); [M+H] calc'd for C$_{29}$H$_{33}$N$_4$O$_5$S, 549.2; found, 549.4.3.

Compound 244: 3-(7-amino-8-methoxy-3-methyl-9H-pyrido[2,3-b]indol-5-yl)-N-cyclopropylbenzamide

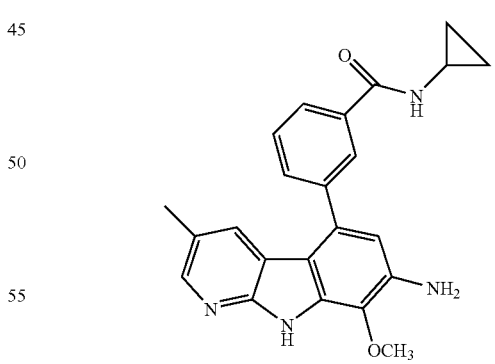

The title compound was prepared from Compound 238 by using an analogous procedure to that outlined in the preparation of Compound 239. $^1$H NMR (400 MHz, DMSO-d$_6$) δ ppm 0.55 (m, 2 H) 0.68 (m, 2 H) 2.23 (s, 3 H) 2.87 (m, 1 H) 3.94 (s, 3 H) 7.40 (s, 1 H) 7.63 (t, J=7.71 Hz, 1 H) 7.72-7.71 (m, 2H) 7.94 (d, J=7.58 Hz, 1 H) 8.01 (s, 1 H) 8.21 (d, J=1.77 Hz, 1 H) 8.54 (d, J=4.04 Hz, 1 H) 9.84 (s, 1 H) 12.00 (s, 1 H); [M+H] calc'd for C$_{23}$H$_{22}$N$_4$O$_2$, 387.2; found, 387.4.

Compound 245: 3-(7-(cyclopropanecarboxamido)-8-methoxy-3-methyl-9H-pyrido[2,3-b]indol-5-yl)-N-cyclopropylbenzamide

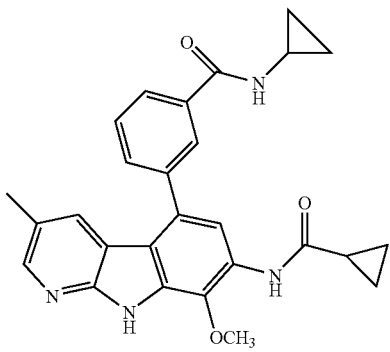

The title compound was prepared from Compound 244 by using an analogous procedure to that outlined in the preparation of Compound 241. $^1$H NMR (400 MHz, DMSO-d$_6$) δ ppm 0.55 (m, 2 H) 0.68 (m, 2 H) 0.81 (br. m, 4 H) 2.17 (m, 1 H) 2.23 (s, 3 H) 2.87 (m, 1 H) 3.94 (s, 3 H) 7.40 (s, 1 H) 7.63 (t, J=7.71 Hz, 1 H) 7.72-7.71 (m, 2H) 7.94 (d, J=7.58 Hz, 1 H) 8.01 (s, 1 H) 8.21 (d, J=1.77 Hz, 1 H) 8.54 (d, J=4.04 Hz, 1 H) 9.84 (s, 1 H) 12.00 (s, 1 H); [M+H] calc'd for C$_{27}$H$_{27}$N$_4$O$_3$, 455.2; found, 455.4.

Compound 246: 7-chloro-5-(3-(ethylsulfonyl)phenyl)-8-methoxy-3-methyl-9H-pyrido[2,3-b]indole

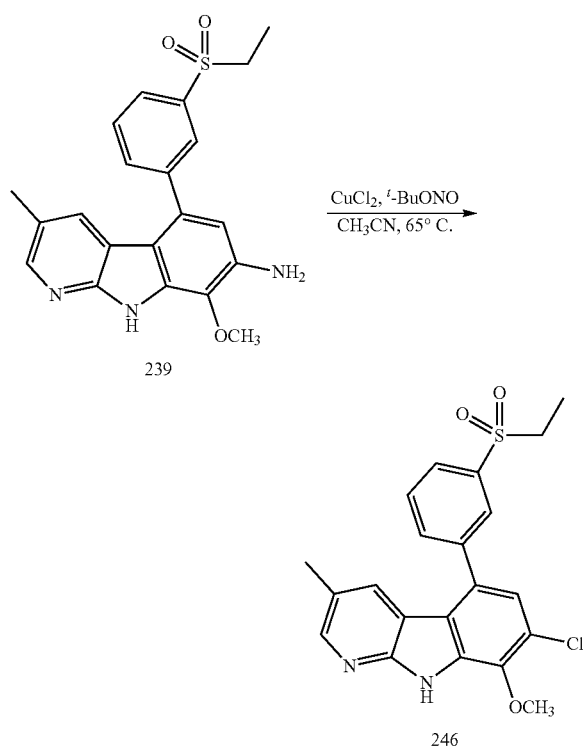

To a suspension of compound 239 (19.0 mg, 0.05 mmol) in CH$_3$CN (1 mL) was taken CuCl$_2$ (9.7 mg, 0.072 mmol) and $^t$-BuONO (12.6 mL, 0.096 mmol). The reaction mixture was heated at 65° C. for 30 min. and quenched with aqueous NH$_4$Cl solution. Organic matter was extracted with EtOAc and washed with brine. The organic extracts were dried (Na$_2$SO$_4$) and concentrated and purified by preparative HPLC to yield the title compound (4.2 mg, 21%). $^1$H NMR (400 MHz, Acetone) δ ppm 1.16 (t, J=7.33 Hz, 3 H) 2.26 (s, 3 H) 4.00 (s, 3 H) 7.24 (s, 1 H) 7.45 (s, 1 H) 7.88 (t, J=7.71 Hz, 1 H) 8.01 (dt, J=1.26, 8.02 Hz, 2 H) 8.11 (s, 1 H) 8.31 (s, 1 H) 12.38 (s, 1 H); [M+H] calc'd for C$_{21}$H$_{20}$ClN$_2$O$_3$, 415.1; found, 415.3.

Compound 247: 7-chloro-5-(3-(ethylsulfonyl)phenyl)-3-methyl-9H-pyrido[2,3-b]indol-8-ol

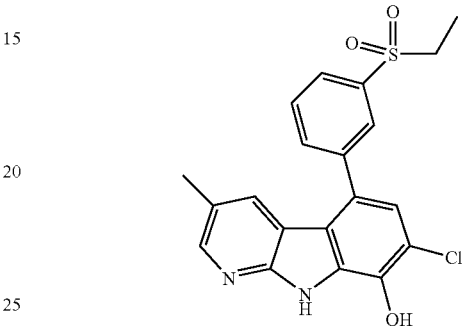

The title compound was prepared from Compound 246 by using an analogous procedure to that outlined in the preparation of Compound 157. $^1$H NMR (400 MHz, DMSO-d$_6$) δ ppm 1.16 (t, J=7.33 Hz, 3 H) 2.25 (s, 3 H) 3.41 (q, J=7.58 Hz, 2 H) 4.26 (t, J=6.44 Hz, 2 H) 7.23 (s, 1 H) 7.46 (s, 1 H) 7.87 (t, J=7.71 Hz, 1 H) 8.03 (t, J=7.20 Hz, 2 H) 8.11 (s, 1 H) 8.31 (s, 1 H) 12.27 (br. s., 1 H); [M+H] calc'd for C$_{20}$H$_{17}$ClN$_2$O$_3$S, 401.1; found, 401.3.

Compound 248: 3-(7-chloro-5-(3-(ethylsulfonyl)phenyl)-3-methyl-9H-pyrido[2,3-b]indol-8-yloxy)propan-1-ol

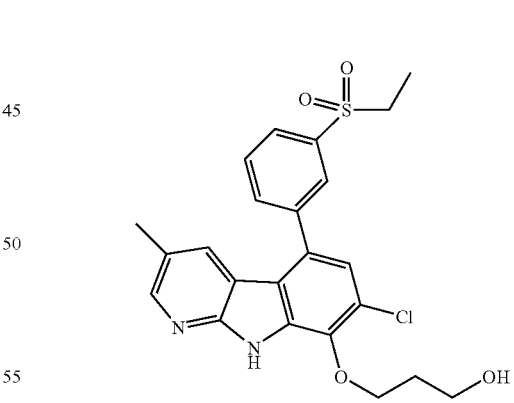

The title compound was synthesized from Compound 247 and 3-(benzyloxy)propan-1-ol using an analogous procedure to that outlined in the preparation of Compound 210 followed by debenzylation using Pd/C—H$_2$. $^1$H NMR (400 MHz, DMSO-d$_6$) δ ppm 1.16 (t, J=7.33 Hz, 3 H) 1.99-2.06 (m, 2 H) 2.25 (s, 3 H) 3.41 (q, J=7.58 Hz, 2 H) 3.71 (br. s., 2 H) 4.26 (t, J=6.44 Hz, 2 H) 4.81 (br. s., 1 H) 7.23 (s, 1 H) 7.46 (s, 1 H) 7.87 (t, J=7.71 Hz, 1 H) 8.03 (t, J=7.20 Hz, 2 H) 8.11 (s, 1 H) 8.31 (s, 1 H) 12.27 (br. s., 1 H); [M+H] calc'd for C$_{23}$H$_{24}$ClN$_2$O$_4$S, 459.1; found, 459.3.

Compound 249: tert-butyl 5-bromo-7-(tert-butoxy-carbonylamino)-8-methoxy-3-methyl-9H-pyrido[2,3-b]indole-9-carboxylate
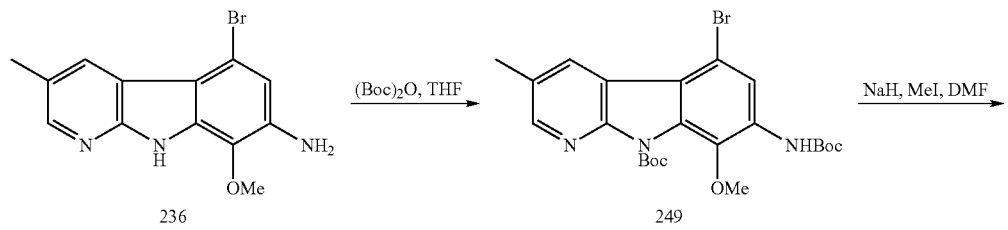
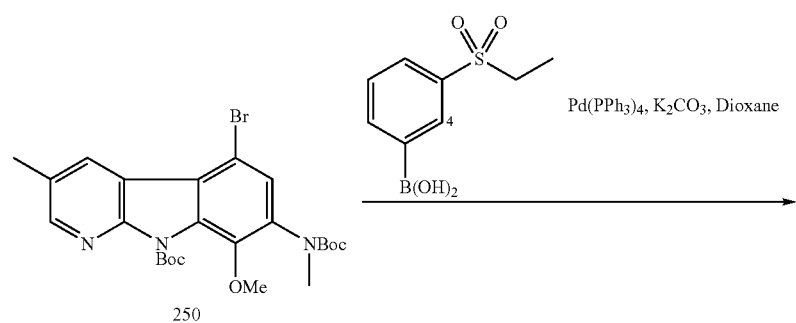
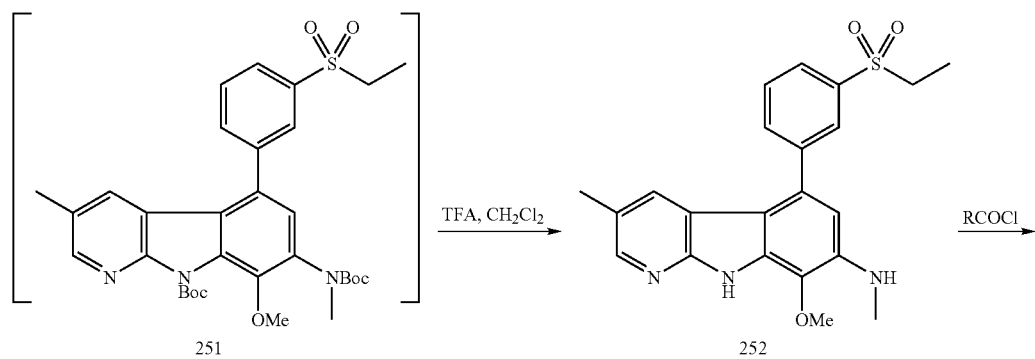
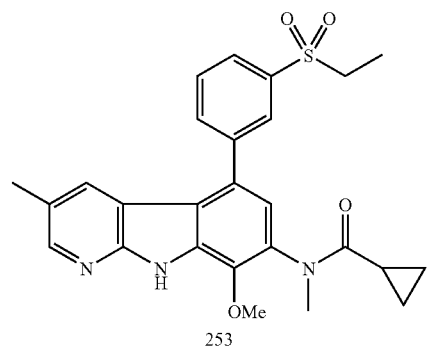

To a solution of Compound 238 (660 mg, 2.15 mmol) in a mixture of CH$_2$Cl$_2$-THF (4 mL, 1:1) was added (Boc)$_2$O (1.24 ml, 5.38 mmol) and the mixture was heated in a sealed tube for 24 h at a temperature of 50° C. Solvents were removed under vacuum and the crude residue was purified by flash chromatography to provide Compound 249 (762 mg, 70%).

Compound 250: tert-butyl 5-bromo-7-(tert-butoxycarbonyl(methyl)amino)-8-methoxy-3-methyl-9H-pyrido[2,3-b]indole-9-carboxylate

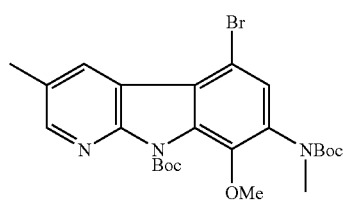

To a solution of Compound 249 (610 mg, 1.2 mmol) in dry DMF (3 mL) was added NaH (60 mg, 1.51 mmol) at 0° C. and the mixture was stirred for 20 min. To this ice cold reaction mixture was added MeI (0.72 ml, 1.44 mmol, 2 M solution) and stirred for another 30 min. at 0° C. Slowly the temperature was raised to room temperature and stirred for an additional hour. Reaction was quenched with water and extracted with ether, washed with brine, dried over Na$_2$SO$_4$ and finally purified flash chromatography to furnish Compound 250 (468 mg, 75%).

Compound 251: tert-butyl 7-(tert-butoxycarbonyl(methyl)amino)-5-(3-(ethylsulfonyl)phenyl)-8-methoxy-3-methyl-9H-pyrido[2,3-b]indole-9-carboxylate

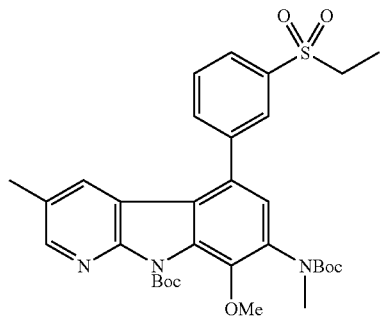

A 5 mL microwave vial was charged with Compound 250 (520 mg, 1.0 mmol), 3-(ethylsulfonyl)phenylboronic acid (321 mg, 1.5 mmol) and Pd(PPh$_3$)$_4$ (116 mg, 0.10 mmol). To the mixture was added dioxane (2 mL) and a saturated aqueous solution of K$_2$CO$_3$ (1 mL). The reaction mixture was heated at 140° C. for 20 min. in microwave. The reaction was diluted with EtOAc and washed with water and brine. The organic extracts were dried (Na$_2$SO$_4$) and concentrated and the crude Compound 251 was taken forward for Boc deprotection.

Compound 252: 5-(3-(ethylsulfonyl)phenyl)-8-methoxy-N,3-dimethyl-9H-pyrido[2,3-b]indol-7-amine

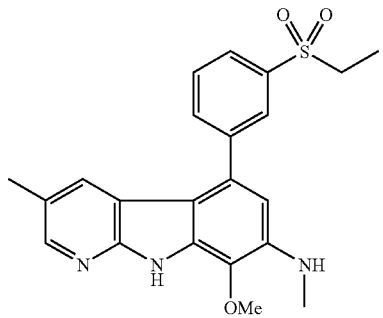

The crude residue from previous step (Compound 251) was dissolved in 3 mL CH$_2$Cl$_2$ and to were sequentially added 0.2 mL of anisole and 1 mL of TFA. The mixture was stirred at room temperature for 2 h. Solvent was removed in vacuum and the residue was basified with saturated aqueous NaHCO$_3$ and extracted with EtOAc. The organic layer was washed with brine, dried over Na$_2$SO$_4$ and finally purified flash chromatography to furnish Compound 252 (287 mg, 70%, for 2 steps).

Compound 253: N-(5-(3-(ethylsulfonyl)phenyl)-8-methoxy-3-methyl-9H-pyrido[2,3-b]indol-7-yl)-N-methylcyclopropanecarboxamide

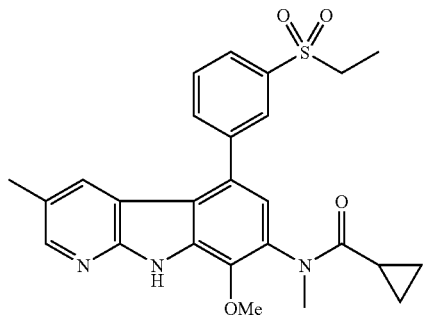

To a solution of Compound 252 (150 mg, 0.37 mmol) in dry THF (3 mL) was added cyclopropylcarbonyl chloride (34 µL, 0.37 mmol) at 0° C. Slowly the temperature was raised to room temperature and stirred for an additional hour. Reaction was quenched with aqueous NaHCO$_3$ solution and extracted with EtOAc, washed with brine, dried over Na$_2$SO$_4$ and finally purified preparative HPLC to provide Compound 253 (132 mg, 75%). $^1$H NMR (400 MHz, DMSO-d$_6$) δ ppm 0.63 (br. d, J=8.1 Hz, 2 H) 0.80 (br. s., 2 H) 1.18 (t, J=7.45 Hz, 3 H) 1.48 (td, J=8.02, 3.92 Hz, 1 H) 2.27 (s, 3 H) 3.26 (s, 3 H) 3.41 (q, J=7.45 Hz, 2 H) 3.98 (s, 3 H) 7.17 (s, 1 H) 7.54 (s, 1 H) 7.88 (t, J=7.71 Hz, 1 H) 8.04 (d, J=8.08 Hz, 2 H) 8.14 (s, 1 H) 8.31 (d, J=1.26 Hz, 1 H) 12.31 (s, 1 H); [M+H] calc'd for C$_{26}$H$_{28}$N$_3$O$_4$S, 478.2; found, 478.3.

Compound 254: 3-(dimethylamino)-N-(5-(3-(ethylsulfonyl)phenyl)-8-methoxy-3-methyl-9H-pyrido[2,3-b]indol-7-yl)-N-methylpropanamide

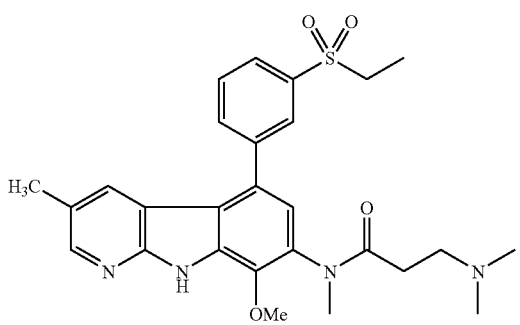

The title compound was prepared from Compound 252 by using an analogous procedure to that outlined in the preparation of C253ompound 241. ¹H NMR (400 MHz, DMSO-d₆) δ ppm 1.17 (t, J=7.33 Hz, 4 H) 2.02 (br. s., 6 H) 2.19-2.33 (m, 7 H) 3.26 (s, 3 H) 3.96 (s, 3 H) 7.14 (s, 1 H) 7.53 (s, 1 H) 7.88 (t, J=7.71 Hz, 1 H) 8.03 (d, J=8.08 Hz, 2 H) 8.12 (s, 1 H) 8.32 (d, J=1.26 Hz, 1 H) 12.31 (s, 1 H); [M+H] calc'd for C₂₇H₃₃N₄O₄S, 509.2; found, 509.3.

Compound 255: 5-(3-(cyclopropylcarbamoyl)phenyl)-3,8-dimethyl-N-(1-methylpiperidin-4-yl)-9H-pyrido[2,3-b]indole-7-carboxamide

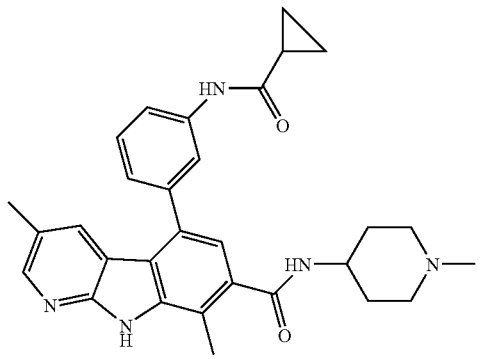

The title compound was synthesized from 5-chloro-3,8-dimethyl-N-(1-methylpiperidin-4-yl)-9H-pyrido[2,3-b]indole-7-carboxamide and 3-(cyclopropylcarbamoyl)phenylboronic acid using an analogous procedure to that described in the preparation of compound 83. [M+H] calc'd for C₃₀H₃₃N₅O₂, 496.3.; found, 496.5.

Compound 256: 4-(2-(3-chloro-5-(3-(ethylsulfonyl)phenyl)-9H-pyrido[2,3-b]indol-8-yloxy)ethyl)morpholine

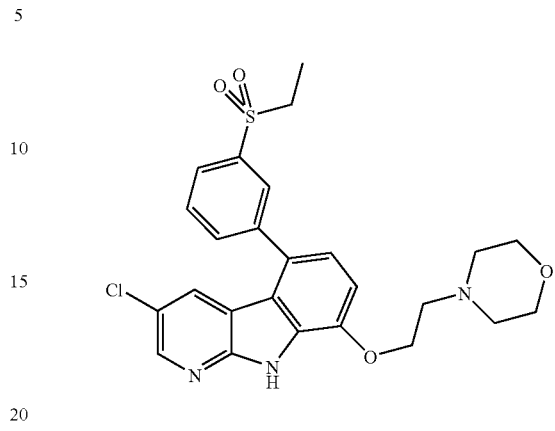

The title compound was prepared from Compound 218 by using an analogous procedure to that outlined in the preparation of Compound 205. ¹H NMR (400 MHz, Methanol-d₄) δ 8.12 (s, 1 H) 8.00(m, 1 H) 7.92 (m, 1 H) 7.74 (t, J=7.84 Hz, 1 H) 7.64 (s, 1 H) 7.09 (m, 1 H) 7.02 (m, 1 H) 6.84 (s, 1 H) 4.40 (t, J=5.0 Hz, 2 H) 4.11 (br, 4 H) 3.80 (br, 4 H) 3.55 (t, J=5.0 Hz, 2 H) 3.30 (q, J=7.32 Hz, 2 H) 1.27 (t, J=7.32 Hz, 3 H). [M+H] calc'd for C₂₅H₂₇ClN₃O₄S, 500; found, 500.

Compound 257: 3-(3-chloro-5-(3-(ethylsulfonyl)phenyl)-9H-pyrido[2,3-b]indol-8-yloxy)propanenitrile

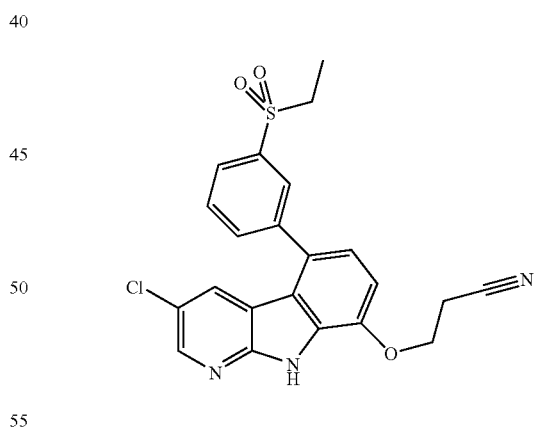

The title compound was prepared from Compound 218 by using an analogous procedure to that outlined in the preparation of Compound 205. ¹H NMR (400 MHz, Methanol-d₄) δ 8.39 (d, J=2.24 Hz, 1 H) 8.08(m, 1 H) 8.06 (m, 1 H) 7.92 (m, 1 H) 7.84 (t, J=7.56 Hz, 1 H) 7.54 (d, J=2.24 Hz, 1 H) 7.08 (d, J=8.08 Hz, 1 H) 7.06 (d, J=8.08 Hz, 1 H) 5.13 (t, J=6.84 Hz, 2 H) 3.30 (q, J=7.32 Hz, 2 H) 3.13 (t, J=6.84 Hz, 2 H) 1.27 (t, J=7.32 Hz, 3 H). [M+H] calc'd for C₂₂H₁₉ClN₃O₃S, 440; found, 440.

Compound 258: 3-chloro-5-(3-(ethylsulfonyl)phenyl)-8-(1-methylpiperidin-4-yloxy)-9H-pyrido[2,3-b]indole

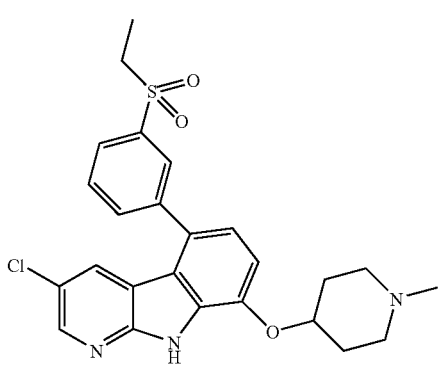

The title compound was prepared from Compound 218 by using an analogous procedure to that outlined in the preparation of Compound 205. $^1$H NMR (400 MHz, Methanol-$d_4$) δ 8.44 (br, 2 H) 8.15 (s, 1 H) 8.05 (m, 2 H) 7.90 (t, J=7.84 Hz, 1 H) 7.70 (s, 1 H) 7.30 (s, 1 H) 4.76 (br, 1 H) 3.56 (m, br, 2 H) 3.33 (m, 4 H) 3.12 (s, 3 H) 2.80 (m, 2 H) 1.30 (m, 5 H). [M+H] calc'd for $C_{25}H_{27}ClN_3O_3S$, 484; found, 484.

Compound 259: 3-(5-(3-(ethylsulfonyl)phenyl)-3-(trifluoromethyl)-9H-pyrido[2,3-b]indol-8-yloxy)-N,N-dimethylpropan-1-amine

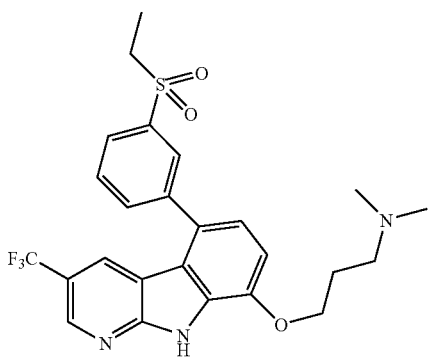

The title compound was synthesized by using an analogous synthetic sequence to that outlined in the preparation of Compound 199. $^1$H NMR (400 MHz, Methanol-$d_4$) δ 8.72 (s, 1 H) 8.15 (s, 1 H) 8.10 (m, 1 H) 7.99 (m, 1 H) 7.93 (s, 1 H) 7.88 (t, J=7.6 Hz, 1 H) 7.28 (d, J=8.08 Hz, 1 H) 7.23 (d, J=8.08 Hz, 1 H) 4.44 (t, J=5.8 Hz, 2 H) 3.72 (t, J=8.0 Hz, 2 H) 3.43 (q, J=7.32 Hz, 2 H) 3.03 (s, 6 H) 2.41 (m, 2 H) 1.34 (t, J=7.32 Hz, 3 H). [M+H] calc'd for $C_{25}H_{27}F_3N_3O_3S$, 506; found, 506.

Compound 260: (3-(8-methoxy-3-methyl-9H-pyrido[2,3-b]indol-5-yl)phenyl)(morpholino)methanone

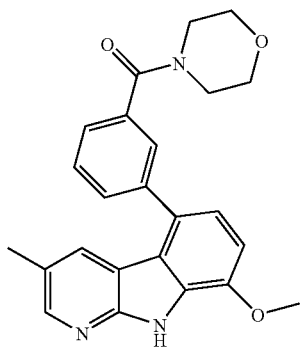

The title compound was synthesized from Compound 155 using an analogous procedure to that outlined in the preparation of Compound 156. $^1$H NMR (400 MHz, Methanol-$d_4$) δ 8.30 (s, 1 H) 8.15 (s, 1 H) 7.73 (m, 2 H) 7.69 (m, 2 H) 7.34 (d, J=8.32 Hz, 1 H) 7.29 (d, J=8.32 Hz, 1 H) 4.14 (s, 3 H) 3.63-3.85 (m, 4 H) 2.44 (s, 3 H). [M+H] calc'd for $C_{24}H_{24}N_3O_3$, 402; found, 402.

Compound 261: N-methoxy-3-(8-methoxy-3-methyl-9H-pyrido[2,3-b]indol-5-yl)benzamide

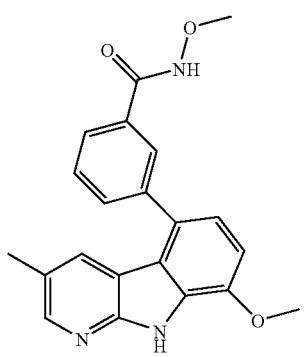

The title compound was synthesized from Compound 155 using an analogous procedure to that outlined in the preparation of Compound 156. $^1$H NMR (400 MHz, Methanol-$d_4$) δ 8.24 (s, 1 H) 8.08 (m, 1 H) 8.03 (m, 1 H) 7.90 (m, 1 H) 7.84 (m, 1 H) 7.68 (t, J=8.08 Hz, 1 H) 7.21 (d, J=8.08 Hz, 1 H) 7.18 (d, J=8.08 Hz, 1 H) 4.11 (s, 3 H) 3.85 (s, 3 H) 2.35 (s, 3 H). [M+H] calc'd for $C_{21}H_{20}N_3O_3$, 362; found, 362.

229

Compound 262: 5-(3-Ethanesulfonyl-phenyl)-8-(cyclopropylmethoxy)-3-methyl-9H-dipyrido[2,3-b;4',3'-d]pyrrole

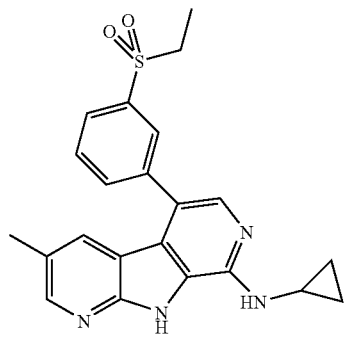

The title compound was prepared using cyclopropanamine in the procedure outlined for the preparation of compound 51. $^1$H NMR (400 MHz, Methanol-d$_4$) δ 8.35 (s, 1 H) 8.20 (s, 1 H) 8.02 (m, 2 H) 7.83 (m, 3 H) 3.43 (q, J=7.32 Hz, 2 H) 3.0 (m, 1 H) 2.37 (s, 3 H) 1.31 (t, J=7.32 Hz, 3 H) 0.93 (m, 2 H) 0.67 (m, 2 H). [M+H] calc'd for C$_{22}$H$_{23}$N$_4$O$_2$S, 407; found, 407.

Compound 263: N-(2-(diethylamino)ethyl)-5-(3-(ethylsulfonyl)phenyl)-3,8-dimethyl-9H-pyrido[2,3-b]indole-7-carboxamide

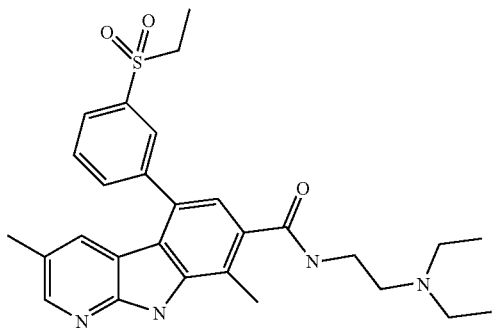

The title compound was synthesized using an analogous procedure to that described in the preparation of compound 87. ESI-MS: m/z calc'd for C28H34N4O3S 506.242; found 507.4 (M+H)$^-$

Compound 264: 5-(3-(ethylsulfonyl)phenyl)-3,8-dimethyl-N-(3-morpholinopropyl)-9H-pyrido[2,3-b]indole-7-carboxamide

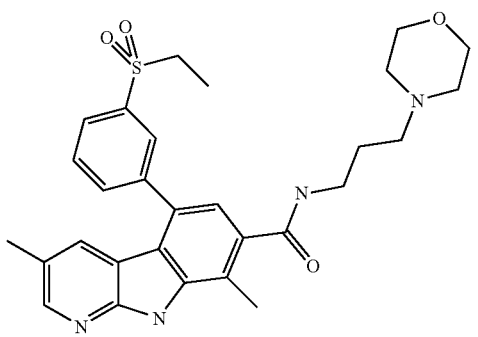

230

The title compound was synthesized using an analogous procedure to that described in the preparation of compound 87. ESI-MS: m/z calc'd for C29H34N4O4S 534.6; found 535.7 (M+H)$^+$ Compounds according to the present invention can also be prepared as pharmaceutically acceptable salts. Salts of compounds of the present inventions can be formed using, for example, the following acids: benzoic acid, fumaric acid, HBr, HCl, hippuric acid, lactic acid, maleic acid, malic acid, MSA, phosphoric acid, p-TSA, succinic acid, sulfuric acid, tartaric acid, and the like. The salts of the above acids can be prepared by adding 0.5 to 2.0 equivalents of the appropriate acid in any of a variety of solvents (such as MECN, ETOH, MEOH, DMA, THF, AcOH, and the like, or mixtures thereof) at a temperature of between about 10° C. and 75° C.

For example, the mono HCl salt of 5-(3-(ethylsulfonyl)phenyl)-3,8-dimethyl-N-(1-methylpiperidin-4-yl)-9H-pyrido[2,3-b]indole-7-carboxamide (Compound 112) was prepared as follows. To a solution of 5-(3-(ethylsulfonyl)phenyl)-3,8-dimethyl-N-(1-methylpiperidin-4-yl)-9H-pyrido[2,3-b]indole-7-carboxamide (2.105 g) in MeOH (20 mL) was added 4.38 mL of 1N aqueous HCl. The mixture was stirred for 15-30 min at 25° C. The solvent was removed to near dryness, and the resultant white solid filtered and dried to provide 2.23 g of the title compound. Mono HCl salts of the following compounds were also prepared using an analogous procedure:

- 5-(3-(ethylsulfonyl)phenyl)-3-methyl-8-((1-methylpiperidin-4-yl)methoxy)-9H-pyrido[2,3-b]indole (Compound 176 and 182);
- 3-chloro-5-(3-(ethylsulfonyl)phenyl)-8-((1-methylpiperidin-4-yl)methoxy)-9H-pyrido[2,3-b]indole (Compound 199);
- 3-(5-(3-(ethylsulfonyl)phenyl)-3-methyl-9H-pyrido[2,3-b]indol-8-yloxy)-N,N-dimethylpropan-1-amine (Compound 205);
- 3-(3-chloro-5-(3-(ethylsulfonyl)phenyl)-9H-pyrido[2,3-b]indol-8-yloxy)-N,N-dimethylpropan-1-amine (Compound 219); and
- N-cyclopropyl-3-(3-methyl-8-((1-methylpiperidin-4-yl)methoxy)-9H-pyrido[2,3-b]indol-5-yl)benzamide (Compound 177).

Biological Testing

The activity of compounds as protein kinase inhibitors may be assayed in vitro, in vivo or in a cell line. In vitro assays include assays that determine inhibition of either the phosphorylation activity or ATPase activity of the activated protein kinase. Alternate in vitro assays quantitate the ability of the inhibitor to bind to the protein kinase. Inhibitor binding may be measured by radiolabelling the inhibitor prior to binding, isolating the inhibitor/protein kinase complex and determining the amount of radiolabel bound. Alternatively, inhibitor binding may be determined by running a competition experiment where new inhibitors are incubated with the protein kinase bound to known radioligands.

A. Determination of Inhibition of AIK

The inhibitory properties of compounds relative to AIK may be determined by the Direct Fluorescence Polarization detection method (FP) using a Greiner small volume black 384-well-plate format under the following reaction conditions: 50 mM Hepes pH 7.3, 10 mM MgCl$_2$, 10 mM NaCl, 1 mM DTT, 0.01% Brij35, 100 nM Fluorescein-LRRASLG peptide (provided by SYNPEP), 5% DMSO, 2.5 µM ATP. Detection of the reaction product is performed by addition of IMAP binding reagent (Molecular Devices). Reaction product may be determined quantitatively by FP using an Analyst HT plate reader (Molecular Devices) with an excitation wavelength at 485 nm and emission at 530 nm and using a Fluorescein 505 dichroic mirror.

The assay reaction may be initiated as follows: 2 ul of (3×) 300 nM Fl-Peptide/7.5 uM ATP was added to each well of the plate, followed by the addition of 2 ul of (3×) inhibitor (2.5 fold serial dilutions for 11 data points for each inhibitor) containing 15% DMSO. 2 ul of (3×) 7.5 nM AIK solution may be added to initiate the reaction (final enzyme concentration was 2.5 nM for AIK). The reaction mixture may then be incubated at room temperature for 45 min, and quenched and developed by addition of 20 ul of 1 to 400 diluted IMAP binding reagent in 1× proprietary IMAP binding buffer. Fluorescence polarization readings of the resulting reaction mixtures may be measured after a 60-minute incubation at room temperature.

IC50 values may be calculated by non-linear curve fitting of the compound concentrations and fluorescent polarization values to the standard $IC_{50}$ equation. As a reference point for this assay, Staurosporin showed an $IC_{50}$ of <10 nM.

B. Determination of Inhibition of c-KIT

The inhibitory properties of compounds relative to c-Kit may be determined by the Time-Resolved Fluorescence Resonance Energy Transfer (TR-FRET) method using a small volume black 384-well-plate (Greiner) format under the following reaction conditions: 50 mM Hepes pH 7.3, 10 mM MgCl2, 10 mM NaCl, 1 mM DTT, 0.01% Brij35, 250 nM Biotin-EGPWLEEEEEAYGWMDF peptide (provided by SYNPEP), 5% DMSO, 100 uM ATP. Detection of the reaction product may be performed by addition of Streptavidin-APC (Prozyme) and Eu-Anti-phosphotyrosine antibody (Perkin Elmer). Reaction product may be determined quantitatively by TR-FRET reading using an Analyst HT plate reader (Molecular Devices) with an excitation wavelength at 330 nm and emission at 615 nm (Europium) compared to 330 nm excitation (Europium) and emission 665 nm (APC) and using an Europium 400 dichroic mirror.

The assay reaction may be initiated as follows: 4 ul of (2.5×) 625 nM Biotin-Peptide/250 uM ATP was added to each well of the plate, followed by the addition of 2 ul of (5×) inhibitor (2.5 fold serial dilutions for 11 data points for each inhibitor) containing 25% DMSO. 4 ul of (2.5×) c-Kit solution may be added to initiate the reaction (final enzyme concentration was 0.13 nM for c-Kit). The reaction mixture may then be incubated at room temperature for 30 min, and quenched and developed by addition of 10 ul of (2×) 3.2 nM Eu-Antibody and 25 nM Streptavidin-APC in 50 nM Hepes pH 7.3, 30 mM EDTA, 0.1% Triton X-100 buffer. TR-FRET reading of the resulting reaction mixtures may be measured after a 60-minute incubation at room temperature on the Analyst HT.

$IC_{50}$ values may be calculated by non-linear curve fitting of the compound concentrations and ration metric Eu:APC values to the standard $IC_{50}$ equation. As a reference point for this assay, Staurosporin showed an $IC_{50}$ of <5 nM. $IC_{50}$ values for select compounds of the invention are given in Table 1.

TABLE 1

$IC_{50}$ of Exemplified Compounds Against AIK

| COMPOUND | $IC_{50}$ (nM) |
|---|---|
| 15 | <20 |
| 17 | 20-50 |
| 41 | 50-100 |
| 48 | >100 |
| 50 | <20 |

TABLE 1-continued $IC_{50}$ of Exemplified Compounds Against AIK

| COMPOUND | $IC_{50}$ (nM) |
|---|---|
| 53 | <20 |
| 87 | 20-50 |
| 110 | <20 |
| 111 | 20-50 |
| 112 | 20-50 |
| 120 | >100 |
| 154 | <20 |
| 161 | 50-100 |
| 174 | <20 |
| 175 | 50-100 |
| 197 | <20 |
| 199 | 20-50 |
| 203 | <20 |
| 217 | <20 |
| 240 | 20-50 |

The following abbreviations have been used:
ATP Adenosine Triphophatase
BAS Bovine Serum Albumin
EDTA Ethylenediaminetetraacetic acid
GSK3 Glycogen synthase kinase 3
MOPS Morpholinepropanesulfonic acid
SPA on Scintillation Proximity Assay It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:
1. A compound consisting of a formula:

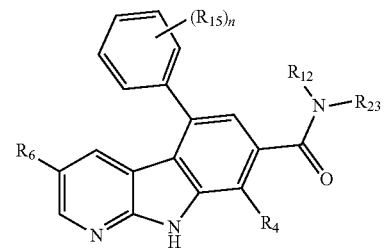

or pharmaceutically acceptable salts thereof,
wherein
$R_4$ is selected from the group consisting of (1) hydrogen (2) halo and (3) $(C_{1-5})$alkyl;
$R_6$ is selected from the group consisting of (1) hydrogen (2) halo (3) alkoxy and (4) $(C_{1-5})$alkyl;
$R_{12}$ is selected from the group consisting of (1) hydrogen, (2) $(C_{1-10})$alkyl optionally substituted with one or more substituents selected from the group consisting of halo; cyano; hydroxy; $(C_{1-10})$alkoxy; amino; $(C_{1-10})$alkylamino; di-$(C_{1-10})$ alkylamino; and hetero$(C_{3-12})$cycloalkyl optionally substituted by a $(C_{1-10})$alkyl (3) hetero$(C_{3-12})$cycloalkyl optionally substituted with one or more substituents selected from the group consisting of halo; cyano; hydroxy; $(C_{1-10})$alkyl; $(C_{1-10})$alkoxy; amino $(C_{1-10})$alkylamino and di-$(C_{1-10})$alkylamino and (4) heteroaryl selected from the group consisting of furyl, imidazoyl, isothiazolyl, isoxazolyl, oxadiazolyl, oxazolyl, 1,2,3-oxadiazoly, pyrazinyl, pyrazolyl, pyridazyl, pyridyl, pyrimidyl, thiazolyl, 1,3,4-thiadiazolyl, triazolyl, and tetrazolyl;

n is selected from the group consisting of 0, 1, 2, 3, 4 and 5;

$R_{15}$ is selected from the group consisting of halo, cyano, hydroxy, amino, $(C_{1-10})$alkyl, —$OR_{22}$, —$C(O)$—$R_{22}$, —$NR_{23}$—$C(O)$—$R_{22}$, —$C(O)$—$NR_{23}$—$R_{22}$, —$SO_2$—$R_{22}$, —$NR_{23}$—$SO_2$—$R_{22}$, and —$SO_2$—$NR_{23}R_{24}$;

$R_{22}$ is selected from the group consisting of $(C_{1-10})$alkyl and $(C_{3-12})$cycloalkyl;

$R_{23}$ is selected from the group consisting of hydrogen and $(C_{1-10})$alkyl; and $R_{24}$ is selected from the group consisting of hydrogen, $(C_{1-10})$alkyl, and $(C_{3-12})$cycloalkyl.

2. The compound according to claim 1, wherein $R_4$ is methyl.

3. The compound according to claim 2, wherein $R_6$ is $(C_{1-5})$alkyl.

4. The compound according to claim 3, wherein $R_{12}$ is selected from the group consisting of (1) hydrogen (2) $(C_{1-10})$alkyl optionally substituted with one or more substituents selected from the group consisting of hydroxy; $(C_{1-10})$alkylamino; di-$(C_{1-10})$alkylamino; and hetero$(C_{3-12})$cycloalkyl optionally substituted by a $(C_{1-10})$alkyl and (3) hetero$(C_{3-12})$cycloalkyl optionally substituted by a $(C_{1-10})$alkyl.

5. The compound according to claim 4, wherein $R_{23}$ is hydrogen.

6. The compound according to any one of claims 1 or 5 consisting of a formula:

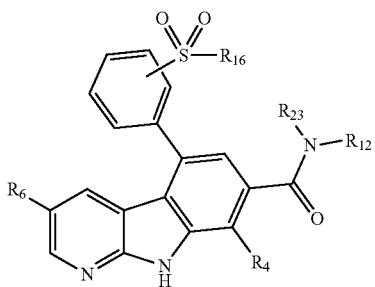

wherein
$R_{16}$ is selected from the group consisting of $(C_{1-10})$alkyl and $(C_{3-12})$cycloalkyl.

7. The compound according to any one of claims 1 or 5 consisting of a formula:

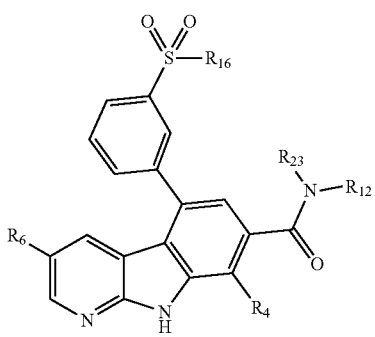

wherein
$R_{16}$ is selected from the group consisting of $(C_{1-10})$alkyl and $(C_{3-12})$cycloalkyl.

8. The compound according to any one of claims 1 or 5 comprising a formula:

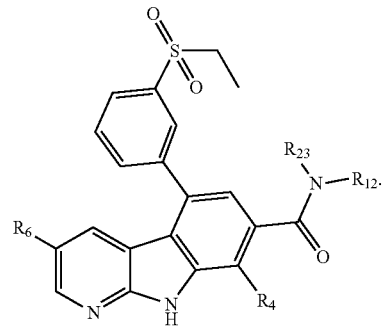

9. The compound according to any one of claims 1 or 5 comprising a formula:

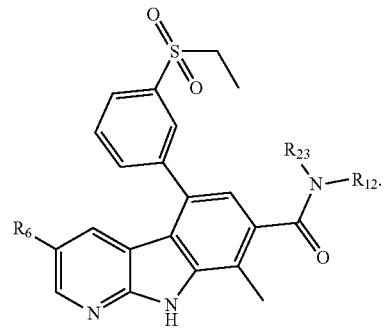

10. The compound according to claim 1 selected from the group consisting of:
- N-(2-(dimethylamino)ethyl)-5-(3-(ethylsulfonyl)phenyl)-3,8-dimethyl-9H-pyrido[2,3-b]indole-7-carboxamide;
- N-(2-(methoxy)ethyl)-5-(3-(ethylsulfonyl)phenyl)-3,8-dimethyl-9H-pyrido[2,3-b]indole-7-carboxamide;
- N-(2-(dimethylamino)ethyl)-N-methyl-5-(3-(ethylsulfonyl)phenyl)-3,8-dimethyl-9H-pyrido[2,3-b]indole-7-carboxamide;
- N,N-dimethyl-5-(3-(ethylsulfonyl)phenyl)-3,8-dimethyl-9H-pyrido[2,3-b]indole-7-methylcarboxamide;
- 5-(3-(ethylsulfonyl)phenyl)-3,8-dimethyl-N-(2-piperazin-1-yl)ethyl)-9H-pyrido[2,3-b]indole-7-carboxamide;
- 5-(3-(ethylsulfonyl)phenyl)-3,8-dimethyl-N-(3-(4-methylpiperazin-1-yl)propyl)-9H-pyrido[2,3-b]indole-7-carboxamide;
- (R)-5-(3-(ethylsulfonyl)phenyl)-N-(2-hydroxypropyl)-3,8-dimethyl-9H-pyrido[2,3-b]indole-7-carboxamide;
- (S)-5-(3-(ethylsulfonyl)phenyl)-N-(2-hydroxypropyl)-3,8-dimethyl-9H-pyrido[2,3-b]indole-7-carboxamide;
- 5-(3-(ethylsulfonyl)phenyl)-N-(2-hydroxyethyl)-3,8-dimethyl-9H-pyrido[2,3-b]indole-7-carboxamide;
- N-(2,3-dihydroxypropyl)-5-(3-(ethylsulfonyl)phenyl)-3,8-dimethyl-9H-pyrido[2,3-b]indole-7-carboxamide;
- 5-(3-(ethylsulfonyl)phenyl)-N-(2-hydroxy-2-methylpropyl)-3,8-dimethyl-9H-pyrido[2,3-b]indole-7-carboxamide;
- 5-(3-(ethylsulfonyl)phenyl)-N-(1-isopropylpiperidin-4-yl)-3,8-dimethyl-9H-pyrido[2,3-b]indole-7-carboxamide;

N-(1-ethylpiperidin-4-yl)-5-(3-(ethylsulfonyl)phenyl)-3,8-dimethyl-9H-pyrido[2,3-b]indole-7-carboxamide;

5-(3-(ethylsulfonyl)phenyl)-3,8-dimethyl-N-thiazol-2-yl)-9H-pyrido[2,3-b]indole-7-carboxamide;

5-(3-(ethylsulfonyl)phenyl)-3,8-dimethyl-N-(piperidin-3-yl)-9H-pyrido[2,3-b]indole-7-carboxamide;

5-(3-(ethylsulfonyl)phenyl)-3,8-dimethyl-N-(piperidin-4-yl)-9H-pyrido[2,3-b]indole-7-carboxamide;

5-(3-(cyclopropanecarboxamido)phenyl)-N-(2-(dimethylamino)ethyl)-3,8-dimethyl-9H-pyrido[2,3-b]indole-7-carboxamide;

5-(3-(ethylsulfonyl)phenyl)-3,8-dimethyl-N-((1-methylpiperidin-4-yl)methyl)-9H-pyrido[2,3-b]indole-7-carboxamide;

N-(3-(dimethylamino)propyl)-5-(3-(ethylsulfonyl)phenyl)-3,8-dimethyl-9H-pyrido[2,3-b]indole-7-carboxamide;

5-(3-(ethylsulfonyl)phenyl)-3,8-dimethyl-N-(2-(pyrrolidin-1-yl)ethyl)-9H-pyrido[2,3-b]indole-7-carboxamide;

(S)-5-(3-(ethylsulfonyl)phenyl)-3,8-dimethyl-N-(1-methylpiperidin-3-yl)-9H-pyrido[2,3-b]indole-7-carboxamide;

(R)-5-(3-(ethylsulfonyl)phenyl)-3,8-dimethyl-N-(1-methylpiperidin-3-yl)-9H-pyrido[2,3-b]indole-7-carboxamide;

5-(3-(cyclopropylcarbamoyl)phenyl)-N-(2-(dimethylamino)ethyl)-3,8-dimethyl-9H-pyrido[2,3-b]indole-7-carboxamide;

5-(3-Ethanesulfonyl-phenyl)-3-methyl-9H-pyrido[2,3-b]indole-7-carboxylic acid (2-dimethylamino-ethyl)-amide;

5-(3-Ethanesulfonyl-phenyl)-3-methyl-9H-pyrido[2,3-b]indole-7-carboxylic acid (3-dimethylamino-propyl)-amide;

5-(3-Ethanesulfonyl-phenyl)-3-methyl-9H-pyrido[2,3-b]indole-7-carboxylic acid amide;

N-ethyl-5-(3-(ethylsulfonyl)phenyl)-3-methyl-9H-pyrido[2,3-b]indole-7-carboxamide;

5-(3-(cyclopropylcarbamoyl)phenyl)-3,8-dimethyl-N-(1-methylpiperidin-4-yl)-9H-pyrido[2,3-b]indole-7-carboxamide; and 5-(3-(ethylsulfonyl)phenyl)-3,8-dimethyl-N-(3-morpholinopropyl)-9H-pyrido[2,3-b]indole-7-carboxamide.

11. A pharmaceutical composition comprising, as an active ingredient, a compound according to claim 1 and a pharmaceutical excipient.

12. The compound according to claim 1, wherein the compound is 5-(3-(ethylsulfonyl)phenyl)-3,8-dimethyl-N-(1-methylpiperidin-4-yl)-9H-pyrido[2,3-b]indole-7-carboxamide HCl salt.

13. The compound according to claim 1, wherein the compound is N-(2-(methylamino)ethyl)-5-(3-(ethylsulfonyl)phenyl)-3,8-dimethyl-9H-pyrido[2,3-b]indole-7-carboxamide.

14. The compound according to claim 1, wherein the compound is 5-(3 -(ethylsulfonyl)phenyl)-3,8-dimethyl-N-(1-methylpiperidin-4-yl)-9H-pyrido[2,3 -b]indole-7-carboxamide.

15. The compound according to claim 1, wherein the compound is 5-(3-(cyclopropanecarboxamido)phenyl)-3,8-dimethyl-N-(1-methyl-piperidin-4-yl)-9H-pyrido[2,3-b]indole-7-carboxamide.

16. The compound according to claim 1, wherein the compound is 5-(3-(cyclopropylsulfonyl)phenyl)-3,8-dimethyl-N-(1-methylpiperidin-4-yl)-9H-pyrido[2,3-b]indole-7-carboxamide.

17. The compound according to claim 1, wherein the compound is N-(2-(diethylamino)ethyl)-5-(3-(ethylsulfonyl)phenyl)-3,8-dimethyl-9H-pyrido[2,3-b]indole-7-carboxamide.

* * * * *